US012653992B2

(12) United States Patent
Shimizu et al.

(10) Patent No.: US 12,653,992 B2
(45) Date of Patent: Jun. 16, 2026

(54) METHODS AND DEVICES FOR TREATING A DISEASE WITH BIOTHERAPEUTICS

(71) Applicant: BIORA THERAPEUTICS, INC., San Diego, CA (US)

(72) Inventors: Jeffrey A. Shimizu, Poway, CA (US); Mitchell Lawrence Jones, La Jolla, CA (US); Mark Sasha Drlik, Victoria (CA); Iman Niknia, Victoria (CA); Nathan John Muller, Victoria (CA); Tuyen Nguyen, Victoria (CA); Christopher Loren Wahl, San Diego, CA (US); Edward Mudge, Cambridgeshire (GB); Nicholas Mark Salt, Cambridgeshire (GB); Nia Eleri Stevens, Cambridgeshire (GB); Stuart Robert Abercrombie, Cambridgeshire (GB); Christopher Ian Bunce, Cambridgeshire (GB); Nelson Quintana, Temecula, CA (US)

(73) Assignee: BT Bidco, Inc., San Diego, CA (US)

( * ) Notice: Subject to any disclaimer, the term of this patent is extended or adjusted under 35 U.S.C. 154(b) by 873 days.

(21) Appl. No.: 17/295,277

(22) PCT Filed: Nov. 19, 2019

(86) PCT No.: PCT/US2019/062261
§ 371 (c)(1),
(2) Date: Mar. 17, 2022

(87) PCT Pub. No.: WO2020/106750
PCT Pub. Date: May 28, 2020

(65) Prior Publication Data
US 2022/0249814 A1     Aug. 11, 2022

Related U.S. Application Data

(60) Provisional application No. 62/932,459, filed on Nov. 7, 2019, provisional application No. 62/819,513, filed
(Continued)

(51) Int. Cl.
*A61M 31/00*     (2006.01)
*A61K 38/17*     (2006.01)
(Continued)

(52) U.S. Cl.
CPC ....... *A61M 31/002* (2013.01); *A61K 38/1796* (2013.01); *A61K 38/26* (2013.01);
(Continued)

(58) Field of Classification Search
CPC ............... A61M 31/002; A61M 11/02; A61M 2210/1042; A61M 2210/106;
(Continued)

(56) References Cited

U.S. PATENT DOCUMENTS 3,057,344 A    10/1962    Alberto
3,118,439 A     1/1964    Barana
(Continued)

FOREIGN PATENT DOCUMENTS

CN           1856290 B      11/2006
CN         108784634 A      11/2018
(Continued)

OTHER PUBLICATIONS

Moroz, Elena, Simon Matoori, and Jean-Christophe Leroux. "Oral delivery of macromolecular drugs: Where we are after almost 100 years of attempts." Advanced drug delivery reviews 101 (2016): 108-121.
(Continued)

*Primary Examiner* — James D Ponton
(74) *Attorney, Agent, or Firm* — Perkins Coie LLP

(57)     ABSTRACT
This disclosure features methods and devices for treating diseases with orally-delivered biotherapeutics.

18 Claims, 73 Drawing Sheets

Related U.S. Application Data on Mar. 15, 2019, provisional application No. 62/818,731, filed on Mar. 14, 2019, provisional application No. 62/769,496, filed on Nov. 19, 2018.

(51) Int. Cl.

| | |
|---|---|
| *A61K 38/26* | (2006.01) |
| *A61K 38/28* | (2006.01) |
| *A61M 11/02* | (2006.01) |
| *A61P 1/04* | (2006.01) |
| *C07K 16/24* | (2006.01) |

(52) U.S. Cl.
CPC ............. *A61K 38/28* (2013.01); *A61M 11/02* (2013.01); *A61P 1/04* (2018.01); *C07K 16/241* (2013.01); *A61M 2210/1042* (2013.01); *A61M 2210/106* (2013.01); *A61M 2210/1064* (2013.01)

(58) Field of Classification Search
CPC .. A61M 2210/1064; A61M 2205/8218; A61M 2205/8281; A61M 2210/1053; A61P 1/04; A61P 1/16; A61P 19/02; A61P 29/00; A61P 35/00; C07K 16/241; A61K 9/0053; A61K 31/4035; A61K 31/69; A61K 31/727; A61K 2039/505
See application file for complete search history.

(56) References Cited

U.S. PATENT DOCUMENTS

| | | | |
|---|---|---|---|
| 3,315,660 A | | 4/1967 | Abella |
| 3,485,235 A | | 12/1969 | Felson |
| 4,036,214 A | | 7/1977 | Bucalo |
| 4,172,446 A | | 10/1979 | Bucalo |
| 4,239,040 A | | 12/1980 | Hosoya |
| 4,425,117 A | | 1/1984 | Hugeman |
| 4,439,197 A | * | 3/1984 | Honda ................ A61M 31/002 |
| | | | D24/117 |
| 4,481,952 A | | 11/1984 | Pawelec |
| 4,507,115 A | | 3/1985 | Kambara |
| 4,522,625 A | | 6/1985 | Edgren |
| 4,596,556 A | * | 6/1986 | Morrow ................... A61M 5/30 |
| | | | 604/70 |
| 5,167,626 A | | 12/1992 | Casper et al. |
| 5,170,801 A | | 12/1992 | Casper |
| 5,217,449 A | | 6/1993 | Yuda et al. |
| 5,279,607 A | * | 1/1994 | Schentag ............. A61B 5/0031 |
| | | | 604/890.1 |
| 5,316,015 A | | 5/1994 | Sinaiko |
| 5,318,557 A | | 6/1994 | Gross |
| 5,395,366 A | | 3/1995 | Andrea |
| 5,604,531 A | | 2/1997 | Iddan et al. |
| 5,738,110 A | | 4/1998 | Beal et al. |
| 5,858,001 A | | 1/1999 | Tsals et al. |
| 5,951,538 A | | 9/1999 | Joshi |
| 5,971,942 A | | 10/1999 | Gu et al. |
| 6,632,216 B2 | | 10/2003 | Houzego |
| 6,884,239 B2 | | 4/2005 | Houzego et al. |
| 6,950,690 B1 | | 9/2005 | Meron et al. |
| 7,144,366 B2 | | 12/2006 | Takizawa et al. |
| 7,160,258 B2 | | 1/2007 | Imran et al. |
| 7,611,480 B2 | | 11/2009 | Levy |
| 7,662,093 B2 | | 2/2010 | Gilad et al. |
| 7,717,862 B2 | | 5/2010 | Stoltz |
| 7,717,874 B2 | | 5/2010 | Landau et al. |
| 7,763,014 B2 | | 7/2010 | Houzeao et al. |
| 7,946,979 B2 | | 5/2011 | Gilad et al. |
| 8,005,536 B2 | | 8/2011 | Imran |
| 8,216,130 B2 | | 7/2012 | Glukhovsky et al. |
| 8,360,976 B2 | | 1/2013 | Imran |
| 8,597,279 B2 | | 12/2013 | Dijksman et al. |
| 8,626,268 B2 | | 1/2014 | Adler |
| 8,696,602 B2 | | 4/2014 | Semler et al. |
| 8,740,774 B2 | | 6/2014 | Takizawa et al. |
| 8,809,271 B2 | | 8/2014 | Imran |
| 8,926,526 B2 | | 1/2015 | Shuck |
| 8,998,881 B2 | * | 4/2015 | Gilbert .................... A61M 5/30 |
| | | | 604/521 |
| 9,072,834 B2 | | 7/2015 | Vogt |
| 9,456,737 B2 | | 10/2016 | Pascal |
| 9,511,121 B2 | | 12/2016 | Imran |
| 10,172,598 B2 | | 1/2019 | Amoako-Tuffour et al. |
| 10,588,608 B2 | | 3/2020 | Jones et al. |
| 10,632,251 B2 | | 4/2020 | Imran et al. |
| 10,765,360 B2 | | 9/2020 | Euliano et al. |
| 10,835,152 B2 | | 11/2020 | Jones et al. |
| 11,007,356 B2 | | 5/2021 | Shimizu et al. |
| 11,439,802 B2 | | 9/2022 | Shimizu et al. |
| 2002/0099310 A1 | | 7/2002 | Kimchy |
| 2002/0198470 A1 | | 12/2002 | Imran et al. |
| 2004/0162469 A1 | | 8/2004 | Imran |
| 2004/0199054 A1 | | 10/2004 | Wakefield et al. |
| 2004/0253304 A1 | | 12/2004 | Gross et al. |
| 2005/0158246 A1 | | 7/2005 | Takizawa |
| 2007/0043320 A1 | | 2/2007 | Kenany |
| 2008/0051635 A1 | | 2/2008 | Tanaka et al. |
| 2008/0086079 A1 | * | 4/2008 | Williamson ............ A61M 5/30 |
| | | | 604/68 |
| 2009/0275923 A1 | | 11/2009 | Shimizu et al. |
| 2010/0049012 A1 | * | 2/2010 | Dijksman ............ A61B 5/4839 |
| | | | 604/890.1 |
| 2010/0049120 A1 | | 2/2010 | Dijksman et al. |
| 2010/0063486 A1 | | 3/2010 | Diiksman et al. |
| 2010/0324381 A1 | | 12/2010 | Glukhovskv et al. |
| 2011/0046458 A1 | | 2/2011 | Pinedo |
| 2011/0087155 A1 | | 4/2011 | Uhland et al. |
| 2011/0092959 A1 | | 4/2011 | Zou et al. |
| 2011/0106063 A1 | | 5/2011 | Diiksman et al. |
| 2012/0136209 A1 | | 5/2012 | Kostenich et al. |
| 2012/0208755 A1 | | 8/2012 | Leung |
| 2013/0172257 A1 | | 7/2013 | Imran |
| 2015/0011874 A1 | | 1/2015 | Amoaka-Tuffour et al. |
| 2015/0051589 A1 | | 2/2015 | Sako et al. |
| 2015/0065926 A1 | | 3/2015 | Nakamura et al. |
| 2015/0209411 A1 | | 7/2015 | Berenbaum et al. |
| 2016/0213234 A1 | | 7/2016 | Poon |
| 2016/0235663 A1 | | 8/2016 | Zou et al. |
| 2016/0375232 A1 | | 12/2016 | Kugler et al. |
| 2017/0050006 A1 | | 2/2017 | Imran et al. |
| 2017/0106099 A1 | | 4/2017 | Bellinger et al. |
| 2017/0246438 A1 | * | 8/2017 | Aran ................. A61K 39/0005 |
| 2017/0296092 A1 | | 10/2017 | Jones et al. |
| 2018/0049725 A1 | | 2/2018 | Jones et al. |
| 2018/0052084 A1 | | 2/2018 | Jones et al. |
| 2018/0070857 A1 | | 3/2018 | Jones et al. |
| 2018/0160950 A1 | | 6/2018 | Rabinovitz et al. |
| 2018/0279908 A1 | | 10/2018 | Jones et al. |
| 2018/0318496 A1 | | 11/2018 | Zou et al. |
| 2019/0083073 A1 | | 3/2019 | Amoaka-Tuffour et al. |
| 2019/0388502 A1 | | 12/2019 | Corvari |
| 2020/0038268 A1 | | 2/2020 | Shrapnel |
| 2020/0094031 A1 | | 3/2020 | Jones et al. |
| 2020/0245897 A1 | | 8/2020 | Jones et al. |
| 2020/0308268 A1 | | 10/2020 | Imran |
| 2020/0316352 A1 | | 10/2020 | Aran et al. |
| 2021/0015398 A1 | | 1/2021 | Jones et al. |
| 2021/0093248 A1 | | 4/2021 | Euliano et al. |
| 2021/0161805 A1 | | 6/2021 | Zou et al. |
| 2022/0072286 A1 | | 3/2022 | Bonner et al. |
| 2022/0080115 A1 | | 3/2022 | Traverso et al. |

FOREIGN PATENT DOCUMENTS

| | | | |
|---|---|---|---|
| DE | 19801573 A1 | 7/1999 | |
| EP | 1530950 A1 | 5/2005 | |
| EP | 2201938 A1 | 6/2010 | |
| EP | 2515992 B1 | 10/2012 | |
| JP | 2005073888 A | 3/2005 | |
| JP | 2008500876 A | 1/2008 | |
| WO | WO0145789 A2 | 6/2001 | |
| WO | WO2008014439 A2 | 1/2008 | |
| WO | WO2008053396 A2 | 5/2008 | |

(56) References Cited

FOREIGN PATENT DOCUMENTS

| | | | |
|----|-----------------|----|---------|
| WO | 2009104110 | A1 | 8/2009 |
| WO | WO2013003824 | A1 | 1/2013 |
| WO | 2018049133 | A1 | 3/2018 |
| WO | WO2018183934 | A1 | 10/2018 |
| WO | 2018213588 | A1 | 11/2018 |
| WO | 2020041774 | A1 | 2/2020 |
| WO | 2020157324 | A1 | 8/2020 |
| WO | 2020160399 | A1 | 8/2020 |
| WO | 2021119482 | A1 | 6/2021 |

OTHER PUBLICATIONS

Caffarel-Salvador, Ester, et al. "Oral delivery of biologics using drug-device combinations." Current opinion in pharmacology 36 (2017): 8-13.
Trietley et al.—"Albiglutide (Tanzeum) for Diabetes Mellitus", Steps, New Drug Reviews, Apr. 15, 2017 (Year: 2017).
Wang, Xing-Chun. "Effects of Glucagon-like Peptide-1 Receptor Agonists on Non-Alcoholic Fatty Liver Disease and Inflammation."
World Journal of Gastroenterology, vol. 20, No. 40, Oct. 28, 2014, p. 14821., doi: 10.3748/wjg.v20.40.14821. (Year: 2014).
Marso, Steven P etal. "Semaglutide and Cardiovascular Outcomes in Patients with Type 2 Diabetes." The New England Journal of Medicine, Nov. 10, 2016. (Year: 2016).
Ambery P, Parker et al. "MEDI0382, a GLP-1 and glucagon receptor dual agonist, in obese or overweight patients with type 2 diabetes: a randomised, controlled, double-blind, ascending dose and phase 2a study". Lancet. Jun. 30, 2018 (Year: 2018).
International Search Report and Written Opinion for International Application No. PCT/US2019/062261; Date of Mailing: Apr. 9, 2020; 16 pages.
Examination Report No. 1 for Australian Application No. 2019383976; Date of Mailing: Jun. 25, 2024; 5 pages.
Examination Report No. 2. for Australian Application No. 2019383976; Date of Mailing: Jan. 20, 2025; 5 pages.
Office Action in Japanese Application No. 2024-073391; Date of Mailing: Dec. 24, 2024; 2 pages.
Notice of Preliminary Rejection of Korean Application No. 10-2021-7018504; Date of Mailing: Mar. 20, 2025, 1 page.

* cited by examiner 2620        2622                    2624            2626

2700

2704  2710        2708  2706

2702A                                2702B

Jet Velocity v Time

——— 320 PSIG Pre-compressed gas pressure 2 Nozzles

····✳···· 320 PSIG Pre-compressed gas pressure 4 Nozzles

— — — 350 PSIG Pre-compressed gas pressure 4 Nozzles

Jet Impact Force v Time

——— 320 PSIG Pre-compressed gas pressure 2 Nozzles

····✳···· 320 PSIG Pre-compressed gas pressure 4 Nozzles

— — — 350 PSIG Pre-compressed gas pressure 4 Nozzles

Log [Antibody] (µg)

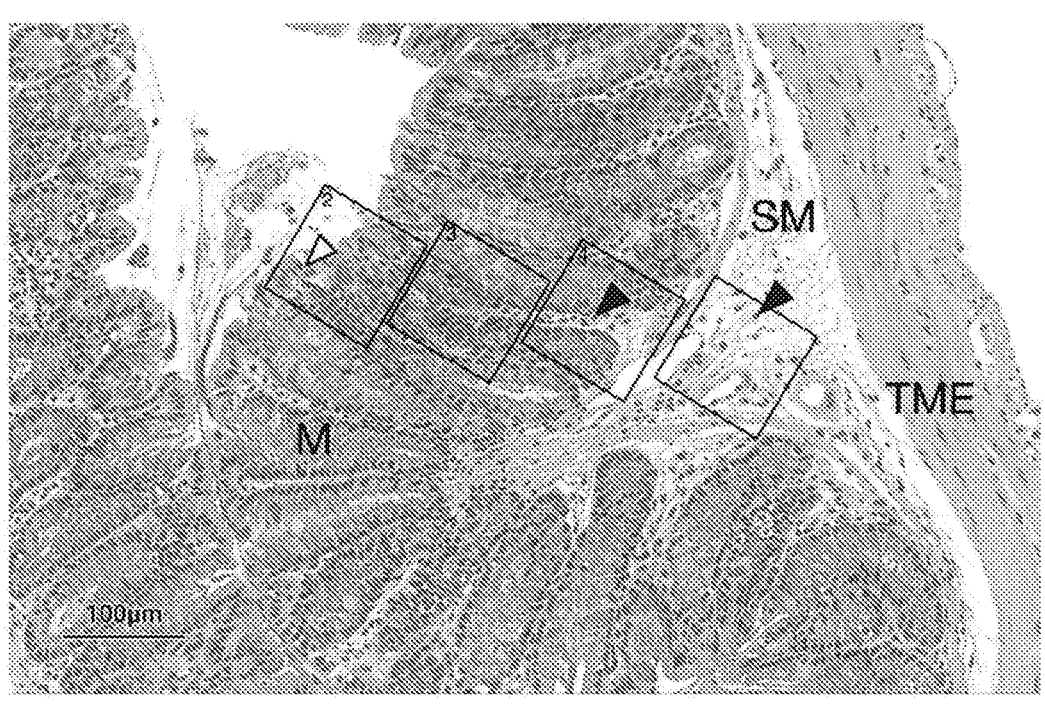
FIG. 71B
Anti-TNFαIC
(IHC. CD4+)
Anti-TNFαlP
(IHC: CD4+)
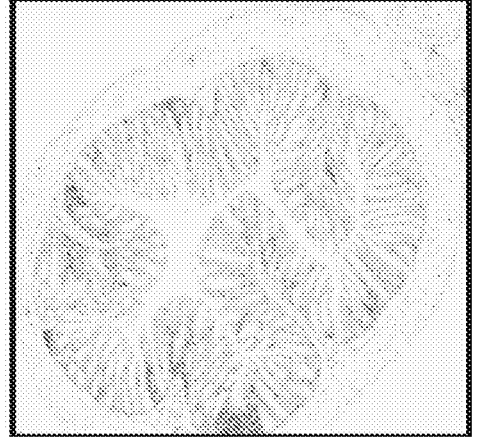
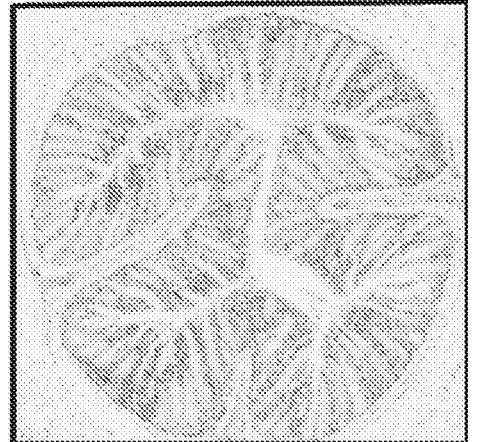
FIG. 71C                FIG. 71D

METHODS AND DEVICES FOR TREATING A DISEASE WITH BIOTHERAPEUTICS

RELATED APPLICATIONS

This application claims the benefit of the following patent applications:

U.S. Ser. No. 62/769,496, filed Nov. 19, 2018, and entitled "Ingestible Device With High Pressure Substance Delivery to the Gastrointestinal Tract";

U.S. Ser. No. 62/818,731, filed Mar. 14, 2019, and entitled "Ingestible Device With High Pressure Substance Delivery to the Gastrointestinal Tract";

U.S. Ser. No. 62/819,513, filed Mar. 15, 2019, and entitled "Ingestible Device With High Pressure Substance Delivery to the Gastrointestinal Tract"; and U.S. Ser. No. 62/932,459, filed Nov. 7, 2019, and entitled "Ingestible Device and Method of Use to Deliver Therapeutic Agent to the Gastrointestinal Tract."

The entire disclosure of each of these applications is incorporated by reference in its entirety.

SEQUENCE LISTING

This application contains a Sequence Listing, which was submitted in ASCII format via EFS-Web and is hereby incorporated by reference in its entirety. The ASCII copy, created on Jun. 7, 2022 is named Biora 144573-8005.US00 Sequence Listing_ST25.txt and is 1 KB in size.

FIELD

The disclosure generally relates to ingestible devices capable of delivering a dispensable substance, such as a therapeutic agent, as well as related components, systems and methods.

BACKGROUND

The gastrointestinal (GI) tract generally provides a therapeutic medium for an individual's body. At times, it is desirable to dispense therapeutic agents to the GI tract to treat a medical condition.

SUMMARY

The disclosure provides ingestible devices that can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

Ingestible devices of the present disclosure are configured to provide at least three different modes of direct delivery of therapeutic agents to the GI tract of a subject, referred to herein as trans-epithelial, epithelial, and topical delivery. Direct delivery, as used herein, refers to a force-driven delivery mechanism.

Thus, in one aspect, this disclosure relates to trans-epithelial delivery of a therapeutic agent to the GI tract of a subject. Accordingly, the disclosure provides an ingestible device that can directly deliver a therapeutic agent past the epithelial cell layer of the mucosa of the GI tract of a subject to yield systemic exposure of the therapeutic agent to the subject. In such embodiments, the ingestible device is configured to directly deliver the therapeutic agent past the epithelial cell layer of the mucosa and into the submucosa and/or into a region of the mucosa beneath the epithelial layer (e.g., into the lamina propria) of the GI tract, where it is available for systemic uptake. This can be particularly relevant when the oral bioavailability of the therapeutic agent is otherwise low. In some embodiments, systemic exposure of the therapeutic agent is achieved by trans-epithelial delivery of the therapeutic agent into the submucosa and/or into a region of the mucosa beneath the epithelial layer (e.g., into the lamina propria) of the small intestine, for example, in the duodenum, the jejunum, and/or the ileum. In further embodiments, the trans-epithelial delivery directly delivers the therapeutic agent into the submucosa submucosa and/or into a region of the mucosa beneath the epithelial layer (e.g., into the lamina propria) of the GI tract such that the percent systemic uptake of the trans-epithelial delivery relative to intravenous or subcutaneous administration is at least about 10% (e.g., at least about 15%, at least about 20%, at least about 25% or more).

As an example, in some embodiments, the ingestible device is configured for trans-epithelial delivery and may provide/exhibit one or more of the following properties. The ingestible device is configured to deliver the dispensable substance to tissue of the GI tract of a subject at a peak jet power of from about one Watt to about three Watts. The ingestible device has a drive force generator that provides an internal pressure of from about 225 psig to about 400 psig. The ingestible device contains the dispensable substance at a peak fluid pressure of from about 200 psig to about 375 psig. The ingestible device is configured to deliver the dispensable substance at a peak jet velocity of from about 25 meters per second to about 45 meters per second. The ingestible device is configured to deliver the dispensable substance as a jet having jet stable length of at least about one millimeter. The ingestible device is configured to deliver the dispensable substance to tissue of the GI tract of a subject at a peak jet pressure of from about 100 psig to about 250 psig. The ingestible device is configured to deliver the dispensable substance to tissue of the GI tract of a subject at a peak jet force of from about 0.09 N to about 0.15 N. The ingestible device has one or more nozzles, each having a diameter of from about 0.1 millimeter to about two millimeters and/or a length of from about one millimeter to about five millimeters.

In another aspect, this disclosure relates to epithelial delivery of a therapeutic agent to the GI tract of a subject. Accordingly, the disclosure provides an ingestible device configured to directly deliver the therapeutic agent into the mucus and/or onto the epithelial layer, but not past the epithelial layer of the mucosa, of the small or large intestine, from which it can act locally, and in some cases away from the site of direct delivery. In some embodiments, the device is configured so that the therapeutic agent is delivered from the device with sufficient force to provide the epithelial delivery, the force being lower than that required for trans-epithelial delivery.

In yet another aspect, this disclosure relates to topical delivery of a therapeutic agent to the GI tract of a subject. Accordingly, the disclosure provides an ingestible device configured to deliver the therapeutic agent into the lumen and/or onto the mucus or other surface of the GI tract facing the lumen of the small or large intestine, from which it can act locally, and in some cases away from the site of delivery. In some embodiments, the device is configured so that the therapeutic agent is delivered from the device with sufficient force so that the therapeutic agent is delivered topically, the force being lower than that required for the epithelial or the trans-epithelial delivery.

The ingestible device, whether configured for trans-epithelial, epithelial or topical delivery, can have a streamlined and/or relatively simple mechanical design, be relatively small, and/or be inexpensive to manufacture. In general, the device protects a dispensable substance (e.g., a therapeutic agent, or a pharmaceutical formulation comprising the therapeutic agent) until the device reaches a desired location of the subject. As an example, the device can be designed to deliver dispensable substance to a desired location in the GI tract of a subject, and the device can be designed so that the dispensable substance is not subject to constituents of the GI tract (e.g., acids, enzymes) prior to reaching the desired location in the GI tract. As another example, the device can be designed to deliver dispensable substance such that the therapeutic properties of the dispensable substance are not altered during delivery (e.g., the dispensable substance is a therapeutic agent that binds its therapeutic target after delivery).

The present disclosure provides ingestible devices that can directly deliver therapeutic agents to desired tissue(s) of the GI tract of a subject (such as the submucosa, the mucosa, and/or the mucus layer of the GI tract), e.g., to treat a particular class of disease, or a specific disease. Relatedly, methods of using the device to deliver the therapeutic agents to desired tissue(s) of the GI tract, e.g., to treat a particular class of disease, or a specific disease, are disclosed. These disclosures also inherently provide disclosures of corresponding medical uses—that is, disclosures of the recited therapeutic agents for use in a method of treating the recited class of disease, or specific disease, by using the device to deliver the recited agents to desired tissue(s) of the GI tract of a subject.

First Group of Aspects of the Disclosure

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to directly deliver the dispensable substance to the GI tract of a subject via trans-epithelial delivery. The ingestible device may be configured to directly deliver the dispensable substance into the lamina propria of the GI tract of the subject, and/or the ingestible device may be to directly deliver the dispensable substance into the submucosa of the GI tract of the subject.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance to tissue of the GI tract of a subject as a jet with a peak jet power of from about one Watt to about three Watts. The peak jet power may be from about 1.3 Watts to about 2.8 Watts, from about 1.5 Watts to about 2.5 Watts, or about 2.3 Watts.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to provide an internal pressure of from about 225 psig to about 425 psig. The internal pressure may be from about 250 psig to about 400 psig, or from about 300 psig to about 375 psig.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to contain the dispensable substance at a peak fluid pressure of from about 200 psig to about 400 psig.

The ingestible device may be configured to deliver the dispensable substance at a mean jet velocity of from about 25 m/s to about 35 m/s.

The ingestible device may be configured to contain the dispensable substance at a peak fluid pressure of: from about 200 psig to about 375 psig.

The ingestible device may be configured to deliver the dispensable substance at a mean jet velocity of from about 20 m/s to about 30 m/s, from about 25 m/s to about 30 m/s, or from about 27 m/s to about 30 m/s or from about 28 m/s to about 30 m/s.

The opening in the ingestible device may comprise a nozzle opening having a diameter of from about 0.1 mm to about 2 mm, from about 0.1 mm to about 1 mm, from about 0.2 mm to about 0.8 mm, from about 0.3 mm to about 0.5 mm, from about 0.3 mm to about 0.4 mm, or about 0.35 mm.

The ingestible device may be 1 to 5 nozzles, 2 to 4 nozzles or 2 nozzles.

The ingestible device may be configured to release a dispensable substance volume ranging from about 50 microliters to about 500 microliters, from about 100 microliters to about 450 microliters, from about 200 microliters to about 400 microliters, from 250 microliters to about 400 microliters, or from about 300 microliters to about 400 microliters.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance as a jet having jet stable length of at least about 0.5 millimeter to 20 millimeters, a peak jet pressure of from about 100 psig to about 250 psig, and a peak jet force of from about 0.1 N to about 0.14 N.

The ingestible device may comprises a nozzle, and the opening may comprise a nozzle opening. The nozzle may have a nozzle diameter of from about 0.1 millimeter to about two millimeters, and/or a nozzle length of from about one millimeter to about five millimeters.

The ingestible device may comprise a plurality of nozzles. The nozzles may be directed perpendicular to a longitudinal axis of the ingestible device. The nozzles may be uniformly distributed relative to a circumference of the ingestible device. The plurality of nozzles may comprise an even number of nozzles or an odd number of nozzles. The plurality of nozzles comprises two nozzles.

The ingestible device may be configured to deliver from about 20 microliters to about 800 microliters of the dispensable substance through each nozzle.

The ingestible device may further include the dispensable substance, wherein the dispensable substance comprises a fluid. The ingestible device may further include the dispensable substance, wherein the dispensable substance comprises a fluid. The dispensable substance may comprise a therapeutic agent. The dispensable substance may comprise a solution. The dispensable substance may comprise a suspension. The dispensable substance may have a viscosity of less than or equal to 10 cP. The dispensable substance may have a viscosity of at least about 0.8 cP. The dispensable substance may a viscosity of at most about 8 cP or at most about 9 cP.

The jet may have an average jet diameter of from about 0.1 millimeter to about two millimeters.

The ingestible device may further comprise a drive force generator configured to apply a force to the dispensable substance to force the dispensable substance out of the ingestible device via the opening. The drive force generator may comprise a member selected from the group consisting of a spring, a gas cell, a compressed gas, and a liquid-gas mixture. The ingestible device may comprise chemicals configured to react to provide a gas as the drive force generator. The drive force generator may be configured to provide an internal pressure of from about 225 psig to about 400 psig.

The ingestible device may further comprise a drive coupling configured to transfer force from the drive force generator to the dispensable substance. The drive coupling may comprise a member selected from the group consisting of a piston and a membrane.

The ingestible device may further comprise a restraining mechanism having a first state and a second state, wherein, when the restraining mechanism is in its first state, the restraining mechanism prevents the dispensable substance from being delivered out of the ingestible device. In some embodiments, when the restraining mechanism is in its second state, the restraining mechanism does not prevent the dispensable substance from being delivered out of the ingestible device. The ingestible device may be configured so that, when the restraining mechanism is in its first state, the drive force generator does not apply an internal pressure to the dispensable substance. The ingestible device may be configured so that, when the restraining mechanism is in its first state, the drive force generator applies an internal pressure to the dispensable substance. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a dowel, a clasp, a clamp, a flange, and a rivet. The restraining mechanism may comprise a cap. The cap may be located at a distal end of the ingestible device.

The ingestible device may be configured to directly deliver the dispensable substance to the GI tract of a subject via trans-epithelial delivery.

In a general aspect, the disclosure provides an ingestible device, comprising: a housing;

an opening in the housing configured to fluidly connect the dispensable substance to an environment outside the housing via the opening; a drive force generator configured to provide a force to the dispensable substance to deliver the dispensable substance through the opening; a drive force coupling configured to transfer the force from the drive force generator to the dispensable substance; and a restraining mechanism having a first state in which the restraining mechanism prevents the dispensable substance from being delivered out of the ingestible device.

The drive force generator may comprise a member selected from the group consisting of a spring, a gas cell, a compressed gas, and a liquid-gas mixture. The ingestible device may comprise chemicals configured to react to provide a gas as the drive force generator. The drive force generator may be configured to provide an internal pressure of from about 225 psig to about 400 psig.

The drive coupling may comprise a member selected from the group consisting of a piston and a membrane.

In some embodiments, when the restraining mechanism is in its first state, the drive force generator does not apply an internal pressure to the dispensable substance. In certain embodiments, when the restraining mechanism is in its first state, the drive force generator applies an internal pressure to the dispensable substance. The restraining mechanism may have second state different from its first state, and, when the restraining mechanism is in its second state, the restraining mechanism does not prevent the dispensable substance from being delivered out of the ingestible device. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a band, a dowel, a clasp, a clamp, a flange, and a rivet. The restraining mechanism may comprise a cap. The cap may be located at a distal end of the ingestible device.

In a general aspect, the disclosure provides a method, comprising: using an ingestible device to directly deliver a dispensable substance to the GI tract of a subject via trans-epithelial delivery. The method may comprise using the ingestible device to directly deliver the dispensable substance into the lamina propria of the GI tract of the subject, and/or using the ingestible device to directly deliver the dispensable substance into the submucosa of the GI tract of the subject.

The details of one or more embodiments of the device and methods are set forth in the accompanying drawings and the description below. Other features and advantages will be apparent from the description and drawings, and from the claims.

BRIEF DESCRIPTION OF THE DRAWINGS

FIG. 55A represents animals treated with adalimumab after ID administration via the endoscopically placed ingestible device having 4 nozzles and an internal pressure of 320 psig. FIG. 55B represents animals treated with adalimumab after ID administration via the endoscopically placed ingestible device having 4 nozzles and an internal pressure of 350 psig.

FIG. 57A shows binding of anti-TNFα to the TNFα receptor without drug, where uninhibited binding brings the Donor and Acceptor beads into close proximity for singlet oxygen transfer detection. FIG. 57B shows binding of anti-TNFα to TNFα that is inhibited by drug binding to TNFα, thus preventing binding to anti-TNFα antibodies and proximity oxygen singlet transfer detection.

FIG. 58A shows the dose response curve after 10,000 μg/mL of adalimumab was dispensed into collection tubes under various conditions as described in Example 8. FIG. 58B is an enlarged view of a section of the graph shown in FIG. 58A.

FIG. 64A shows IL-6 concentrations in colon tissue at various timepoints on Study Day 12. FIG. 64B shows the relationship between tofacitinib concentration in colon tissue (open shapes and dotted lines; right y-axis) and % IL-6 in colon tissue after treatment with tofacitinib citrate, normalized to DSS vehicle control (Group 2) (solid shapes and solid lines; left y-axis).

FIG. 69A shows the influence of anti-TNF-alpha; FIG. 69B shows the influence of anti-IL12p40. The AUC was calculated using the trapezoidal rule and is shown in the figure inset. Differences in body weight loss were calculated as AUC for individual mouse from Days 0 to 42. Two-tailed Mann-Whitney U-Test; p<0.05*; p<0.01; p<0.005*; n=5-9.

FIGS. 71A-71D show mean lymphocyte counts from luminal to external submucosa of proximal colon and represented images of H&E stains and IHC stains of the proximal colon. FIG. 71A shows the mean lymphocyte count from most inner lumen to submucosal of the proximal colon in groups treated with Vehicle controls, anti-TNFα

(IP) and anti-TNFα (IC), Group mean+/−SEM. Kruskal-Wallis Test with Dunn's multiple comparison for treatment effects; p<0.05*.

Figure 71A:
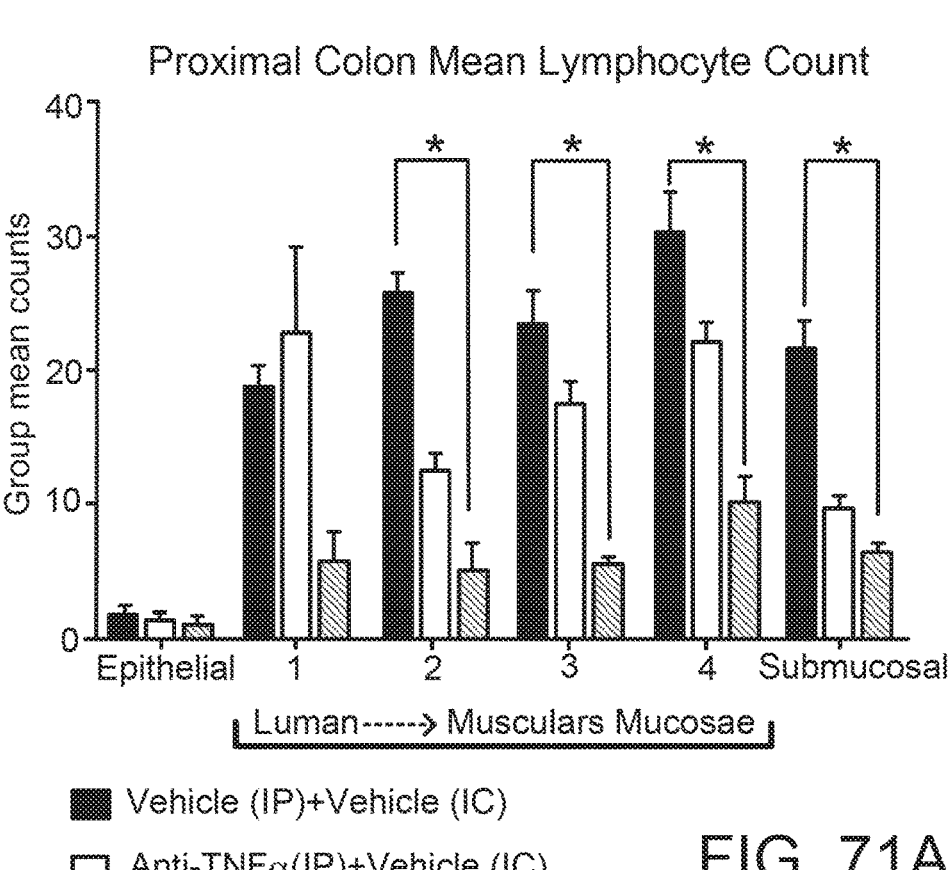

FIG. 71B is a representative image of H&E stain of proximal colon in proximal colon of anti-TNFα (IC) group. An intraepithelial lymphocyte (white arrowhead), example lamina proprial lymphocytes (black arrowheads), and the tunica muscularis externa (TME) are indicate. FIGS. 71C and 71D are representative images of IHC stain of CD4 marker for lymphocytes in proximal colon of anti-TNFα (IC) (FIG. 71C) or anti-TNFα (IP) (FIG. 71D) group.

Figure 72A:
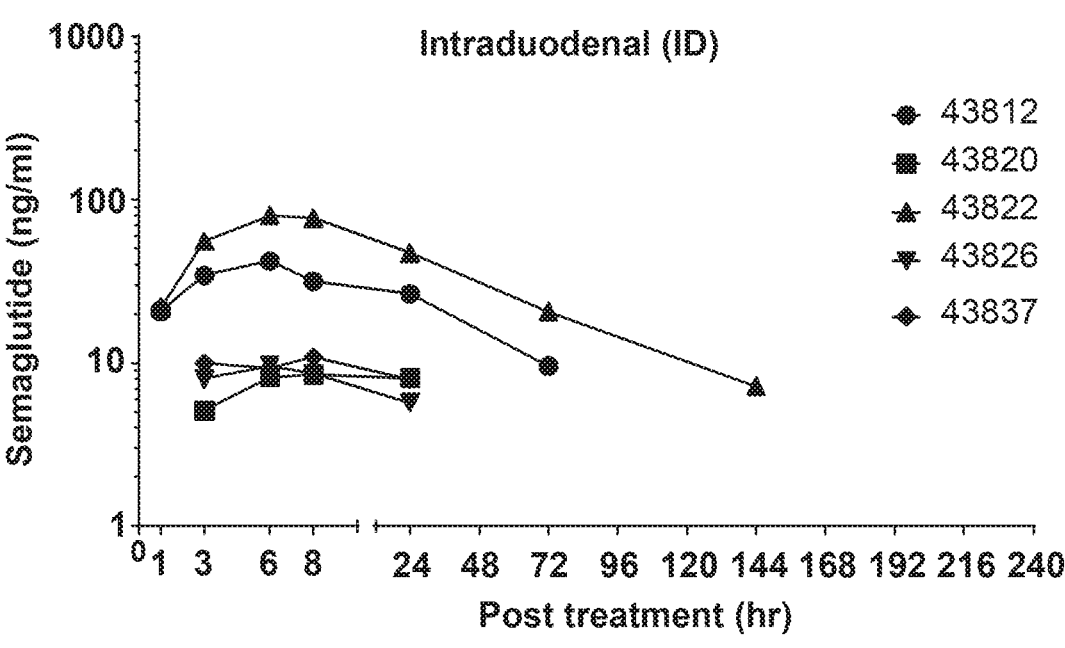
Figure 72B:
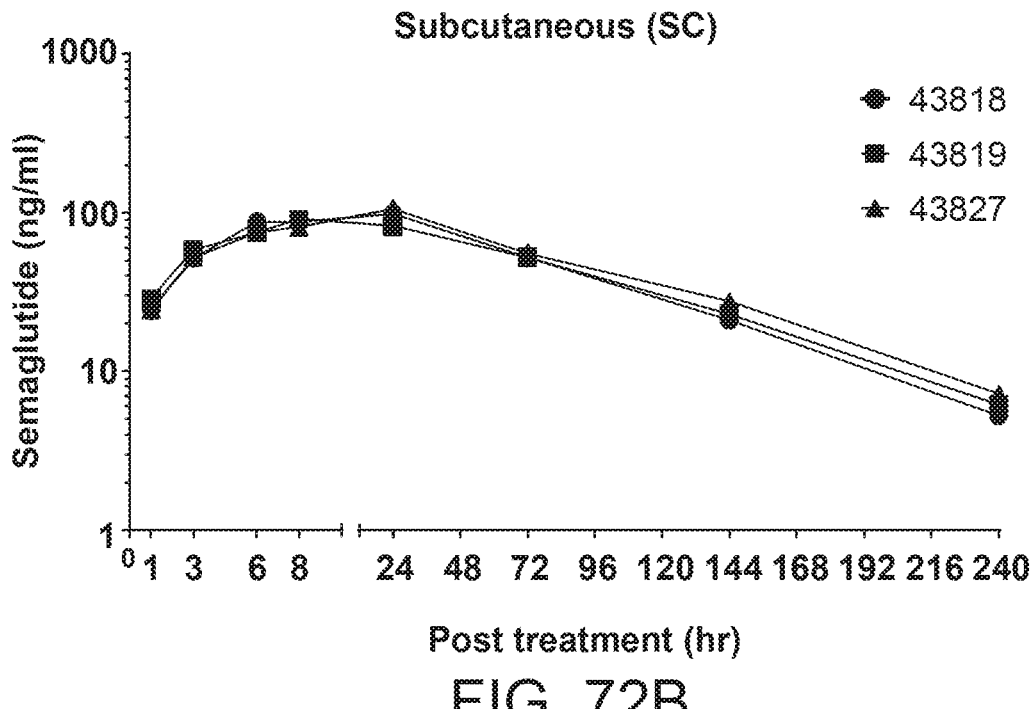
Figure 72C:
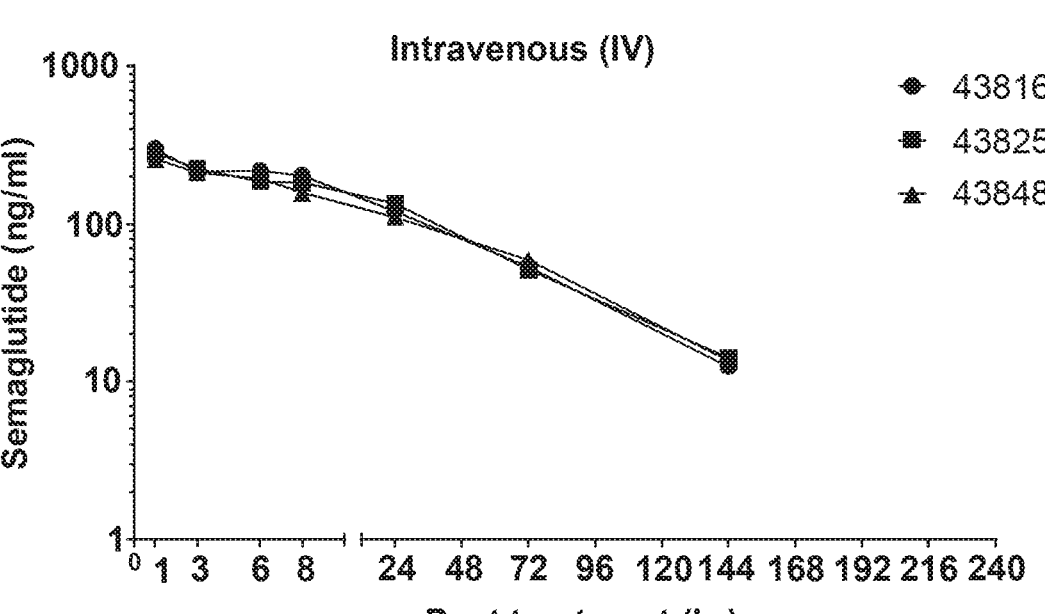

FIGS. 72A-72C show semaglutide concentration in blood over time after: ID administration via the endoscopically placed ingestible jet delivery device (FIG. 72A); SC administration (FIG. 72B); and IV administration (FIG. 72C).

Figure 73:
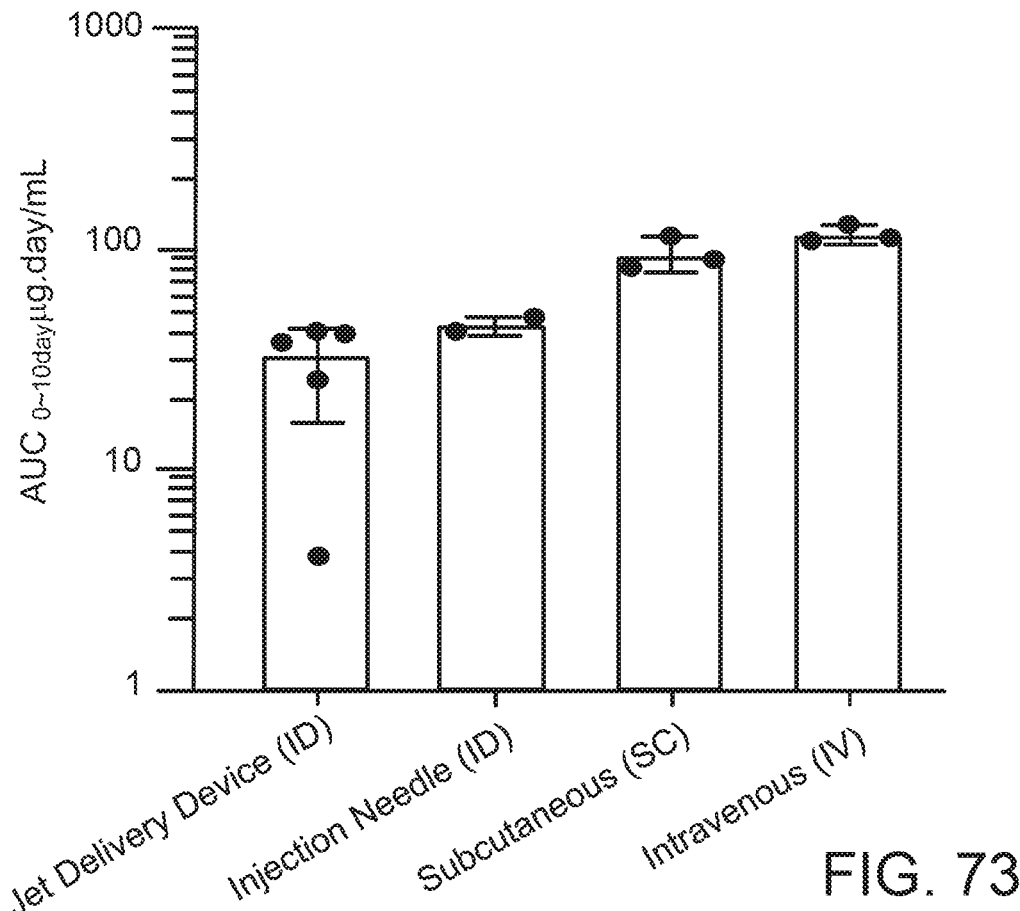

FIG. 73 shows the $(AUC)_{T0-T10d}$ observed after administration of adalimumab intraduodenally (ID) via an ingestible jet delivery device having an internal pressure of 320 psig (Example 5, Group 3), ID via an endoscopic injection needle (Example 12), subcutaneously (Example 5, Group 4) and intravenously (Example 5, Group 5).

DETAILED DESCRIPTION

1. Definitions

"Ingestible," as used herein in reference to the device, means that the device can be swallowed whole.

"Bioavailability," as used herein, may be reported based on the ratio of the area under a curve (AUC) of the therapeutic agent concentration in systemic circulation versus time that is achieved when the drug is administered by another form of administration (e.g., trans-epithelial administration [hereinafter, $AUC_{TE}$] or topical administration [hereinafter, $AUC_{TOP}$], respectively) versus the AUC of the therapeutic agent concentration in systemic circulation versus time that is achieved when the same amount of the drug is administered intravenously [hereinafter, $(AUC)_{IV}$], or subcutaneously [hereinafter, $(AUC)_{SC}$], expressed as a percentage. In some aspects, especially when the pharmacokinetic data are derived from more than one subject, the AUC is a mean AUC. In some embodiments, the mean is a geometric mean. In other aspects, as used herein, drug exposure may be reported based on a different pharmacokinetic parameter. For example, drug exposure may be reported as a ratio of maximum therapeutic agent concentration $(C_{max})$ in systemic circulation that is achieved when the drug is administered by another form of administration (e.g., trans-epithelial administration [hereinafter, $(C_{max})_{TE}$] or topical administration [hereinafter, $(C_{max})_{TOP}$]), versus the $C_{max}$ of the therapeutic agent concentration in systemic circulation that is achieved when the same amount of the drug is administered intravenously [hereinafter, $(C_{max})_{IV}$], or subcutaneously [hereinafter, $(C_{max})_{SC}$], expressed as a percentage.

As used herein, "non-oral," when used in reference to a therapeutic suitable for use with the devices and methods of the present disclosure, refers to a therapeutic or active agent that has poor bioavailability and/or is not administered by an oral route of administration.

"Effective amount" as used herein refers to an amount of therapeutic agent that offers beneficial response to a patient receiving the treatment. For example, an effective amount may be a Human Equivalent Dose (HED). The phrase "therapeutically effective amount," as used herein, refers to the amount of the therapeutic agent that is effective for producing a desired therapeutic effect. In some embodiments, a therapeutically effective amount treats or prevents a disease or condition disclosed herein.

As used herein, each listed small molecule, peptide or nucleic acid agent optionally includes a pharmaceutically acceptable salt thereof, whether or not such a form is expressly indicated. Each listed antibody agent optionally includes a biosimilar thereof, or a glycosylation variant thereof, whether or not such a biosimilar or glycosylation variant is expressly indicated.

"Dispensable" as used herein with reference to any substance, refers to any substance that may be released from an ingestible device as disclosed herein, or from a component of the device such as a reservoir. For example, a dispensable substance may be a therapeutic agent as disclosed herein, and/or a formulation that includes a therapeutic agent as disclosed herein. A dispensable substance may be a fluid, such as a liquid, a suspension or a semi-solid. For example, a dispensable substance can be a liquid in the form of a solution, such as an aqueous solution. In some embodiments, when disposed in an ingestible device, a substance is a non-fluid, such as a solid. In such embodiments, the substance may be converted to a fluid prior to being delivered from the ingestible device. In some embodiments, the therapeutic agent is a small molecule. In other embodiments, the therapeutic agent is a large molecule, such as a biologic drug. Nonlimiting examples of biologic drugs include antibodies (including monoclonal antibodies), proteins (including fusion proteins), peptides (including cyclic peptides), cells (including stem cells), and nucleic acids (including inhibitory nucleic acids, antisense nucleic acids, siRNA, ribozymes). In some embodiments, the dispensable substance is a pharmaceutical formulation comprising a therapeutic agent and a liquid carrier. In some embodiments, the pharmaceutical formulation comprising the therapeutic agent and the liquid carrier is a solution formulation. In other embodiments, the pharmaceutical formulation comprising the therapeutic agent and the liquid carrier is a suspension formulation, or an emulsion formulation. In some embodiments, a dispensable substance delivered as described herein is particularly well-suited for treatment of diseases and conditions of the endoderm, for example, it may be more efficacious in gut-associated lymphoid tissue (GALT) or the hepatic system as compared to subcutaneous or intravenous administration. In general, the viscosity of a dispensable substance can be selected as appropriate. In some embodiments, the dispensable substance has a viscosity of at least about 0.5 centiPoise (cP) and/or at most about 10 cP.

As used herein, the term "enteric" refers a material that permits transition to a desired location in the GI tract (e.g., through the stomach to the intestine) before being dissolved/degraded/eroded due to exposure of certain conditions (e.g., pH, temperature, enzymes) of the GI tract. An enteric material may prevent a drug from degradation by gastric fluid and enzymes.

The term "jet," as used herein, refers to a collimated stream of fluid, e.g., liquid or suspension, that is stable without breaking up into a spray. A jet may be formed by forcing the fluid, e.g., liquid or suspension, through an opening in an ingestible device. Generally, a jet maintains a stable form and is capable of achieving its intended purpose by maintaining appropriate properties (e.g., to penetrate a surface), such as its diameter and/or velocity.

As used herein, "jet diameter" is the cross-sectional diameter of a jet at a given location.

As used herein, "average jet diameter" refers to the average cross-sectional diameter of a jet between the location where the jet is formed (e.g., a nozzle opening through which the dispensable substance is delivered from the ingestible device) and the location where the jet impacts the GI tissue of the subject.

"Jet stable length," as used herein, refers to the distance from an opening (e.g., nozzle opening) of an ingestible device that a dispensable substance delivered through the opening remains in the form of a jet.

"Jet velocity," as used herein is the average fluid velocity across the cross-section of a jet at a given point in time.

As used herein, "peak jet velocity," refers to the maximum jet velocity of a jet at the interface of the lumen and the surface of the GI tract facing the lumen. In general, the peak jet velocity is achieved at the time of initial delivery of the dispensable substance from the ingestible device.

As used herein, "minimum jet velocity," refers to the minimum velocity of a jet at the interface of the lumen and the surface of the GI tract facing the lumen. In general, the minimum jet velocity is achieved at the end of delivery of the dispensable substance from the ingestible device.

"Mean jet velocity" and "average jet velocity," as used herein, refer to the average velocity of a jet at the interface of the lumen and the surface of the GI tract facing the lumen as determined over the time that the ingestible device delivers the dispensable substance.

As used herein, "peak jet power" refers to the maximum power of a jet at the interface of the lumen and the surface of the GI tract facing the lumen. In general, the peak jet power is achieved at the time of initial delivery of the dispensable substance from the ingestible device.

As used herein, "minimum jet power," refers to the minimum power of a jet at the interface of the lumen and the surface of the GI tract facing the lumen. In general, the minimum jet power is achieved at the end of delivery of the dispensable substance from the ingestible device.

"Mean jet power" and "average jet power," as used herein, refer to the average power of a jet at the interface of the lumen and the surface of the GI tract facing the lumen as determined over the time that the ingestible device delivers the dispensable substance.

"Jet power during delivery," as used herein, refers to the power of a jet at the interface of the lumen and the mucosa of the GI tract of a subject.

"Jet pressure," as used herein, refers to the pressure of a jet at the interface of the lumen and the surface of the GI tract facing the lumen. As an example, the jet pressure can be the pressure by the jet measured at the intestinal wall. In some embodiments, jet pressure is referred to herein as "impact pressure."

"Peak jet pressure," as used herein, refers to the maximum pressure of a jet at the interface of the lumen and the surface of the GI tract facing the lumen. In general, the peak jet pressure is achieved at the time of initial delivery of the dispensable substance from the ingestible device.

As used herein, "minimum jet pressure," refers to the minimum pressure of a jet at the interface of the lumen and the surface of the GI tract facing the lumen. In general, the minimum jet pressure is achieved at the end of delivery of the dispensable substance from the ingestible device.

"Mean jet pressure" and "average jet pressure," as used herein, refer to the average pressure of a jet at the interface of the lumen and the surface of the GI tract facing the lumen as determined over the time that the ingestible device delivers the dispensable substance.

"Jet force," as used herein, refers to the force of a jet at the interface of the lumen and the surface of the GI tract facing the lumen. In some embodiments, jet force is referred to herein as "impact force."

"Peak jet force," as used herein, refers to the maximum force of a jet at the interface of the lumen and the surface of the GI tract facing the lumen. In general, the peak jet force is achieved at the time of initial delivery of the dispensable substance from the ingestible device. In some embodiments, peak jet force is referred to herein as "impact force."

As used herein, "minimum jet force," refers to the minimum force of a jet at the interface of the lumen and the mucosa of the GI tract of a subject. In general, the minimum jet force is achieved at the end of delivery of the dispensable substance from the ingestible device.

"Mean jet force" and "average jet force," as used herein, refer to the average pressure of a jet at the interface of the lumen and the surface of the GI tract facing the lumen as determined over the time that the ingestible device delivers the dispensable substance.

As used herein, "fluid volume" refers to the volume of the dispensable substance contained in the ingestible device.

"Initial fluid volume," as used herein, refers to the volume of the dispensable substance contained in the ingestible device just prior to delivery of the dispensable substance from the ingestible device.

"Final fluid volume," as used herein, refers to the volume of the dispensable substance contained in the ingestible device just after delivery of the dispensable substance from the ingestible device has ended.

As herein, "delivered fluid volume" refers to the volume of dispensable substance delivered from the ingestible device. In some embodiments, the delivered fluid volume is less than the fluid volume.

"End round" as used herein is the radius on the curve at the end of the housing of the ingestible device.

"Fluid pressure" as used herein refers to the pressure in the fluid volume.

As used herein, "peak fluid pressure" refers to maximum pressure generated in the fluid volume. Generally, the peak fluid pressure is achieved at initial delivery of the dispensable substance from the ingestible device. In some embodiments, peak fluid pressure is referred to herein as "internal pressure on the pharmaceutical formulation in the device, prior to release from the device."

As used herein, "minimum fluid pressure" refers to minimum pressure generated in the fluid volume. Generally, the minimum fluid pressure is achieved at the end of delivery of the dispensable substance from the ingestible device.

"Fluid pressure during delivery," as used herein, refers to the pressure in the fluid volume as it decreases during the delivery process.

As used herein, "nozzle" refers to a channel between a fluid reservoir space and an external environment. Generally, in embodiments in which a nozzle is used, pressure in the fluid volume generates a high speed flow of fluid through the nozzle to produce a fluid jet at the opening of the nozzle through which the dispensable substance leaves the ingestible device and enters an environment exterior to the ingestible device.

"Nozzle diameter," as used herein, refers to the diameter of the opening of the nozzle at the opening of the nozzle through which the dispensable substance leaves the ingestible device and enters an environment exterior to the ingestible device.

As used herein, "nozzle length" refers to the length of the opening of the nozzle.

"Nozzle stand-off distance," as used herein, refers to the distance between: 1) the opening of the nozzle through which the dispensable substance leaves the ingestible device and enters an environment exterior to the ingestible device; and 2) the interface of the lumen and the surface of the GI tract facing the lumen.

As used herein, the "internal pressure" of an ingestible device refers to the pressure applied to a dispensable substance, such as a therapeutic agent, or a formulation containing a therapeutic agent, contained in the ingestible device prior to delivery of the dispensable substance from the ingestible device. In some embodiments, the internal pressure is provided by the drive force generator of the ingestible device. In certain embodiments, the internal pressure is greater than the fluid pressure. This may be due, for example, to friction, such as O-ring friction, acting on the drive coupling of the ingestible device. This friction is referred to herein as the "piston friction."

"Nozzle pressure" as used herein refers to the pressure of a dispensable substance at a nozzle opening as measured at the surface facing the interior of the nozzle as the dispensable substance is delivered from the ingestible device. In general, for a given ingestible device at a given point in time, the nozzle pressure is approximately the same as the fluid pressure.

"Topical delivery" or "topical administration," as used herein, refers to a route of administration of a dispensable substance (for example, a therapeutic agent or a pharmaceutical formulation containing a therapeutic agent) where the dispensable substance is delivered to a localized area of the body or to the surface of a body part, regardless of the location of the effect; more particularly, the topical administration of the dispensable substance comprises releasing the dispensable substance to the lumen of the GI tract, a surface of the GI tract facing the lumen, a mucous membrane and/or a lining of the gastrointestinal tract of a subject, including, but not limited to, a surface, mucous membrane or lining containing one or more disease sites, such as gastrointestinal mucosal lesions. The effect of the topical delivery or topical administration of the dispensable substance may be local to, or away from (e.g., distal to), the site of the topical administration.

"Epithelial delivery" or "epithelial administration," as used herein, refers to a route of administration of a dispensable substance (for example, a therapeutic agent or a pharmaceutical formulation containing a therapeutic agent) where the dispensable substance is directly delivered into the mucus or onto the epithelium, but not past the epithelial layer, of the GI tract of a subject, such as the small or large intestine, from which the dispensable substance can act locally or peripherally. In some embodiments of epithelial delivery or epithelial administration, the therapeutic agent can move deeper into the GI tissue (i.e., past the epithelial layer) away from the site of direct delivery, such as, for example, via diffusion or active transport.

"Trans-epithelial delivery" or "trans-epithelial administration," as used herein, refers to a route of administration of a dispensable substance (for example, a therapeutic agent or a pharmaceutical formulation containing a therapeutic agent) where the dispensable substance is directly delivered through the epithelial layer of the mucosa of the GI tract to the submucosa of the GI tract of a subject; optionally, at least a portion of the dispensable substance is directly delivered past the epithelial layer to a region of the mucosa beneath the epithelial layer. In embodiments of trans-epithelial delivery in which a portion of the dispensable substance is directly delivered to a region of the mucosa beneath the epithelial layer, at least some (e.g., all) of the portion of the dispensable substance is directly delivered to the lamina propria. Once the therapeutic agent or a pharmaceutical formulation containing a therapeutic agent is directly delivered past the epithelial layer of the GI tract, it is available for systemic exposure of the therapeutic agent to the subject.

The term "response" refers to a measurable response, including complete response (CR) and partial response (PR).

"Complete response" or "CR" as used herein refers to the disappearance of all signs of disease or remission in response to treatment. This does not necessarily mean the disease has been cured.

"Partial response" or "PR" as used herein refers to a decrease of at least 50% in the severity of disease in response to treatment.

"Beneficial response" of a patient to treatment with a therapeutic agent, as used herein, and similar wording, refers to the clinical or therapeutic benefit imparted to a patient at risk for or suffering from a disease or condition. Such benefit includes cellular or biological responses, a complete response, a partial response, a stable disease (without progression or relapse), or a response with a later relapse of the patient from or as a result of the treatment with the agent.

A patient's response can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

General Introduction

Figure 1A:
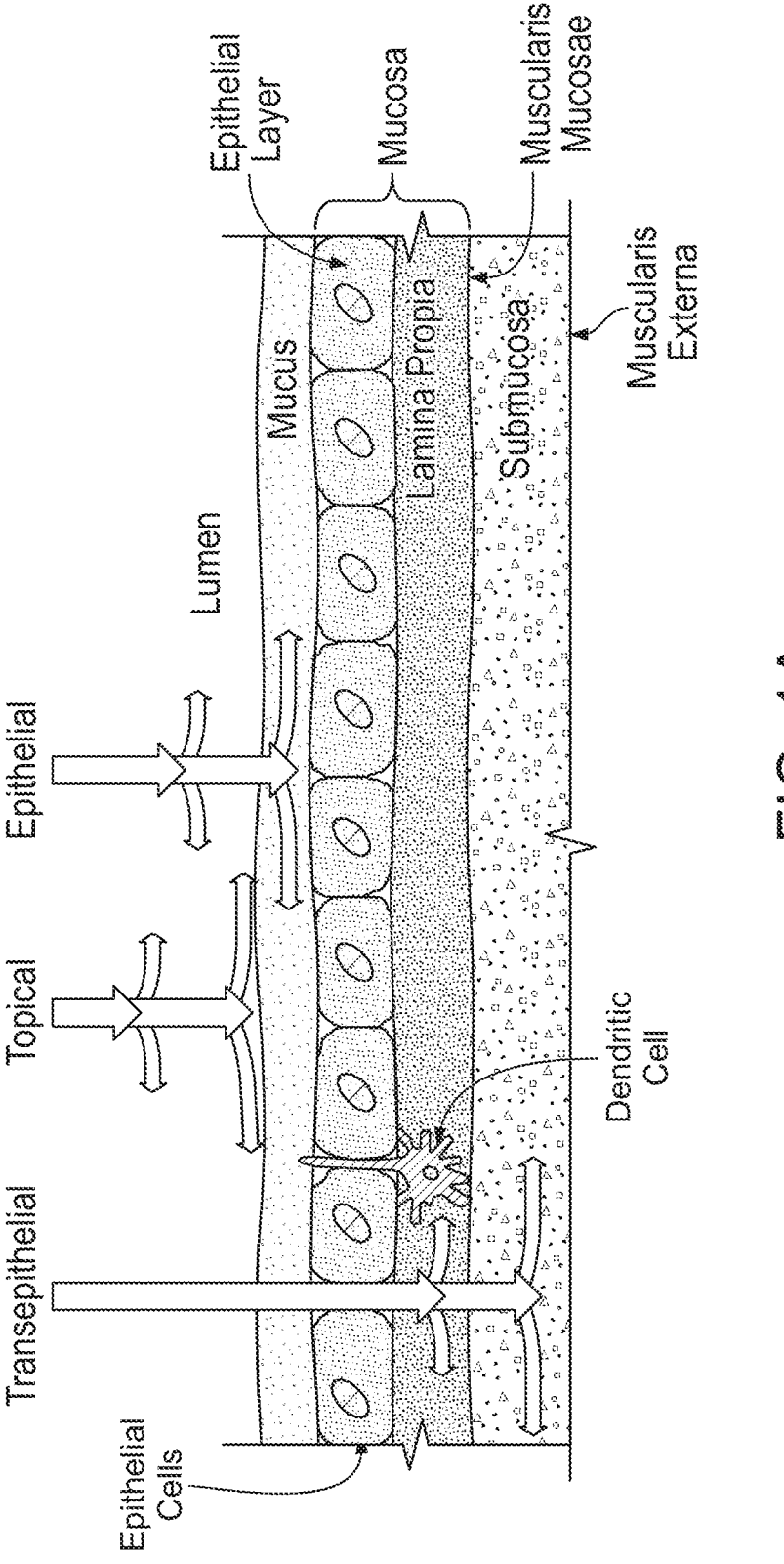
FIG. 1A is a schematic cross section of the different regions of healthy intestinal tissue.
Figure 1B:
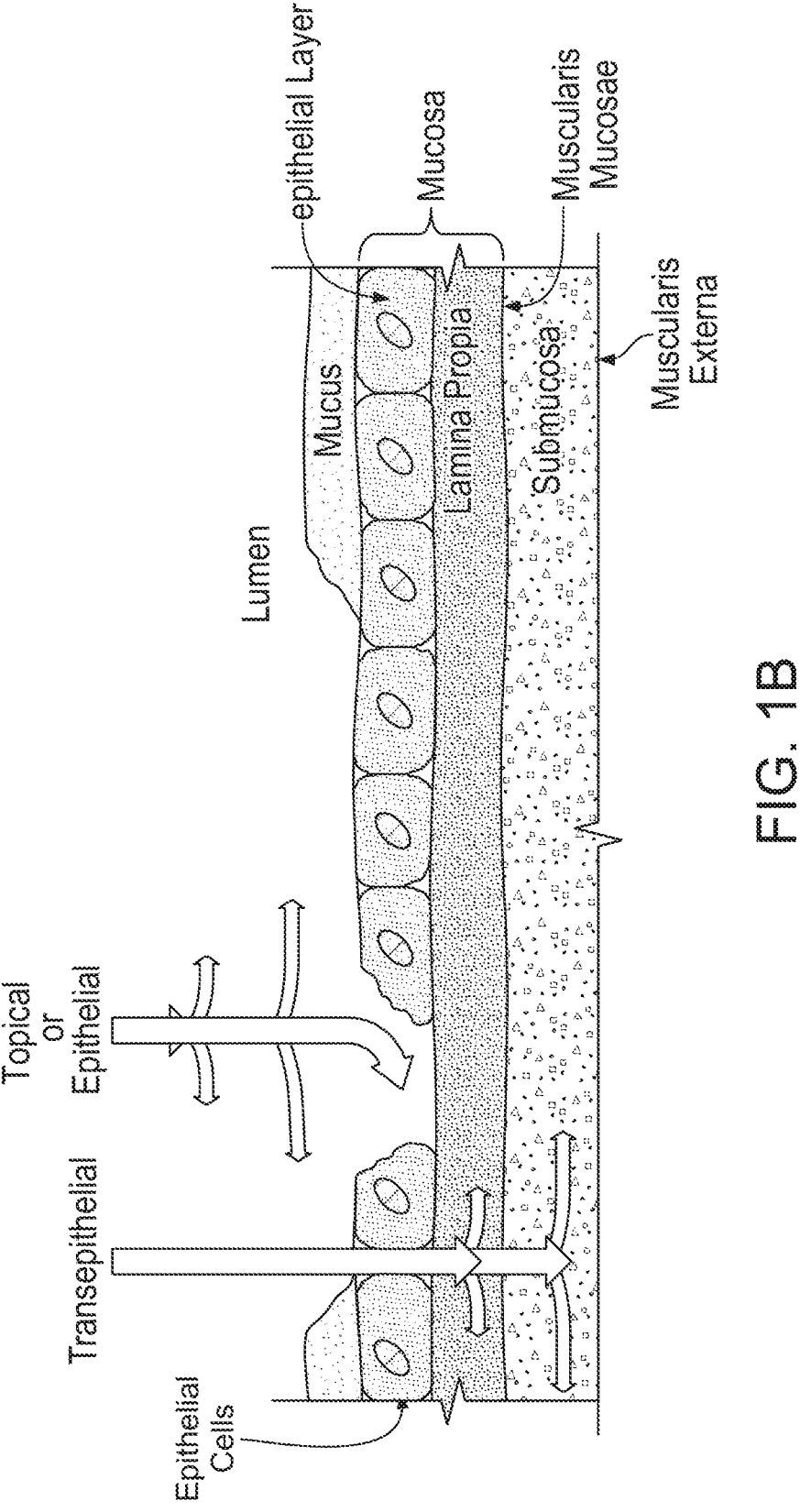
FIG. 1B is a schematic cross section corresponding to FIG. 1A but for diseased intestinal tissue.

FIG. 1A schematically describes the different regions of healthy intestinal tissue, presented in a cross section. The regions include the lumen of the GI tract, the mucus of the GI tissue, the mucosa of the GI tissue and the submucosa of the GI tissue. The mucosa of the GI tissue includes epithelial layer and the lamina propria. The muscularis mucosae separates the mucosa from the submucosa. The muscularis extrema is below the submucosa. FIG. 1B schematically describes corresponding regions of diseased intestinal tissue, presented in a cross section.

An ingestible device described herein can deliver a therapeutic agent via topical delivery (without being directly delivered to the mucus, mucosa or submucosa), epithelial delivery (directly delivered to the mucus or epithelium without being directly delivered past the epithelial layer to the mucosa or submucosa) or trans-epithelial delivery (directly delivered to the submucosa and/or into a region of the mucosa beneath the epithelial layer, such as the lamina propria.

In general, the form of delivery may depend on the design of the ingestible device and parameters used with the device (e.g., internal pressure, fluid pressure, number of nozzles, design of nozzles). Holding other parameters constant, at relatively low fluid pressures and/or internal pressures, the therapeutic agent may be topically delivered, while higher fluid pressures and/or internal pressures may result in epithelial delivery, and still higher fluid pressures and/or internal pressure may result in trans-epithelial delivery. During trans-epithelial delivery, a bolus of the therapeutic agent initially contained in the dispensable substance may form within the submucosa and/or into a region of the mucosa beneath the epithelial layer, such as the lamina propria.

In some embodiments, the following holds. The ingestible device is designed to deliver a dispensable substance, for example, a therapeutic agent or a pharmaceutical formulation containing a therapeutic agent through the epithelial layer of the mucosa of the GI tract. In some embodiments, the dispensable substance is a solution formulation; optionally, a suspension. In some embodiments, the dispensable substance enters the submucosa and/or into a region of the mucosa beneath the epithelial layer, such as the lamina propria, of the small intestine, where it can be absorbed systemically. After the patient swallows the device, it passes through the GI tract and eventually reaches the small intestine. The device includes a restraining mechanism, an optionally a triggering mechanism (e.g., a degradable and/or erodible coating, such as an enteric coating, that partially or completely degrades and/or erodes when the device reaches the desired location in the GI tract). The desired location can be the small intestine or the large intestine. When the device is configured for trans-epithelial GI tract delivery to the submucosa submucosa and/or into a region of the mucosa beneath the epithelial layer, such as the lamina propria, the preferred location can be the small intestine. With the restraining element is removed, relative movement between certain components (e.g., sliding of a component) occurs such that one or more openings in the ingestible device (e.g., in a compartment containing the dispensable substance, such as a reservoir, sometimes referred to herein as the "drug reservoir," "storage reservoir" or "substance reservoir") become aligned with one or more additional openings (e.g., one or more nozzles) in the ingestible device (e.g., in the housing). With the ingestible device now in this open position, a force (e.g., generated by a force generator and/or transferred by a drive coupling, such as a membrane or a piston) forces the dispensable substance from the drug reservoir out of the device via the one or more openings (e.g., the one or more nozzles). The dispensable substance is delivered as a jet of fluid (e.g., liquid) through the epithelial layer of the mucosa and directly into the submucosa and/or into a region of the mucosa beneath the epithelial layer, such as the lamina propria, of the GI tract in the form of single or multiple boluses. After swallowing the device, the device travels through the GI tract (mouth, esophagus, stomach, duodenum, jejunum, ileum, cecum and colon), ultimately exiting the GI tract via the anus.

Thus, in general, the ingestible devices disclosed herein provide delivery of therapeutic agent to the GI tract of a subject. In one aspect, the disclosure relates to trans-epithelial delivery of a dispensable substance (e.g., a therapeutic agent or a formulation comprising a therapeutic agent) to the GI tract of a subject. Accordingly, the disclosure provides an ingestible device that can directly deliver a dispensable substance (e.g., a therapeutic agent or a formulation comprising a therapeutic agent) to the submucosa and/or into a region of the mucosa beneath the epithelial layer, such as the lamina propria, of the GI tract of a subject, which may result in systemic exposure of the therapeutic agent to the subject. In such embodiments, the ingestible device is configured to directly deliver the dispensable substance past the epithelial cell layer of the mucosa and into the submucosa and/or into a region of the mucosa beneath the epithelial layer, such as the lamina propria, of the GI tract, where the therapeutic agent so delivered is available for systemic uptake. In some embodiments, systemic exposure of the therapeutic agent is achieved by trans-epithelial delivery of the dispensable substance into the submucosa and/or into a region of the mucosa beneath the epithelial layer, such as the lamina propria, of the small intestine, for example, in the duodenum, the jejunum, and/or the ileum. In some further embodiments, the trans-epithelial delivery directly delivers the dispensable substance into the submucosa and/or into a region of the mucosa beneath the epithelial layer, such as the lamina propria, of the GI tract such that the percent systemic uptake of the therapeutic agent via the trans-epithelial delivery relative to intravenous or subcutaneous administration is at least about 10% (e.g., at least about 15%, at least about 20%, at least about 25% or more).

In some embodiments, the direct delivery of the therapeutic agent to the submucosa and/or into a region of the mucosa beneath the epithelial layer, such as the lamina propria, via trans-epithelial delivery may also or alternatively provide therapeutic effects locally and/or away from (e.g., distal to) the site of the direct delivery.

In some embodiments, the trans-epithelial delivery may directly deliver a first portion of the dispensable substance to the submucosa of the GI tract, and a second portion of the dispensable substance to the mucosa, all or a further portion of which may be directly delivered to the lamina propria. In some embodiments, the second portion of the dispensable substance delivered to the mucosa, such as the lamina propria, of the GI tract via the trans-epithelial delivery may provide therapeutic effects locally and/or away from (e.g., distal to) the site of the direct delivery.

In another aspect, the disclosure relates to epithelial delivery of a dispensable substance (e.g., a therapeutic agent or a formulation comprising a therapeutic agent) to the GI tract of a subject. Accordingly, the disclosure provides an ingestible device configured to directly deliver a dispensable substance (e.g., a therapeutic agent or a formulation comprising a therapeutic agent) into the mucus, but not past the epithelial layer of the mucosa, of the small or large intestine, from which it may provide therapeutic effects locally and/or away from (e.g., distal to) the site of the direct delivery. In some further embodiments, the ingestible device directly delivers the dispensable substance such that it contacts the surface of the epithelial cell layer of the mucosa facing the lumen, but as previously noted, the epithelial delivery does not directly delivery the dispensable substance past the epithelial layer of the mucosa. In some embodiments, the device is configured so that the dispensable substance is delivered from the device with sufficient force to provide the epithelial delivery, the force being lower than that required for trans-epithelial delivery to the GI tract. In some further embodiments, the epithelial delivery directly delivers the dispensable substance into the mucus of the GI tract such that the percent systemic uptake of the therapeutic agent via the epithelial delivery relative to intravenous or subcutaneous administration is greater than that for topical delivery, but less than for trans-epithelial delivery. In other embodiments, the epithelial delivery directly delivers the dispensable substance into the mucus of the GI tract such that the percent systemic uptake of the therapeutic agent via the epithelial delivery relative to intravenous or subcutaneous administration is about 0.5% to about 10% or more).

In some embodiments of epithelial delivery, the therapeutic agent directly delivered into the mucus of the GI tract via the epithelial delivery may undergo active or passive transport or diffusion past the epithelial layer. Once past the epithelial layer, the therapeutic agent may provide therapeutic effects locally and/or away from (e.g., distal to) the site of the direct delivery. In some embodiments, the therapeutic agent binds to a therapeutic target present in the GI epithelial layer or elicits other pharmacodynamic effects locally or away from the site of delivery via immune cells or tissue in the GI tract (e.g., dendritic cells, lymphocytes, mucosa-associated lymphoid tissue).

In yet another aspect, this disclosure relates to topical delivery of a dispensable substance (e.g., a therapeutic agent or a formulation comprising a therapeutic agent) to the GI tract of a subject. Accordingly, the disclosure provides an ingestible device configured to deliver the dispensable substance (e.g., a therapeutic agent or a formulation comprising a therapeutic agent) into the lumen and/or onto the mucus or other surface (e.g., a diseased surface) of the GI tract facing the lumen of the small or large intestine, from which it may provide therapeutic effects locally and/or away from (e.g., distal to) the site of delivery. In some embodiments, the device is configured so that the dispensable substance is delivered from the device with sufficient force so that the dispensable substance is delivered topically, the force being lower than that required for the epithelial or the trans-epithelial delivery to the GI tract. In some embodiments, the topical delivery to the GI tract results in reduced systemic uptake of the therapeutic agent compared to trans-epithelial delivery to the GI tract, intravenous or subcutaneous delivery.

In some further embodiments, topical delivery delivers the dispensable substance into the lumen and/or onto the mucus or the other surface facing the lumen of the GI tract such that the percent systemic uptake of the therapeutic agent via the topical delivery relative to intravenous or subcutaneous administration is less than about 20%, less than about 10%, less than about 5%, less than about 4%, less than about 3%, less than about 2% or less than about 1%. In some embodiments, the topical delivery to the GI tract results in negligible or no systemic uptake of the therapeutic agent compared to trans-epithelial delivery to the GI tract, intravenous or subcutaneous delivery.

In some embodiments, the topically delivered dispensable substance may spread over the mucus or other surface facing the lumen of the GI tract, thereby coating the surface of the GI tract at or away from (e.g., distal to) the site of delivery. In some embodiments, upon or after the dispensable substance has been topically delivered, the therapeutic agent may undergo transport (e.g., diffusion) from the surface of the mucus into the mucus, and optionally, active or passive transport or diffusion past the epithelial layer of the mucosa.

In some embodiments, the mucus and/or epithelial layer of the mucosa may be disrupted or even absent, such as in a patient having a disease or condition of the GI tract. In such embodiments, the topical delivery of the dispensable substance to the GI tract of the patient may provide direct delivery of the dispensable substance to the surface of the GI tract facing the lumen, such as mucosal tissue exposed by said disruption and/or absence (e.g., both the mucus layer and/or epithelial layer are completely or partially absent or compromised in portions of the GI tract due to a disease or condition). For example, in some embodiments, the topical delivery of the dispensable substance to the GI tract of the patient may provide topical delivery to one or more lesions of the GI tract. In some embodiments, the disease or condition is an inflammatory bowel disease. In some further embodiments, the inflammatory bowel disease is ulcerative colitis. In some other embodiments, the inflammatory bowel disease is Crohn's disease.

Accordingly, provided herein are new systemic delivery devices and methods that deliver therapeutic agents into the small intestinal mucosa and/or submucosa by jet injection. Current methods of administration for most large molecule therapeutic agents are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

Also, by providing a higher concentration of therapeutic in GI tissue, the devices and methods described herein are particularly well-suited for treatment of diseases and conditions of the endoderm, including the liver.

In some embodiments of any of the devices or methods described herein, the pharmaceutical composition is an ingestible device, that includes: a housing; a drug reservoir located within the housing and containing the therapeutic; a pre-pressurized air reservoir; a sliding mechanism; and an exit nozzle configured to allow the therapeutic agent to be released out of the housing from the reservoir and into the submucosa and/or the mucosa (e.g., into the lamina propria) of the gastrointestinal tract.

2. In Some Embodiments of any of the Devices or Methods Described Herein, the Therapeutic is Released at a Location in the Small Intestine or in the Jejunum of the Subject. Device Description

3. General

In general, the ingestible device is suitable for swallowing by a patient and for safely and effectively passing through the GI tract of the patient. Generally, the device can be in the shape of a capsule, a pill or any other swallowable form that may be orally consumed by the subject. In some embodiments, the ingestible device can be swallowed voluntarily under medical supervision or in a home use environment with instruction provided ahead of subsequent ingestion. Generally, ingestible devices are intended for single subject, single use. The ingestible device can have a density high enough to cause the ingestible device to sink within human stomach fluid, e.g., the unfilled ingestible device can have a density of greater than 1.01 $g/cm^3$. The ingestible device can have maximum dimensions that allow the ingestible device to pass through an average human GI tract. In some embodiments, the ingestible device is configured to prevent tumbling in the small intestine of a human. For example, the ingestible device is of sufficient length whereby it will not tumble in the small intestine of a human before, during, or after the dispensable substance is released. Generally, the ingestible device is configured to deliver a sufficient amount of therapeutic agent contained in the dispensable substance to be effective for its intended purpose. In general, the ingestible device's patient-contacting portions (e.g., exterior surface) and dispensable substance-contacting portions are biocompatible. Preferably, the device can withstand an indirect bite force without damaging the housing damage or resulting in leakage. As an example, when containing the dispensable substance, the ingestible device can withstand a bite force of at least about 60 Newtons (N). Generally, unless otherwise intended (see discussion below) components of the ingestible device can withstand exposure to a pH range expected in the human GI tract without substantial loss of functionality, substantial structural damage, or substantial leakage. As an example, in some embodiments, the ingestible device can withstand submersion in a pH 1.5±0.5 fluid environment for at least about 24 hours without substantial loss of functionality, substantial structural damage, or substantial leakage. In general, the ingestible device can maintain an external fluid barrier between the inside of the ingestible device and the GI tract of the subject during transit therethrough. Generally, the ingestible device can withstand external fluid pressures to which it is exposed during use without substantial loss of functionality, substantial structural damage, or substantial leakage. As an example, in some embodiments, the ingestible device undergoes no substantial loss of functionality, substantial structural damage, or substantial leakage when exposed to a sustained pressure of at least about 2 psig for at least about 24 hours and/or when exposed to a momentary pressure of at least about 5 psig momentary pressure for at least about 1 minute.

In general, an ingestible device disclosed herein includes the following features.

Housing

In some embodiments, the ingestible device comprises a housing configured to maintain its mechanical integrity during use of the ingestible device. In some embodiments, the housing has a first portion and a second portion. In some further embodiments, the housing has a first actuation component on the housing, and a second actuation component within the housing. In some embodiments, a storage reservoir is located within the housing, wherein the storage reservoir is configured to store a dispensable substance. In some embodiments, the housing has an opening in fluid communication with the storage reservoir. In some embodiments, the ingestible device employs an electrolytic mechanism for creating one or more openings in the ingestible device, wherein a substance can be dispensed through said opening as described in PCT Application Number PCT/US2019/021814, which published as WO2019178071, and which is incorporated by reference herein. For example, the housing may comprise an external electrolytic circuit (electrolytically erodible surface being on the exterior of the device), whereby the surrounding gastric fluids are the electrolyte that completes an electrolytic circuit between anode and cathode. With sufficient bias voltage (e.g., 1.5-15 volts, such as 3-5 volts), the anode will dissolve or erode electrolytically and thus create an opening in the housing within a desired time interval. In some embodiments, the one or more openings created by an electrolytic mechanism are coupled to one or more nozzles, thereby allowing for trans-epithelial, epithelial, or topical delivery as described herein. In some embodiments an ingestible device includes an enteric coating on the housing. In certain embodiments, the enteric coating covers only certain regions of the housing. The housing may be designed to withstand the chemical and mechanical environment of the GI tract (e.g., effects of muscle contractile forces and concentrated hydrochloric acid in the stomach).

Fluid Volume

The ingestible device includes a fluid volume to contain a dispensable substance (e.g., a liquid, a suspension). In some embodiments, the fluid volume is completely disposed within the housing. Optionally, the fluid volume can be defined by a storage reservoir. Such a storage reservoir can be a component that can be prepared separately from the housing. In such a storage reservoir, the dispensable substance can be disposed in the storage reservoir before the storage reservoir is associated with the ingestible device.

Dispensable Substance

The device may include one or more dispensable substances, with each dispensable substance including one or more therapeutic agents and/or one or more pharmaceutical formulations including one or more therapeutic agents.

Nozzles

In some embodiments, an ingestible device includes one or more nozzles in fluid communication with the one or more openings in the ingestible device. The nozzle(s) is (are) configured so that the dispensable substance through the nozzle(s) when the dispensable substance is delivered from the ingestible device. In general, a nozzle can have any desired size and shape appropriate for the desired type of delivery of a dispensable substance from the ingestible device. In certain embodiments, a nozzle has a shape and/or size appropriate for trans-epithelial delivery, epithelial delivery or topical delivery. In some embodiments, an ingestible device includes more than one nozzle. In certain embodiments, an ingestible device includes 2 nozzles, three nozzles, four nozzles, five nozzles, six nozzles, seven nozzles, eight nozzles, 10 nozzles, 20 nozzles, 30 nozzles, 36 nozzles, 40 nozzles, 50 nozzles). In some embodiments, the nozzles are arranged at even intervals (optionally pairwise if an even number of nozzles are used) around the circumference of the device.

Restraining Mechanism

In some embodiments, the ingestible device comprises a restraining mechanism. Generally, a restraining mechanism has a first state in which it is configured to prevent the dispensable substance from exiting the ingestible device via the opening(s), and a second state in which it is configured so that it does not prevent the dispensable substance from exiting the ingestible device via the opening(s). The restraining mechanism can be configured to transition from its first state to its second state when it is exposed to a triggering condition. The restraining mechanism may be provided by one or more restraining elements. The restraining elements can have a first state in which they are configured to prevent the dispensable substance from exiting the ingestible device via the openings, and a second state in which they are configured to allow the dispensable substance to exit the ingestible device via the openings. The restraining elements can be configured to transition from the first state to the second state when the restraining elements are exposed to a triggering condition. In some embodiments, the restraining elements comprise a first type of restraining element and a second type of restraining element different from the first type of restraining element. The first type of restraining element can be configured to transition to its second state before the second type of restraining element transitions to its second state. In some embodiments, a restraining elements comprises a lid, a pin, a band, a plug, a dowel, a clasp, a clamp, a flange, a rivet, or any combination thereof. In some embodiments, the restraining elements comprise a plasticizer such as triethyl citrate (TEC). In some embodiments, the restraining elements comprise a degradable and/or erodible material, such as, for example, an enteric material. The enteric material may be degradable and/or erodible in the small intestine of the GI tract, or may be degradable and/or erodible in the large intestine of the GI tract, for example, the colon. In some embodiments, a restraining mechanism can be a mechanism that prevents the dispensable substance from being delivered from the ingestible device even when the drive force generator (or optionally the drive coupling) applies an internal force. For example, such a restraining can be an element (e.g., a pin, a band, a plug) in the opening (e.g., nozzle opening) through which the dispensable substance can be delivered from the ingestible device. Such a restraining element can be formed, for example, of a material that degrades and/or erodes as discussed above.

Triggering Mechanism

In some embodiments, the ingestible device comprises a triggering mechanism. In some embodiments, a triggering mechanism is configured to cause the dispensable substance within the fluid volume to be released under one or more triggering conditions. In some embodiments, a triggering mechanism initiates a drive force generator. In some embodiments, a triggering mechanism incorporates a mechanical feature like a restraining mechanism. As an example, one or more restraining elements degrade and/or erode in the presence of certain GI tract conditions (e.g., pH greater than 5), thereby triggering a drive force generator, such as a compressed spring. As another example, a spring may have a piercing element that pierces a cylinder with compressed gas, whereby the released gas acts as a force applied to a dispensable substance. In certain embodiments, a triggering mechanism incorporates an electrical feature. For example, an enteric coating degrades and/or erodes in the presence of certain GI tract conditions (e.g., pH greater than 5), thereby exposing conductors to intestinal fluid, which acts as a liquid conductor to triggering the drive force generator. In some embodiments, a triggering condition relates to a condition of the GI tract. In some embodiments, the condition of the GI tract comprises at least one condition selected from the group consisting of temperature, pH, presence of one or more enzymes, and time. In some more particular embodiments, the condition of the GI tract is a pH of greater than 5. In certain embodiments, the triggering mechanism is configured so that the release mechanism is autonomously triggered (e.g., due to degradation, dissolution and/or erosion of the restraining mechanism due to conditions in the GI tract).

Drive Force Generator

The drive force generator is configured to provide the requisite force to the dispensable substance such that, when the restraining mechanism is removed, the dispensable substance is delivered from the ingestible device as desired. The drive force generator can apply force using different mechanisms, including, for example, a compressed gas, a gas generated by chemical reaction, a spring, a liquid-gas mixture, an impact ram, a sudden expansion caused by a controlled exothermic reaction, or the like. When the drive force generator is a spring, the spring can have one or more of the following properties: the outer diameter of the spring is smaller than the inner diameter of the ingestible device; the compressed length of the spring is minimized to leave more space for dispensable substance; the spring is of a conical shape, potentially with a reduction in the solid length of the spring; the free length of the spring is maximized and larger than the free length of the inner cavity of the ingestible device to ensure an acceptable driving pressure is provided throughout the entire time step of delivery; and the spring rate is large enough to provide acceptable pressure from the beginning until the end of delivery of the dispensable substance. Examples of springs include parallel springs, wave springs and conical springs. Examples of chemical reactants include an airbag inflator, a hydrogen cell (e.g., a Varta hydrogen cell), sodium bicarbonate and acid (e.g., alka seltzer and water on board the ingestible device, alka seltzer and GI tract fluid). Examples of compressed gas include a gas charged within the ingestible device, and a container (e.g., cylinder) of compressed gas. In some embodiments, the compressed gas is a gas cylinder from Picocyl. Exemplary gas cylinders are disclosed, for example, in US 2017-0258583, which is incorporated by reference herein. An example of a liquid-gas mixture is liquid nitrogen/HFA (hexafluoroacetone)/propane. An example of an impact ram is a two-phase spring/ram. Other examples of drive force generators include a wax actuator, heat generated by electric power (Peltier effect-based mechanism), and a mechanical puncture of tissue followed by delivery.

Drive Coupling

In general, the drive force coupling transfers a force from the drive force generator to the dispensable substance. Examples of a drive coupling include a piston and a membrane. Examples of membranes include balloons and elastomeric materials. An example of a piston is an O-ring sealed piston. In some embodiments, a piston is provided by a gas cylinder, e.g., with added O-rings or a custom housing. In some embodiments, a drive coupling is a vein, such as a rotating vein. In certain embodiments, a drive coupling is a double piston configured to counteract cap impact. In certain embodiments, a drive coupling is a collapsing bag, such as a collapsing foil bag. In some embodiments, a drive coupling is a collapsing bellows.

Storage Reservoir

In some embodiments, an ingestible device includes a storage reservoir configured to store a dispensable substance. In some embodiments, the storage reservoir stores the dispensible substance. In some embodiments, the storage reservoir is completely disposed within the housing.

Figure 2:
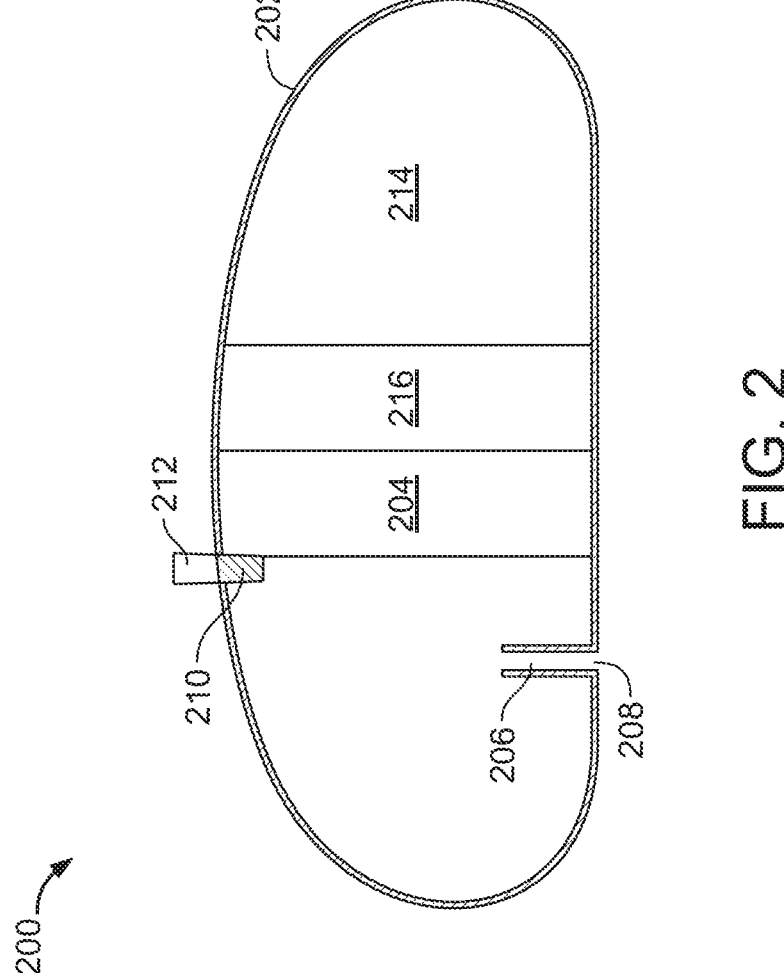
FIG. 2 is a cross section of an ingestible device.

FIG. 2 is a schematic representation of an ingestible device 200 which includes a housing 202, a fluid volume 204 containing a dispensable substance, a nozzle 206 with a nozzle opening 208, a restraining mechanism 210, a triggering mechanism 212, a drive force generator 214 and drive coupling 216. During use, ingestible device 200 is swallowed by a subject and traverses the GI tract. At an appropriate location, the triggering mechanism 212 is triggered, allowing the drive force generator to apply pressure to the drive coupling 216, which then applies pressure to the fluid volume such that at least some of the dispensable substance is delivered out of fluid volume 204, through the nozzle 206, and out of the device 200 via the nozzle opening 208. In some embodiments, the internal pressure is applied, even before the triggering mechanism 212 is triggered. As an example, at an appropriate location, the triggering mechanism 212 is triggered, allowing the drive coupling 216 to apply pressure to the fluid volume 204. In certain embodiments, the internal pressure is not applied until the triggering mechanism 212 is triggered.

Device for Trans-Epithelial Delivery

Generally, trans-epithelial delivery can be achieved at any desired location within the GI tract of a subject. In some embodiments, trans-epithelial delivery is achieved in the small intestine of the subject, such as, for example, in the duodenum, the jejunum and/or the ileum. In certain embodiments, trans-epithelial delivery is achieved in the large intestine of the subject, such as, for example, the cecum or the colon.

In some embodiments, an ingestible device for trans-epithelial delivery is configured to deliver a jet of the dispensable substance having a peak jet power of from about 1 Watt to about 3 Watts (e.g., of from about 1.3 Watts to about 2.8 Watts, of from about 1.5 Watts to about 2.5 Watts).

Figure 3:
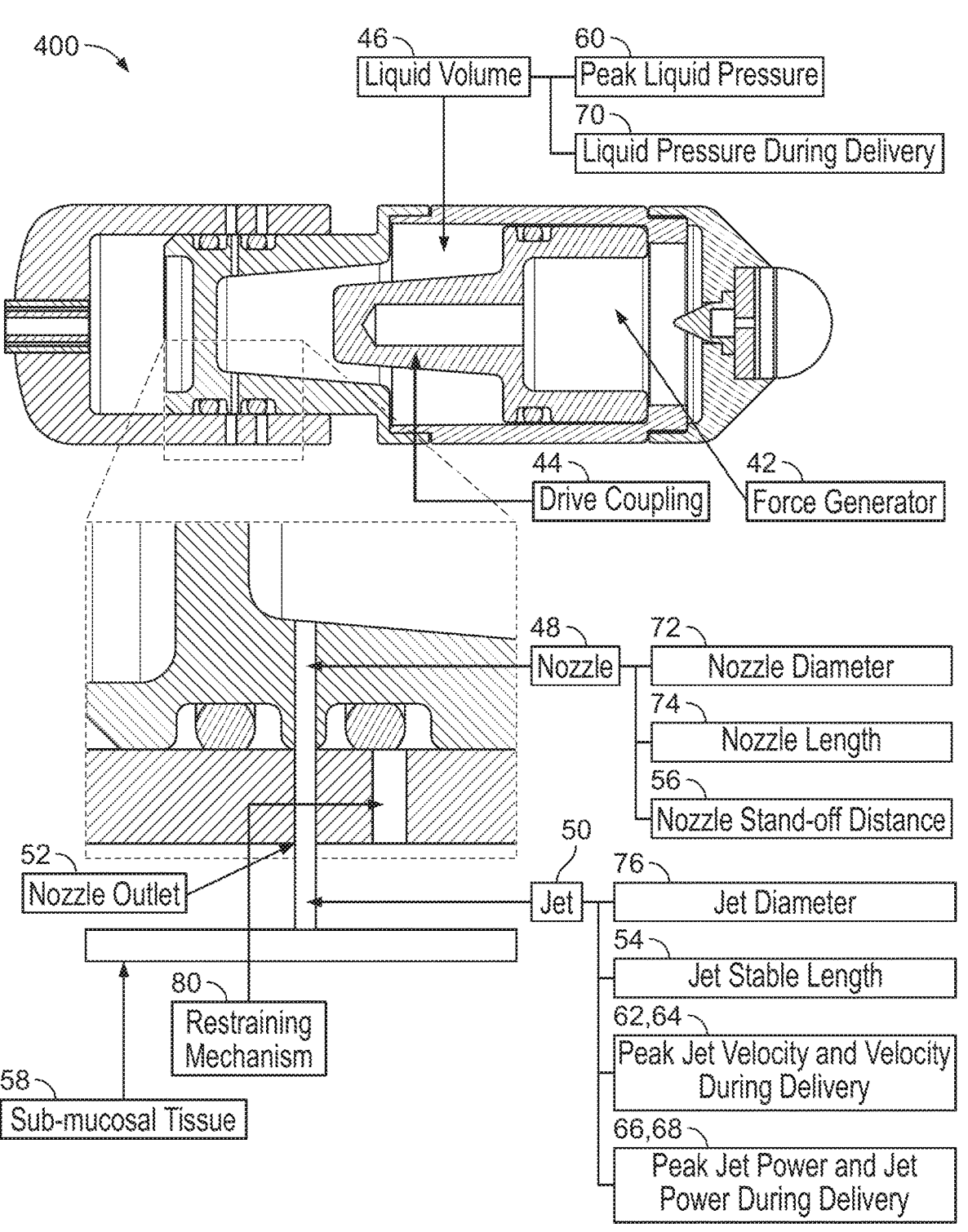
FIG. 3 is a cross section of an ingestible device.

In certain embodiments, an ingestible device for trans-epithelial delivery is configured to have a nozzle pressure of from about 280 psig to about 400 psig or from about 300 psig to about 375 psig In some embodiments, each nozzle can have a nozzle diameter of from about 0.1 mm to about 2 mm (e.g., from about 0.1 mm to about 1 mm, from about 0.15 mm to about 0.5 mm, from about 0.2 mm to about 0.8 mm, from about 0.25 mm to about 0.45 mm. FIG. 3 shows cross sectional views of a representative ingestible device 400 for trans-epithelial delivery, schematically illustrating certain parameters and components of action for the device 400. These include a drive force generator 42 which applies a force (resulting in an internal pressure) to a drive coupling 44. The drive coupling 44 transfers force from the force generator 42 to a fluid volume 46 containing a dispensable substance (e.g., a liquid, a suspension). The force applied to the fluid volume 46 by the drive coupling 44 generates pressure in the fluid volume 46 (fluid pressure). The pressure in the fluid volume 46 generates high-speed flow through an open nozzle 48 to produce a jet 50 of fluid at the nozzle outlet 52 that has a nozzle diameter 72 and the nozzle has a nozzle length 74.

During trans-epithelial delivery, the fluid jet 50 has a jet stable length 54 that is sufficient for the fluid jet 50 to travel across a nozzle stand-off distance 56 to reach the interface of the lumen of the GI tract and the surface of the GI tract facing the lumen. Ultimately, the fluid (e.g., liquid, suspension) impacts the mucosal layer of the GI tract (e.g., the epithelial layer and any mucus that may be present on the epithelial layer) as a stable stream of fluid with little breakup into a spray and is deposited in the submucosal and/or the mucosal tissue 58. That is, between the nozzle outlet 52 and the site of impact at the mucosa, the jet 50 has a jet diameter 76 that can vary in the manner discussed above with respect to the average jet diameter.

The fluid volume 46 experiences a peak fluid pressure 60 that generates the fluid jet 50 that exits the device 40 with a peak jet velocity, and impacts the interface of the lumen of the GI tract and the surface of the GI tract facing the lumen with a peak jet power, peak jet pressure and peak jet force. One of ordinary skill in the art recognizes that these three parameters are interconnected.

The pressure in the fluid volume 46 decreases during delivery so that the fluid pressure during delivery 70 varies, as does the jet power, jet force, and jet pressure. The fluid pressure during delivery 70 maintains the fluid jet 50 at sufficient jet impact force during delivery to continue fluid (dispensable substance including one or more therapeutic agents) delivery from the fluid volume 46 into the submucosal and/or mucosal tissue 58. The surrounding tissue can then absorb the delivered therapeutic agents for systemic delivery of the therapeutic agent.

Even prior to when the subject swallows the ingestible device, the drive coupling 44 transmits force from the force generator 42 to the fluid volume 46. The drive coupling 44 is prevented from moving by a restraining mechanism 80 (e.g., a pin or plug that selectively degrades and/or selectively erodes) until movement of the drive coupling is triggered by a triggering mechanism, and/or an opening becomes open.

FIGS. 4A-5B show cross sections of an example ingestible device 100.

Figure 4A:
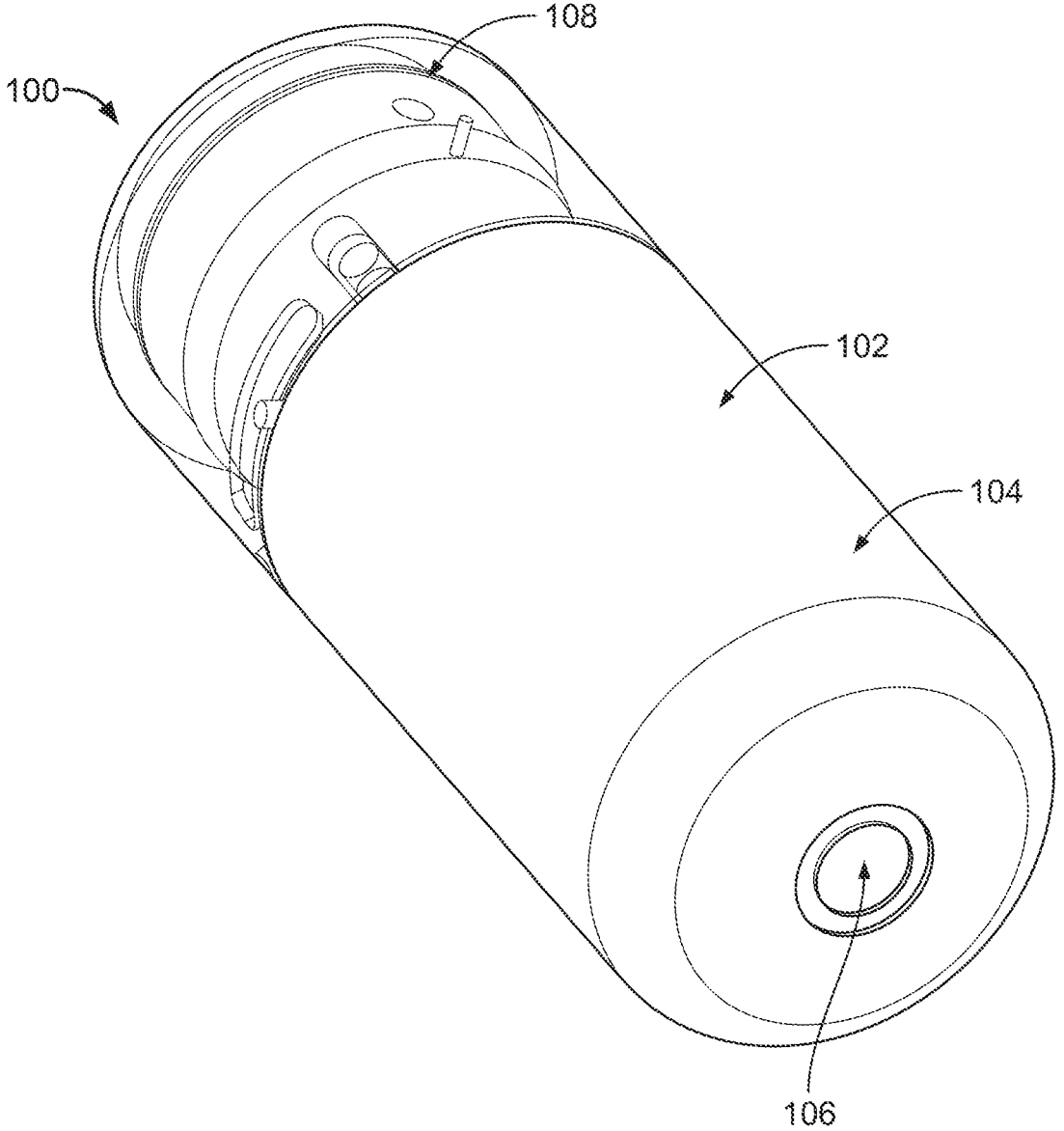
FIG. 4A shows the exterior surface of an ingestible device.

FIG. 4A shows an exterior view of the ingestible device 100. The device 100 is generally cylindrical with a longitudinal axis and a generally smooth exterior surface 102. The exterior surface 102 includes a bottom housing 104 with an inlet 106 at one end, and a slider 108 (shown transparent) at the opposite end from the inlet 106 (e.g., a pressurization inlet port). The device 100 is a purely mechanical device for the delivery of a therapeutic agent to the GI tract, and does not contain any electronics.

Figure 4B:
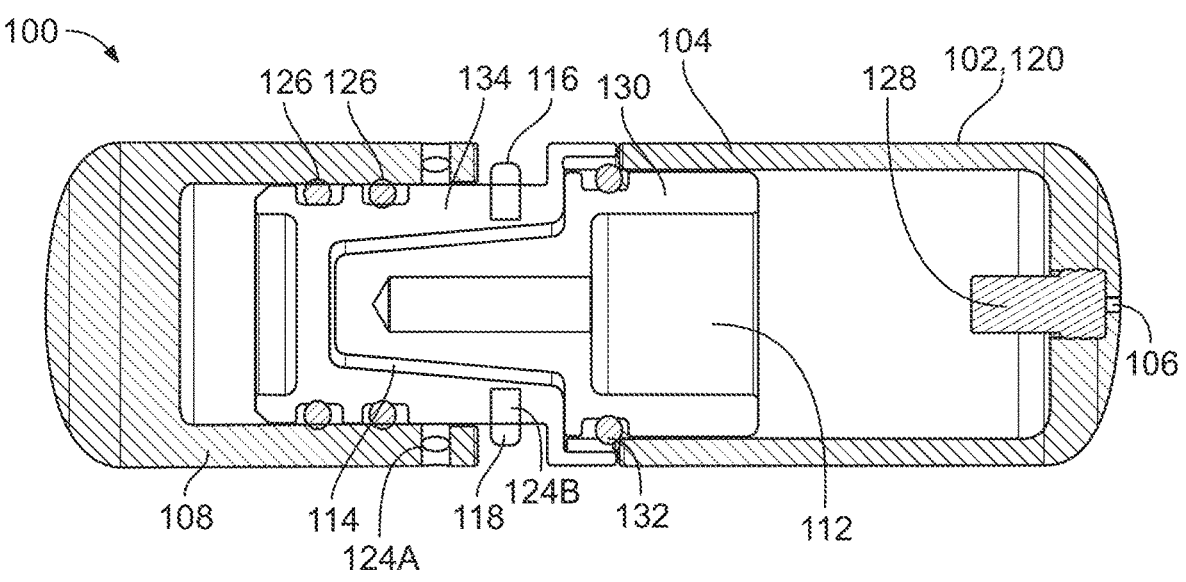
FIG. 4B is a top view cross section of the ingestible device in an open position.

FIG. 4B shows an embodiment of the device 100. The device 100 includes a gas reservoir 112, a dispensable substance reservoir 114 that contains the substance to be dispensed (e.g., a pharmaceutical formulation), a slider 108, degradable and/or erodible elements 116 (e.g., shear pins), and structural elements 118 (e.g., structural shear pins). In general, the degradable and/or erodible elements 116 are configured to degrade and/or erode under certain conditions, while the structural elements 118 are configured to provide additional mechanical strength beyond that provided by the degradable and/or erodible elements 116. Together, the degradable and/or erodible elements 116 and structural elements 118 are able to hold back the force of the force generator (e.g., a pressurized gas within the gas reservoir 112). However, when the degradable and/or erodible elements 116 begin to or completely degrade and/or erode in the presence of GI fluid, the structural elements 118 cannot alone hold back the force of the force generator (e.g., the pressurized gas), and the slider 108 moves to the open position. In some embodiments, the degradable and/or erodible elements 116 and structural elements 118 are placed in pairs with like elements on opposite sides of the device. In some embodiments, the degradable and/or erodible elements 116 are made of an enteric material. For example, the enteric material may be degradable and/or erodible in the small intestine of the GI tract, or the enteric material may be degradable and/or erodible in the large intestine of the GI tract, such as the colon. Although shown in FIGS. 2A-4B as including both the degradable and/or erodible elements 116 and the structural elements 118, in some embodiments, the device 100 includes the degradable and/or erodible elements 116 but does not include the structural elements 118.

FIGS. 4A-5B show cross sections of an embodiment of the device 100, which includes gas reservoir 112, a dispensable substance reservoir 114 that contains the substance to be dispensed (e.g., a pharmaceutical formulation), a slider 108, degradable and/or erodible elements 116 (e.g., shear pins), and structural elements 118 (e.g., structural shear pins). In general, the degradable and/or erodible elements 116 are configured to degrade and/or erode under certain conditions, while the structural elements 118 are configured to provide additional mechanical strength beyond that provided by the degradable and/or erodible elements 116. Together, the degradable and/or erodible elements 116 and structural elements 118 are able to hold back the force of the force generator (e.g., a pressurized gas within the gas reservoir 112). However, when the degradable and/or erodible elements 116 begin to or completely degrade and/or erode in the presence of GI fluid, the structural elements 118 cannot alone hold back the force of the force generator (e.g., the pressurized gas), and the slider 108 moves to the open position. In some embodiments, the degradable and/or erodible elements 116 and structural elements 118 are placed in pairs with like elements on opposite sides of the device. In some embodiments, the degradable and/or erodible elements 116 are made of an enteric material. For example, the enteric material may be degradable and/or erodible in the small intestine of the GI tract, or the enteric material may be degradable and/or erodible in the large intestine of the GI tract, such as the colon. Although shown in FIGS. 2A-4B as including both the degradable and/or erodible elements 116 and the structural elements 118, in some embodiments, the device 100 includes the degradable and/or erodible elements 116 but does not include the structural elements 118.

As shown in FIGS. 4A-5B, the ingestible device 100 is encased by a coating 120, such as a degradable and/or erodible coating, for example, an enteric coating, that covers the exterior surface 102. Optionally, the ingestible device 120 does not include the coating 120. Further, in certain embodiments, only certain portions of the ingestible device 100 include the coating 120. As an example, in some embodiments, only the pockets 124 (described below) are coated, e.g., coated with a degradable and/or erodible material, for example, an enteric material.

Figure 4C:
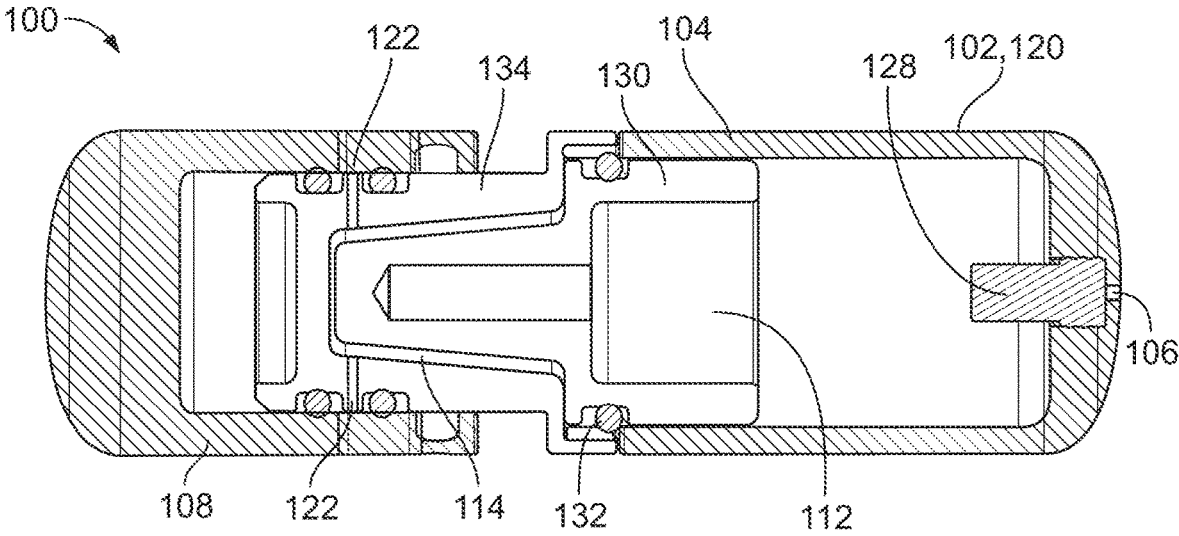
FIG. 4C is a front view cross section of the ingestible device in the open position.

FIGS. 4B and 4C show the device 100 in its open position, where the substance reservoir 114 is fluidly connected to the outside of the device via the nozzles 122 (visible in FIG. 3C). To prepare the device for use, the dispensable substance (e.g., a therapeutic agent or a pharmaceutical formulation containing a therapeutic agent) is loaded into the substance reservoir 114 via the nozzles 122 with the device in this open position. Once the dispensable substance is loaded into the substance reservoir 114, the slider 108 is shut by sliding it axially, disconnecting the nozzles 122 from the exterior of the device so that the device 100 is in its closed position. Note that the location of the structural elements 118 and elements 116 are depicted in FIGS. 4B and 4C as these elements are not yet on the device 100 while it is in the open position depicted. The device 100 may also include a guide pin that provides alignment of nozzles 122 to the hole provided by the slider 108, and may also prevent the slider from continuing to translate axially.

Figure 5A:
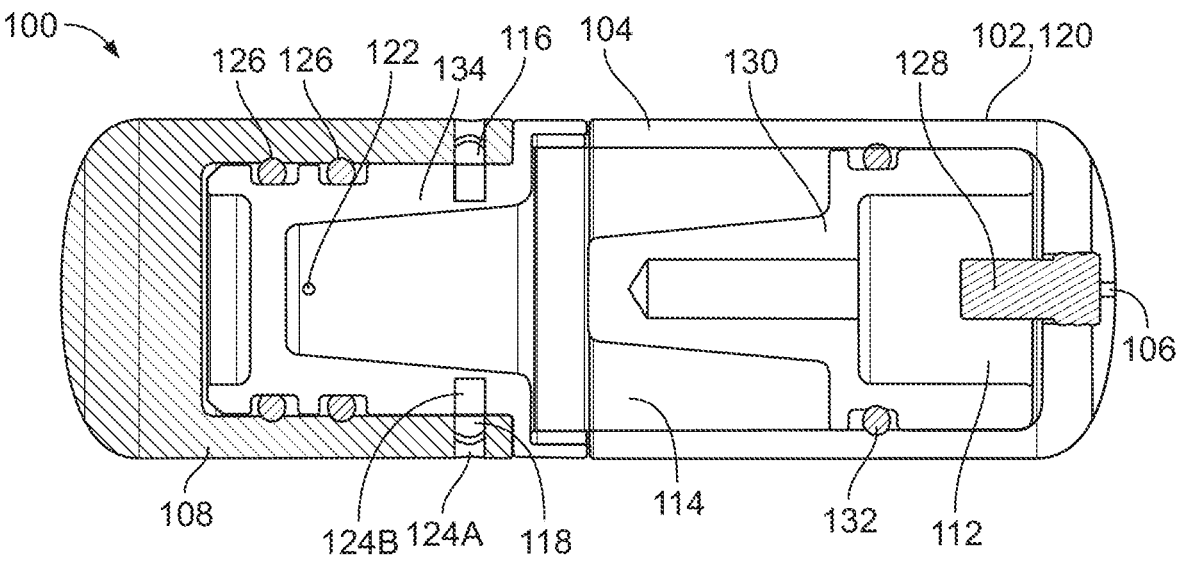
FIG. 5A is a top view cross section of the ingestible device in the closed position.
Figure 5B:
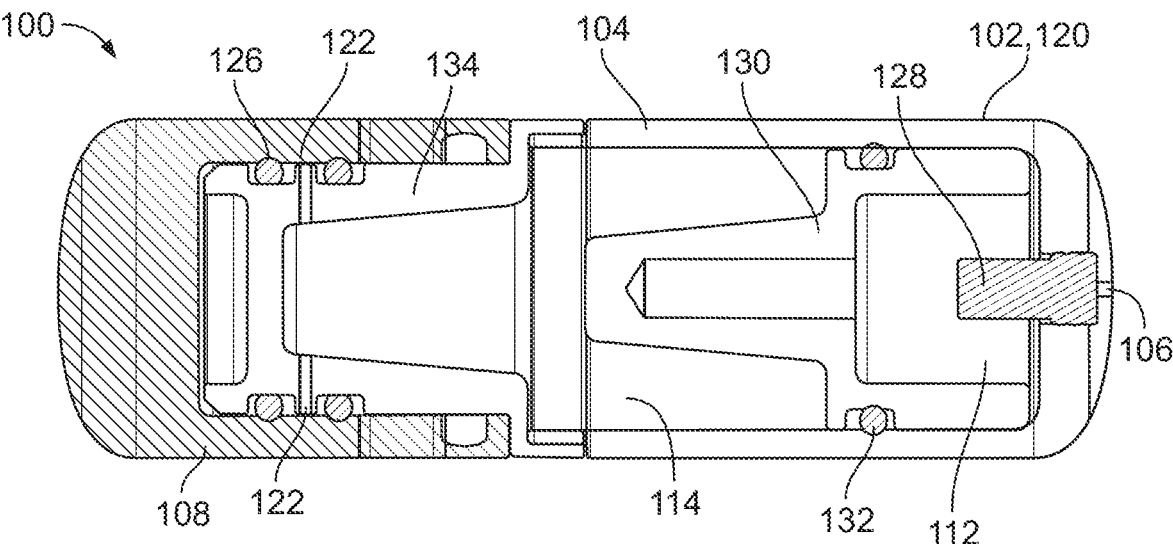
FIG. 5B is a front view cross section of the ingestible device of in the closed position.

FIGS. 5A and 5B show the device in its closed position in which the slider 108 is held in place by a number of elements 116 and 118 that mate with pockets (e.g., pin pockets) 124. The location of elements 116 extend through the housing at the positions indicated while the device 100 is in the closed position. A single nozzle 122 is shown in the view of FIG. 5A and two nozzles are shown in the view of FIG. 5B. One or more top housing seals (e.g., sealing O-rings) 126 assist in containing the dispensable substance behind the slider 108 so that the dispensable substance does not leak to the environment external to the device 100. A piston (e.g., substance/gas piston) 130 and a seal (e.g., sealing O-ring) 132 assist in separating the gas in the gas reservoir 112 from the dispensable substance in the substance reservoir 114. The piston 130 surrounds the gas reservoir 112 and is configured to slide axially within the bottom housing 104. In some embodiments, the slider 108 is not an external sliding mechanism as shown, but is an internal slider.

With the dispensable substance loaded within the substance reservoir 114, the slider 108 is held in place with respect to the top housing 134 with the elements 116 and structural elements 118 within the pockets 124. The pockets 124 each have a through-portion 124A piercing the slider 108, and a blind hole portion 124B within the top housing 134. In the closed position (FIGS. 5A and 5B), the through-portion 124A and the blind hole portion 124B of each of the pockets 124 align, allowing the elements 116 and/or 118 to be inserted through the slider 108 and fasten it to the top housing 134. Once in this fixed position, the gas reservoir 112 is charged with pressurized gas up to a predetermined pressure (e.g., about 300 psig) via the inlet 106. The inlet 106 includes a valve 128 that allows gas to flow into the gas reservoir 112, but prevents the pressurized gas from travelling back out through the inlet 106. In general, any appropriate valve may be used. Examples of valves include check valves, ball check valves, umbrella valves, duckbill valves, or the like. In some embodiments, the valve 128 is replaced by a static plug (e.g., an adhesive applied to the inlet 106) that can withstand the pressure of the pressurized gas reservoir 112.

The elements 116 and 118 are generally made of materials and are sized and shaped such that they, in combination, provide enough rigidity to hold the slider 108 in the closed position under the internal pressure of the pressurized air in the gas reservoir 112, e.g., in the range of about 150-400 psig. Upon dissolution, degradation and or erosion of the elements 116, the maximum pressure that the remaining structural elements 118 can withstand without breaking drops below the internal pressure within the gas reservoir 112. In some embodiments, the structural elements 118 are made from a relatively brittle material, and thereby fail and release the slider 108 and allow the dispensable substance to forcefully leave the device via the nozzles 122. Although FIGS. 4A-5B show a single element 116 and a single element 118, the disclosure is not limited in this sense. For example, the device 100 can include more than one (e.g., two, three, four, etc.) elements 116, and/or more than one (e.g., two, three, four, etc.) elements 118. In some embodiments, there is an even number of elements 116 and of structural elements 118, and the elements 116 and 118 are arranged in an alternating configuration around the longitudinal axis of the device 100. In other embodiments, there is an even number of elements 116 and of structural elements 118, and the elements 116 and 118 are arranged such that elements 116 are opposite other elements 116 and structural elements 118 are opposite other structural elements 118 around the longitudinal axis of the device 100. In certain embodiments, elements 116 and 118 are co-located within the same pocket 124 and may comprise a matrix of materials such as 118 consisting of fibers, or consisting of a coaxial pin 118 surrounded by an annulus of element 116. In some embodiments, the coating 120 may be placed only in the region of the elements 116 and/or 118, e.g., in an annulus. Alternatively, enteric material may be in the pocket portions 124A and/or 124B as a plug separating the elements 116 and/or 118 from the exterior environment.

The properties of the elements 116 can be varied to select the desired performance. For example, their effective force-restraining area can be increased by increasing the diameter and thus the cross section of each element 116, and/or by increasing the number of the elements 116. Increasing the area allows for a safety factor to permit longer periods of storage and shipping, variation in dissolvability, degradability and or erodability between batches of elements 116 and/or 118, and variations in the pressure within the gas reservoir 112, or the like. In some embodiments, elements 116 and 118 are pins having a diameter of about 0.9 mm, but can be thinner (e.g., about 0.8 mm) or wider.

In some embodiments, the elements 116 and/or the structural elements 118 have configurations other than straight pins. For example, one or more elements 116 can be an annular member that fits within a grooved pocket (rather than the discrete pockets 124 shown) that encircles the circumference of the slider 108. The element(s) can be cotters, shear pins, linchpins, split pins, straight pins, dowels, biscuits, clasps, clamps, flanges, rivets, or the like. In some embodiments one or more of the elements 116 is a restraining device other than a pin, such as a clamp, a spacer, or the like.

The gas reservoir 112 contains pressurized gas. In some embodiments, the gas is air, however gases other than air are possible. Nonlimiting examples of compressed gases include, nitrogen ($N_2$), oxygen ($O_2$), argon (Ar), krypton (Kr), helium (He) or other inert or noble gases that do not interact or are compatible with the GI tract, with preference to higher molecular weight gasses that would decrease any permeation of the drive gas out of the device and therefore increase shelf life. In some embodiments, the gas is carbon dioxide ($CO_2$).

The device 100 maintains a gas/fluid barrier internally, and the gas reservoir 112 can keep pressurized gas from interacting with a fluid dispensable substance (e.g., dispensable substance in the substance reservoir 114). The substance reservoir 114 may have a residual volume of <0.050 mL after the dispensing period is complete, and does not induce agglomeration that would prevent therapeutic agent delivery.

The device 100 also can have several characteristics that make it safe to be stored and transported before being swallowed by a patient. The device 100 can maintain an internal pressure of about 350 psig over the shelf life of the device, e.g., hold a pressure of about 350 psig for about 6 months. The dispensable substance-contacting substance reservoir 114 does not have an effect on the therapeutic agent contained within, and the device and the therapeutic agent are not affected (in efficacy, safety, consistency, or bioavailability) by each other during device storage, transit, and dispensing (e.g., with a storage time up to about six months, or up to about 12 months). The substance reservoir 114 can resist contamination from outside sources prior to dispensing.

Figures 6A, 6B, 6C, 6D, 6E, 6F, 6G, 6H, 6I, 6J, 6K, 6L:
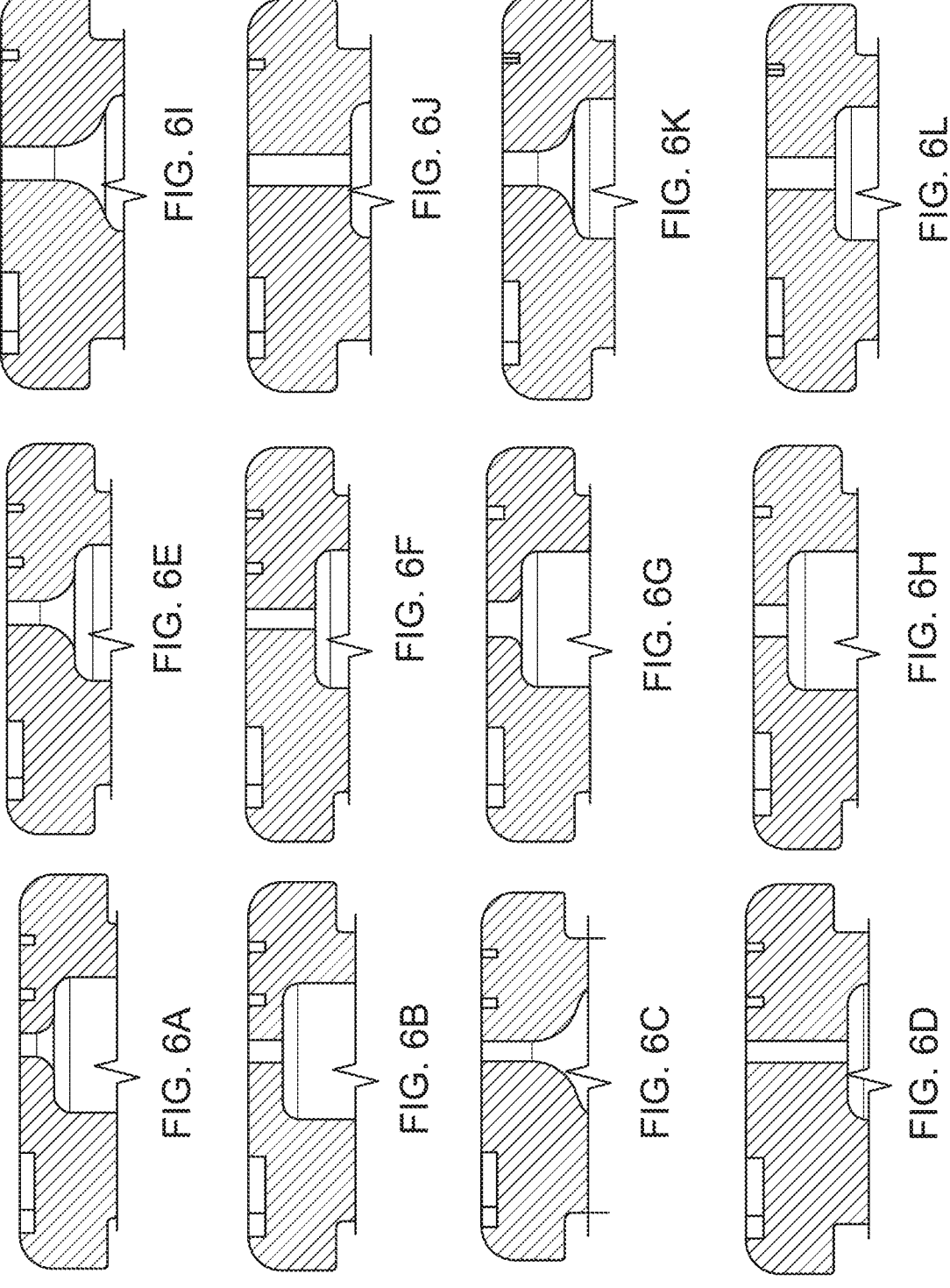
FIGS. 6A-6L shows exemplary nozzle cross sections for the ingestible device.

In some embodiments, as shown in FIG. 6, the diameter of a nozzle as measured at the point of interface with the dispensable substance reservoir can be the same as, smaller than, or larger than the diameter as measured at the nozzle opening (location of delivery of the dispensable substance from the ingestible device). Table 1 provides nozzle diameter (in millimeters) and nozzle length (in millimeters) for the nozzle designs shown in FIG. 6.

TABLE 1

| FIG. 6 | Nozzle diameter | Nozzle length |
|---|---|---|
| A | 0.35 | 0.5 |
| B | 0.35 | 0.5 |
| C | 0.35 | 1.5 |
| D | 0.35 | 1.5 |
| E | 0.35 | 1 |
| F | 0.35 | 1 |
| G | 0.5 | 0.5 |
| H | 0.5 | 0.5 |
| I | 0.5 | 1.5 |
| J | 0.5 | 1.5 |
| K | 0.5 | 1 |

In some embodiments, a tapered nozzle may exhibit enhanced jetting properties. In certain embodiments, a non-tapered nozzle relatively may be relatively inexpensive and simple to manufacture. In some embodiments, a small reducing in certain jet properties with a relatively simplified (e.g., non-tapered) nozzle can be compensated with variation of more easily controlled parameters such as the internal pressure and/or fluid pressure. In some embodiments where the jet exhibits turbulent flow, considering the variations in the flow profile which is inherent to the turbulent nature of the flow, and small impacts of nozzle length variations on the jet velocity, the length of the nozzle may be selected based on mechanical design constraints and required thickness of the ingestible devices.

In some embodiments, a smaller nozzle diameter (e.g., about 0.35 millimeter) is can result in longer dispensing time (~120 milliseconds), which can better align with achievable opening times of ~10 milliseconds and higher velocity for a given peak internal pressure. In some embodiments, a smaller nozzle diameter can also provide actual dispensing times and jet velocities that are closer to the predicted values.

FIG. 6 shows exemplary cross sections of the nozzles 122 within the slider 108 (although nozzles depicted in FIG. 6 may be used in one or more of other embodiments of ingestible devices disclosed herein). In some embodiments, the nozzles are about 0.15-0.5 mm in diameter and about 0.3-1.5 mm in length. The throat (e.g., the narrowing portion) of the nozzle can be rounded (as in the top right) or sharp (as in the bottom left) and the neck can have varying lengths. Each of these parameters have an effect on the jet(s) generated by the nozzle, modulating, for example, average jet diameter, jet velocity, peak jet power, peak jet pressure, peak jet force, and average dispensing time. These characteristics can affect the efficacy of delivery and/or subject uptake of the therapeutic agent.

Figure 7:
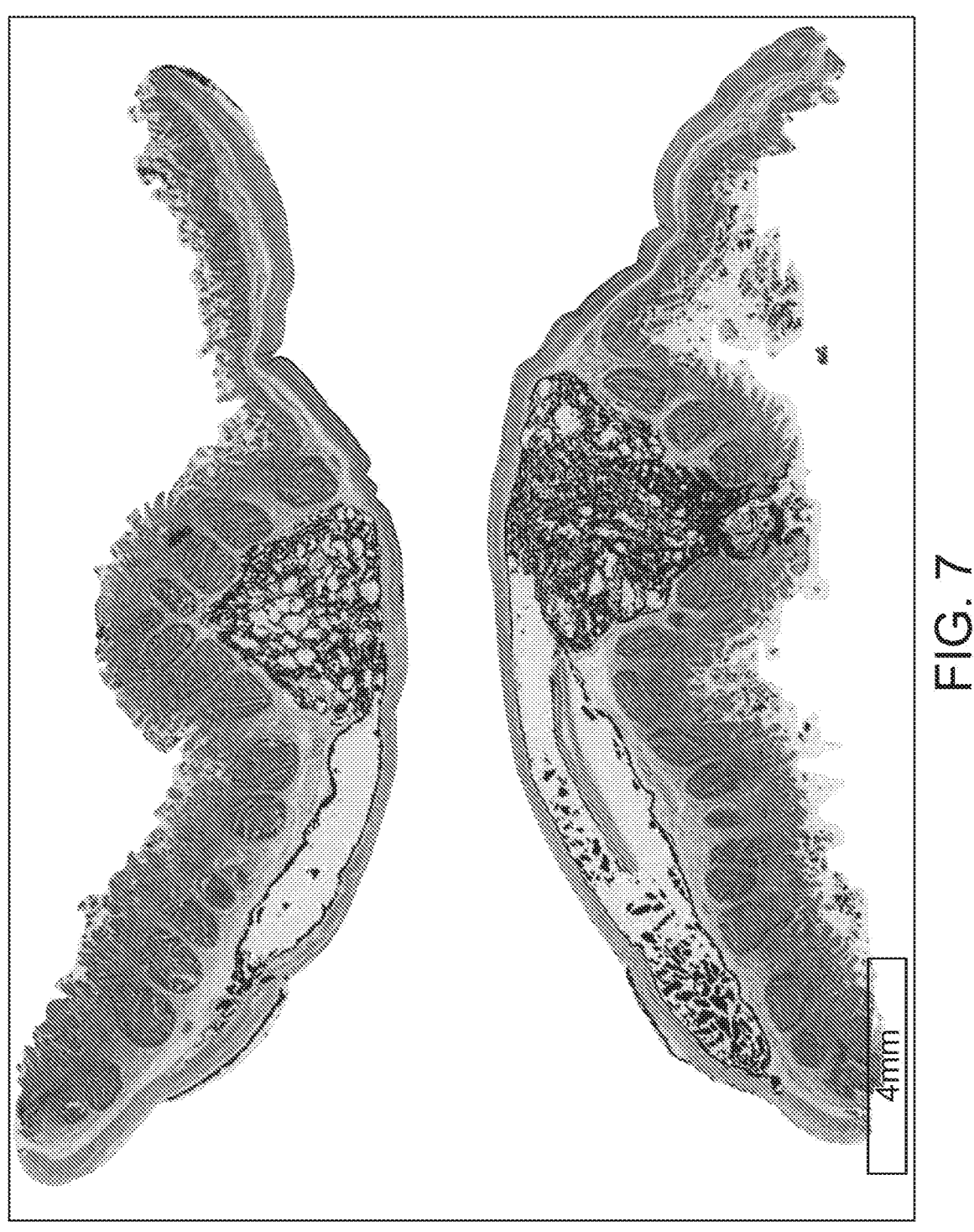
FIG. 7 shows an exemplary histology slide resulting from a bolus of therapeutic agent in situ.

FIG. 7 shows a histologic example of a jetted fluid in situ. This result was achieved with a 0.35 mm nozzle and jetting pressure of 250 psig, and an estimated 181 μL bolus volume. The fluid passed through the mucosa and is within the submucosal region. In this example, the complete bolus was not delivered, possibly due to the physical volume constraints of the region. This indicates that multiple nozzles each delivering a smaller bolus of therapeutic agent may be preferred to maximize the bioavailability of the therapeutic agent.

Referring back to FIGS. 4A-5B, the ingestible device 100 has a triggering mechanism that causes the device 100 to release the dispensable substance within the substance reservoir 114 when the ingestible device reaches the desired location within the GI tract. The trigger that initiates dispensable substance release can have two parts: the enteric coating 120 enrobing the exterior surface 102 of the device 100, and the elements 116. The elements 116 are either covered with an enteric coating or are themselves are made of an enteric material. The enteric material may be degradable and/or erodible in the small intestine of the GI tract, or may be degradable and/or erodible in the large intestine of the GI tract, for example, the colon. Such a two-stage release mechanism allows the device 100 to transit through the GI tract to the desired location intact before releasing the therapeutic agent.

In the first stage, the enteric coating 120 dissolves, degrades and/or erodes while the device 100 is within a desired portion of the GI tract, e.g., the small intestine or the large intestine. The enteric coating 120 is chosen such that it is stable in the acidic environment of the stomach and dissolves, degrades and/or erods only when exposed to the more neutral environment of the small intestines (e.g., pH>5) or the slightly acidic to neutral environment of the large intestine (e.g., pH 5.5-7). The thickness of the coating 120 is chosen such that it dissolves, degrades and/or erodes (either entirely, or enough to expose the elements 116) when the swallowed device 100 is predicted to have transited through the stomach and be within the small intestine or large intestine.

Once the enteric coating 120 has dissolved, degraded and/or eroded from the exterior surface 102 of the device 100, the elements 116 of the device 100 are exposed to the GI tract. The elements 116 are configured to dissolve, degrade and/or erod upon exposure to the environment of the small intestine (e.g., a water soluble material). Generally, the elements 116 dissolve, degrade and/or erode more rapidly than does the enteric coating 120. The elements 116 can dissolve, for example, within about 1 minute of the enteric coating 120 dissolving, degrading and/or eroding and exposing the elements 116 to the small intestine environment, compared to, for example, about 30 minutes for the enteric coating 120 to degrade. It is not necessary that the enteric coating 120 dissolves, degrades and/or erodes in its entirety. As the enteric coating 120 starts to degrade water or other luminal contents may pass through it and cause the elements 116 to dissolve and thereby lose their mechanical holding strength.

Materials for the elements 116 can be isomalt, sugars like maltose or sucrose, or degrading materials of different sorts.

The elements 116 and the structural elements 118 can be made of materials and are sized and shaped such that they, in combination, provide enough rigidity to hold the slider 108 in the closed position under the pressure of the pressurized gas in the gas reservoir 112, which can be in the range of 150-400 psig. For example, if the gas reservoir 112 is to be pressurized to 260 psig, the elements 116 and the structural elements 118 can be designed to hold back 300 psig of pressure. In one arrangement, the retaining strength of the elements 116 is 80 psig, and the retaining strength of the structural elements 118 is 220 psig. Upon dissolution, degradation and/or erosion of the elements 116, the structural elements 118 are exposed to the pressure of 260 psig within the gas reservoir 112. As the 260 psig within the gas reservoir 112 exceeds the reduced restraining strength of 220 psig, the remaining structural elements 118 break. The combination of the dissolution, degradation and/or erosion of the elements 116 followed by the breaking of the structural elements 118 releases the slider 108.

In some embodiments, the elements 116 and the structural elements 118 are made of the same material. The elements 116 have a smaller cross sectional area than the structural elements 118 and thus fail more quickly than the structural elements 118. In other embodiments, the elements 116 and the structural elements 118 are made of different materials, where the structural elements 118 are stronger but more brittle than the elements 116.

In some embodiments, only elements 116 are present, without structural elements 118. In such instances, the elements 116 are configured to break and release the piston 130 and slider 108 in a single step (following dissolving, degrading and/or eroding of the enteric coating 120).

To dispense the therapeutic agent, the device 100 moves from the closed position in FIGS. 5A and 5B back to the open position of FIGS. 3B and 3C where the substance reservoir 114 is fluidly connected to the outside of the device (in this instance, with the GI tract). Once the shear pins dissolve/degrade/erode and/or are sheared, the piston 130 is released to slide axially within the bottom housing 104, and the slider 108 slides relative to the top housing 134. The motion of the slider 108 positions the nozzles 122 such that the portion of the nozzles 122 within the top housing 134 aligns with the fluid outlet portion of the nozzles 122 within the slider 108. The movement of the piston 130, driven by the now-unrestrained pressure within the air reservoir 122, forces the therapeutic within the substance reservoir 114 out through the nozzles 122. The elements 116 and 118 may remain only in the blind hole portion 124B of the pockets 124. In some embodiments, the dispensing time is approximately 120 ms. In some embodiments, the time for the slider 108 to move from the closed to the open position is approximately 10 ms.

Figure 8:
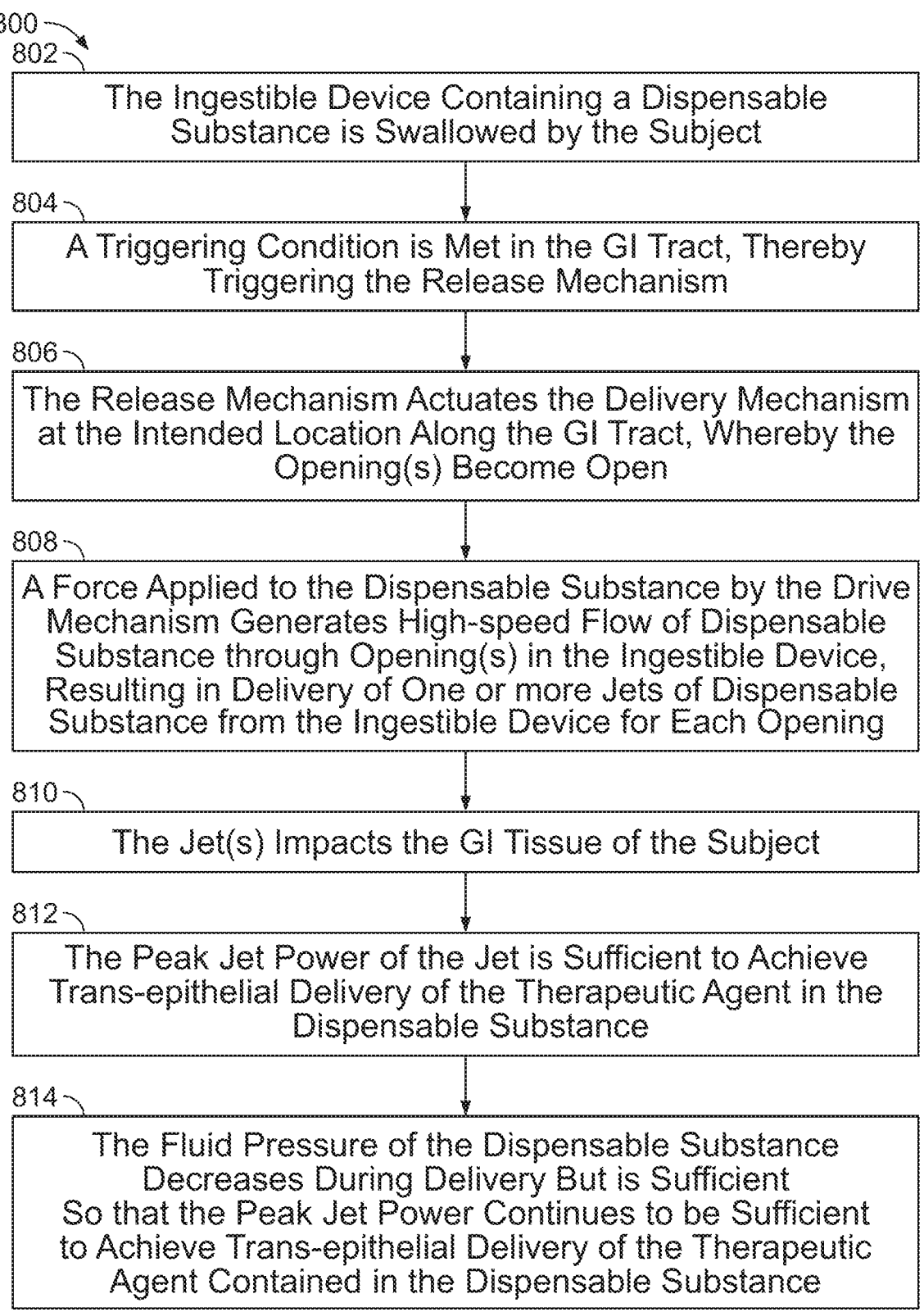
FIG. 8 shows an exemplary process flow chart for use of an ingestible device in which pressure is applied to the dispensable substance before the subject swallows the ingestible device.

FIG. 8 shows an exemplary process flow chart 800 for use of an ingestible device in which pressure is applied to the dispensable substance before the subject swallows the ingestible device. The process begins at step 802, when the patient swallows the ingestible device. In step 804, a triggering condition (e.g., pH, change in pH, presence of certain enzyme, concentration of certain enzyme) is met in the GI tract, thereby triggering the release mechanism. In step 806, the release mechanism actuates the delivery mechanism at the intended location of the GI tract, whereby the opening(s) of the ingestible device become open. In step 808, force applied to the dispensable substance by the drive mechanism generates high-speed flow of the dispensable substance through the opening(s) in the ingestible device, resulting in delivery of a jet of the dispensable substance from the ingestible device for each opening. In step 810, the jet has a sufficient jet stable length for the jet to impact the GI tissue of the subject. In step 812, the peak jet power of the jet is sufficient to achieve trans-epithelial delivery of the therapeutic agent contained in the dispensable substance. In step 814, the fluid pressure of the dispensable substance decreases during delivery but is sufficiently so that the peak jet power continues to be sufficient to achieve trans-epithelial delivery of the therapeutic agent contained in the dispensable substance.

Figure 9A:
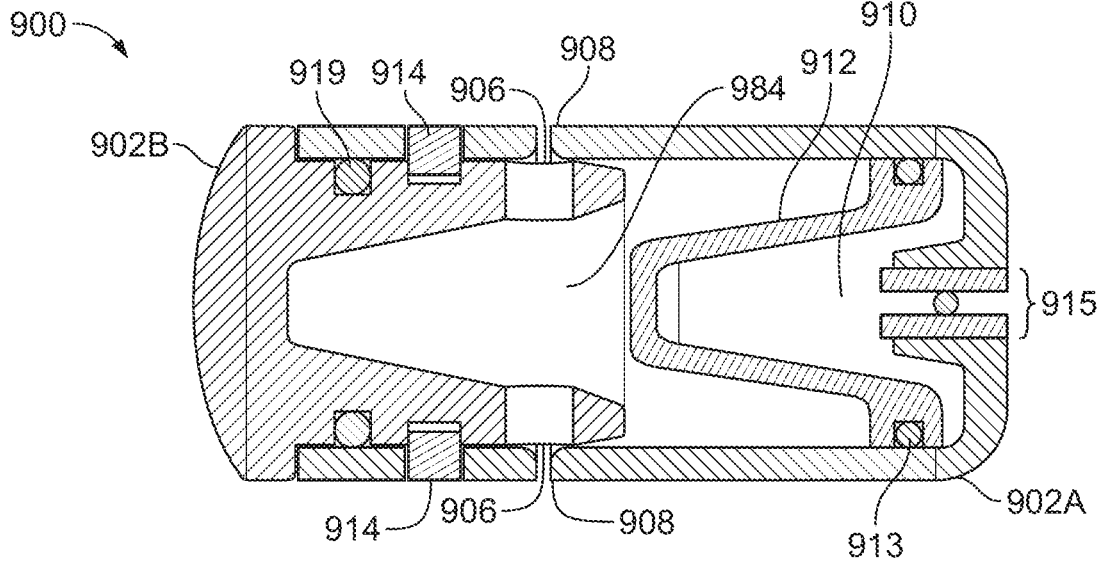
FIG. 9A shows an ingestible device.
Figure 9B:
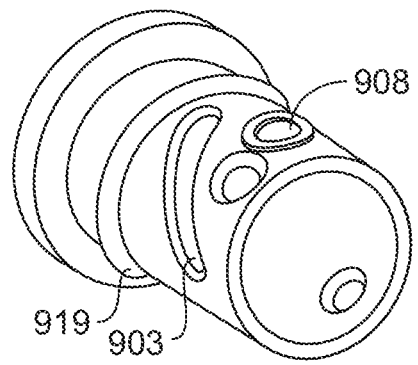
FIG. 9B shows certain elements of the ingestible device of FIG. 9A.

FIG. 9A shows an embodiment of an ingestible device 900 for trans-epithelial delivery. The device 900 includes housing parts 902A and 902B, a fluid volume 904 containing a dispensable substance, nozzles 906 with nozzle openings 908, pressurized gas as a drive force generator 910, a drive coupling 912 with an O-ring 913 seal, a ring 914 and a valve 915 (inlet for compressed gas). Similar to the device shown in FIGS. 4A-5B, when the device 900 is swallowed by the subject, the dispensable substance in the device is already pressurized. However, the ring 914 prevents the pressure of the drive force generator 910 and the drive coupling 912 from forcing the dispensable substance in the fluid volume 904 through the nozzle openings 908. When the device 900 reaches the appropriate location in the GI tract, the ring 914 erodes, degrades and/or dissolves. Thus, the pressure of the drive force generator 910 and the drive coupling 912 is applied to the dispensable substance 904, forcing the cap to move to expose openings 908. As shown in FIG. 9B, the housing part 902B has a slot 903 into which a portion of housing part 902A fits such that the motion of the housing part 902A is both axial and rotational (e.g., a track and cam arrangement). This arrangement can result in relatively reduced axial movement of the housing part 902B during delivery of the dispensable substance, which can result in maintenance of a relatively high internal pressure during delivery of the dispensable substance.

Figure 10A:
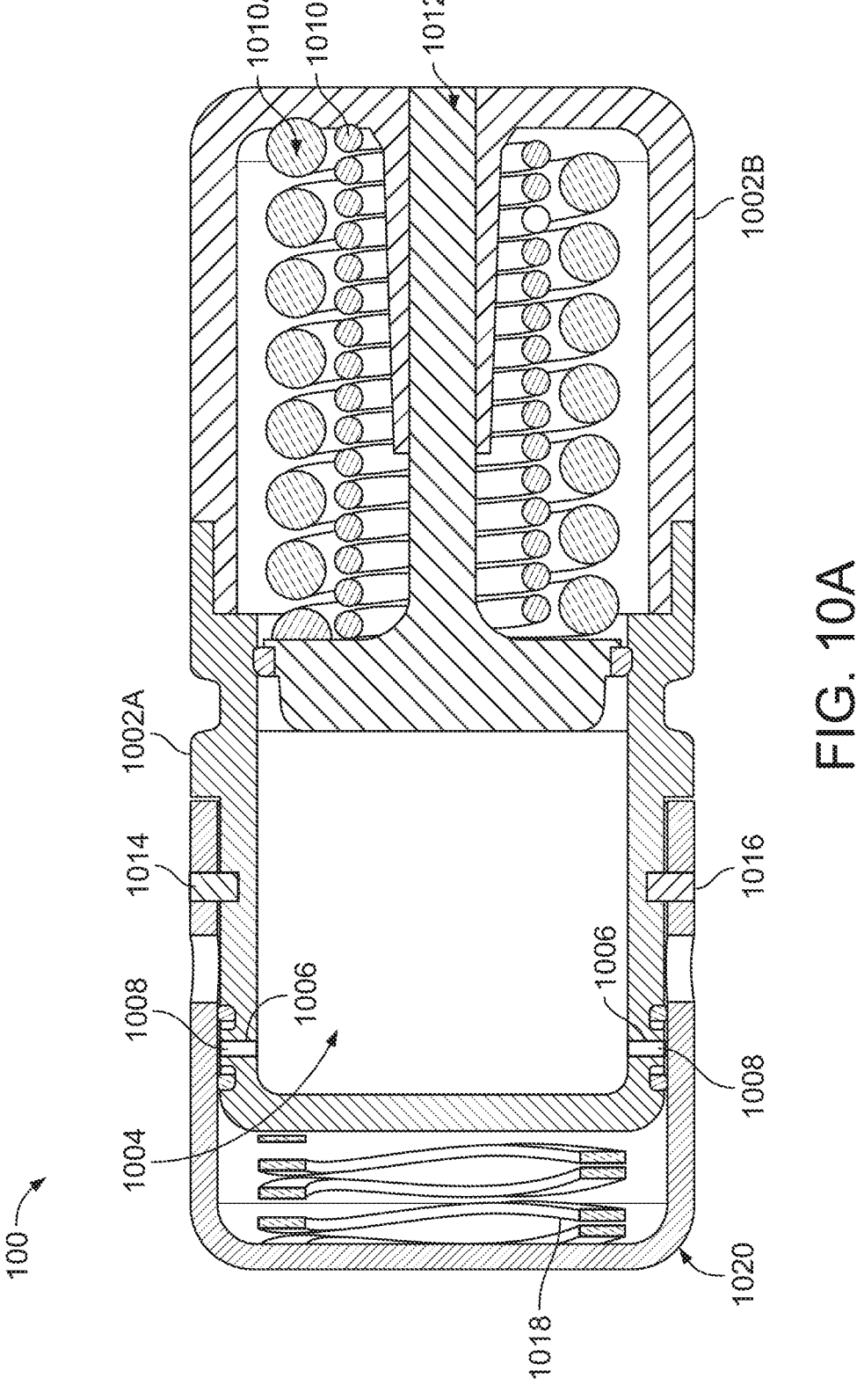
FIG. 10A shows an ingestible device.
Figure 10B:
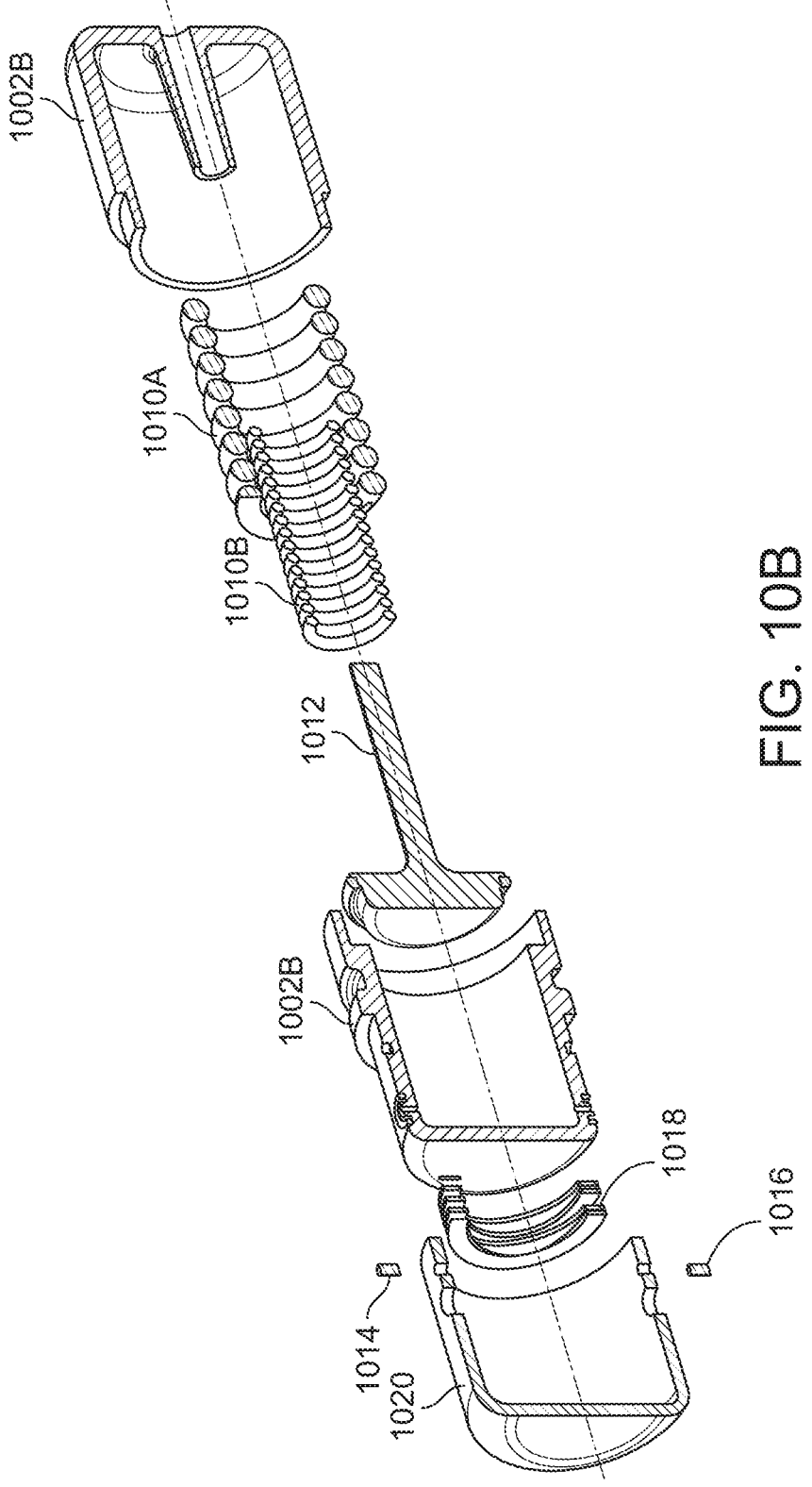
FIG. 10B shows an exploded view of the ingestible device of FIG. 10A.

FIG. 10A shows an embodiment of an ingestible device 1000 for trans-epithelial delivery. FIG. 10B is an exploded view of the ingestible device 1000. The ingestible device 1000 has housing parts 1002A and 1002B, a fluid volume 1004 containing a dispensable substance, nozzles 1006, nozzle openings 1008, parallel springs 1010A and 1010B, a piston 1012, a pin 1014, a pin 1016, a spring 1018 and a cap 1020. Similar to the device shown in FIGS. 4A-5B, when the device 1000 is swallowed by the subject, the dispensable substance in the device is already pressurized. However, the pins 1014 and 1016 prevent the pressure of the springs 1010A and 1010B and the piston 1012 from forcing the dispensable substance in the fluid volume 1004 through the nozzle openings 1008. When the device 1000 reaches the appropriate location in the GI tract, the pin 1014 erodes, degrades and/or dissolves, and the pin 1016 is not sufficient to hold back the pressure from the springs 1010A and 1010B and the piston 1012. Thus, the pressure of the springs 1010A an 1010B and the piston 1012 is applied to the dispensable substance, forcing the spring 1020 to quickly move the cap 1018 forward. This rapidly exposes the nozzle openings 1008 to the environment exterior to the device 1000 so that the dispensable substance is delivered out of the openings 1008 in the form of a jet. This results in in trans-epithelial delivery of the therapeutic agent contained in the dispensable substance. In some embodiments, the housing of the ingestible device 1000 has a diameter of about 11 mm, a length of about 26 mm, a wall thickness of about 0.8 mm, an end round of about 1.5 mm and an internal volume of about 1685 μL. In such embodiments, the fluid volume 1004 can be about 325 μL.

Figure 10C:
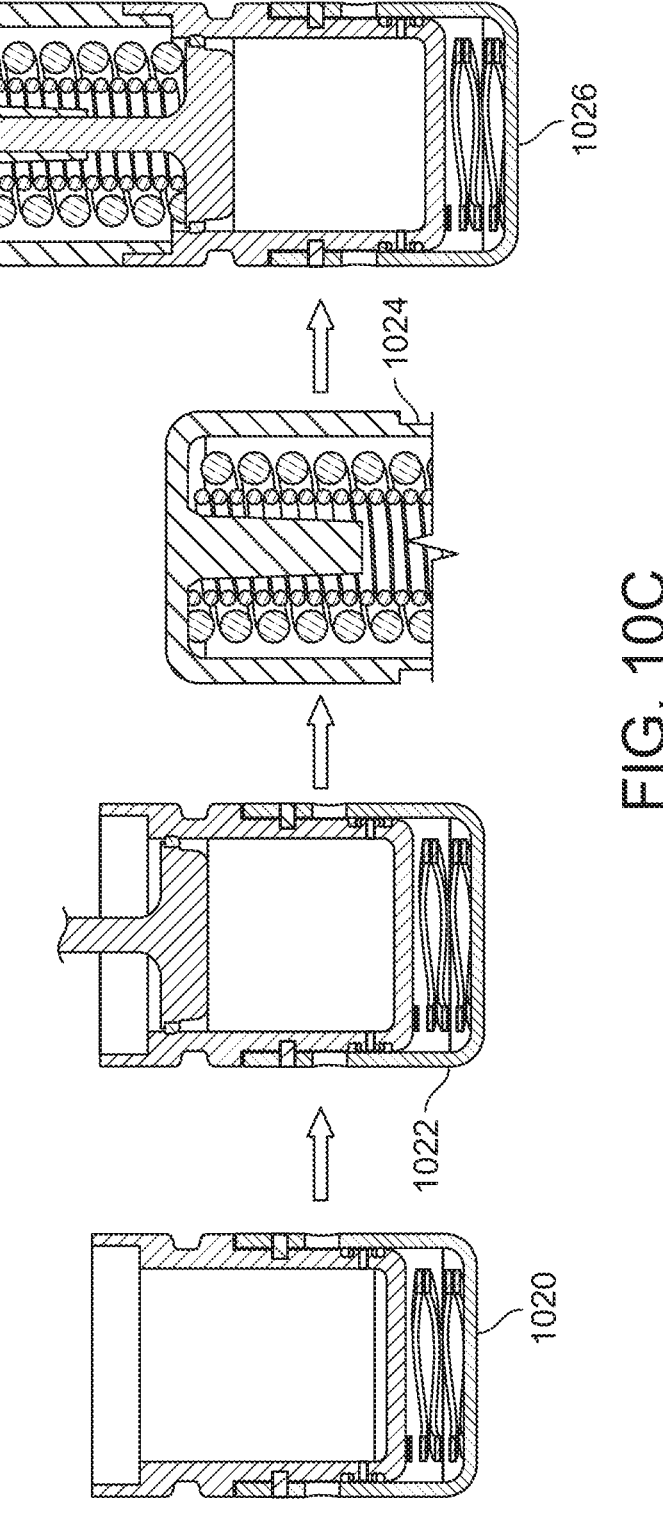
FIG. 10C shows aspects of steps in assembling the ingestible device of FIG. 10A.

FIG. 10C shows aspects of steps in assembling the ingestible device 1000. In step 1020, the cap 1020 and spring 1018 are combined with the housing part 1002B and pins 1014 and 1016, and this module is sterilized. In step 1022, the dispensable substance 1004 is disposed in the housing part 1002B in an aseptic environment and then sealed within the housing part 1002B via the piston 1012. In step 1024, the housing part 1002A and its components are assembled in a clean environment. In step 1026, the resulting modules are joined together in a clean environment to compress the springs 1010A and 1010B to provide the ingestible device 1000. As shown in step 1026, the assembly process can include using a jig to hold the housing part 1002A to prevent over-loading of the cap 1020/spring 1018/pin 1014/pin 1016 combination.

Figures 10D, 10E:
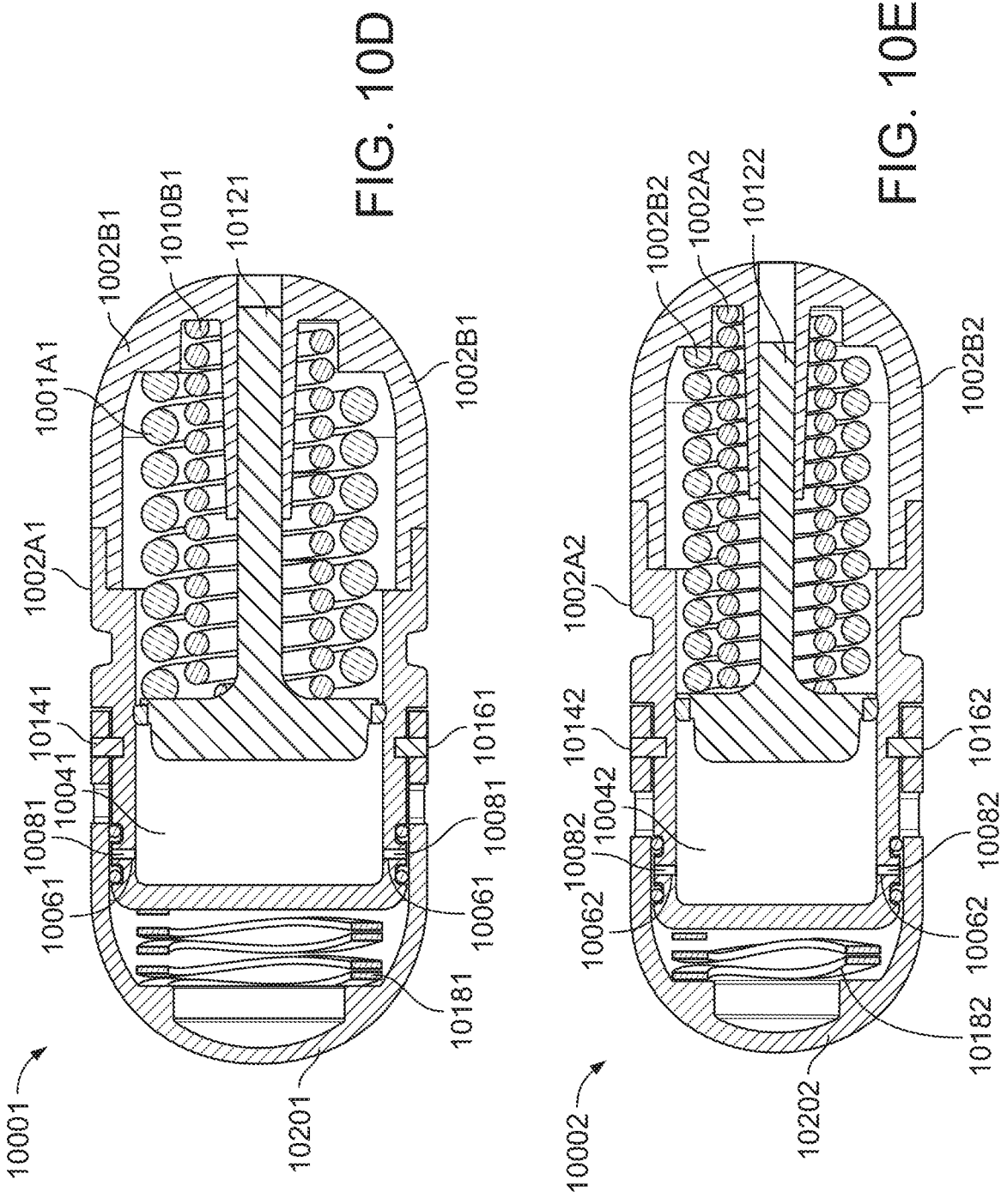
FIG. 10D shows an ingestible device with aspects similar to those shown in FIG. 10A.
FIG. 10E shows an ingestible device with aspects similar to those shown in FIG. 10A.

FIG. 10D shows an embodiment of an ingestible device 10001 for trans-epithelial delivery. The ingestible device 10001 has housing parts 1002A1 and 1002B1, a fluid volume 10041 containing a dispensable substance, nozzles 10061, nozzle openings 10081, parallel springs 1010A1 and 1010B1, a piston 10121, a pin 10141, a pin 10161, a spring 10181 and a cap 10201. Similar to the device shown in FIGS. 4A-5B, when the device 10001 is swallowed by the subject, the dispensable substance in the device is already pressurized. However, the pins 10141 and 10161 prevent the pressure of the springs 1010A1 and 1010B1 and the piston 10121 from forcing the dispensable substance in the fluid volume 10041 through the nozzle openings 10081. When the device 10001 reaches the appropriate location in the GI tract, the pin 10141 erodes, degrades and/or dissolves, and the pin 10161 is not sufficient to hold back the pressure from the springs 1010A1 and 1010B1 and the piston 10121. Thus, the pressure of the springs 1010A1 an 1010B1 and the piston 10121 is applied to the dispensable substance, forcing the spring 10201 to quickly remove move the cap 10181 forward. This rapidly exposes the nozzle openings 10081 to the environment exterior to the device 10001 so that the dispensable substance is delivered out of the openings 10081 in the form of a jet. This results in in trans-epithelial delivery of the therapeutic agent contained in the dispensable substance. In some embodiments, the spring force of the spring 10181 has a force of about 30 Newtons, the parallel springs 1010A1 and 1010B1 have a force of 110 Newtons to provide an internal pressure of about 320 psig with about 50 Newtons of force at the end of the stroke, and the fluid volume 10041 is about 225 μL. In some embodiments, the housing of the ingestible device 10001 has a diameter of about 11 mm, a length of about 26 mm, a wall thickness of about 0.8 mm, an end round of about 5.5 mm (spherical) and an internal volume of about 1475 μL. In such embodiments, the fluid volume 10041 can be about 225 μL.

FIG. 10E shows an embodiment of an ingestible device 10002 for trans-epithelial delivery. The ingestible device 10002 has housing parts 1002A2 and 1002B2, a fluid volume 10042 containing a dispensable substance, nozzles 10062, nozzle openings 10082, parallel springs 1010A2 and 1010B2, a piston 10122, a pin 10142, a pin 10162, a spring 10182 and a cap 10202. Similar to the device shown in FIGS. 4A-5B, when the device 10002 is swallowed by the subject, the dispensable substance in the device is already pressurized. However, the pins 10142 and 10162 prevent the pressure of the springs 1010A2 and 1010B2 and the piston 10122 from forcing the dispensable substance in the fluid volume 10042 through the nozzle openings 10082. When the device 10002 reaches the appropriate location in the GI tract, the pin 10142 erodes, degrades and/or dissolves, and the pin 10162 is not sufficient to hold back the pressure from the springs 1010A2 and 1010B2 and the piston 10122. Thus, the pressure of the springs 1010A2 an 1010B2 and the piston 10122 is applied to the dispensable substance, forcing the spring 10202 to quickly remove move the cap 10182 forward. This rapidly exposes the nozzle openings 10082 to the environment exterior to the device 10002 so that the dispensable substance is delivered out of the openings 10082 in the form of a jet. This results in in trans-epithelial delivery of the therapeutic agent contained in the dispensable substance. In some embodiments, the spring force of the spring 10182 has a force of about 12 Newtons, the parallel springs 1010A2 and 1010B2 have a force of 58 Newtons to provide an internal pressure of about 320 psig with about 25 Newtons of force at the end of the stroke, and the fluid volume 10042 is about 120 μL. In some embodiments, the housing of the ingestible device 10002 has a diameter of about 8.5 mm, a length of about 23.3 mm, a wall thickness of about 0.75 mm, an end round of about 4.25 mm (spherical) and an internal volume of about 775 μL. In such embodiments, the fluid volume 10042 can be about 120 μL.

Figure 11:
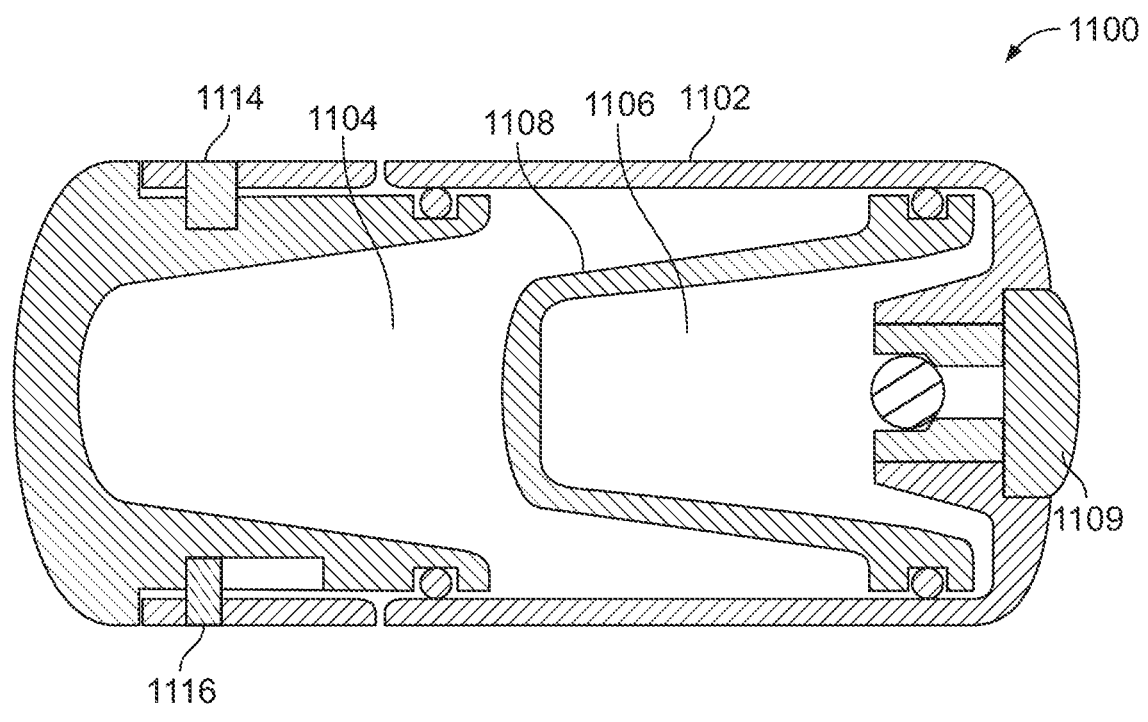
FIG. 11 shows an ingestible device.

FIG. 11 shows an ingestible device 1100 which includes a housing 1102, a fluid volume 1104, a liquid-gas reservoir (drive force generator) 1106, a drive coupling 1108, a seal 1109, a pin 1114 and a pin 1116. The ingestible device 1100 is configured so that, before the subject swallows the device, the dispensable substance in fluid volume 1104 is under pressure from the liquid-gas reservoir 1106 via the drive coupling 1108, but the pins 1114 and 1116 prevent the dispensable substance in fluid volume 1004 from being delivered from the device 1100 via nozzle(s) with nozzle opening(s) (not shown). When the device 1100 reaches the appropriate location in the GI tract, the pin 1114 erodes, degrades and/or dissolves (e.g., due to pH, change in pH, presence of certain enzyme, and/or concentration of certain enzyme), and the pin 1116 is no longer sufficient to hold back the pressure from the liquid-gas reservoir 1106 and the drive coupling 1108. Thus, this pressure is applied to the dispensable substance in the fluid volume 1104, forcing the dispensable substance out of the nozzle openings (not shown) in the form of a jet. This results in in trans-epithelial delivery of the therapeutic agent contained in the dispensable substance.

Figure 12:
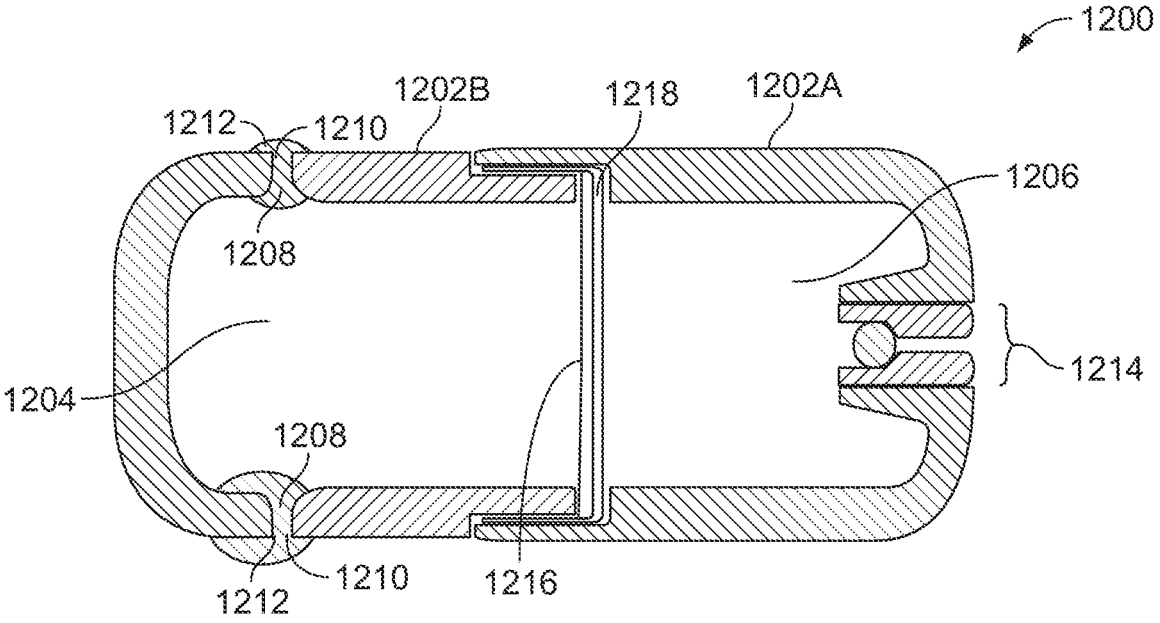
FIG. 12 shows an ingestible device.

FIG. 12 shows an ingestible device 1200 which includes a first housing part 1202A, a second housing part 1202B, a fluid volume 1204, a drive force generator 1206, nozzles 1208 with nozzle openings 1210, plugs 1212, a seal 1214, a seal 1216 and a membrane 1218. The ingestible device 1200 is configured so that, before the subject swallows the device, the dispensable substance in fluid volume 1204 is under pressure from the drive force generator 1206, but the plugs 1212 prevent the dispensable substance in fluid volume 1204 from being delivered from the device 1200 via nozzle openings 1210. When the device 1200 reaches the appropriate location in the GI tract, the plugs 1212 erode, degrade and/or dissolve (e.g., due to pH, change in pH, presence of certain enzyme, and/or concentration of certain enzyme), so that the pressure from the drive force generator 1206 breaks the seal 1216 (made of a relatively low mechanical strength material, such as a seal), which causes the membrane 1218 to expand into the fluid volume 1204, forcing the dispensable substance out of the nozzle openings 1210 in the form of a jet. This results in in trans-epithelial delivery of the therapeutic agent contained in the dispensable substance.

The housing parts 1202A and (including the membrane 1218) are initially separate from each other. The plugs are disposed in the nozzles 1210, the dispensable substance is disposed in the fluid volume 1204, and the seal 1216 is added. The dispensable substance (including the therapeutic agent) is first sterilized, and then disposed in the fluid volume 1204 under aseptic conditions. The drive force generator 1206 is manufactured in a clean environment and then incorporated with the housing part 1202B, after which the membrane 1218 is added. Subsequently, the housing parts 1202A and 1202B are joined in a clean environment to produce the ingestible device 1200.

Figure 13:
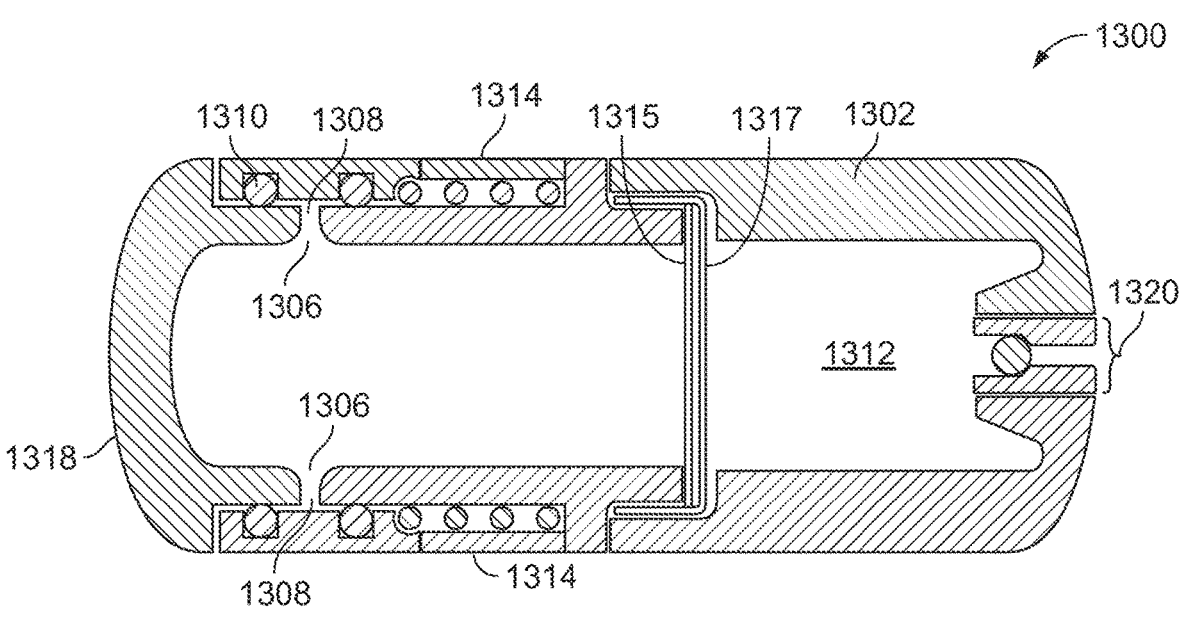
FIG. 13 shows an ingestible device.

FIG. 13 shows an embodiment of an ingestible device 1300 for trans-epithelial delivery. The device 1300 has a housing 1302 with a fluid volume 1304 containing a dispensable substance, nozzles 1306, nozzle openings 1308, a tensioned spring 1310, a drive force generator 1312, a band 1314 around the device, a seal 1315, a cap 1318, a membrane 1317 and a seal 1320. When the device 1300 is swallowed by the subject, the dispensable substance in the device is already pressurized. However, the band 1314 prevents the pressure of the drive force generator 1312 from relieving the tension in the spring 1310 so that the dispensable substance in the fluid volume 1304 is prevented from going through the nozzle openings 1308. When the device 1300 reaches the appropriate location in the GI tract, the band 1314 erodes, degrades and/or dissolves. Thus, the tension in the spring 1310 is relieved, and the spring moves to where the band 1314 was located, thereby rapidly exposing the nozzle openings 1308 to the environment exterior to the device 1300 so that the dispensable substance is delivered out of the openings 1308 in the form of a jet. This results in in trans-epithelial delivery of the therapeutic agent contained in the dispensable substance.

Figure 14:
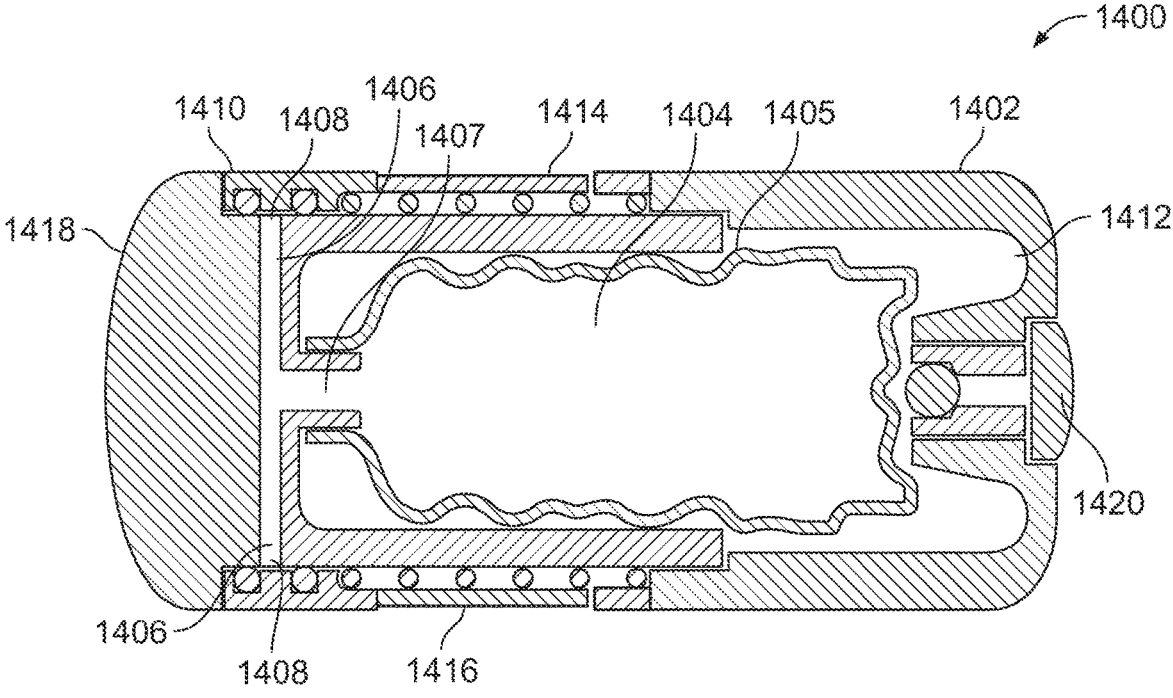
FIG. 14 shows an ingestible device.

FIG. 14 shows an embodiment of an ingestible device 1400 for trans-epithelial delivery. The device 1400 has a housing 1402 with a fluid volume 1404 containing a dispensable substance, a membrane 1405 defining the fluid volume 1404, an opening 1407 leading to nozzles 1406, nozzle openings 1408, a tensioned spring 1410, a pressurized gas (drive force generator) 1412, a band 1414, a cap 1418 and a seal 1420. When the device 1400 is swallowed by the subject, the dispensable substance in the device is already pressurized. However, the band 1414 keeps the spring 1410 tensioned so that the dispensable substance in the fluid volume 1404 is prevented from going through the nozzle openings 1408. When the device 1400 reaches the appropriate location in the GI tract, the band 1414 erodes, degrades and/or dissolves, relieving the tension in the spring 1410, which moves to where the band 1414 had been located, thereby rapidly exposing the nozzle openings 1408 to the environment exterior to the device 1400 so that the dispensable substance is delivered out of the openings 1408 in the form of a jet. This results in in trans-epithelial delivery of the therapeutic agent contained in the dispensable substance.

In some embodiments, the dispensable substance is not under pressure when the subject swallows the ingestible device. The following are illustrative examples of such ingestible devices.

Figure 15A:
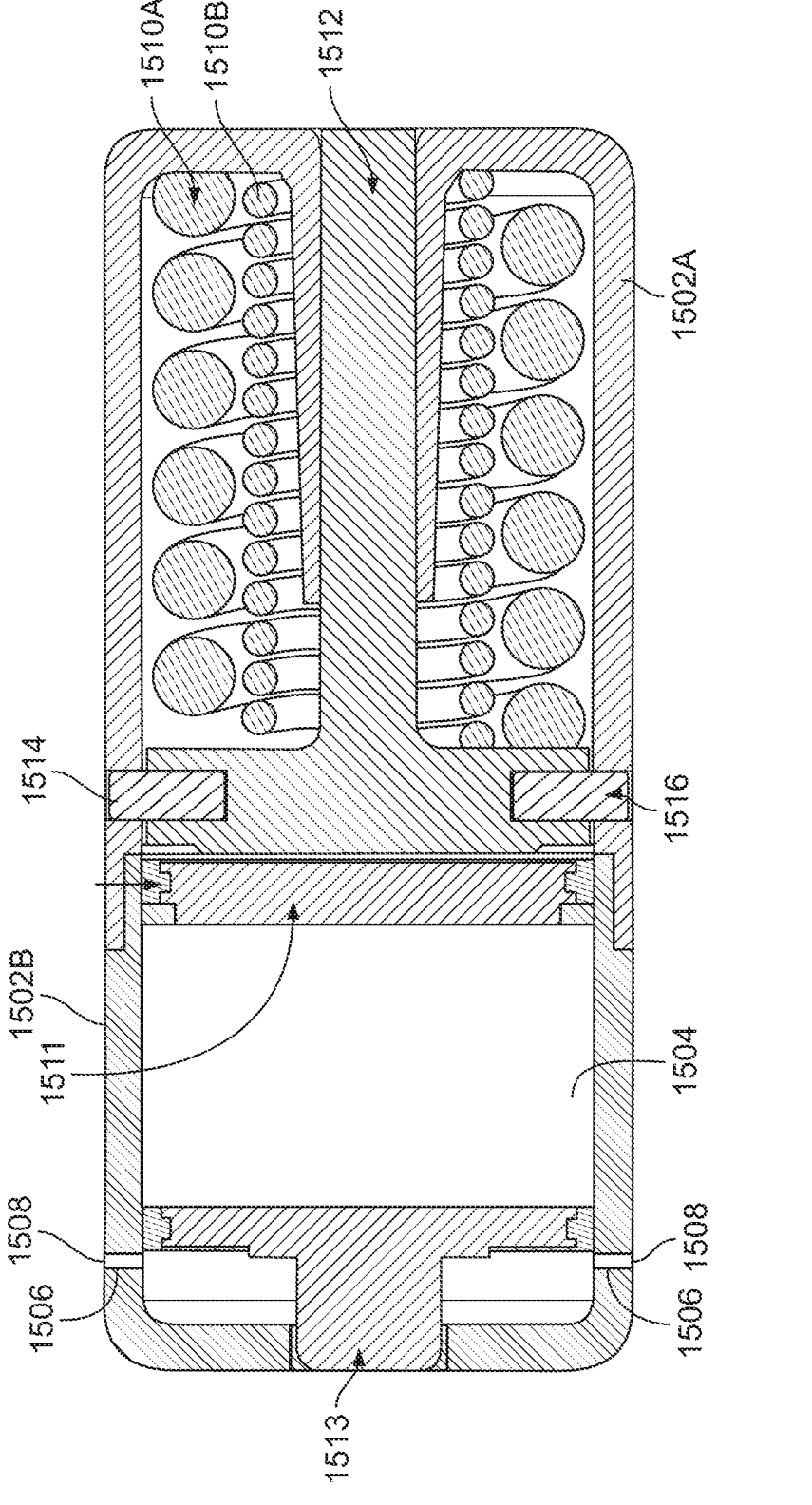
FIG. 15A shows an ingestible device.
Figure 15B:
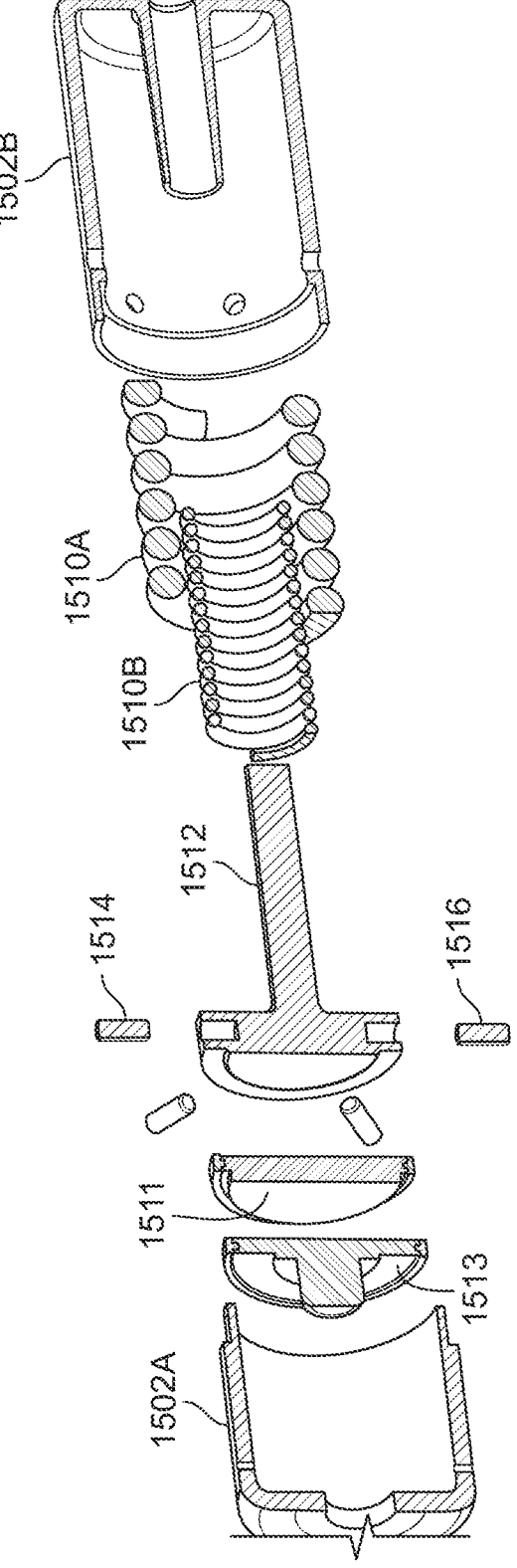
FIG. 15B shows an exploded view of the ingestible device of FIG. 15A.

As an example, FIG. 15A shows an embodiment of an ingestible device 1500 for trans-epithelial delivery. FIG. 15B shows an exploded view of the ingestible device 1500. The ingestible device 1500 has housing parts 1502A and 1502B, a fluid volume 1504 containing a dispensable substance, nozzles 1506, nozzle openings 1508, parallel springs 1510A and 1510B, a plunger 1511, a piston 1512, a piston 1513, a pin 1514 and a pin 1516. When the device 1500 is swallowed by the subject, the pins 1514 and 1516 prevent the dispensable substance in fluid volume 1504 from being under pressure from the springs 1510A and 1510B, the plunger 1511 and the piston 1512. Thus, the pins 1514 and 1516 prevent the pressure of the springs 1510A and 1510B, the plunger 1511 and the piston 1512 from forcing the dispensable substance in the fluid volume 1504 through the openings 1508. When the device 1500 reaches the appropriate location in the GI tract, the pin 1514 erodes, degrades and/or dissolves (e.g., due to pH, change in pH, presence of certain enzyme, and/or concentration of certain enzyme), and the pin 1516 is no longer sufficient to hold back the pressure from the springs 1510A and 1510B, the plunger 1511 and the piston 1512. Thus, the pressure of the springs 1510A and 1510B, the plunger 1511 and the piston 1512 is applied to the dispensable substance in the fluid volume 1504, forcing the dispensable substance out of the nozzle openings 1508 in the form of a jet. This results in in trans-epithelial delivery of the therapeutic agent contained in the dispensable substance.

Figure 15C:
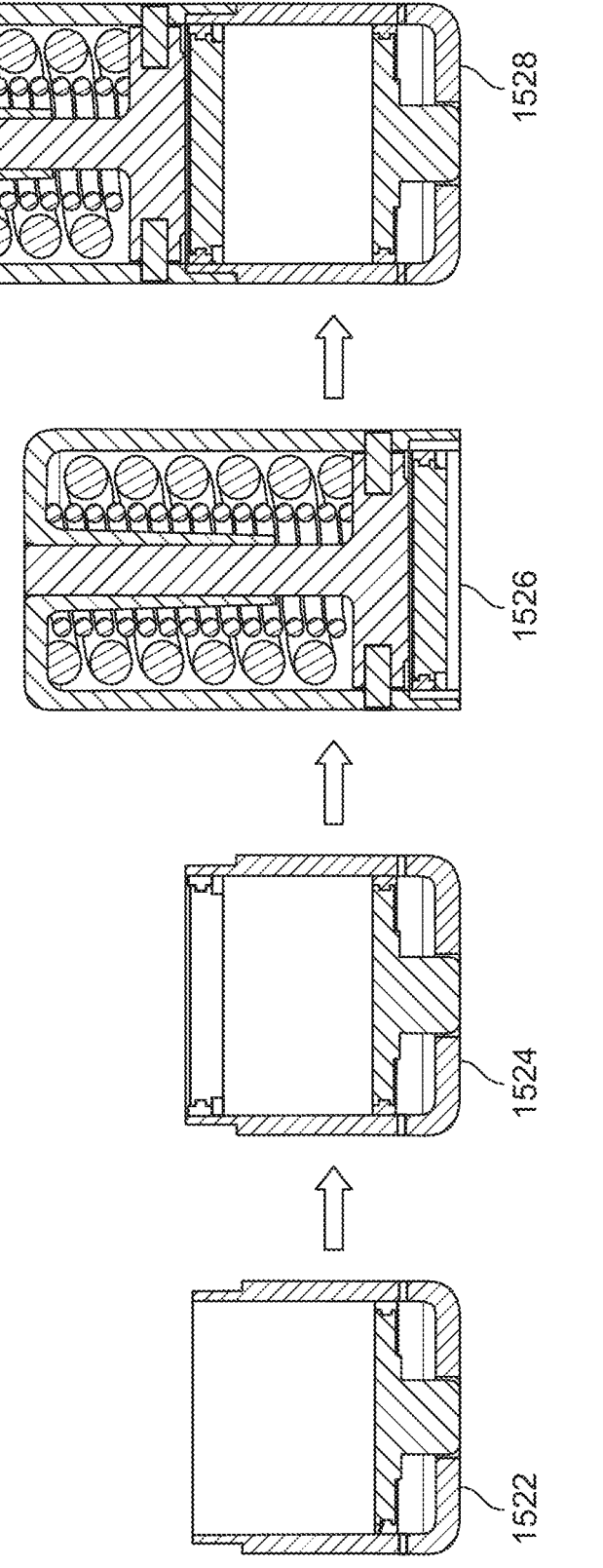
FIG. 15C shows aspects of steps in assembling the ingestible device of FIG. 15A.

FIG. 15C shows aspects of a process of assembling the ingestible device of 1500. In steps 1520 and 1522, the housing part 1502B and piston 1513 are combined and sterilized, the dispensable substance 1504 is added to the housing part 1502B in an aseptic environment, and drive piston 1511 is added to the housing part 1502B to seal the dispensable substance 1504 in the housing part 1502B. In step 1524, the housing part 1502A and its components are assembled in a clean environment. The drive plunger 1512 is used to compress the springs 1510A and 1510B, and the drive plunger 1512 is held in place via the pins 1514 and 1516. In step 1526, the resulting modules are assembled in a clean environment to produce the ingestible device 1500.

Figure 16:
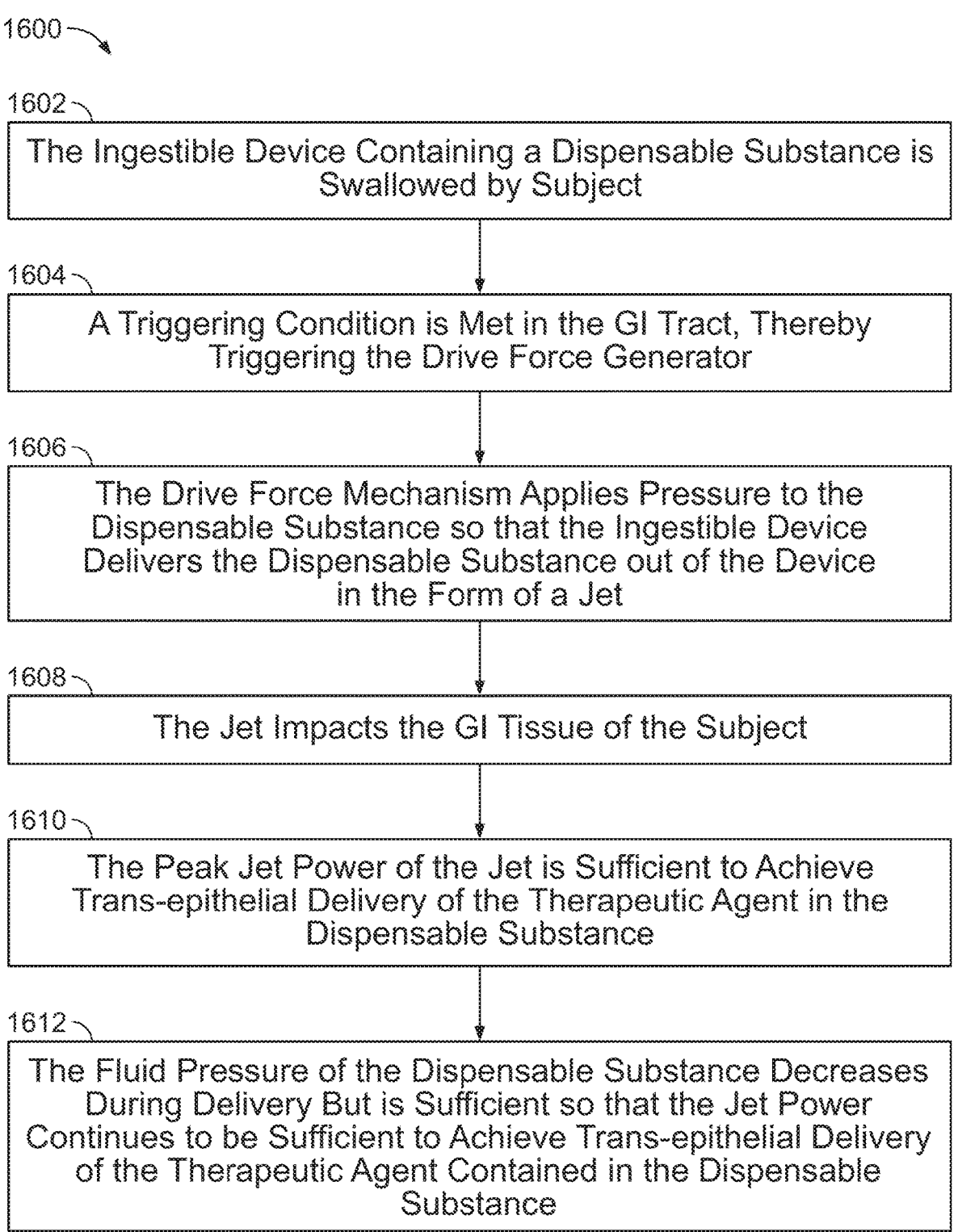
FIG. 16 shows an exemplary process flow chart for use of an ingestible device in which pressure is not applied to the dispensable substance before the subject swallows the ingestible device.

FIG. 16 shows an exemplary process flow chart 1600 for use of an ingestible device in which pressure is not applied to the dispensable substance before the subject swallows the ingestible device. The process beings at step 1602, when the patient swallows the ingestible device. In step 1604, a triggering condition (e.g., pH, change in pH, presence of certain enzyme, concentration of certain enzyme) is met in the GI tract, thereby triggering the drive force generator. In step 1606, the drive force mechanism applies pressure to the dispensable substance, resulting delivery of a jet of the dispensable substance from the ingestible device for each opening. In step 1608, the jet has a sufficient jet stable length for the jet to impact the GI tissue of the subject. In step 1610, the peak jet power of the jet is sufficient to achieve trans-epithelial delivery of the therapeutic agent contained in the dispensable substance. In step 1612, the fluid pressure of the dispensable substance decreases during delivery but is sufficiently so that the peak jet power continues to be sufficient to achieve trans-epithelial delivery of the therapeutic agent contained in the dispensable substance.

Figure 17:
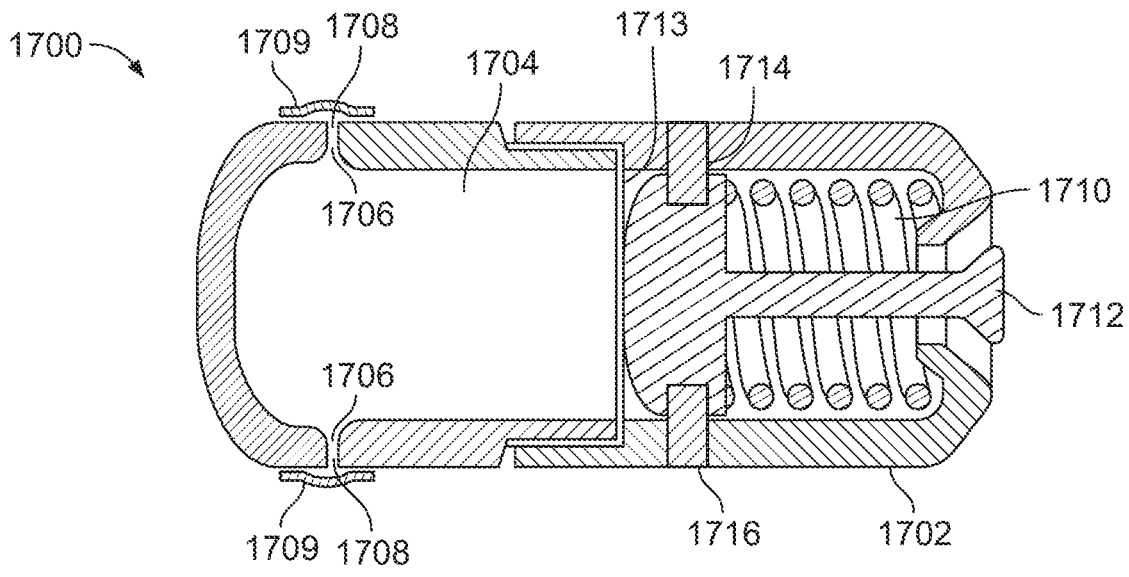
FIG. 17 shows an ingestible device.

FIG. 17 shows an embodiment of an ingestible device 1700 for trans-epithelial delivery, which contains a dispensable substance that is not under pressure when the subject swallows the ingestible device. The device 1700 has a housing 1702 with a fluid volume 1704 containing a dispensable substance, nozzles 1706, nozzle openings 1708, coverings 1709 over openings 1708, a spring 1710, a piston 1712, a fluid barrier 1713 (to prevent the dispensable substance from contacting the piston 1712 or the spring 1710), a pin 1714 and a pin 1716. When the device 1700 is swallowed by the subject, the pins 1714 and 1716 prevent the dispensable substance in fluid volume 1704 from being under pressure from the spring 1710 and the piston 1712, and the coverings 1709 prevent the dispensable substance from exiting the device via openings 1708. When the device 1700 reaches the appropriate location in the GI tract, the pin 1714 erodes, degrades and/or dissolves (e.g., due to pH, change in pH, presence of certain enzyme, and/or concentration of certain enzyme), and the pin 1716 is no longer sufficient to hold back the pressure from the spring 1710 and the piston 1712. Thus, the pressure of the spring 1710 and the piston 1712 is applied to the dispensable substance in the fluid volume 1704, forcing the seals 1709, which are made of a relatively low mechanical strength material (e.g., a foil or a film) to break so that the dispensable substance is delivered out of the nozzle openings 1708 in the form of a jet. This results in in trans-epithelial delivery of the therapeutic agent contained in the dispensable substance.

Figure 18:
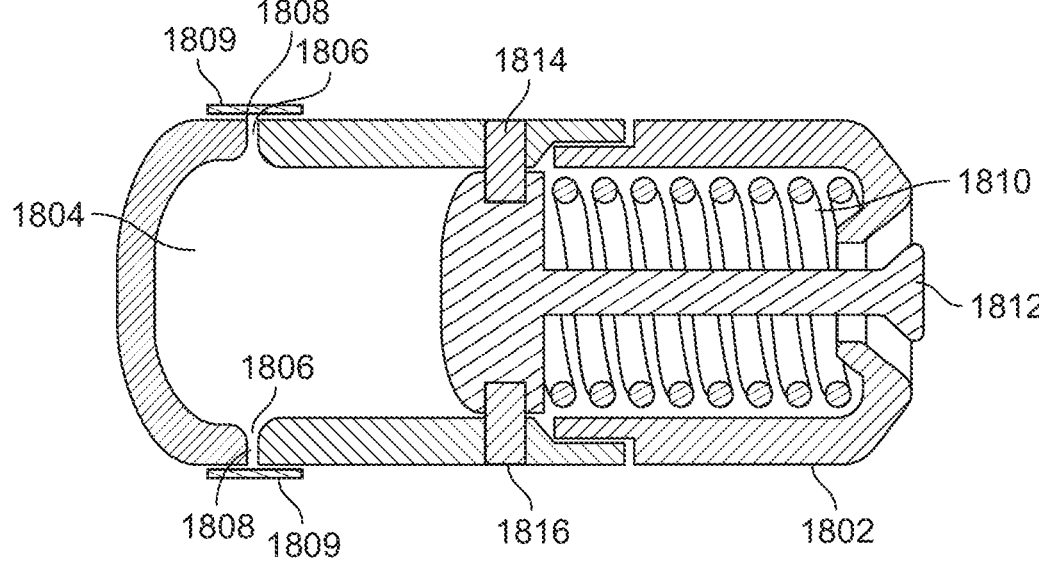
FIG. 18 shows an ingestible device.

FIG. 18 shows an embodiment of an ingestible device 1800 for trans-epithelial delivery, which contains a dispensable substance that is not under pressure when the subject swallows the ingestible device. The device 1800 has a housing 1802 with a fluid volume 1804 containing a dispensable substance, nozzles 1806, nozzle openings 1808, coverings 1809 over openings 1808, a spring 1810, a piston 1812, a pin 1814 and a pin 1816. When the device 1800 is swallowed by the subject, the pins 1814 and 1816 prevent the dispensable substance in fluid volume 1804 from being under pressure from the spring 1810 and the piston 1812, and the coverings 1809 prevent the dispensable substance from exiting the device via openings 1808. When the device 1800 reaches the appropriate location in the GI tract, the pin 1814 erodes, degrades and/or dissolves (e.g., due to pH, change in pH, presence of certain enzyme, and/or concentration of certain enzyme), and the pin 1816 is no longer sufficient to hold back the pressure from the spring 1810 and the piston 1812. Thus, the pressure of the spring 1810 and the piston 1812 is applied to the dispensable substance in the fluid volume 1804, forcing the seals 1809, which are made of a relatively low mechanical strength material (e.g., a foil or a film) to break so that the dispensable substance is delivered out of the nozzle openings 1808 in the form of a jet. This results in in trans-epithelial delivery of the therapeutic agent contained in the dispensable substance.

Figures 19A, 19B:
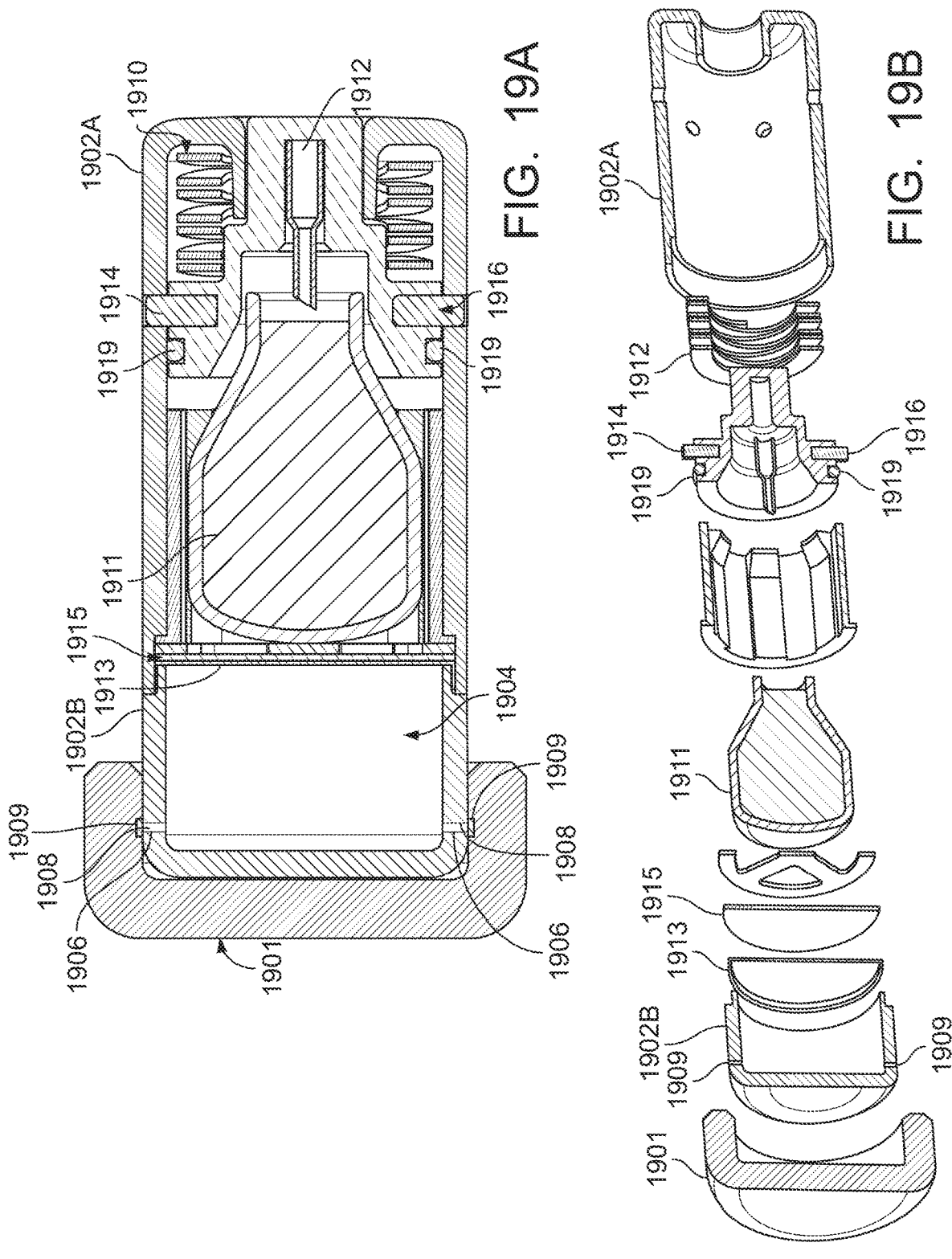
FIG. 19A shows an ingestible device.
FIG. 19B shows an exploded view of the ingestible device of FIG. 19A.

FIG. 19A shows an embodiment of an ingestible device 1900 for trans-epithelial delivery, which contains a dispensable substance that is not under pressure when the subject swallows the ingestible device. FIG. 19B is an exploded view of the ingestible device 1900. The ingestible device 1900 has a cap 1901, housing parts 1902A and 1902B with a fluid volume 1904 containing a dispensable substance, nozzles 1906, nozzle openings 1908, coverings 1909 over openings 1908, a seal 1913, a spring 1910, a gas cylinder 1911, a membrane 1915 surrounding the gas cylinder 1911, a piercer 1912, a pin 1914, a pin 1916, and an O-ring 1919. The cap 1901 is removed before the subject swallows the ingestible device 1900. When the device 1900 is swallowed by the subject, the pins 1914 and 1916 prevent the dispensable substance in fluid volume 1904 from being under pressure by holding the spring 1910 and the piercer 1912 in place. When the device 1900 reaches the appropriate location in the GI tract, the pin 1914 erodes, degrades and/or dissolves (e.g., due to pH, change in pH, presence of certain enzyme, and/or concentration of certain enzyme), and the pin 1916 is no longer sufficient to hold back the pressure from the spring 1910. The spring forces the piercer 1912 into the gas cylinder 1911, puncturing the gas cylinder 1911 and causing gas at elevated pressure to leave the cylinder 1911. This causes the cylinder to press against the membrane 1915, which expands against the seal 1913. The seal 1913 is made of a relatively low mechanical strength material (e.g., a foil or a film), which breaks when pressed against by the expanding membrane 1915. This causes the expanding membrane 1915 to apply pressure against the dispensable substance in the fluid volume 1904. This causes the coverings 1909, which are made of a relatively low mechanical strength material (e.g., a foil or a film), to break so that the dispensable substance is delivered out of the nozzle openings 1908 in the form of a jet. This results in in trans-epithelial delivery of the therapeutic agent contained in the dispensable substance. In some embodiments, the housing of the ingestible device 1900 is about 26 millimeters long, has a diameter of about 11 mm, a wall thickness of about 0.8 mm Newtons, an end round of about 1.5 mm, an internal volume of about 1685 µL. In such embodiments, the fluid volume 1904 can be about 425 µL. In some embodiments, the ingestible device 1900 does not include coverings 1909.

Figure 19C:
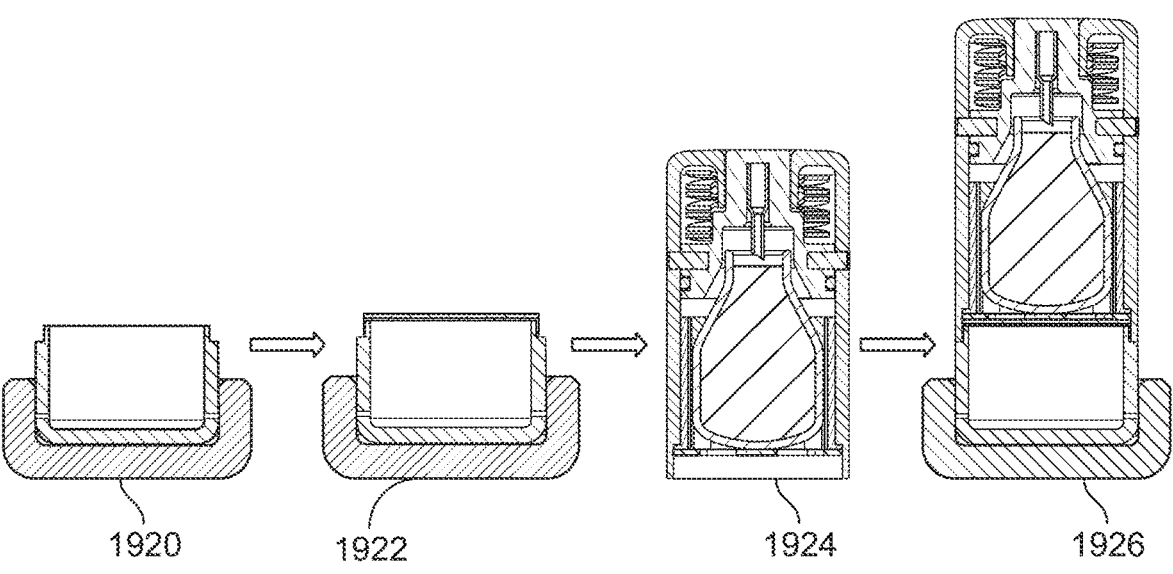
FIG. 19C shows aspects of steps in assembling the ingestible device of FIG. 19A.

FIG. 19C schematically shows certain aspects of a process for the assembly of the ingestible device 1900. In step 1920, the housing part 1902 is combined with the cap 1901 and coverings 1909. In step 1922, the dispensable substance 1904 is added to the housing part 1902B in an aseptic environment, and the seal 1913 is added. In step 1924, the housing part 1902A and its components are assembled in a clean environment. The piercer 1912 is held in place by pins 1914 and 1916, and the gas cylinder 1911 is held in place by components of this assembly. In step 1926, the resulting modules are combined to provide the ingestible device 1900.

Figure 19D:
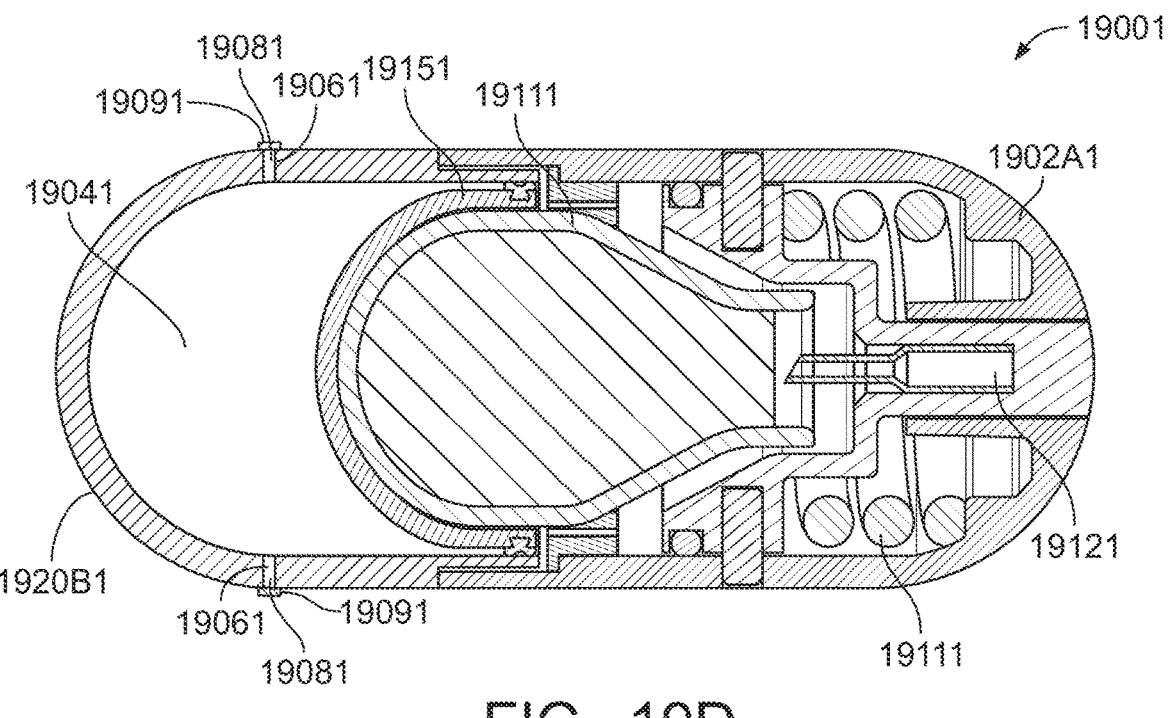
FIG. 19D shows an ingestible device with aspects similar to those shown in FIG. 19A.

FIG. 19D shows an ingestible device 19001 for trans-epithelial delivery, which contains a dispensable substance that is not under pressure when the subject swallows the ingestible device. The ingestible device 19001 has housing parts 1902A1 and 1902B1 with a fluid volume 19041 containing a dispensable substance, nozzles 19061, nozzle openings 19081, coverings 19091 over openings 19081, a spring 19101, a gas cylinder 19111, a piston 19151, a piercer 19121, and an O-ring 19191. The pins used as the triggering mechanism are not shown in FIG. 19D but are similarly configured as pins 1914 and 1916 in FIG. 19A. When the device 19001 is swallowed by the subject, the pins prevent the dispensable substance in fluid volume 19041 from being under pressure by holding the spring 19101 and the piercer 19121 in place. When the device 19001 reaches the appropriate location in the GI tract, one of the pins erodes, degrades and/or dissolves (e.g., due to pH, change in pH, presence of certain enzyme, and/or concentration of certain enzyme), and the other pin is no longer sufficient to hold back the pressure from the spring 19101. The spring forces the piercer 19121 into the gas cylinder 19111, puncturing the gas cylinder 19111 and causing gas at elevated pressure to leave the cylinder 19111. This causes the gas cylinder 19111 to press against the piston 19151 and apply pressure to the fluid volume 19041. This causes the coverings 19091, which are made of a relatively low mechanical strength material (e.g., a foil or a film), to break so that the dispensable substance is delivered out of the nozzle openings 19081 in the form of a jet. This results in in trans-epithelial delivery of the therapeutic agent contained in the dispensable substance. In some embodiments, the housing of the ingestible device 19001 has a diameter of about 11 mm, a length of about 26 mm, a wall thickness of about 0.8 mm, an end round of about 5.5 mm (spherical), and an internal volume of about 1475 µL. In such embodiments, a fluid volume 19041 can be about 400 µL, and a gas volume in the gas cylinder 19111 can be about 255 µL.

Figure 19E:
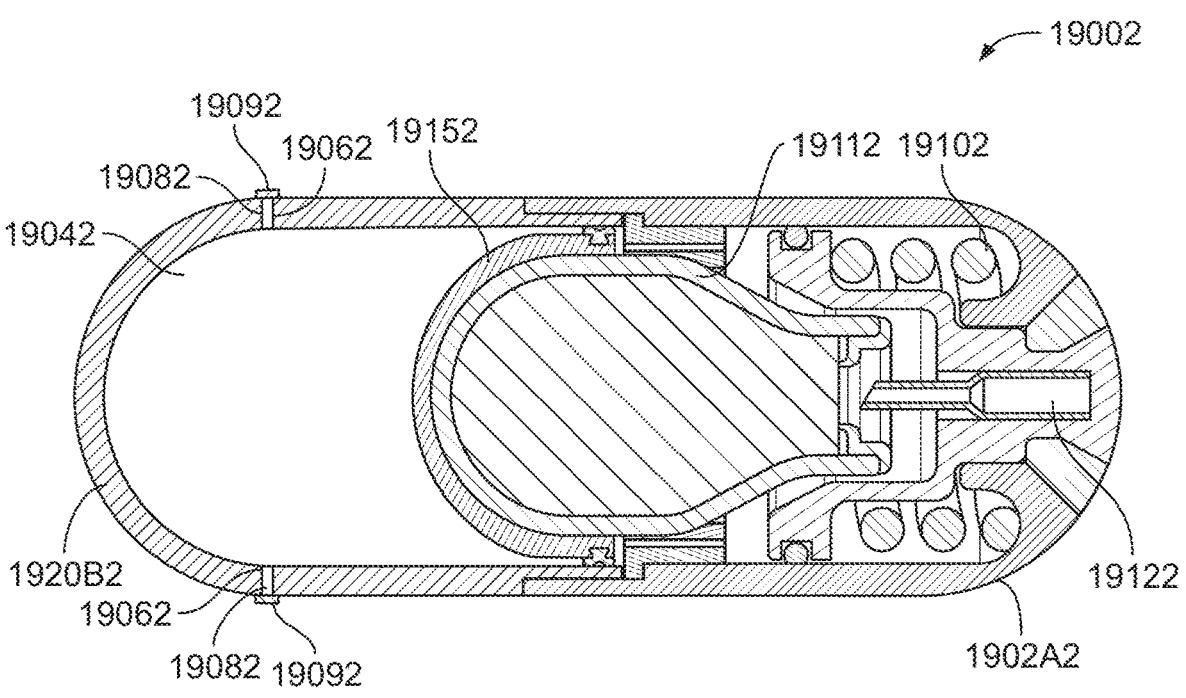
FIG. 19E shows an ingestible device with aspects similar to those shown in FIG. 19A.

FIG. 19E shows an ingestible device 19002 for trans-epithelial delivery, which contains a dispensable substance that is not under pressure when the subject swallows the ingestible device. The ingestible device 19002 has housing parts 1902A2 and 1902B2 with a fluid volume 19042 containing a dispensable substance, nozzles 19062, nozzle openings 19082, coverings 19092 over openings 19082, a spring 19102, a gas cylinder 19112, a piston 19152, a piercer 19122, and an O-ring 19192. The pins used as the triggering mechanism are not shown in FIG. 19E but are similarly configured as pins 1914 and 1916 in FIG. 19A. When the device 19002 is swallowed by the subject, the pins prevent the dispensable substance in fluid volume 19042 from being under pressure by holding the spring 19102 and the piercer 19122 in place. When the device 19002 reaches the appropriate location in the GI tract, one of the pins erodes, degrades and/or dissolves (e.g., due to pH, change in pH, presence of certain enzyme, and/or concentration of certain enzyme), and the other pin is no longer sufficient to hold back the pressure from the spring 19102. The spring forces the piercer 19122 into the gas cylinder 19112, puncturing the gas cylinder 19112 and causing gas at elevated pressure to leave the cylinder 19112. This causes the gas cylinder 19112 to press against the piston 19152 and apply pressure to the fluid volume 19042. This causes the coverings 19092, which are made of a relatively low mechanical strength material (e.g., a foil or a film), to break so that the dispensable substance is delivered out of the nozzle openings 19082 in the form of a jet. This results in in trans-epithelial delivery of the therapeutic agent contained in the dispensable substance. In some embodiments, the housing of the ingestible device 19002 has a diameter of about 9.9 mm, a length of about 26.1 mm, a wall thickness of about 0.7 mm, a fluid volume 19042 of about 445 µL, a gas volume in the gas cylinder 19112 of about 193 µL.

Figure 19F:
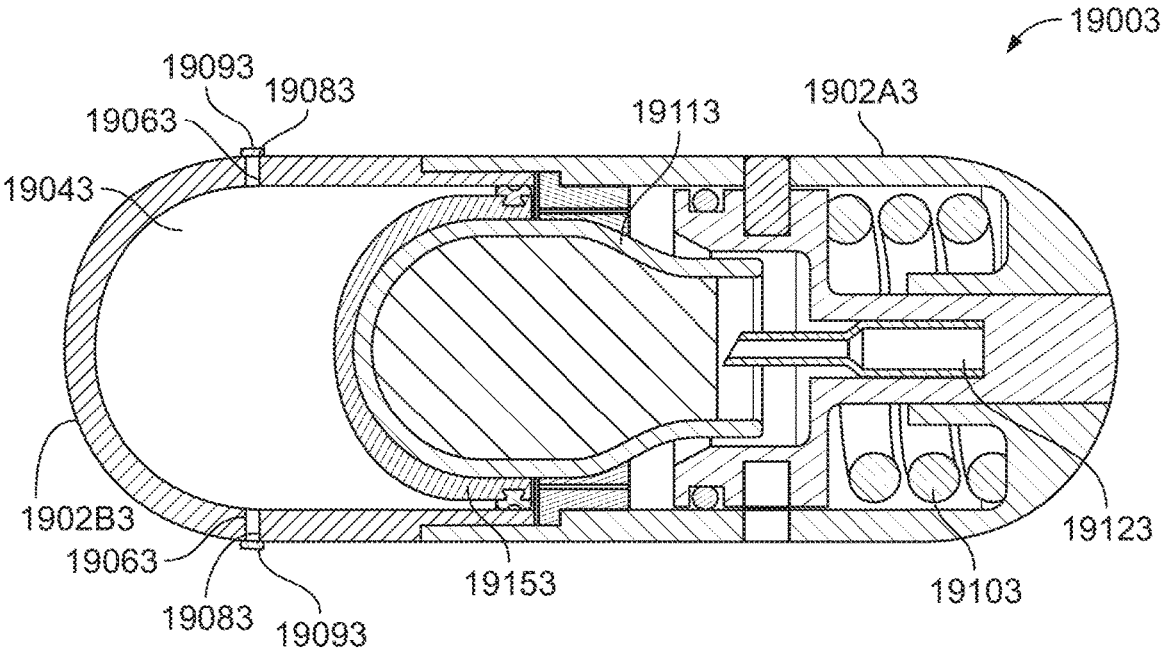
FIG. 19F shows an ingestible device with aspects similar to those shown in FIG. 19A.

FIG. 19F shows an ingestible device 19003 for trans-epithelial delivery, which contains a dispensable substance that is not under pressure when the subject swallows the ingestible device. The ingestible device 19003 has housing parts 1902A3 and 1902B3 with a fluid volume 19043 containing a dispensable substance, nozzles 19063, nozzle openings 19083, coverings 19093 over openings 19083, a spring 19103, a gas cylinder 19113, a pin 19143, a pin 19163, a piston 19153, a piercer 19123, and an O-ring 19193. When the device 19003 is swallowed by the subject, the pins 19143 ad 19163 prevent the dispensable substance in fluid volume 19043 from being under pressure by holding the spring 191033 and the piercer 19123 in place. When the device 19003 reaches the appropriate location in the GI tract, the pin 19143 erodes, degrades and/or dissolves (e.g., due to pH, change in pH, presence of certain enzyme, and/or concentration of certain enzyme), and the pin 19163 is no longer sufficient to hold back the pressure from the spring 19103. The spring forces the piercer 19123 into the gas cylinder 19113, puncturing the gas cylinder 19113 and causing gas at elevated pressure to leave the cylinder 19113. This causes the gas cylinder 19113 to press against the piston 19153 and apply pressure to the fluid volume 19043. This causes the coverings 19093, which are made of a relatively low mechanical strength material (e.g., a foil or a film), to break so that the dispensable substance is delivered out of the nozzle openings 19083 in the form of a jet. This results in in trans-epithelial delivery of the therapeutic agent contained in the dispensable substance. In some embodiments, the housing of the ingestible device 19003 has a diameter of about 8.5 mm, a length of about 23.3 mm, a wall thickness of about 0.7 mm, an end round of about 4.25 mm (spherical), and an internal volume of about 775 µL. In such embodiments, the fluid volume 19043 can be about 205 μL, and a gas volume in the gas cylinder 19113 can be about 160 μL.

Figure 19G:
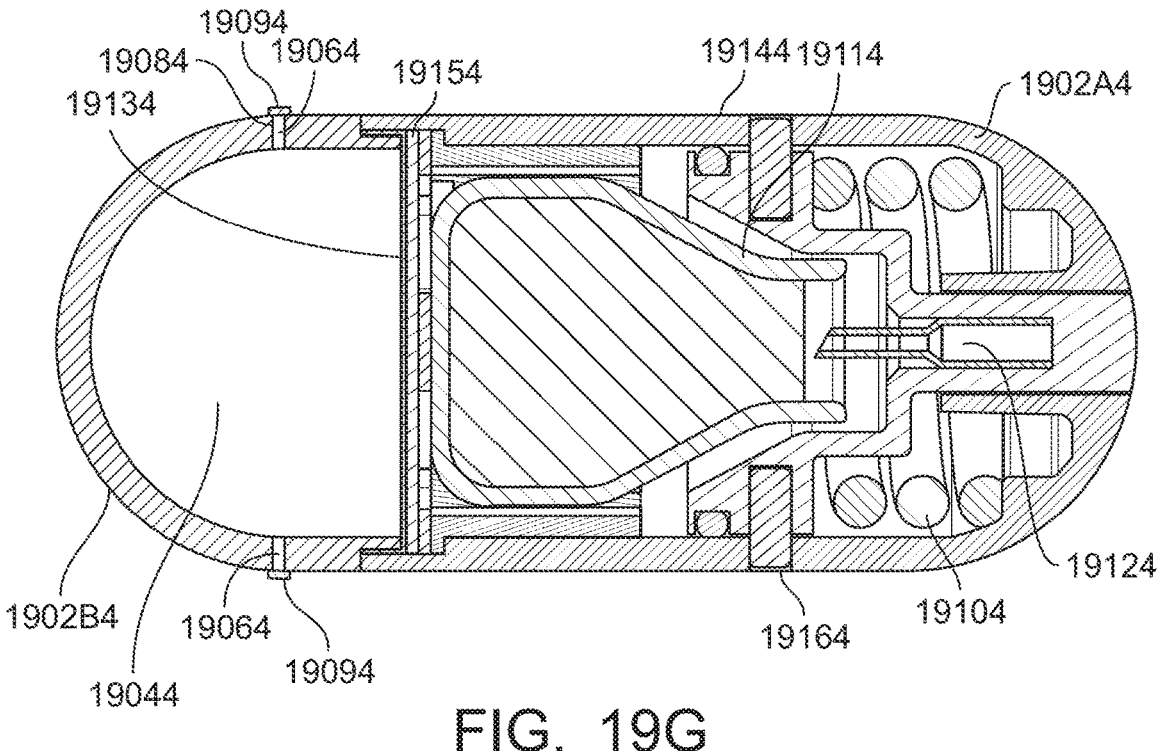
FIG. 19G shows an ingestible device with aspects similar to those shown in FIG. 19A.

FIG. 19G shows an ingestible device 19004 for trans-epithelial delivery, which contains a dispensable substance that is not under pressure when the subject swallows the ingestible device. The ingestible device 19004 has housing parts 1902A4 and 1902B4 with a fluid volume 19044 containing a dispensable substance, nozzles 19064, nozzle openings 19084, coverings 19094 over openings 19084, a spring 19104, a gas cylinder 19114, a pin 19144, a pin 19164, a gas cylinder 19114, a seal 19134, a membrane 19154, a piercer 19124, a pin 19144, and a pin 19164, and an O-ring 19194. When the device 19004 is swallowed by the subject, the pins 19144 and 19164 prevent the dispensable substance in fluid volume 19044 from being under pressure by holding the spring 19104 and the piercer 19124 in place. When the device 19004 reaches the appropriate location in the GI tract, the pin 19144 erodes, degrades and/or dissolves (e.g., due to pH, change in pH, presence of certain enzyme, and/or concentration of certain enzyme), and the pin 19164 is no longer sufficient to hold back the pressure from the spring 19104. The spring forces the piercer 19124 into the gas cylinder 19114, puncturing the gas cylinder 19114 and causing gas at elevated pressure to leave the cylinder 19114. This causes the cylinder to press against the membrane 19154, which expands against the seal 19134. The seal 19134 is made of a relatively low mechanical strength material (e.g., a foil or a film), which breaks when pressed against by the expanding membrane 19154. This causes the expanding membrane 19154 to apply pressure against the dispensable substance in the fluid volume 19044. This causes the coverings 19094, which are made of a relatively low mechanical strength material (e.g., a foil or a film), to break so that the dispensable substance is delivered out of the nozzle openings 19084 in the form of a jet. This results in in trans-epithelial delivery of the therapeutic agent contained in the dispensable substance. In some embodiments, the housing of the ingestible device 19004 is about 26 millimeters long, has a diameter of about 11 mm, and a wall thickness of about 0.8 mm Newtons. In such embodiments, the fluid volume 19044 can be about 410 μL. In such embodiments, the gas volume of the gas cylinder 19114 can be about 216 μL, and the spring 19104 can provide a force of about 80 Newtons.

Figure 19H:
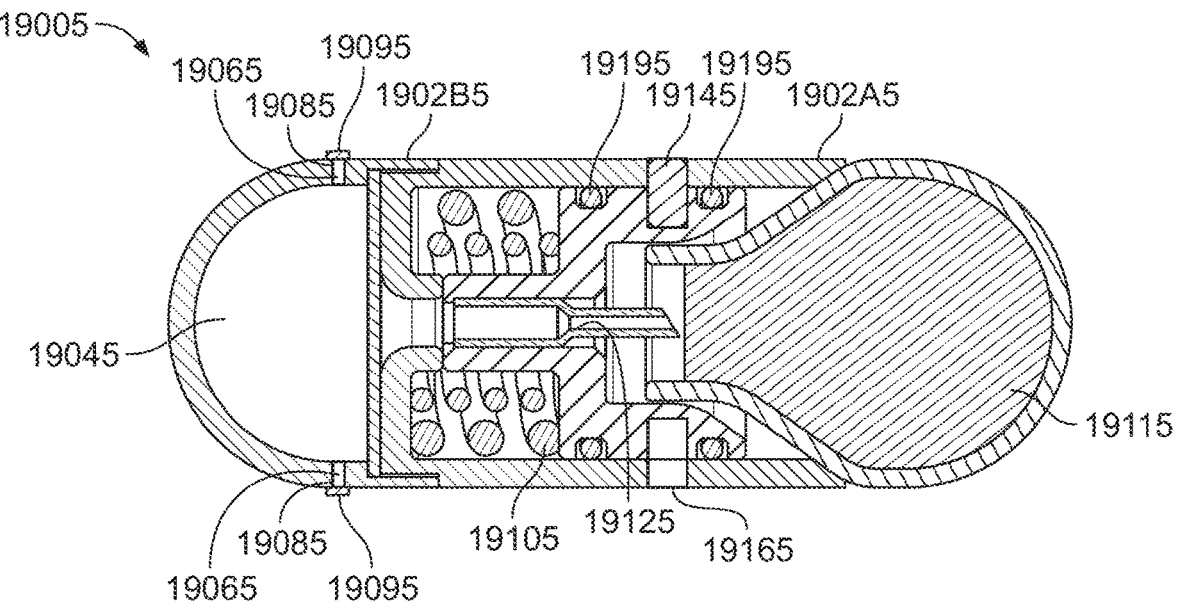
FIG. 19H shows an ingestible device with aspects similar to those shown in FIG. 19A.

FIG. 19H shows an ingestible device 19005 for trans-epithelial delivery, which contains a dispensable substance that is not under pressure when the subject swallows the ingestible device. The ingestible device 19005 has housing parts 1902A5 and 1902B5 with a fluid volume 19045 containing a dispensable substance, nozzles 19065, nozzle openings 19085, coverings 19095 over openings 19085, a spring 19105, a gas cylinder 19115, a pin 19145, a pin 19165, a gas cylinder 19115, a membrane 19155, a piercer 19125, a pin 19145, and a pin 19165, and O-rings 19195. When the device 19005 is swallowed by the subject, the pins 19145 and 19165 prevent the dispensable substance in fluid volume 19045 from being under pressure by holding the spring 19105 and the piercer 19125 in place. When the device 19005 reaches the appropriate location in the GI tract, the pin 19145 erodes, degrades and/or dissolves (e.g., due to pH, change in pH, presence of certain enzyme, and/or concentration of certain enzyme), and the pin 19165 is no longer sufficient to hold back the pressure from the spring 19105. The spring forces the piercer 19125 into the gas cylinder 19115, puncturing the gas cylinder 19115 and causing gas at elevated pressure to leave the cylinder 19115. This causes the cylinder to press against the membrane 19155, which causes the expanding membrane 19155 to apply pressure against the dispensable substance in the fluid volume 19045. This causes the coverings 19095, which are made of a relatively low mechanical strength material (e.g., a foil or a film), to break so that the dispensable substance is delivered out of the nozzle openings 19085 in the form of a jet. This results in in trans-epithelial delivery of the therapeutic agent contained in the dispensable substance. In some embodiments, the housing of the ingestible device 19005 is about 23.3 millimeters long, has a diameter of about 8.5 mm, and a wall thickness of about 0.7 mm. In such embodiments, the fluid volume 19045 can be about 300 μL. In such embodiments, the gas volume of the gas cylinder 19115 can be about 247 μL.

Figure 19I:
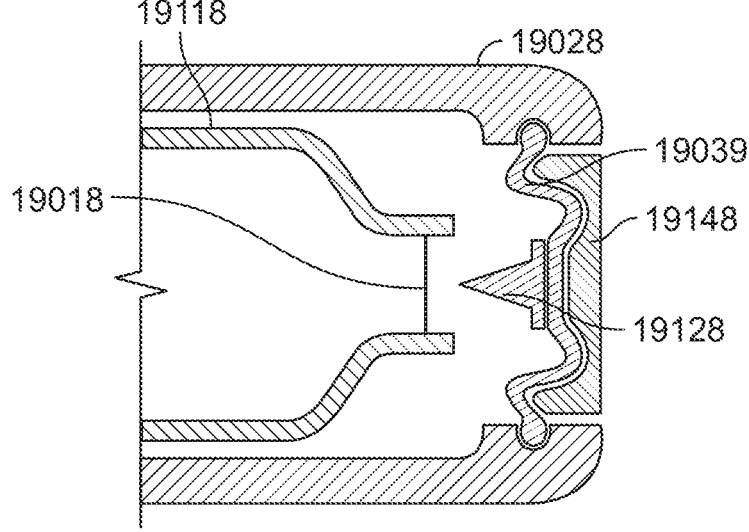
FIGS. 19I and 19J show aspects of states of an ingestible device.
Figure 19J:
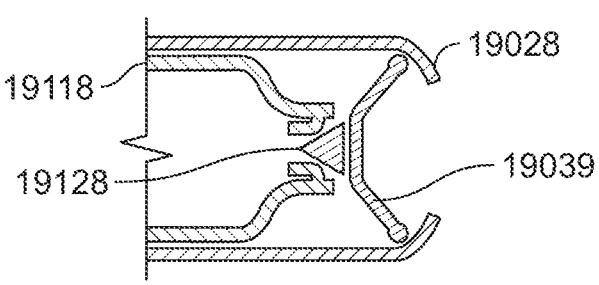

FIG. 19I shows a portion of an ingestible device including a housing part 19028, a gas cylinder 19118 with a membrane 19018, a piercer 19128 that is held in place via an enteric material 19148, and a biased diaphragm 19039. FIG. 19J shows corresponding portions of the ingestible device after the enteric material 19148 degrades/dissolves/erodes. The diaphragm 19038 has moved so that the piercer 19126 has pierced the membrane 19016, causing the gas in the gas cylinder 19116 to escape. Although not shown, the gas pressure causes another housing part (e.g., the housing part of the drug module) to move, to expose nozzle openings so that the dispensable substance leaves the ingestible device in the form jets for trans-epithelial delivery.

Figure 19K:
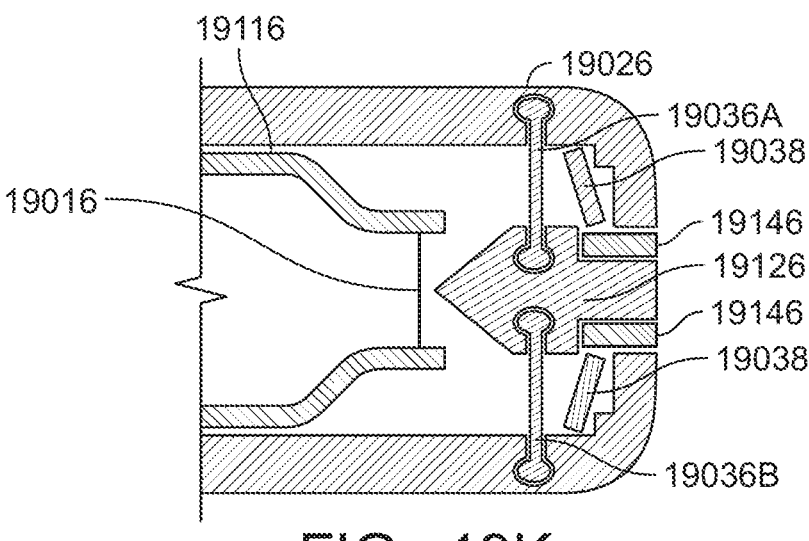
FIGS. 19K and 19L show aspects of states of an ingestible device.
Figure 19L:
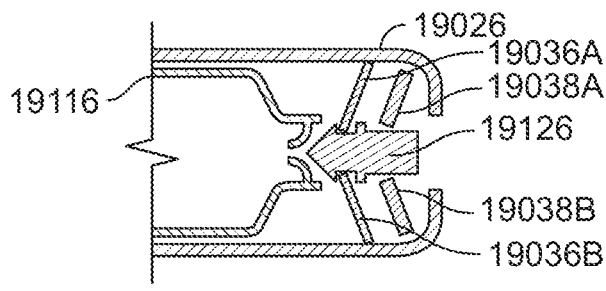

FIG. 19K shows a portion of an ingestible device including a housing part 19026, a gas cylinder 19116 with a membrane 19016, a piercer 19126 that is held in place via an enteric material 19146, stabilizing elements 19036A and 19036B, and a biasing element 19038 (e.g., a disc spring). FIG. 19K shows corresponding portions of the ingestible device after the enteric material 19146 degrades/dissolves/erodes. The spring biasing element 19038 has moved so that the piercer 19126 has pierced the membrane 19016, causing the gas in the gas cylinder 19116 to escape. Although not shown, the gas pressure causes another housing part (e.g., the housing part of the drug module) to move, to expose nozzle openings so that the dispensable substance leaves the ingestible device in the form jets for trans-epithelial delivery.

Figure 20A:
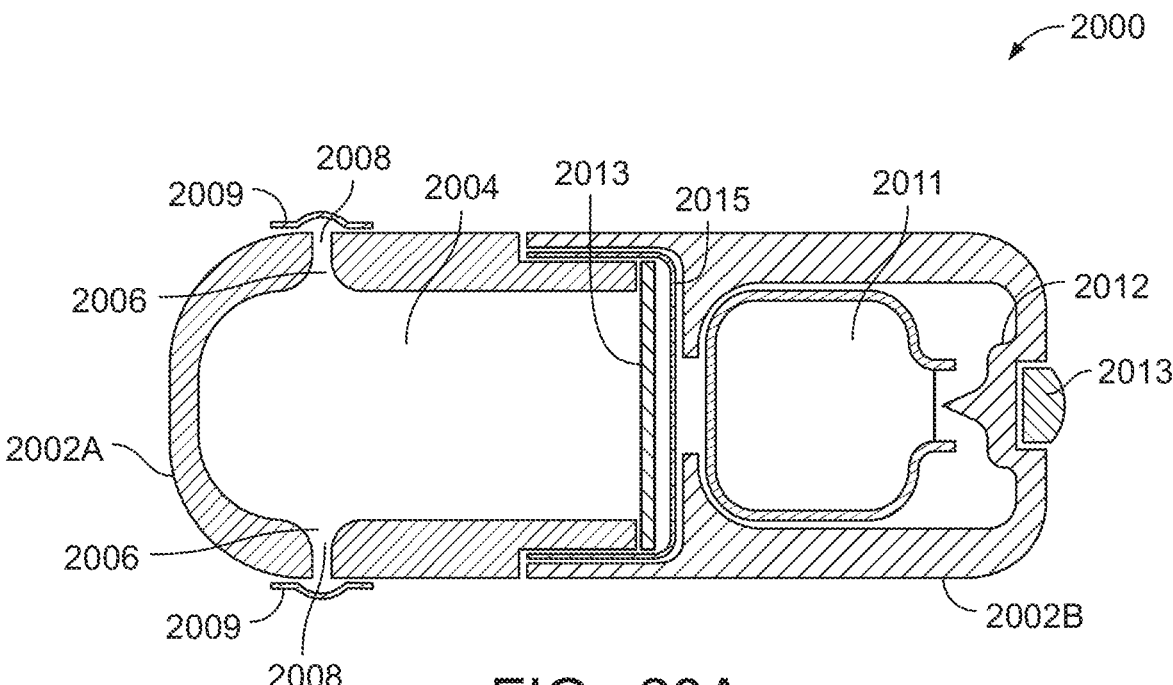
FIGS. 20A and 20B show an ingestible device.

FIG. 20A shows an embodiment of an ingestible device 2000 for trans-epithelial delivery, containing a dispensable substance that is not under pressure when the subject swallows the ingestible device. The device 2000 has housing parts 2002A and 2002B with a fluid volume 2004 containing a dispensable substance, nozzles 2006, nozzle openings 2008, seals 2009 over openings 2008, a seal 2013, a gas cylinder 2011, a membrane 2015 between the seal 2013 and the gas cylinder 2011, a biased piercer 2012, and a plug 2013. When the device 2000 is swallowed by the subject, the plug 2013 keeps the piercer in its biased position as shown in FIG. 20A. When the device 2000 reaches the appropriate location in the GI tract, the plug 2013 erodes, degrades and/or dissolves (e.g., due to pH, change in pH, presence of certain enzyme, and/or concentration of certain enzyme), and the piercer 2012 moves axially to pierce the gas cylinder 2011 and cause gas at elevated pressure to leave the cylinder 2011. This causes the cylinder to press against the membrane 2015, which breaks the seal 2013 so that the pressure is applied against the dispensable substance in the fluid volume 2004. This causes the coverings 2009, which are made of a relatively low mechanical strength material (e.g., a foil or a film), to break so that the dispensable substance is delivered out of the nozzle openings 2008 in the form of a jet. This results in trans-epithelial delivery of the therapeutic agent contained in the dispensable substance.

Figure 20B:
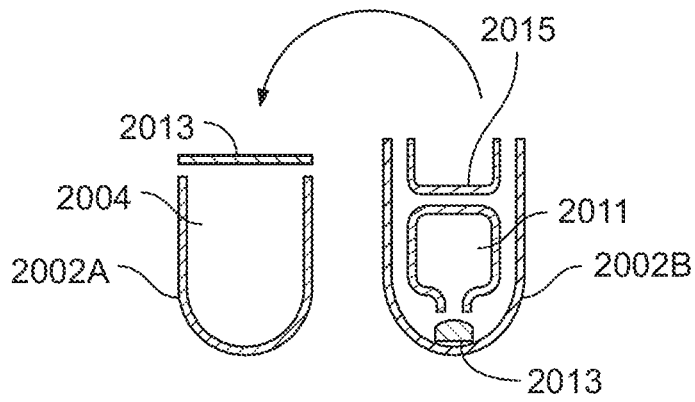

FIG. 20B schematically shows certain aspects of the assembly of the ingestible device 2000. The housing parts 2002A (including the seal 2013) and 2002B (including the membrane 2015, the gas cylinder 2011 and the piercer 2012) are initially separate from each other. The dispensable substance (including the therapeutic agent) is first sterilized, and then disposed in the fluid volume 2004 under aseptic conditions. The components in housing part 2002B are assembled in a clean environment. Subsequently, the housing parts 2002A and 2002B are joined in a clean environment to produce the ingestible device 2000.

Figures 21A, 21B:
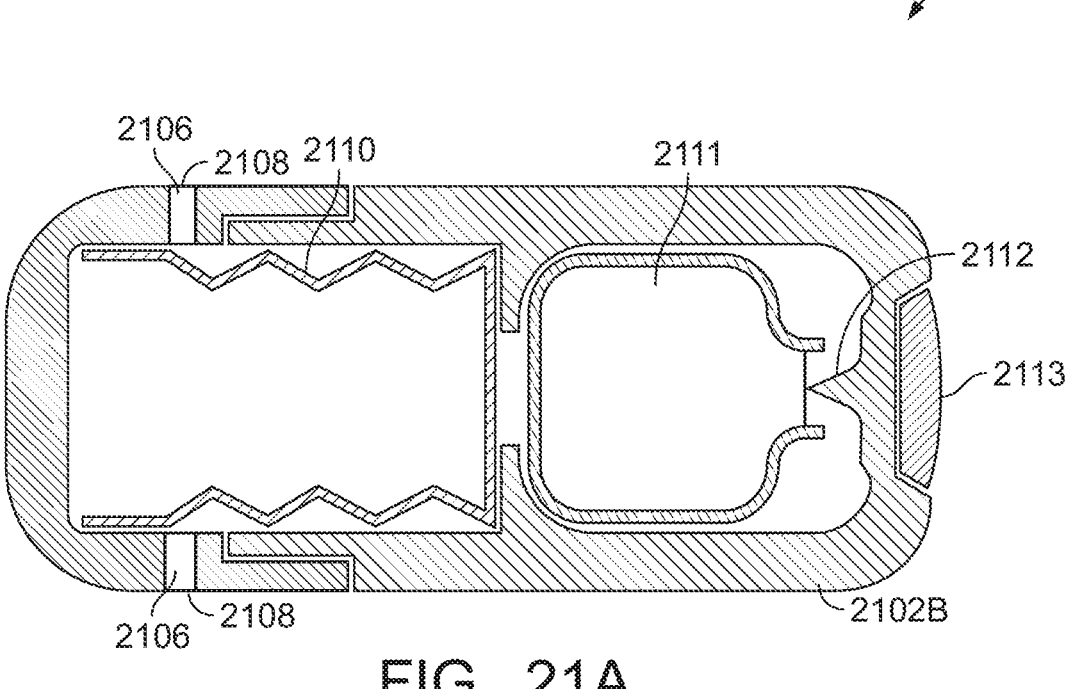
FIGS. 21A and 21B show an ingestible device.
Figure 22:
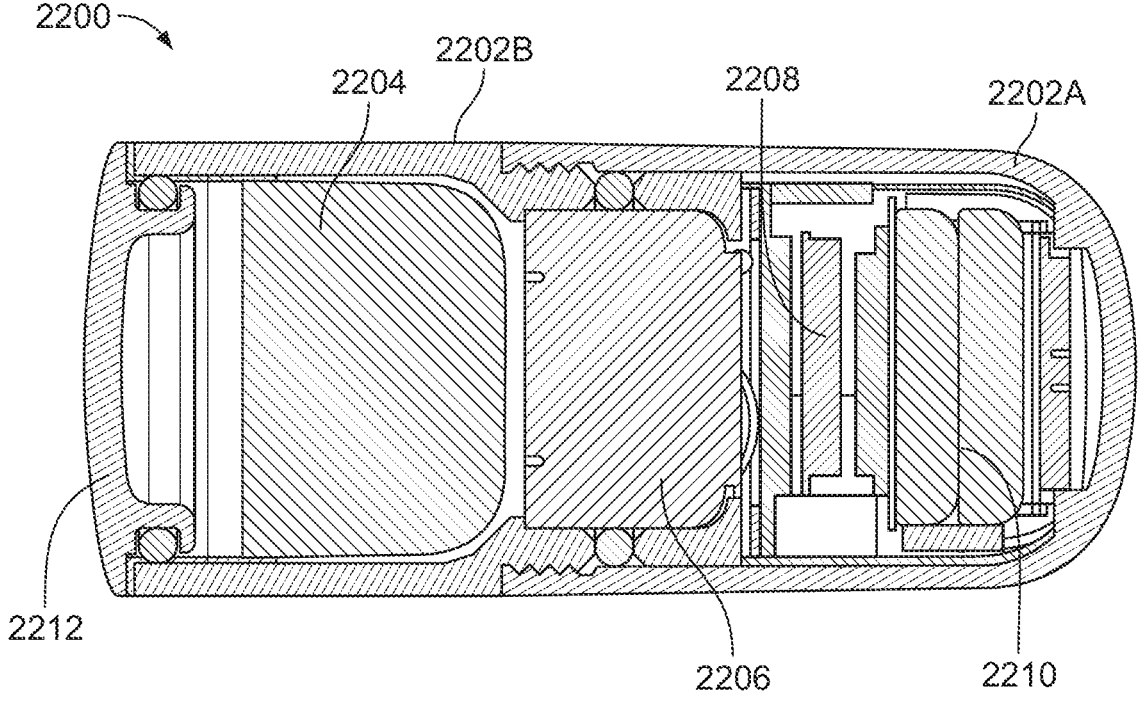
FIG. 22 shows an ingestible device.

FIG. 21A shows an embodiment of an ingestible device 2100 for trans-epithelial delivery, containing a dispensable substance that is not under pressure when the subject swallows the ingestible device. The device 2100 has housing parts 2102A and 2102B with a fluid volume 2104 containing a dispensable substance, nozzles 2106, nozzle openings 2108, a bellows 2110, a gas cylinder 2111, a biased piercer 2112, and a plug 2113. When the device 2100 is swallowed by the subject, the plug 2113 keeps the piercer in its biased position as shown in FIG. 20A. When the device 2100 reaches the appropriate location in the GI tract, the plug 2113 erodes, degrades and/or dissolves (e.g., due to pH, change in pH, presence of certain enzyme, and/or concentration of certain enzyme), and the piercer 2112 moves axially to pierce the gas cylinder 2111 and cause gas at elevated pressure to leave the cylinder 2111. This gas pressure is applied against press against the bellows 2110, causing the bellows 2110 such that holes in the bellows 21120 (not shown) align with the nozzles 2106 so that the dispensable substance is delivered out of the nozzle openings 2008 in the form of a jet. This results in trans-epithelial delivery of the therapeutic agent contained in the dispensable substance.

FIG. 21B schematically shows certain aspects of the assembly of the ingestible device 2100. The housing parts 2102A (including the bellows 2110) and 2102B (including the gas cylinder 2111 and the piercer 2112) are initially separate from each other. The dispensable substance (including the therapeutic agent) is first sterilized, and then disposed in the fluid volume 2104 under aseptic conditions. The components in housing part 2102B are assembled in a clean environment. Subsequently, the housing parts 2102A and 2102B are joined in a clean environment to produce the ingestible device 2100.

Figure 23A:
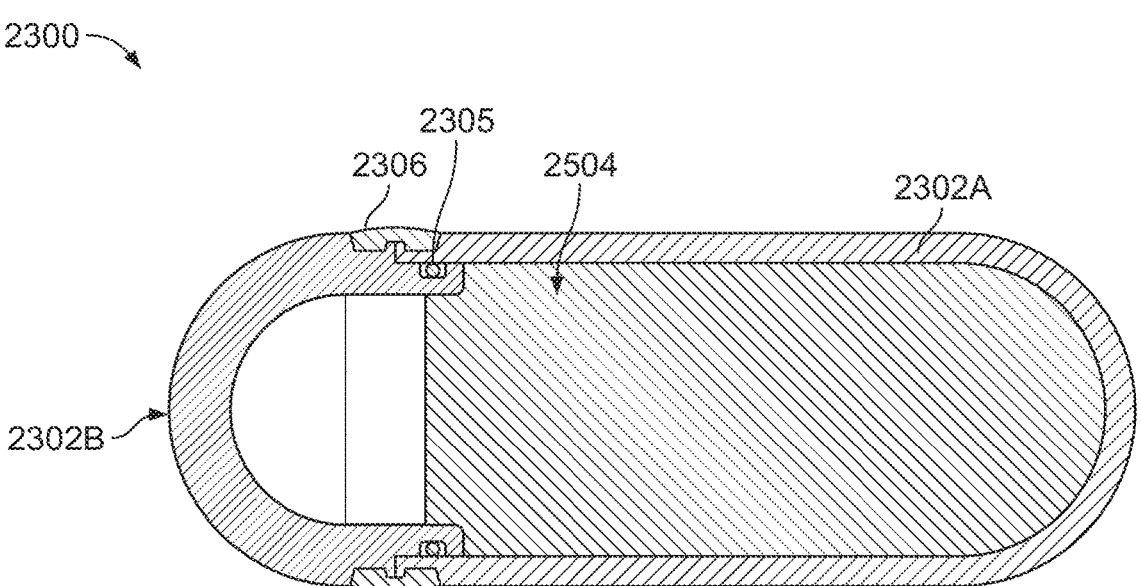
FIG. 23A shows an ingestible device.
Figure 23B:
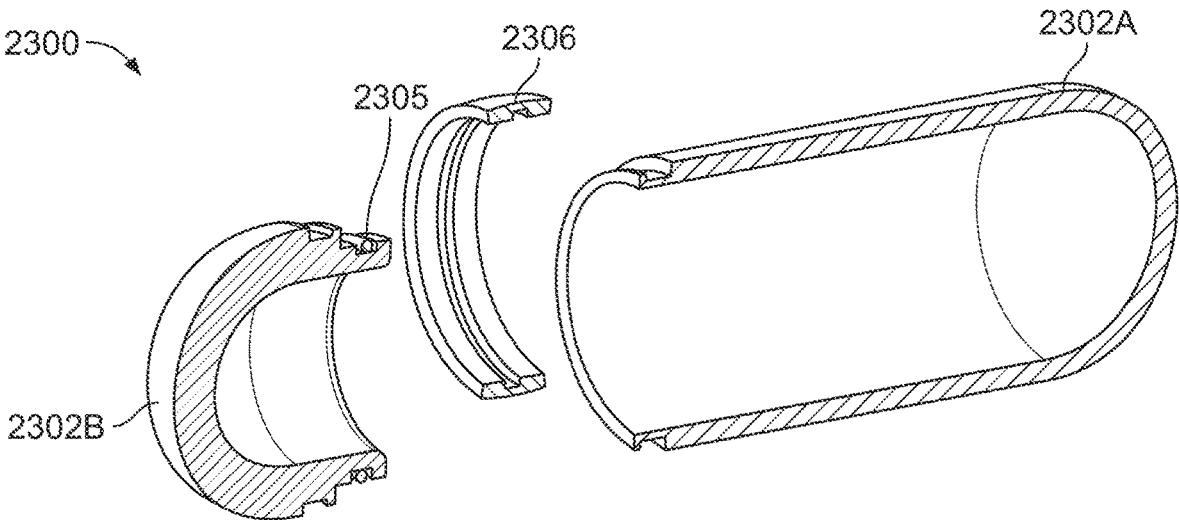
FIG. 23B shows an exploded view of the device of FIG. 23A.

FIG. 23A shows an embodiment of an ingestible device 2300 for topical delivery. FIG. 23B is an exploded view of the ingestible device 2300. The ingestible device 2300 has housing parts 2302A and 2302B, a fluid volume 2304 containing a dispensable substance, an O-ring 2305, and a band 2306. The device 2300 has a head space pressure in the housing part 2302B, but the band 2306 holds the components of device 2300 in place when the device 2300 is swallowed by the subject. When the device 2300 reaches the appropriate location in the GI tract, the band 2306 erodes, degrades and/or dissolves, and the head space pressure causes the housing part 2302B to leave device 2300, resulting in the therapeutic agent in the dispensable substance being topically delivered to the GI tract of the subject. In embodiments having a design substantially similar to the ingestible device 2300, the head space pressure is provided by a gas, such as, for example, air nitrogen ($N_2$), oxygen ($O_2$), an inert gas (e.g., argon (Ar), krypton (Kr), helium (He)), and/or carbon dioxide ($CO_2$). In embodiments having a design substantially similar to the ingestible device 2300, the head space pressure can correspond to the internal pressure of the ingestible device. In embodiments having a design substantially similar to the ingestible device 2300, the head space pressure can correspond to the fluid pressure of the ingestible device.

Figure 24:
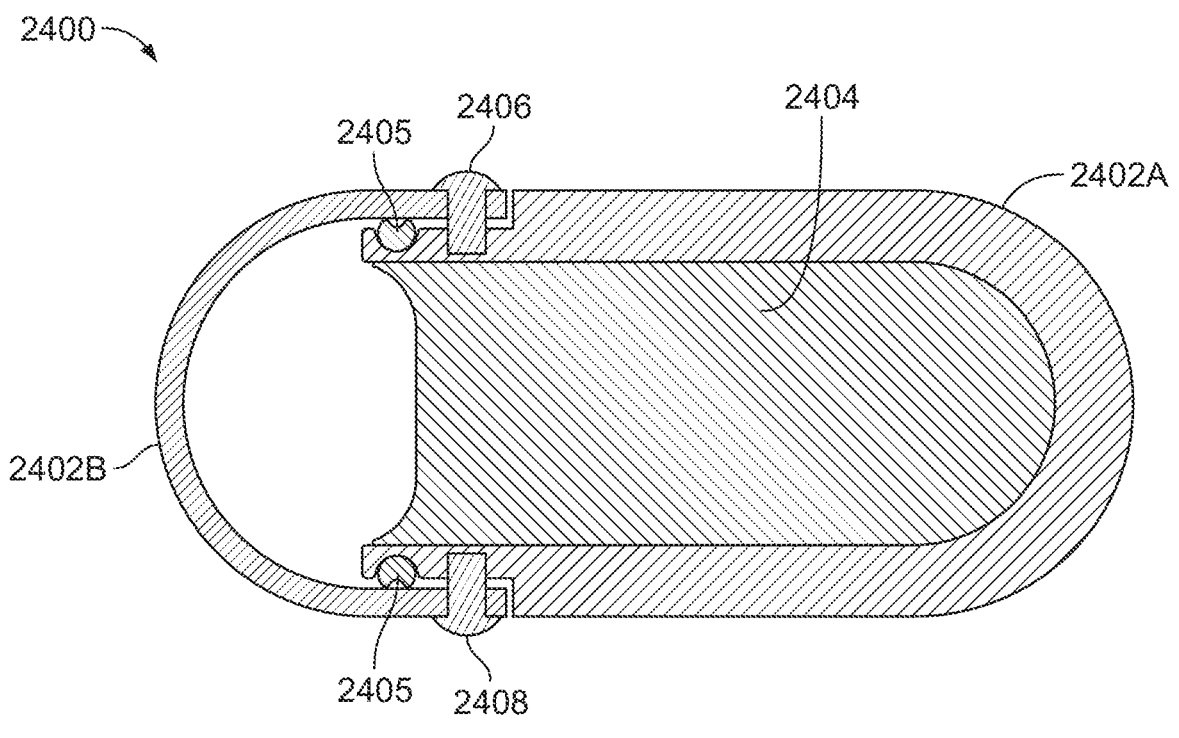
FIG. 24 shows an ingestible device.

FIG. 24 shows an embodiment of an ingestible device 2400 for topical delivery. The ingestible device 2400 has housing parts 2402A and 2402B, a fluid volume 2404 containing a dispensable substance, an O-ring 2405, and pins 2406 and 2408. The device 2400 has a head space pressure in the housing part 2402B, but the pins 2406 and 2408 hold the components of device 2400 in place when the device 2400 is swallowed by the subject. When the device 2400 reaches the appropriate location in the GI tract, the pins 2406 and 2408 erode, degrade and/or dissolve, and the head space pressure causes the housing part 2402B to leave device 2400, resulting in the therapeutic agent in the dispensable substance being topically delivered to the GI tract of the subject. In embodiments having a design substantially similar to the ingestible device 2400, the head space pressure is provided by a gas, such as, for example, air nitrogen ($N_2$), oxygen ($O_2$), an inert gas (e.g., argon (Ar), krypton (Kr), helium (He)), and/or carbon dioxide ($CO_2$). In embodiments having a design substantially similar to the ingestible device 2400, the head space pressure can correspond to the internal pressure of the ingestible device. In embodiments having a design substantially similar to the ingestible device 2400, the head space pressure can correspond to the fluid pressure of the ingestible device.

Figure 25:
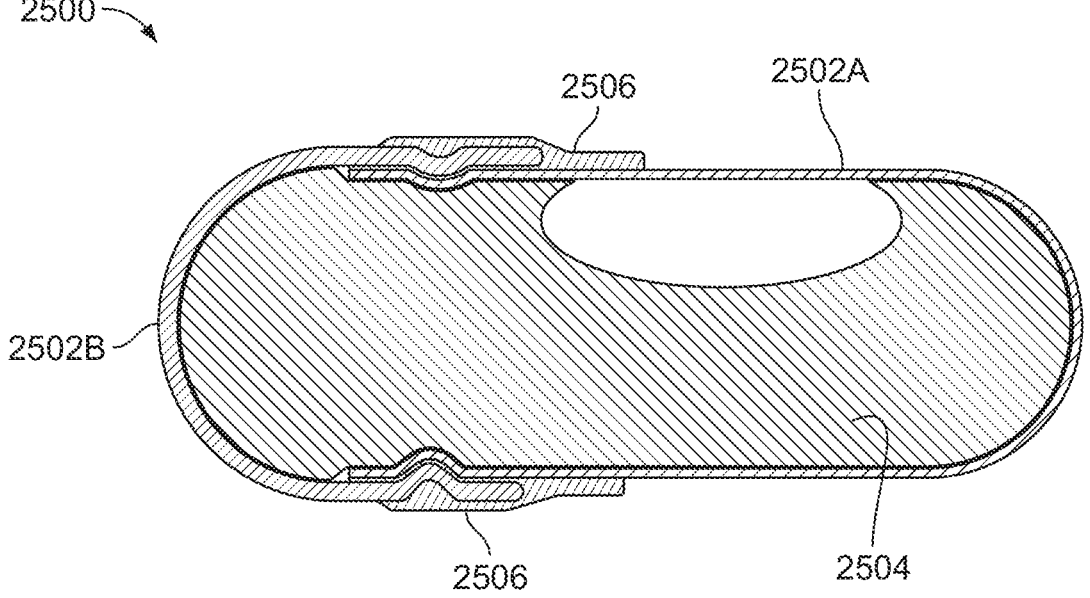
FIG. 25 shows an ingestible device.

FIG. 25 shows an embodiment of an ingestible device 2500 for topical delivery. The ingestible device 2500 has housing parts 2502A and 2502B, a fluid volume 2504 containing a dispensable substance, and a partial coating 2506. The device 2500 has a head space pressure within the housing part 2502A, but the partial coating 2506 holds the components of device 2500 in place when the device 2500 is swallowed by the subject. When the device 2500 reaches the appropriate location in the GI tract, the partial coating 2506 erodes, degrades and/or dissolves, and the head space pressure causes the housing parts 2502A and 2502B to separate from each other, resulting in the therapeutic agent in the dispensable substance being topically delivered to the GI tract of the subject. In embodiments having a design substantially similar to the ingestible device 2500, the head space pressure is provided by a gas, such as, for example, air nitrogen ($N_2$), oxygen ($O_2$), an inert gas (e.g., argon (Ar), krypton (Kr), helium (He)), and/or carbon dioxide ($CO_2$). In embodiments having a design substantially similar to the ingestible device 2500, the head space pressure can correspond to the internal pressure of the ingestible device. In embodiments having a design substantially similar to the ingestible device 2500, the head space pressure can correspond to the fluid pressure of the ingestible device.

Figure 26A:
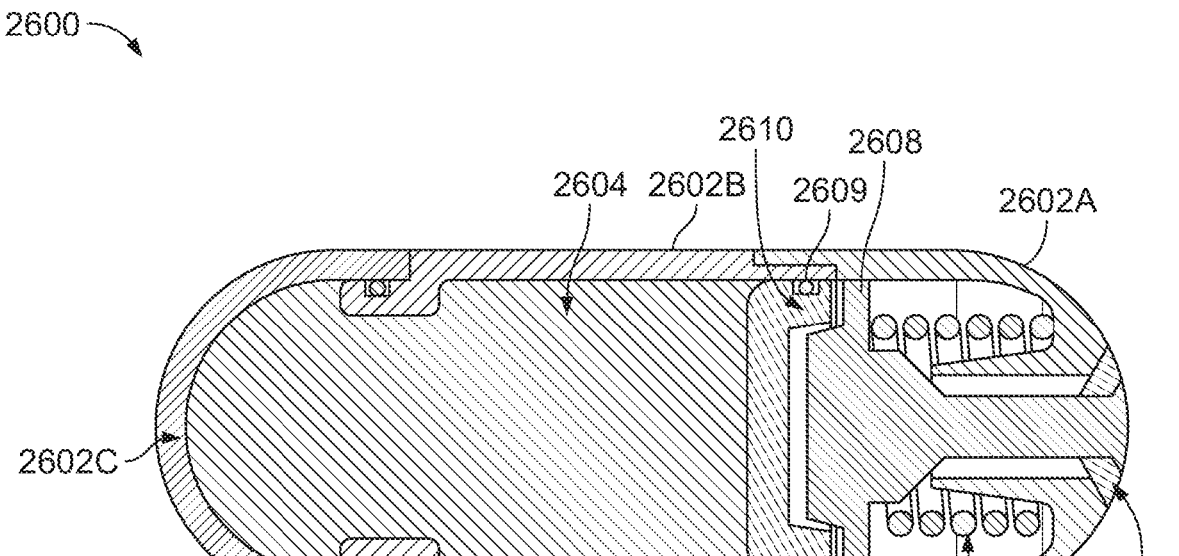
FIG. 26A shows an ingestible device.
Figure 26B:
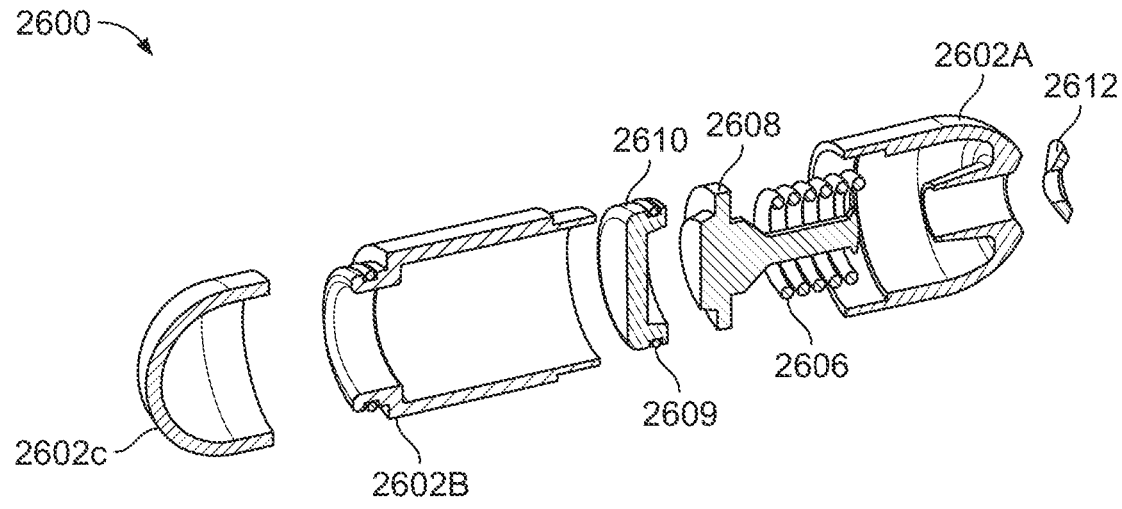
FIG. 26B shows an exploded view of the device of FIG. 26A.

FIG. 26A shows an ingestible device 2600 that can be used for topical delivery. FIG. 26B is an exploded view of the device 2600. The device 2600 includes a first housing part 2602A, a second housing part 2602B and a third housing part 2602C. The device 2600 further includes a fluid volume 2604 containing a dispensable substance, a spring 2606, a plunger 2608, a piston 2610, an O-ring 2609, and a stopper pin 2612 which holds the components of the device 2600 when the subject swallows the device 2600. When the device 2600 reaches the appropriate location in the GI tract, the pin 2612 erodes, degrades and/or dissolves. Thus, the pressure of the spring 2606 is applied to the plunger 2608, which moves the piston 2610 axially. This pressure is transferred to the dispensable substance in the fluid volume 2604, which forces the housing part 2602C to be removed from the device 2600, and the therapeutic agent in the dispensable substance is topically delivered.

Figure 26C:
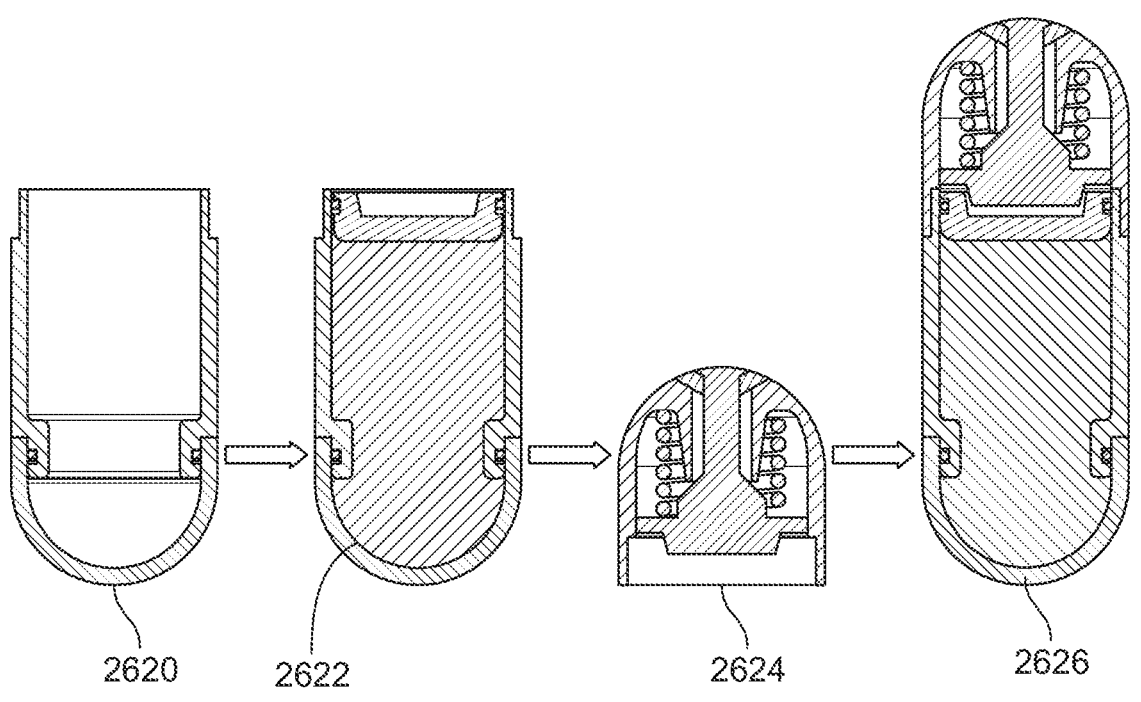
FIG. 26C shows aspects of states of the ingestible device of FIG. 26A.

FIG. 26C shows aspects of steps in assembling the ingestible device 2600. In step 2620, the housing parts 2602B and 2602C are combined and then sterilized. In step 2622, the dispensable substance 2604 is disposed in the housing parts 2602B and 2602C in an aseptic environment and then sealed within the piston 2610. In step 2624, the housing part 2602A and its components are assembled in a clean environment. In step 2626, the resulting modules are joined together in a clean environment to provide the ingestible device 2600.

Figure 27:
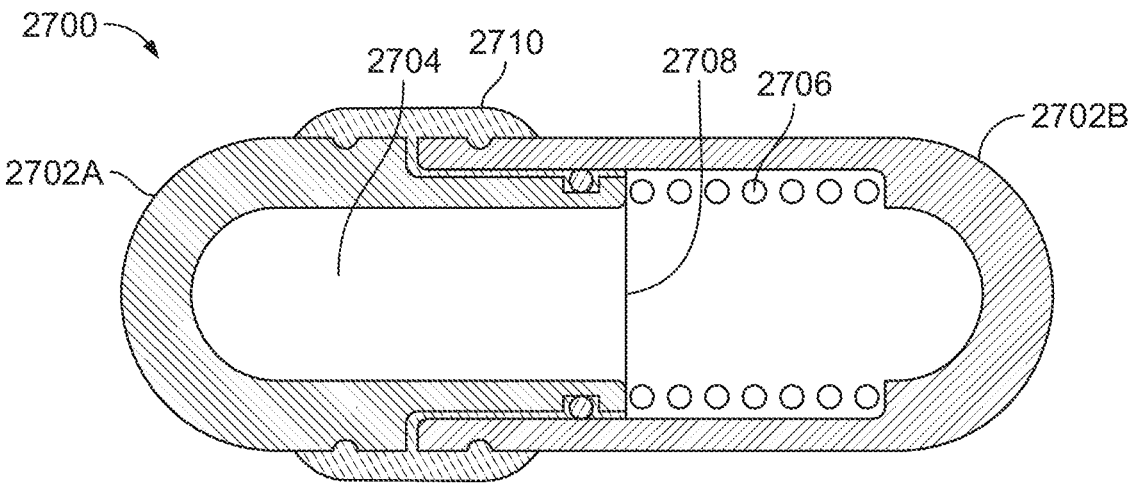
FIG. 27 shows an ingestible device.

FIG. 27 shows an ingestible device 2700 that can be used for topical delivery. The device 2700 includes a first housing part 2702A and a second housing part 2702B. The device 2700 further includes a fluid volume 2704 containing a dispensable substance, a spring 2706, a seal 2708 (e.g., a foil or a film) and a partial coating 2710 which holds the components of the device 2700 when the subject swallows the device 2700. When the device 2700 reaches the appropriate location in the GI tract, the partial coating 2710 erodes, degrades and/or dissolves. The spring 2706 then exerts a pressure axially against the dispensable substance 2704, breaking the seal 2708 and also causing the housing parts 2702A and 2702B to separate, which results in topical delivery of the therapeutic agent in the dispensable substance.

Figure 28A:
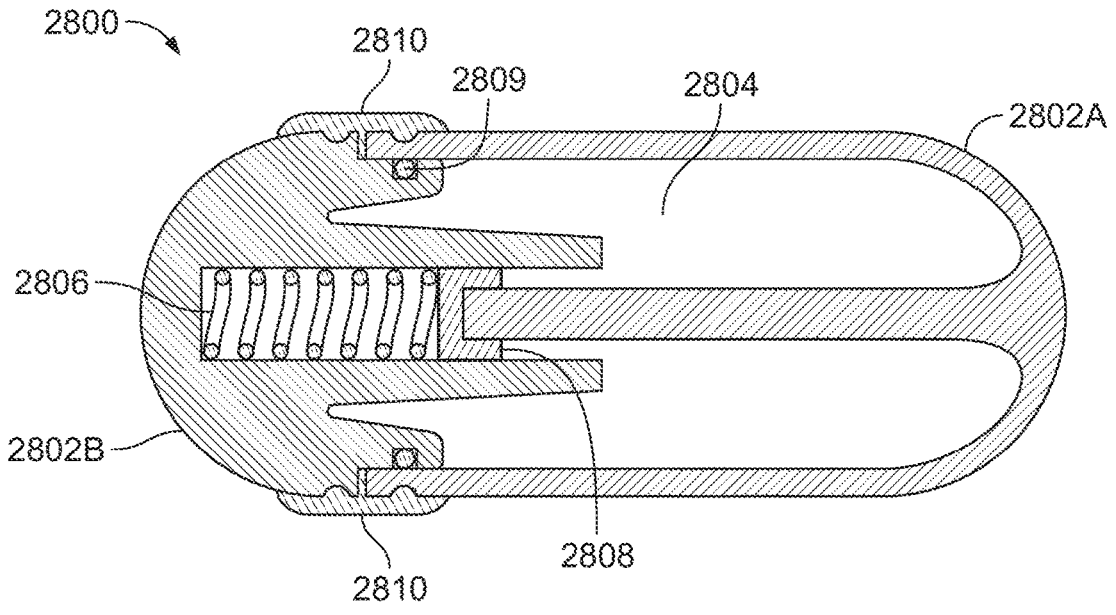
FIG. 28A shows an ingestible device.
Figure 28B:
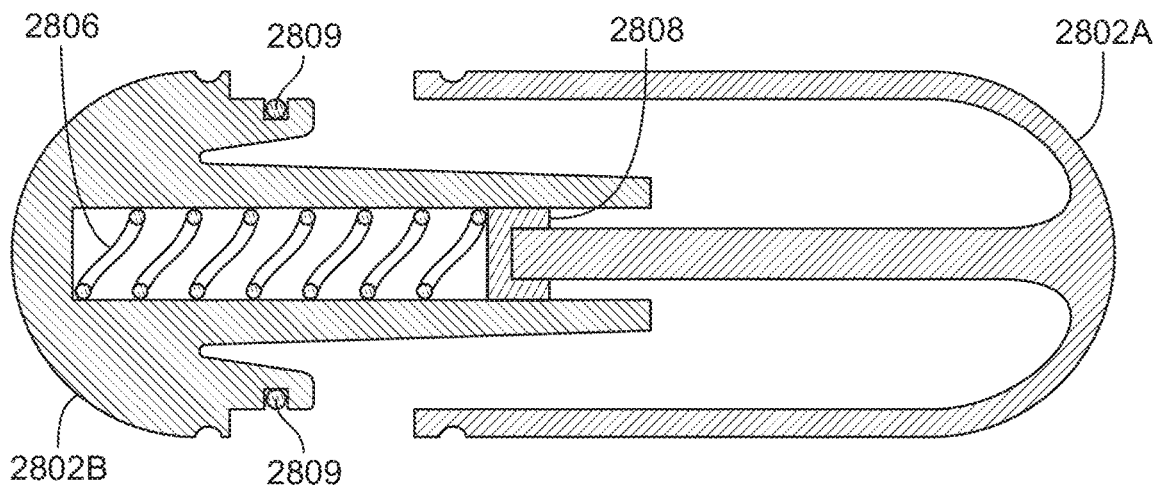
FIG. 28B shows an exploded view of the device of FIG. 28A.

FIG. 28A shows an ingestible device 2800 that can be used for topical delivery. The device 2800 includes a first housing part 2802A and a second housing part 2802B. The device 2800 further includes a fluid volume 2804 containing a dispensable substance, a spring 2806, a seal 2808, an O-ring 2809, and a partial coating 2810 which holds the components of the device 2800 when the subject swallows the device 2800. When the device 2800 reaches the appropriate location in the GI tract, the partial coating 2810 erodes, degrades and/or dissolves. As shown in FIG. 28B, this causes the spring 2806 to expand so that housing parts 2802A and 2802B separate, resulting in topical delivery of the therapeutic agent in the dispensable substance.

Figure 29A:
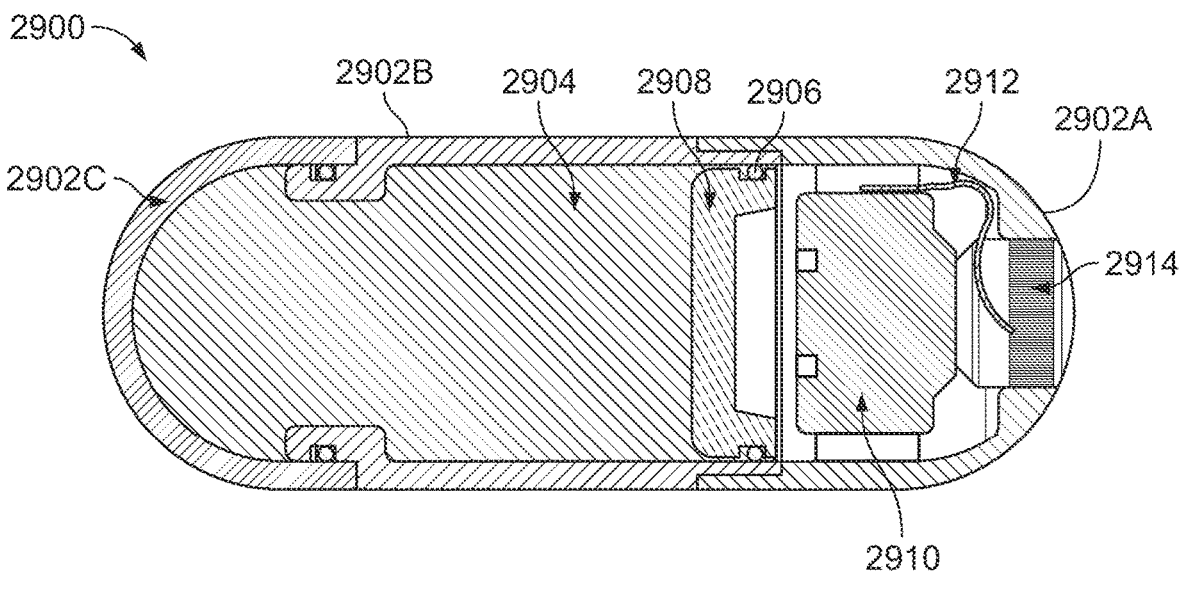
FIG. 29A shows an ingestible device.
Figure 29B:
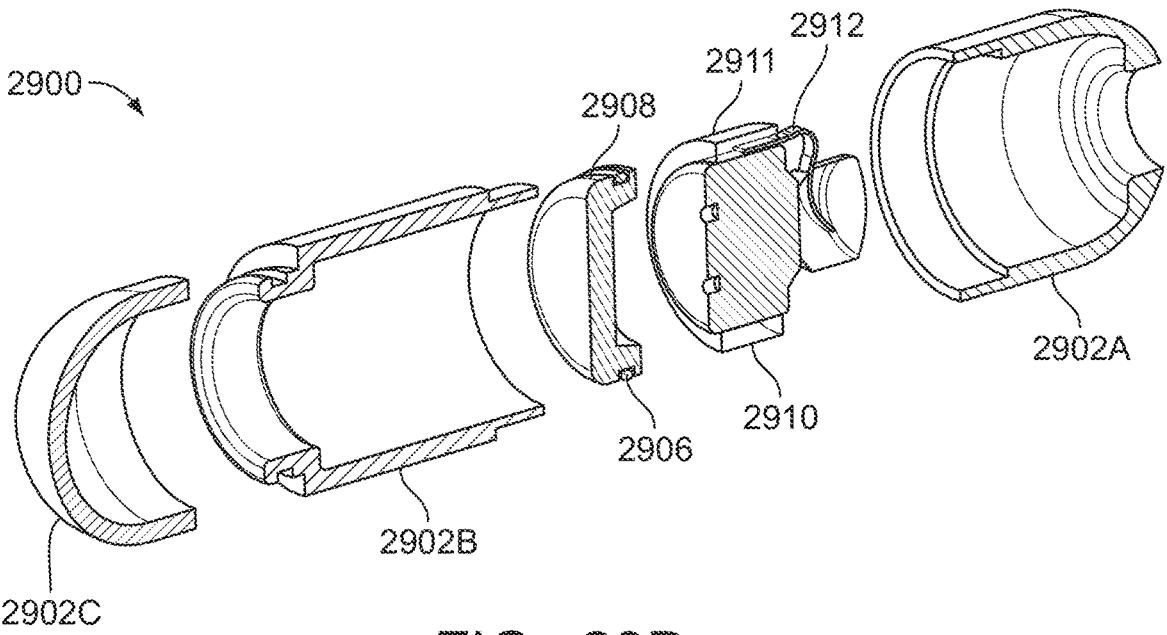
FIG. 29B shows an exploded view of the device of FIG. 29A.

FIG. 29A shows an ingestible device 2900 for topical delivery. FIG. 29B is an exploded view of the device 2900. The device 2900 includes housing parts 2902A, 2902B and 2902C. The device also includes a fluid volume 2904 containing a dispensable substance, an O-ring 2906, a piston 2908 a gas cell 2910 (e.g., a hydrogen cell), a potting material 2911, an electrical contact 2912, and a plug 2914. The subject swallows the device 2900, and, when the device 2900 reaches an appropriate location in the GI tract of the subject, the plug 2914 erodes, degrades and/or dissolves. This causes the electrical contact 2912 to energize the gas cell 2910, which produces a pressurized gas (e.g., pressurized hydrogen) that pushes the piston 2908 axially. This movement applies a pressure to the fluid volume 2904, which transfers the pressure to the housing part 2902C. This causes the housing part 2902C to separate from the device 2900 so that the therapeutic agent in the dispensable substance is topically delivered.

Figure 29C:
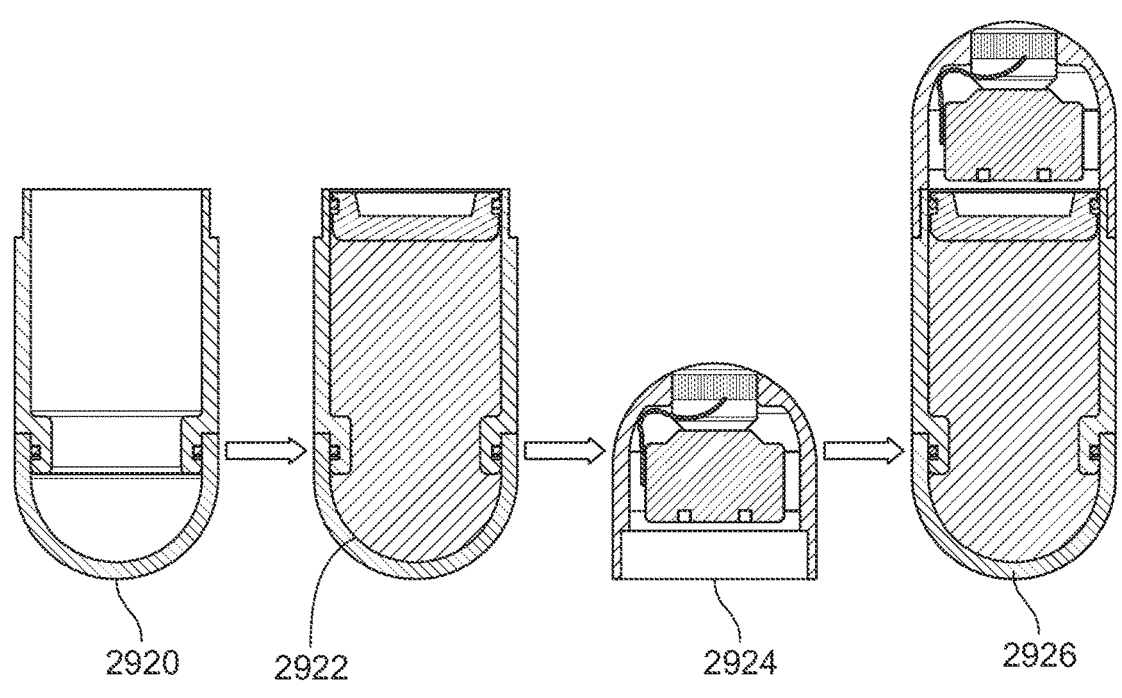
FIG. 29C shows aspects of states of the ingestible device of FIG. 29A.

FIG. 29C shows aspects of steps in assembling the ingestible device 2900. In step 2920, the housing parts 2902B and 2902C are combined and then sterilized. In step 2922, the dispensable substance 2904 is disposed in the housing parts 2902B and 2902C in an aseptic environment and then sealed within the piston 2908. In step 2924, the housing part 2902A and its components are assembled in a clean environment. In step 2926, the resulting modules are joined together in a clean environment to provide the ingestible device 2900.

Figure 30:
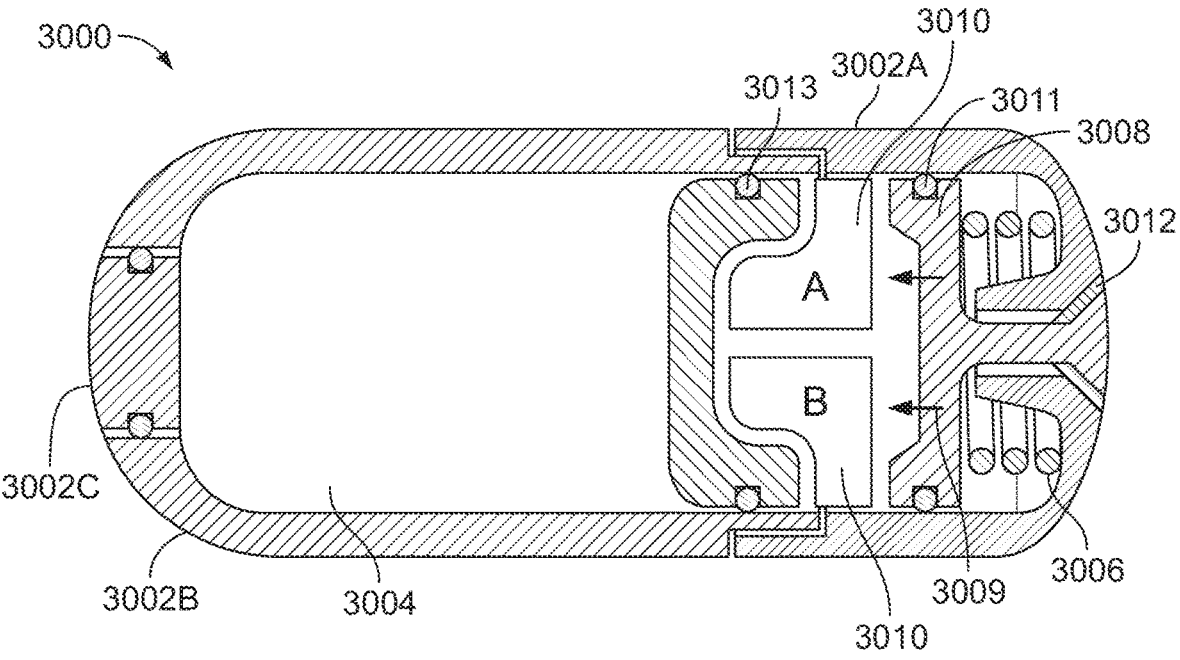
FIG. 30 shows an ingestible device.

FIG. 30 shows an ingestible device 3000 that can be used for topical delivery. The device 3000 includes housing parts 3002A, 3002B and 3002C. The device 2800 further includes a fluid volume 3004 containing a dispensable substance, a spring 3006, a plunger 3008 with piercing elements 3009, an O-Ring 3011, a sealed compartment 3010 containing separated reactants A and B, a piston 3010, and O-ring 3013, and a stopper pin 3012 which holds the components of the device 3000 when the subject swallows the device 3000. When the device 3000 reaches the appropriate location in the GI tract, the pin 3012 erodes, degrades and/or dissolves. This causes the spring 3006 to expand axially, moving the plunger 3008 axially so that the piercing elements 3009 puncture the sealed compartment 3010. This causes the reactants A and B to chemically react and form a pressurized gas which moves the piston axially, thereby applying a pressure against the fluid volume 3004. This pressure is transferred to the housing part 3002C, which forces the housing part 3002C to be removed from the device 3000, and the therapeutic agent in the dispensable substance is topically delivered.

Figures 31A, 31B, 32:
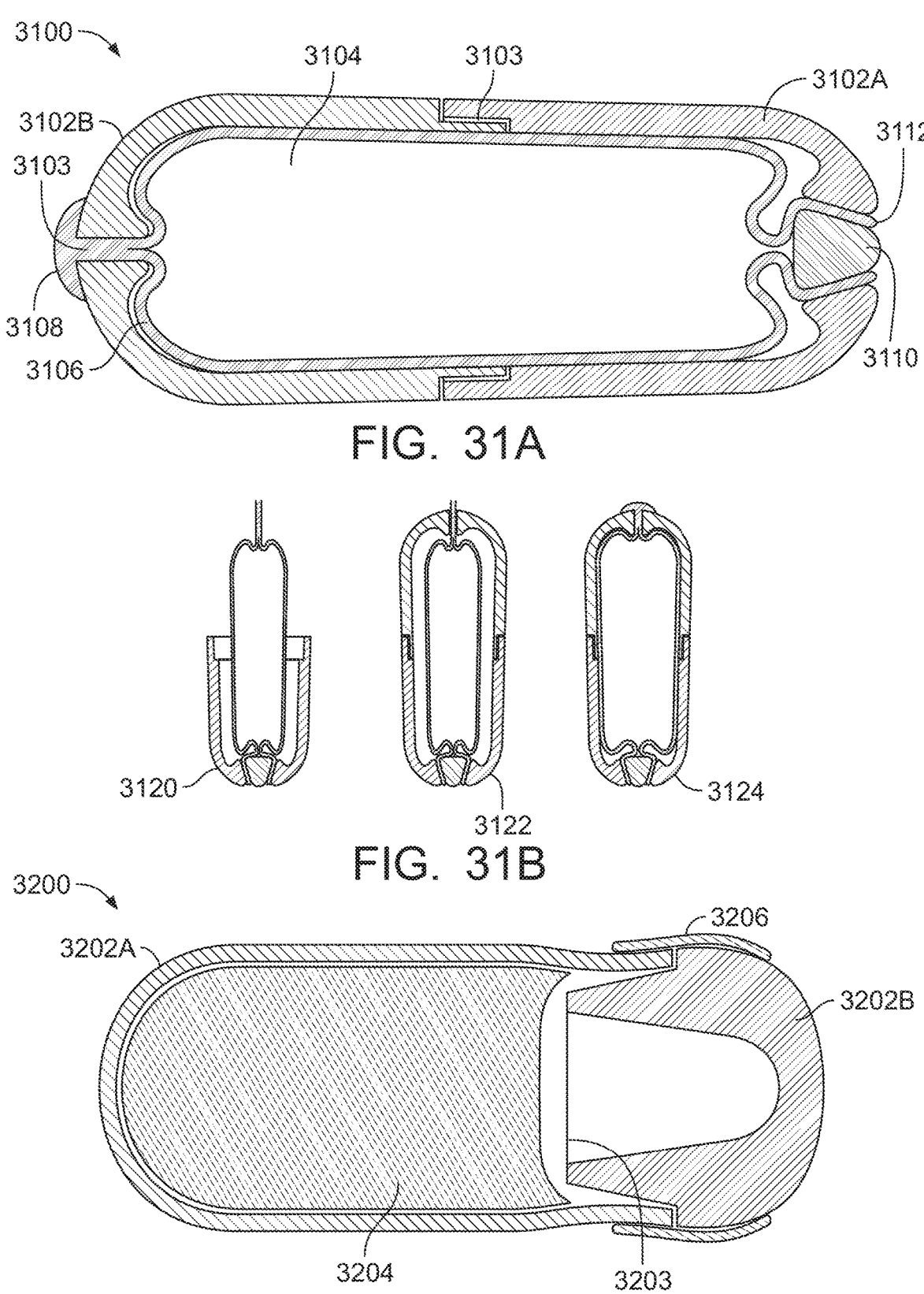
FIG. 31A shows an ingestible device.
FIG. 31B shows aspects of states of the ingestible device of FIG. 31A.
FIG. 32 shows an ingestible device.
Figure 33:
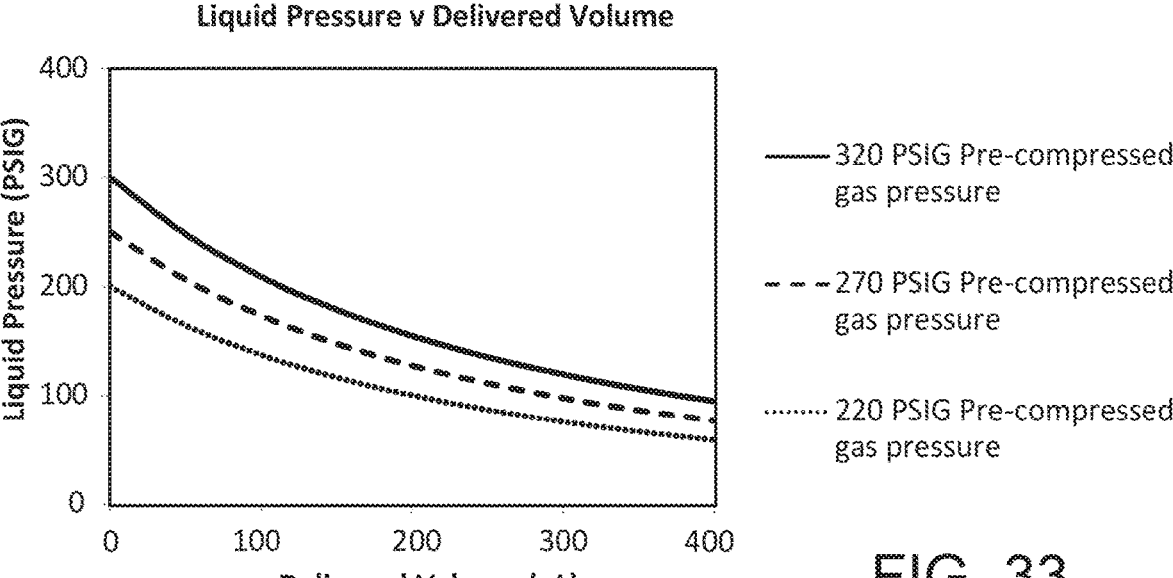
FIGS. 33-37 are graphs showing modelling results for ingestible devices having two nozzles.
Figure 34:
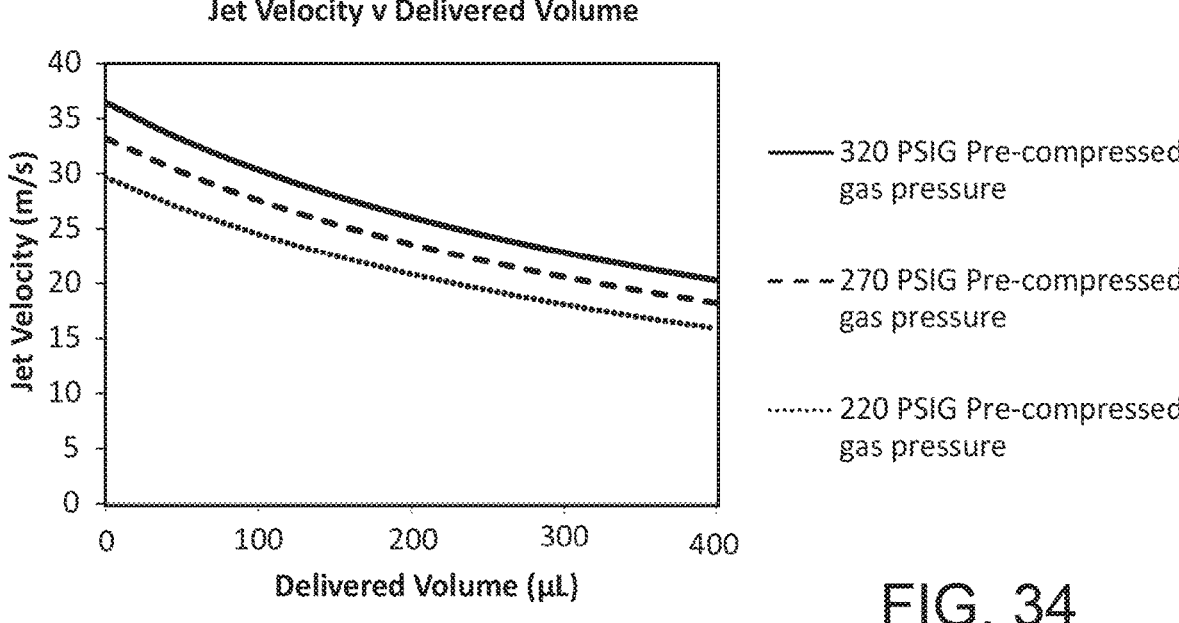
Figure 35:
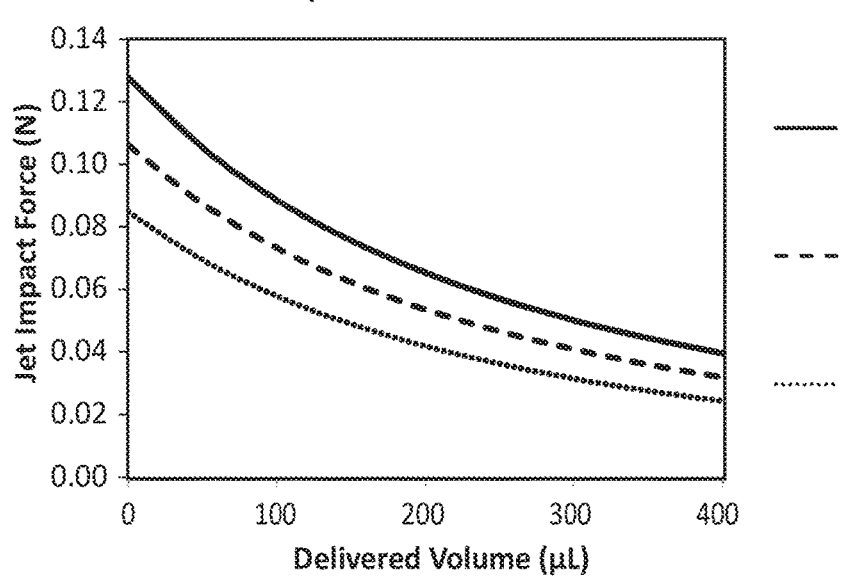
Figure 36:
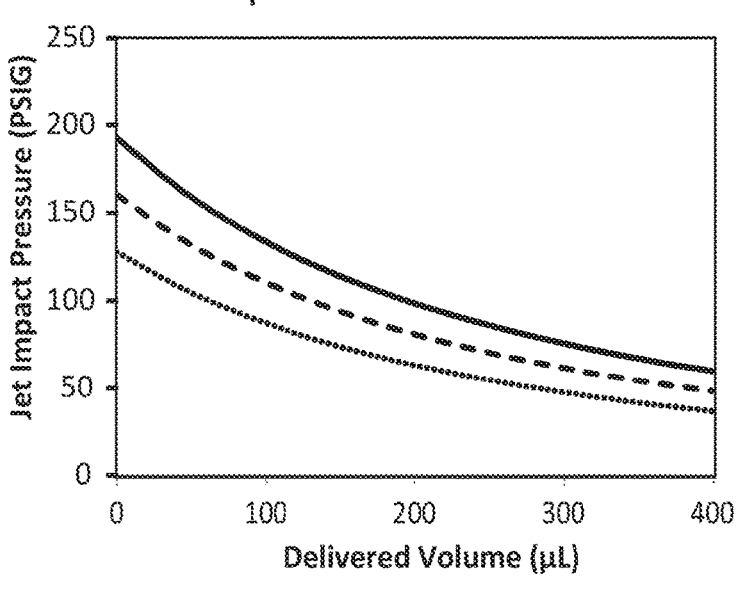
Figure 37:
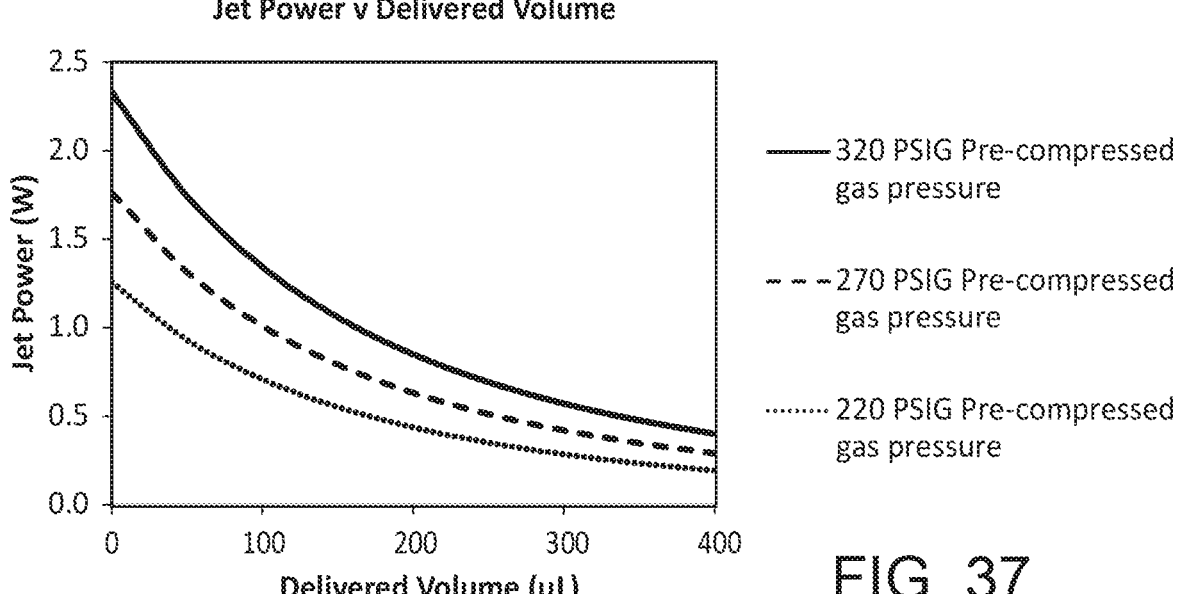
Figure 38:
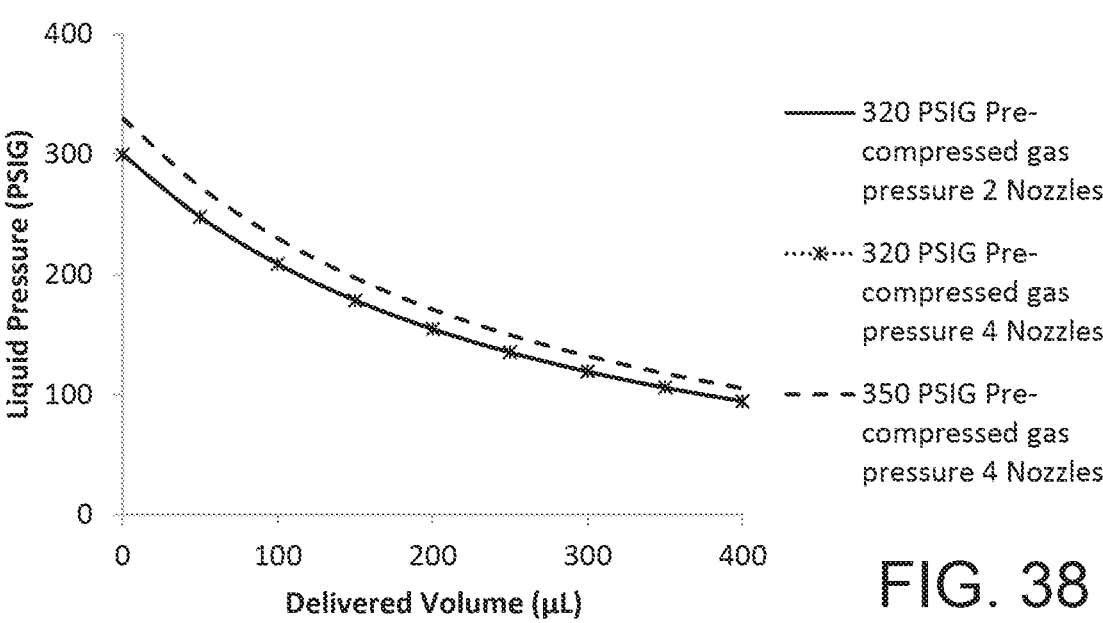
FIGS. 38-47 are graphs showing modelling results for ingestible devices having two or four nozzles.
Figure 39:
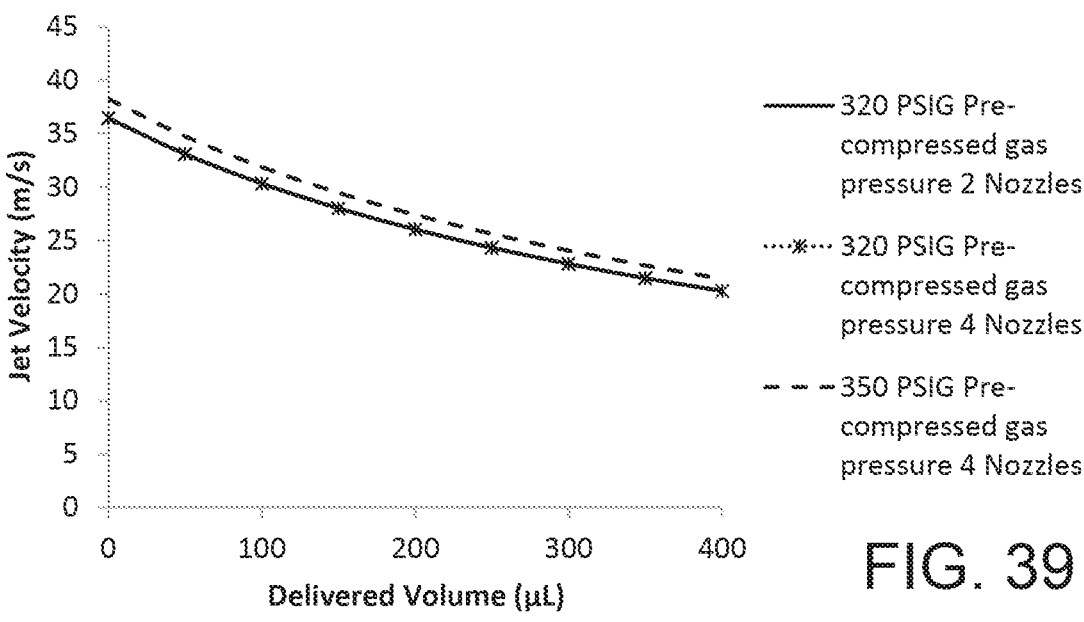
Figure 40:
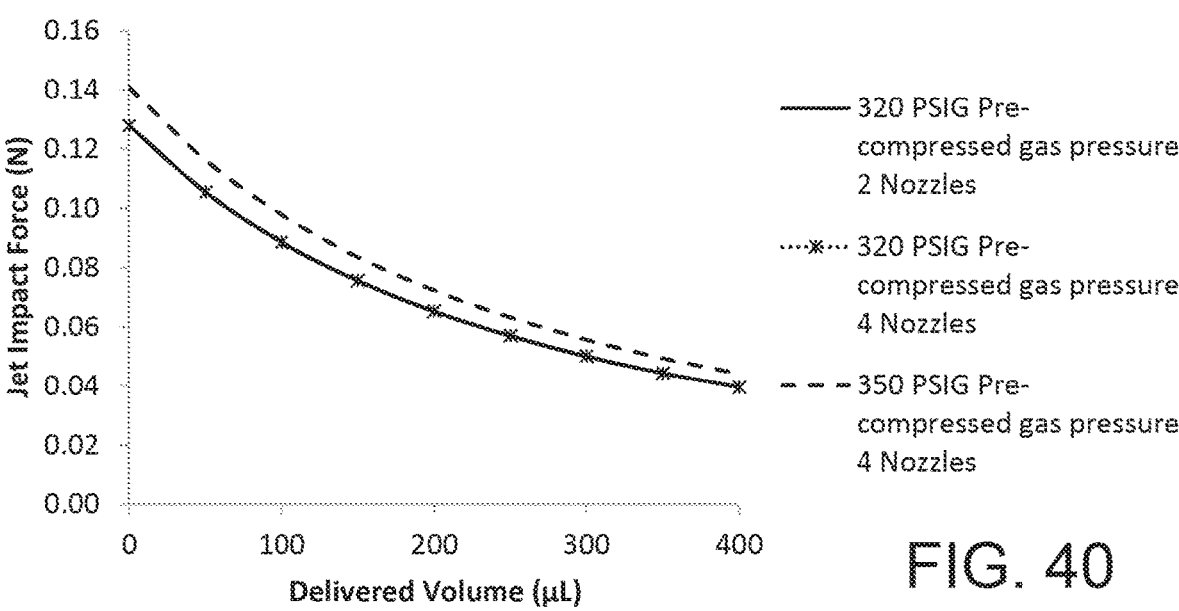
Figure 41:
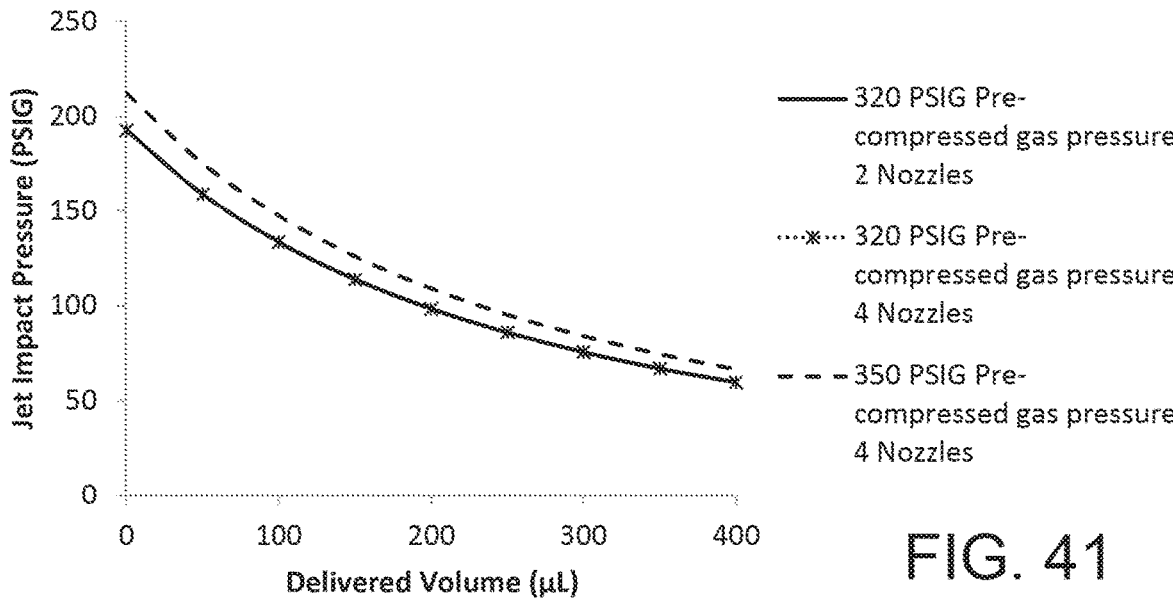
Figure 42:
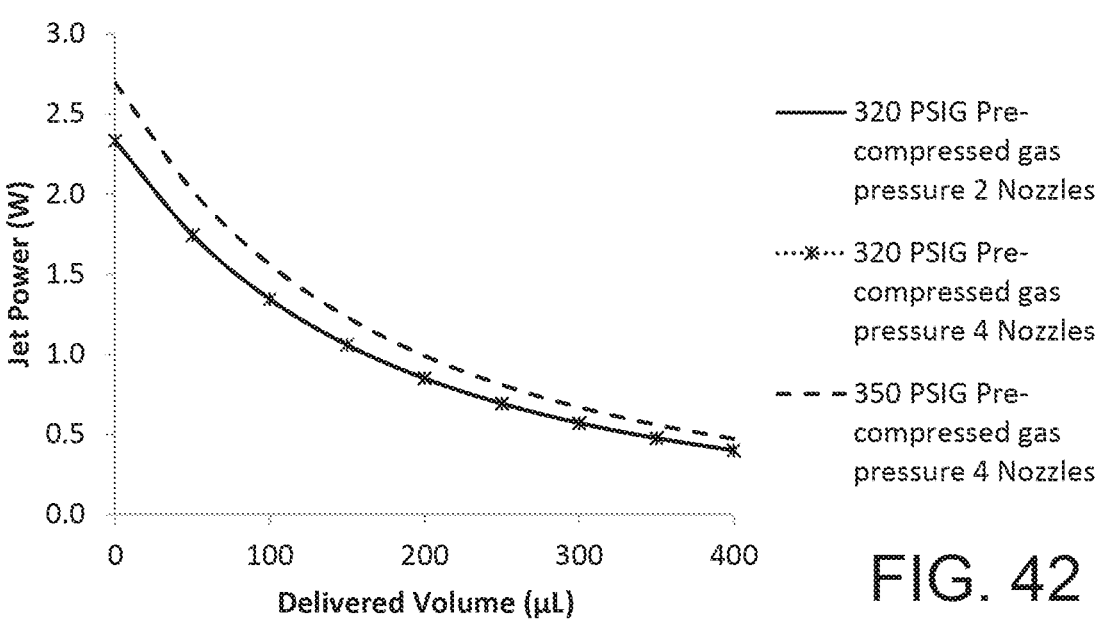
Figure 43:
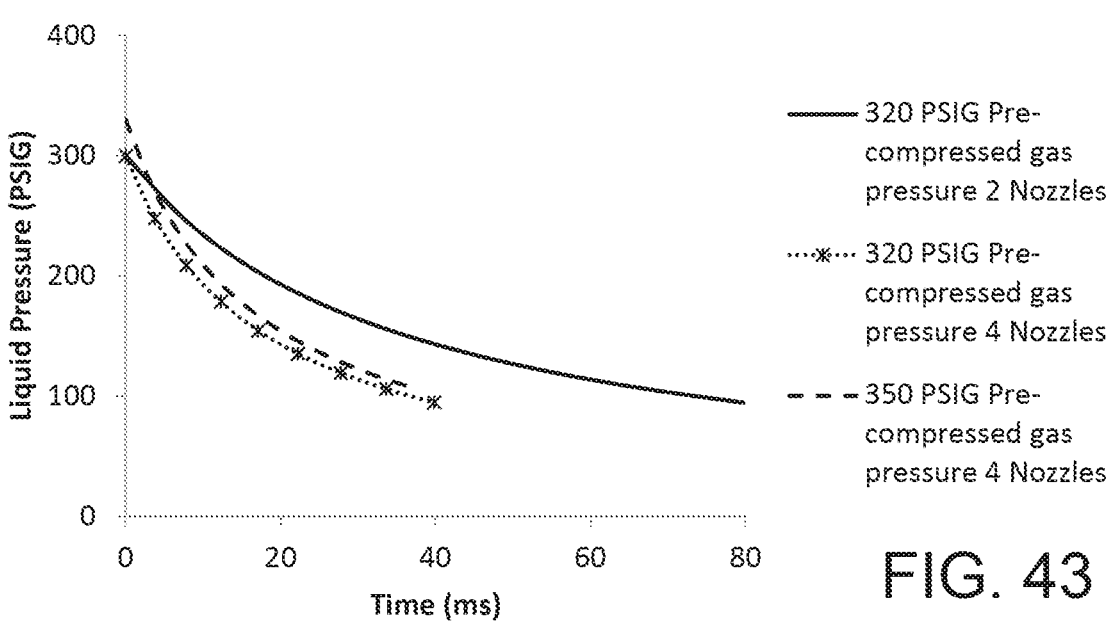
Figure 44:
Figure 45:
Figure 45:
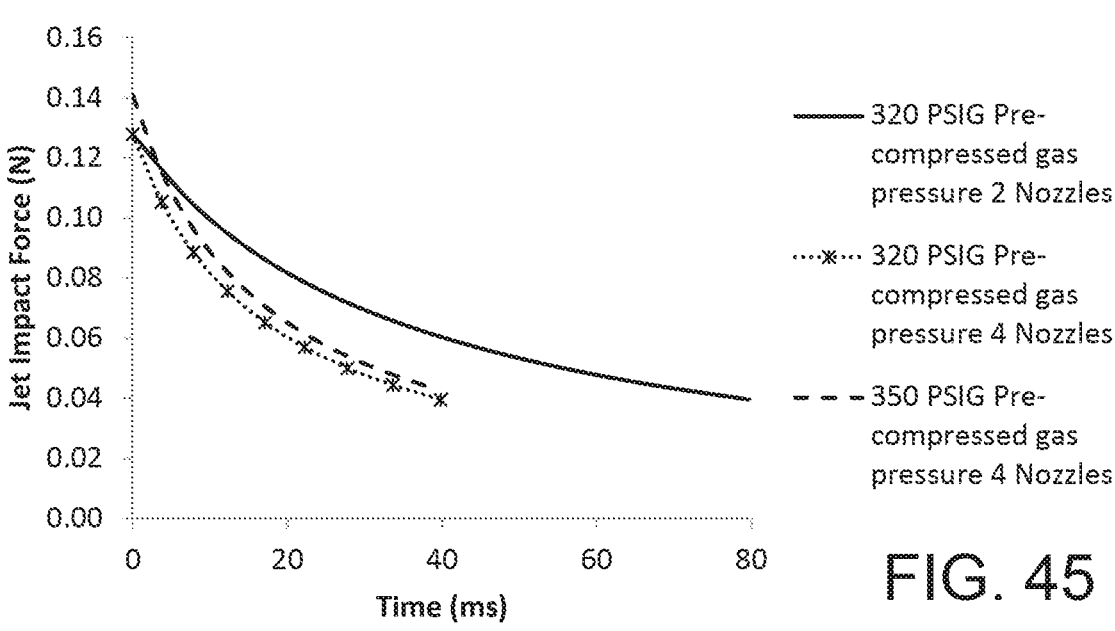
Figure 46:
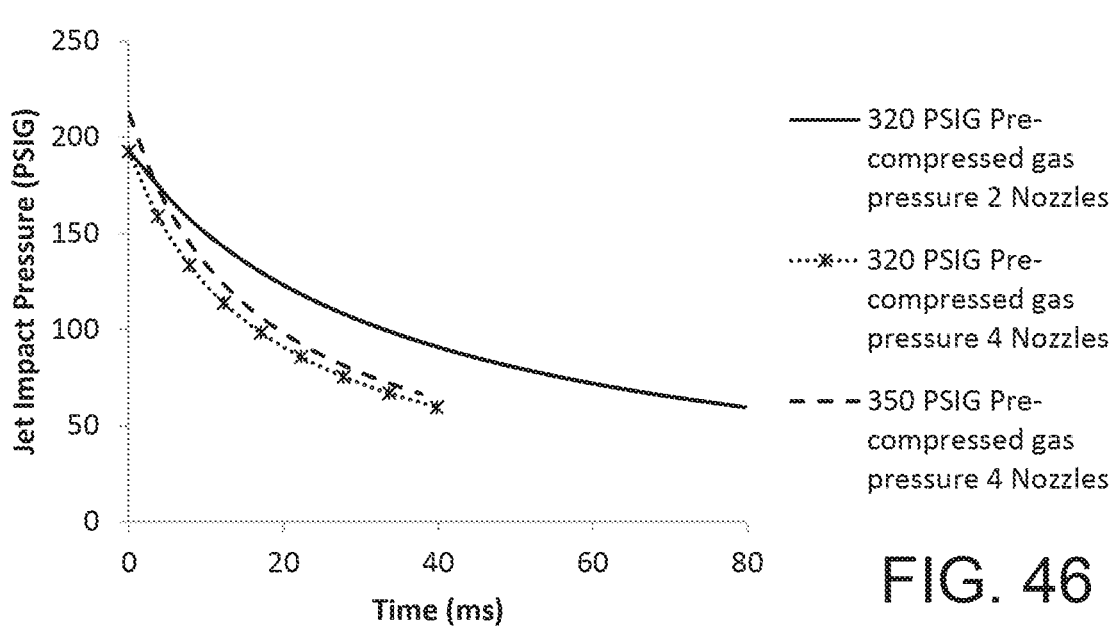
Figure 47:
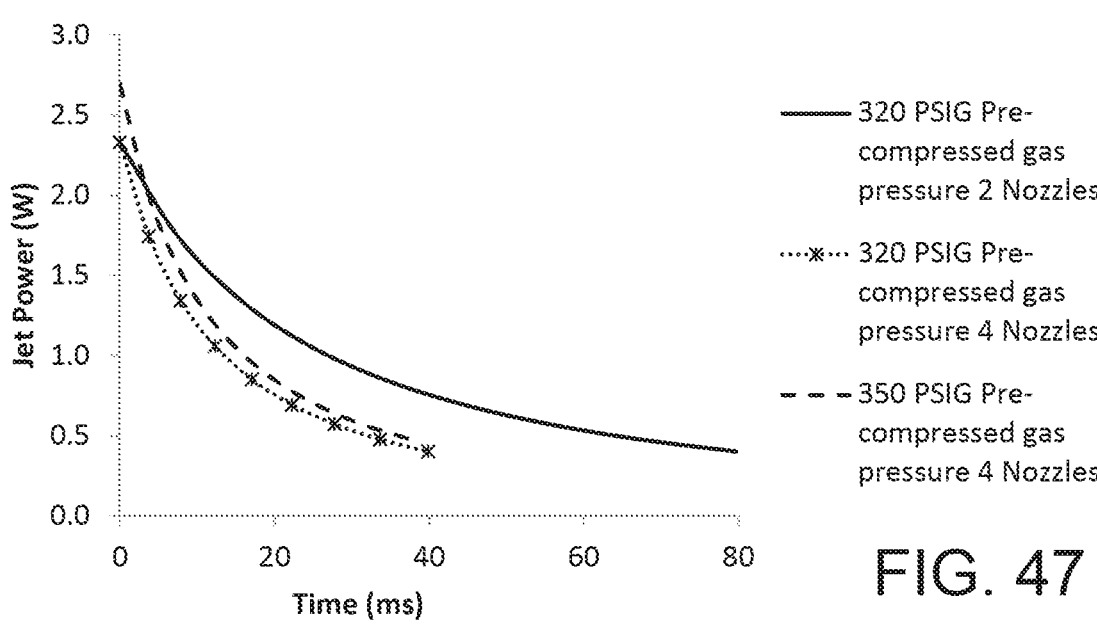

FIG. 31A shows an ingestible device 3100 for topical delivery. The device 3100 includes housing parts 3102A and 3102B, a joint 3103, a pressurized fluid volume 3104 containing a dispensable substance, a membrane 3106 (e.g., balloon) containing the dispensable substance, a seal 3108 located in an opening 3103 of the housing part 3102B, and a plug 3110 in an opening 3112 of the housing part 3102A. The subject swallows the ingestible device 3100. When the device 3100 reaches the appropriate location in the GI tract, the plug 3110 erodes, degrades and/or dissolves. This causes the pressurized fluid 3104 in the membrane 3104 to leave the device 3100 via the opening 3112 so that the therapeutic agent in the dispensable substance is topically delivered.

FIG. 31B shows aspects of steps in assembling the ingestible device 3100. In step 3120, the plug 3112 is formed in the opening 3112 of the housing part 3102A, the membrane 3104 is put inside the housing part 3102A, and the dispensable substance is disposed in the membrane 3104 under aseptic conditions. In step 3122, the housing part 3102B is combined with the housing part 3102A, and the open portion of the membrane 3104 is sealed (e.g., hot sealed) within the opening 3103, thereby forming the ingestible device 3100.

FIG. 32 shows an ingestible device 3200 for topical delivery. The device 3200 includes housing parts 3202A and 3202B. The housing part 3202B includes a seal 3203. The housing part 3202A is made from a flexible material that is biased against the housing part 3202B and joined to the housing part 3202B by a partial coating 3206 such that housing. The device 3200 also includes a fluid volume 3204 containing a dispensable substance. The subject swallows the ingestible device 3200. When the device 3200 reaches the appropriate location in the GI tract, the partial coating 3206 erodes, degrades and/or dissolves. This causes the flexible housing part 3202A to expand radially so that the housing parts 3202A and 3202B are separated, resulting in topical delivery of the therapeutic agent in the dispensable substance.

FIG. 32B shows aspects of steps in assembling the ingestible device 3200. In step 3220, the housing plug 3212 is formed in the opening 3212 of the housing part 3202A, the membrane 3204 is put inside the housing part 3202A, and the dispensable substance is disposed in the membrane 3204 under aseptic conditions. In step 3222, the housing part 3202B is combined with the housing part 3202A, and the open portion of the membrane 3204 is sealed (e.g., hot sealed) within an opening 3203 in the housing part 3202B, thereby forming the ingestible device 3200.

In certain embodiments, an ingestible device for topical delivery is configured as disclosed in the above-discussion regarding trans-epithelial delivery, but with a relatively large number of nozzles and a relatively large nozzle diameter such that performance properties for topical delivery (discussed above) can be achieved. As an example, in some embodiments, an ingestible device for topical delivery has at least 25 nozzles (e.g., at least 30 nozzles, at least 40 nozzles, 50 nozzles). In some embodiments, such an ingestible device for topical delivery has 30 nozzles, 31 nozzles, 32 nozzles, 33 nozzles, 34 nozzles, 35 nozzles, 36 nozzles, 37 nozzles, 38 nozzles or 40 nozzles. Each nozzle can have a diameter, for example, of at least about 1 mm (e.g., at least about 1.5 mm, at least about 2 mm) and/or at most about 3 mm (e.g., at most about 2.5 mm). For example, in such an ingestible device, each nozzle can have a diameter of from about 1 mm to about 3 mm (e.g., from about 1 mm to about 2.5 mm, from about 2 to 2.5 mm).

4. Delivery of Therapeutics

Provided herein are ingestible devices and methods that deliver therapeutic agents into the intestinal lumen, mucus, mucosa and/or submucosa by topical, epithelial or trans-epithelial administration to the GI tract of a subject. Current methods of administration for most large molecule therapeutic agents or small molecule therapeutic agents with poor oral bioavailability are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

a. Therapeutics for Delivery

Therapeutics suitable for use with the devices and methods described herein include both small molecules and large molecules. In some embodiments, the therapeutic agent is a large molecule. Examples of large molecules include, but are not limited to, biologic drugs, proteins including fusion proteins, peptides including cyclic peptides, cells including stem cells, and nucleic acids such as inhibitory nucleic acids, antisense nucleic acids, siRNA, ribozymes, and the like. In some embodiments, the therapeutic agent is a large molecule with a molecular weight of at least about 60 kilodaltons (kDa), or about 60 kDa to about 200 kDa, about 60 kDa to about 175 kDa, or about 60 kDa to about 150 kDa. In some other embodiments, the therapeutic agent has a molecular weight of at least about 20 kDa, at least about 30 kDa, at least about 40 kDa, or at least about 50 kDa, or from about 20 kDa to about 200 kDa, about 20 kDa to about 175 kDa or about 20 kDa to about 150 kDa.

In some embodiments, the therapeutic agent is a molecule with a molecular weight of greater than about 1.5 kDa and less than about 20 kDa, less than about 30 kDa, less than about 40 kDa, less than about 50 kDa or less than about 60 kDa. In some other embodiments, the therapeutic agent has a molecular weight of from about 5 kDa to about 10 kDa, 20 kDa, 30 kDa, 40 kDa or 50 kDa. In some embodiments, the therapeutic agent is a molecule with a molecular weight of about 5 kDa to about 10 kDa, such as about 6 kDa. In some embodiments, the therapeutic agent is a protein or peptide. In some embodiments, the therapeutic agent is insulin.

In some embodiments, the therapeutic agent is a small molecule. A "small molecule," as used herein, is a compound, typically an organic compound, having a molecular weight of about 50 Da to about 1500 Da, about 60 Da to about 1500 Da, about 500 Da to about 1000 Da, or no more than about 1500 Da, about 1000 Da, about 750 Da, or about 500 Da. In some embodiments, the therapeutic agent is a small molecule with a molecular weight of about 50 Da to about 1500 Da. In some embodiments, the therapeutic agent is a small molecule with a molecular weight of about 150 Da to about 1500 Da.

Exemplary therapeutic agents for use in the devices and methods provided herein include, but are not limited to abatacept, teriparatide, emicizumab, pegfilgrastim, semaglutide, dulaglutide, sargramostim, ustekinumab, secukinumab, tocilizumab, vedolizumab, natalizumab, interferon beta-1a, denosumab, alirocumab, evolocumab, adalimumab, etanercept, golimumab, and certolizumab pegol; and biosimilars thereof; and glycosylation variants thereof. In some aspects, the device configured for trans-epithelial delivery delivers the dispensable substance to tissue of the GI tract of a subject as a jet having a diameter of from about 0.3 mm to about 0.5 mm.

EXAMPLES

Example 1—Modelling Device Performance

In this Example, modelling was used to determine the performance parameters of an ingestible device for delivering a dispensable substance.

Model

The driving pressure, for a given point in the dose delivery, is related to the delivered liquid volume, and the resulting increase in gas volume, by equations of state for adiabatic expansion. The velocity (e.g., peak jet velocity, average jet velocity, or minimum jet velocity) through the orifice is in turn given by the driving pressure. This is a steady state approximation in which transient effects of fluid acceleration/deceleration are ignored. In other words, the gas expansion is rapid allowing little time for heat transfer/ thermal equilibration to the surroundings. Thus, this is treated as an adiabatic (no energy loss).

For an adiabatic process, Pressure P and Volume V of a gas are related as follows, assuming that fluid (liquid) pressure is equal to gas pressure (frictionless piston).

$$\frac{P_2}{P_1} = \left(\frac{V_1}{V_2}\right)^\gamma,$$

where P is pressure, V is volume, and $\gamma$ is the ratio of specific heats.

Pipe shear pressure is given by the Darcy-Weisbach equation:

$$P_{Pipe} = f \frac{\rho L v_o^2}{2 d_o},$$

where $\rho$ is the density of a liquid, L is the nozzle length, $u_o$ is the velocity through the nozzle orifice, $d_o$ is the diameter of an nozzle orifice, and f is the Darcy friction factor for pipe flow.

The friction factor for rough pipes is given by:

$$\frac{1}{f^{1/2}} = -2.0\log\left(\frac{\epsilon/d_o}{3.7} + \frac{2.51}{Re f^{1/2}}\right),$$

where $\epsilon$ is the pipe surface roughness, and Re is the Reynolds number for the fluid.

Haaland proposed the following explicit approximation, which differs by less than 2% from Colebrook:

$$f^{-1/2} = \frac{1}{f^{1/2}} = -1.8\log\left(\left(\frac{\epsilon/d_o}{3.7}\right)^{1.11} + \frac{6.9}{Re}\right)$$

$$f = \frac{1}{\left(-1.8\log\left(\left(\frac{\epsilon/d_o}{3.7}\right)^{1.11} + \frac{6.9}{Re}\right)\right)^2}$$

Therefore, pipe pressure is:

$$P_{Pipe} = \frac{\rho L v_o^2}{2d_o\left(-1.8\log\left(\left(\frac{\epsilon/d_o}{3.7}\right)^{1.11} + \frac{6.9}{Re}\right)\right)^2}$$

This explicit approximation requires iterative solution if Re is unknown.

Pipe exit and entry losses are assumed as being given by:

$$P_{Entry} = \frac{1}{2}C_{Entry}\rho_l v^2$$

$$P_{Exit} = \frac{1}{2}C_{Exit}\rho_l v^2$$

Thus, overall pressure drop across the orifice is:

$$P_{Orifice} = f\frac{\rho L v_o^2}{2d_o} + \frac{1}{2}(C_{Entry} + C_{Exit})\rho_l v_o^2,$$

Where $C_{entry}$ is the coefficient of discharge on entry, and $C_{exit}$ is the coefficient of discharge on exit.

The total flowrate is:

$$Q = N\pi d_o^2 v_o,$$

where Q is the volumetric flow rate through a single orifice.

Accounting for piston friction, the liquid delivery pressure through the orifice is related to the gas pressure as follows. The force balance on the piston is given by:

$$\frac{\pi}{4}d_{Piston}^2(P_{gas} - P_{Liquid}) - F_{Friction} = a_{Piston}m_{Piston}$$

Applying a steady state assumption yields:

$$\frac{\pi}{4}d_{Piston}^2(P_{gas} - P_{Liquid}) - F_{Friction}$$

Rearranging, results in:

$$P_{Orifice} = P_{Gas} - \frac{F_{Friction}}{\frac{\pi}{4}d_{Piston}^2}$$

The jet impact force is given by the rate of change of the jet momentum at the impact surface:

$$F = dp/dt = d(mv)/dt = v(dm/dt) + m(dv/dt),$$

Where p is momentum, v is velocity and m is mass.

Assuming constant jet velocity for a given time step, the dV/dt term goes to zero, yielding:

$$F = V(dm/dt), \text{ or } F = \text{velocity*mass flow rate}$$

$$F = \text{density*area*velocity\textasciicircum 2}$$

$$F = 1/4\text{*pi*density*diameter\textasciicircum 2*velocity\textasciicircum 2}$$

The jet power has been shown to correlate with needle-free penetration and dispersion by:

$$\text{Power} = \frac{1}{8}\text{"pi*density*diameter\textasciicircum 2*velocity\textasciicircum 3}$$

Device and Fluid Properties
  Nozzle diameter=0.35 mm
  Nozzle length=2 mm
  Number of nozzles=2 or 4
  Nozzle throat geometry=circular, sharp-edged orifice (similar to FIG. 6D)
  Piston diameter=9.6 mm
  Piston friction=10 N due to one O-ring surrounding the piston
  Friction pressure loss=about 20 psig
  Dispensable substance (fluid)=100 mg/mL adalimumab formulation
  Fluid density=1000 kg/m³
  Fluid viscosity=7.5 centiPoise
  Ratios of specific heat (air)=1.4
Results—Initial Internal Pressure of 320 psig—2 Nozzles
  The following properties were used in the model.
  Initial internal pressure=320 psig
  Fluid pressure=about 300 psig (peak; initial)
  Nozzle pressure=about 300 psig (peak; initial)
  Initial dose volume of dispensable substance=450 μL
  Initial gas volume=370 μL
  With these parameters, the modelling yielded the results shown in Tables 2A-2D (liquid pressure is the same as fluid pressure).

TABLE 2A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 22.1 | 20.7 | 300.0 | 36.5 |
| 2 | 50 | 420 | 18.5 | 17.1 | 247.9 | 33.1 |
| 3 | 100 | 470 | 15.8 | 14.4 | 208.9 | 30.3 |
| 4 | 150 | 520 | 13.7 | 12.3 | 178.7 | 28.0 |
| 5 | 200 | 570 | 12.0 | 10.7 | 154.7 | 26.0 |
| 6 | 250 | 620 | 10.7 | 9.3 | 135.3 | 24.3 |
| 7 | 300 | 670 | 9.6 | 8.2 | 119.3 | 22.8 |
| 8 | 350 | 720 | 8.7 | 7.3 | 160.0 | 21.5 |
| 9 | 400 | 770 | 7.9 | 6.5 | 94.7 | 20.3 |

TABLE 2B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.70E+03 | 7.23E−02 | 2.07E+06 | 20.68 | 0.00 |
| 2 | 1.54E+03 | 7.37E−02 | 1.71E+06 | 17.09 | 0.00 |
| 3 | 1.42E+03 | 7.51E−02 | 1.44E+06 | 14.40 | 0.00 |
| 4 | 1.31E+03 | 7.65E−02 | 1.23E+06 | 12.32 | 0.00 |
| 5 | 1.22E+03 | 7.78E−02 | 1.07E+06 | 10.67 | 0.00 |
| 6 | 1.14E+03 | 7.92E−02 | 9.33E+05 | 9.33 | 0.00 |
| 7 | 1.06E+03 | 8.05E−02 | 8.23E+05 | 8.23 | 0.00 |
| 8 | 1.00E+03 | 8.18E−02 | 7.31E+05 | 7.31 | 0.00 |
| 9 | 9.46E+02 | 8.31E−02 | 6.53E+05 | 6.53 | 0.00 |

TABLE 2C

| Model No. | Jet Impact Force (N) | Jet Impact Pressure (psi) | Jet Power (W) |
|---|---|---|---|
| 1 | 0.128 | 192.7 | 2.3 |
| 2 | 0.105 | 158.9 | 1.7 |
| 3 | 0.089 | 133.5 | 1.3 |
| 4 | 0.076 | 113.9 | 1.1 |
| 5 | 0.065 | 98.4 | 0.8 |
| 6 | 0.057 | 85.8 | 0.7 |
| 7 | 0.050 | 75.5 | 0.6 |
| 8 | 0.044 | 66.9 | 0.5 |
| 9 | 0.040 | 59.6 | 0.4 |

TABLE 2D

| Model No. | Flowrate per Orifice (m/s) | Total Flowrate (µL/s) | Time for Delivered Vol (ms) | Time from Start of Dose (ms) |
|---|---|---|---|---|
| 1 | 3.51E−06 | 7014.2 | | 0.0 |
| 2 | 3.18E−06 | 6368.4 | 7.47 | 7.5 |
| 3 | 2.92E−06 | 5838.1 | 8.19 | 15.7 |
| 4 | 2.70E−06 | 5392.7 | 8.90 | 24.6 |
| 5 | 2.51E−06 | 5011.8 | 9.61 | 34.2 |
| 6 | 2.34E−06 | 4681.3 | 10.32 | 44.5 |
| 7 | 2.20E−06 | 4390.9 | 11.02 | 55.5 |
| 8 | 2.07E−06 | 4133.0 | 11.73 | 67.3 |
| 9 | 1.95E−06 | 3901.7 | 12.45 | 79.7 |

The minimum (final) fluid pressure is about 95 psig, and the minimum (final) nozzle pressure is about 95 psig. The delivered volume of dispensable substance is 400 µL, and the final gas volume is 770 µL. The average velocity is 27.0 m/s. The total delivery time is 79.7 ms. The average velocity based on dispense time is 26.1 m/s.

Results—Initial Internal Pressure of 300 psig—2 Nozzles

The following properties were used in the model.

Initial internal pressure=300 psig

Fluid pressure=about 280 psig (peak; initial)

Nozzle pressure=about 280 psig (peak; initial)

Initial dose volume of dispensable substance=450 µL

Initial gas volume=370 µL

With these parameters, the modelling yielded the results shown in Tables 3A-3D (liquid pressure is the same as fluid pressure).

TABLE 3A

| Model No. | Delivered Dose (µL) | Gas Vol. (µL) | Gas Pressure (bar) | Liquid Pressure (bar) | Liquid pressure (psi) | Velocity (m/s) |
|---|---|---|---|---|---|---|
| 1 | 0 | 370 | 20.7 | 19.3 | 280.0 | 35.2 |
| 2 | 50 | 420 | 17.3 | 15.9 | 231.2 | 31.9 |

TABLE 3A-continued

| Model No. | Delivered Dose (µL) | Gas Vol. (µL) | Gas Pressure (bar) | Liquid Pressure (bar) | Liquid pressure (psi) | Velocity (m/s) |
|---|---|---|---|---|---|---|
| 3 | 100 | 470 | 14.8 | 13.4 | 194.6 | 29.3 |
| 4 | 150 | 520 | 12.8 | 11.5 | 166.3 | 27.0 |
| 5 | 200 | 570 | 11.3 | 9.9 | 143.8 | 25.1 |
| 6 | 250 | 620 | 10.0 | 8.7 | 125.6 | 23.4 |
| 7 | 300 | 670 | 9.0 | 7.6 | 110.6 | 22.0 |
| 8 | 350 | 720 | 8.1 | 6.8 | 98.1 | 20.6 |
| 9 | 400 | 770 | 7.4 | 6.0 | 87.5 | 19.5 |

TABLE 3B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.64E+03 | 7.28E−02 | 1.93E+06 | 19.30 | 0.00 |
| 2 | 1.49E+03 | 7.43E−02 | 1.59E+06 | 15.94 | 0.00 |
| 3 | 1.37E+03 | 7.57E−02 | 1.34E+06 | 13.42 | 0.00 |
| 4 | 1.26E+03 | 7.71E−02 | 1.15E+06 | 11.46 | 0.00 |
| 5 | 1.17E+03 | 7.85E−02 | 9.91E+05 | 9.91 | 0.00 |
| 6 | 1.09E+03 | 7.99E−02 | 8.66E+05 | 8.66 | 0.00 |
| 7 | 1.02E+03 | 8.13E−02 | 7.63E+05 | 7.63 | 0.00 |
| 8 | 9.64E+02 | 8.26E−02 | 6.76E+05 | 6.76 | 0.00 |
| 9 | 9.09E+02 | 8.40E−02 | 6.03E+05 | 6.03 | 0.00 |

TABLE 3C

| Model No. | Jet Impact Force (N) | Jet Impact Pressure (psi) | Jet Power (W) |
|---|---|---|---|
| 1 | 0.119 | 179.7 | 2.10 |
| 2 | 0.098 | 148.0 | 1.57 |
| 3 | 0.082 | 124.2 | 1.21 |
| 4 | 0.070 | 105.9 | 0.95 |
| 5 | 0.061 | 91.3 | 0.76 |
| 6 | 0.053 | 79.6 | 0.62 |
| 7 | 0.046 | 69.9 | 0.51 |
| 8 | 0.041 | 61.8 | 0.42 |
| 9 | 0.037 | 55.0 | 0.36 |

TABLE 3D

| Model No. | Flowrate per Orifice (m/s) | Total Flowrate (µL/s) | Time for Delivered Vol (ms) | Time from Start of Dose (ms) |
|---|---|---|---|---|
| 1 | 3.39E−06 | 6773.1 | | 0.0 |
| 2 | 3.07E−06 | 6146.4 | 7.74 | 7.7 |
| 3 | 2.82E−06 | 5631.4 | 8.49 | 16.2 |
| 4 | 2.60E−06 | 5198.7 | 9.23 | 25.5 |
| 5 | 2.41E−06 | 4828.6 | 9.97 | 35.4 |
| 6 | 2.25E−06 | 4507.1 | 10.71 | 46.1 |
| 7 | 2.11E−06 | 4224.5 | 11.45 | 57.6 |
| 8 | 1.99E−06 | 3973.3 | 12.20 | 69.8 |
| 9 | 1.87E−06 | 3747.9 | 12.95 | 82.8 |

The minimum (final) fluid pressure is about 87.5 psig, and the minimum (final) nozzle pressure is about 87.5 psig. The delivered volume of dispensable substance is 400 µL, and the final gas volume is 770 UL. The average velocity is 26.0 m/s. The total delivery time is 82.8 ms. The average velocity based on dispense time is 25.1 m/s.

Results—Initial Internal Pressure of 270 psig—2 Nozzles

The following properties were used in the model.

Initial internal pressure=270 psig

Fluid pressure=about 250 psig (peak; initial)

Nozzle pressure=about 250 psig (peak; initial)

Initial dose volume of dispensable substance=450 UL

Initial gas volume=370 UL

With these parameters, the modelling yielded the results shown in Tables 4A-4D (liquid pressure is the same as fluid pressure).

TABLE 4A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 18.6 | 17.2 | 250.0 | 33.2 |
| 2 | 50 | 420 | 15.6 | 14.2 | 206.1 | 30.1 |
| 3 | 100 | 470 | 13.3 | 11.9 | 173.1 | 27.6 |
| 4 | 150 | 520 | 11.6 | 10.2 | 147.6 | 25.4 |
| 5 | 200 | 570 | 10.2 | 8.8 | 127.4 | 23.6 |
| 6 | 250 | 620 | 9.0 | 7.7 | 111.0 | 22.0 |
| 7 | 300 | 670 | 8.1 | 6.7 | 97.5 | 20.6 |
| 8 | 350 | 720 | 7.3 | 5.9 | 86.3 | 19.3 |
| 9 | 400 | 770 | 6.7 | 5.3 | 76.7 | 18.2 |

TABLE 4B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.55E+03 | 7.36E−02 | 1.72E+06 | 17.23 | 0.00 |
| 2 | 1.41E+03 | 7.52E−02 | 1.42E+06 | 14.21 | 0.00 |
| 3 | 1.29E+03 | 7.68E−02 | 1.19E+06 | 11.94 | 0.00 |
| 4 | 1.19E+03 | 7.83E−02 | 1.02E+06 | 10.18 | 0.00 |
| 5 | 1.10E+03 | 7.98E−02 | 8.78E+05 | 8.78 | 0.00 |
| 6 | 1.03E+03 | 8.12E−02 | 7.66E+05 | 7.66 | 0.00 |
| 7 | 9.61E+02 | 8.27E−02 | 6.73E+05 | 6.73 | 0.00 |
| 8 | 9.02E+02 | 8.42E−02 | 5.95E+05 | 5.95 | 0.00 |
| 9 | 8.50E+02 | 8.57E−02 | 5.29E+05 | 5.29 | 0.00 |

TABLE 4C

| Model No. | Jet Impact Force (N) | Jet Impact Pressure (psi) | Jet Power (W) |
|---|---|---|---|
| 1 | 0.106 | 160.2 | 1.8 |
| 2 | 0.087 | 131.7 | 1.3 |
| 3 | 0.073 | 110.3 | 1.0 |
| 4 | 0.062 | 93.8 | 0.8 |
| 5 | 0.054 | 80.7 | 0.6 |
| 6 | 0.047 | 70.2 | 0.5 |
| 7 | 0.041 | 61.5 | 0.4 |
| 8 | 0.036 | 54.2 | 0.3 |
| 9 | 0.032 | 48.1 | 0.3 |

TABLE 4D

| Model No. | Flowrate per Orifice (m/s) | Total Flowrate (pL/s) | Time for Delivered Vol (ms) | Time from Start of Dose (ms) |
|---|---|---|---|---|
| 1 | 3.20E−06 | 6394.9 | | 0.0 |
| 2 | 2.90E−06 | 5797.8 | 8.20 | 8.2 |
| 3 | 2.65E−06 | 5306.7 | 9.01 | 17.2 |
| 4 | 2.45E−06 | 4893.8 | 9.80 | 27.0 |
| 5 | 2.27E−06 | 4540.1 | 10.60 | 37.6 |
| 6 | 2.12E−06 | 4232.7 | 11.40 | 49.0 |
| 7 | 1.98E−06 | 3962.1 | 12.20 | 61.2 |
| 8 | 1.86E−06 | 3721.2 | 13.02 | 74.2 |
| 9 | 1.75E−06 | 3504.9 | 13.84 | 88.1 |

The minimum (final) fluid pressure was about 77 psig, and the minimum (final) nozzle pressure was about 77 psig. The delivered volume of dispensable substance was 400 μL, and the final gas volume was 770 μL. The average velocity was 24.5 m/s. The total delivery time was 88.1 ms. The average velocity based on dispense time was 23.6 m/s.

Results—Initial Internal Pressure of 220 psig—2 Nozzles

The following properties were used in the model.

Initial internal pressure-220 psig

Fluid pressure=about 200 psig (peak; initial)

Nozzle pressure=about 200 psig (peak; initial)

Initial dose volume of dispensable substance=450 μL

Initial gas volume=370 μL

With these parameters, the modelling yielded the results shown in Tables 5A-5D (liquid pressure is the same as fluid pressure).

TABLE 5A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 15.2 | 13.8 | 200.0 | 29.7 |
| 2 | 50 | 420 | 12.7 | 11.3 | 164.2 | 26.8 |
| 3 | 100 | 470 | 10.9 | 9.5 | 137.3 | 24.5 |
| 4 | 150 | 520 | 9.4 | 8.0 | 116.6 | 22.6 |
| 5 | 200 | 570 | 8.3 | 6.9 | 100.1 | 20.9 |
| 6 | 250 | 620 | 7.4 | 6.0 | 86.8 | 19.4 |
| 7 | 300 | 670 | 6.6 | 5.2 | 75.8 | 18.1 |
| 8 | 350 | 720 | 6.0 | 4.6 | 66.6 | 16.9 |
| 9 | 400 | 770 | 5.4 | 4.1 | 58.8 | 15.9 |

TABLE 5B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.38E+03 | 7.55E−02 | 1.38E+06 | 13.79 | 0.00 |
| 2 | 1.25E+03 | 7.73E−02 | 1.13E+06 | 11.32 | 0.00 |
| 3 | 1.14E+03 | 7.90E−02 | 9.47E+05 | 9.47 | 0.00 |
| 4 | 1.05E+03 | 8.07E−02 | 8.04E+05 | 8.04 | 0.00 |
| 5 | 9.74E+02 | 8.24E−02 | 6.90E+05 | 6.90 | 0.00 |
| 6 | 9.05E+02 | 8.41E−02 | 5.98E+05 | 5.98 | 0.00 |
| 7 | 8.45E+02 | 8.58E−02 | 5.22E+05 | 5.22 | 0.00 |
| 8 | 7.90E+02 | 8.75E−02 | 4.59E+05 | 4.59 | 0.00 |
| 9 | 7.42E+02 | 8.93E−02 | 4.06E+05 | 4.06 | 0.00 |

TABLE 5C

| Model No. | Jet Impact Force (N) | Jet Impact Pressure (psi) | Jet Power (W) |
|---|---|---|---|
| 1 | 0.085 | 127.7 | 1.3 |
| 2 | 0.069 | 104.5 | 0.9 |
| 3 | 0.058 | 87.2 | 0.7 |
| 4 | 0.049 | 73.8 | 0.6 |
| 5 | 0.042 | 63.1 | 0.4 |
| 6 | 0.036 | 54.6 | 0.4 |
| 7 | 0.032 | 47.5 | 0.3 |
| 8 | 0.028 | 41.6 | 0.2 |
| 9 | 0.024 | 36.6 | 0.2 |

TABLE 5D

| Model No. | Flowrate per Orifice (m/s) | Total Flowrate (μL/s) | Time for Delivered Vol (ms) | Time from Start of Dose (ms) |
|---|---|---|---|---|
| 1 | 2.86E−06 | 5710.0 | | 0.0 |
| 2 | 2.85E−06 | 5165.8 | 9.19 | 9.2 |
| 3 | 2.36E−06 | 4717.3 | 10.12 | 19.3 |
| 4 | 2.17E−06 | 4339.2 | 11.04 | 30.4 |
| 5 | 2.01E−06 | 4014.7 | 11.97 | 42.3 |
| 6 | 1.87E−06 | 3731.9 | 12.91 | 55.2 |

TABLE 5D-continued

| Model No. | Flowrate per Orifice (m/s) | Total Flowrate (μL/s) | Time for Delivered Vol (ms) | Time from Start of Dose (ms) |
|---|---|---|---|---|
| 7 | 1.74E−06 | 3482.2 | 13.86 | 69.1 |
| 8 | 1.63E−06 | 3259.4 | 14.83 | 83.9 |
| 9 | 1.53E−06 | 3058.5 | 15.83 | 99.8 |

The minimum (final) fluid pressure was about 59 psig, and the minimum (final) nozzle pressure was about 59 psig. The delivered volume of dispensable substance was 400 μL, and the final gas volume was 770 μL. The average velocity was 21.6 m/s. The total delivery time was 99.8 ms. The average velocity based on dispense time was 20.8 m/s.

Results—Initial Internal Pressure of 350 psig—4 Nozzles

The following properties were used in the model.

Initial internal pressure=350 psig

Fluid pressure=about 330 psig (peak; initial)

Nozzle pressure=about 330 psig (peak; initial)

Initial dose volume of dispensable substance=450 μL

Initial gas volume=370 μL

With these parameters, the modelling yielded the results shown in Tables 6A-6D (liquid pressure is the same as fluid pressure).

TABLE 6A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 24.1 | 22.8 | 330.0 | 38.3 |
| 2 | 50 | 420 | 20.2 | 18.8 | 273.1 | 34.8 |
| 3 | 100 | 470 | 17.3 | 15.9 | 230.4 | 31.9 |
| 4 | 150 | 520 | 15.0 | 13.6 | 197.3 | 29.5 |
| 5 | 200 | 570 | 13.2 | 11.8 | 171.1 | 27.4 |
| 6 | 250 | 620 | 11.7 | 10.3 | 149.9 | 25.6 |
| 7 | 300 | 670 | 10.5 | 9.1 | 132.4 | 24.1 |
| 8 | 350 | 720 | 9.5 | 8.1 | 117.8 | 22.7 |
| 9 | 400 | 770 | 8.6 | 7.3 | 105.4 | 21.4 |

TABLE 6B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.79E+03 | 7.16E−02 | 2.28E+06 | 22.75 | 0.00 |
| 2 | 1.62E+03 | 7.30E−02 | 1.88E+06 | 18.83 | 0.00 |
| 3 | 1.49E+03 | 7.43E−02 | 1.59E+06 | 15.88 | 0.00 |
| 4 | 1.38E+03 | 7.56E−02 | 1.36E+06 | 13.60 | 0.00 |
| 5 | 1.28E+03 | 7.69E−02 | 1.18E+06 | 11.80 | 0.00 |
| 6 | 1.20E+03 | 7.81E−02 | 1.03E+06 | 10.33 | 0.00 |
| 7 | 1.12E+03 | 7.94E−02 | 9.13E+05 | 9.13 | 0.00 |
| 8 | 1.06E+03 | 8.06E−02 | 8.12E+05 | 8.12 | 0.00 |
| 9 | 1.00E+03 | 8.18E−02 | 7.27E+05 | 7.27 | 0.00 |

TABLE 6C

| Model No. | Jet Impact Force (N) | Jet Impact Pressure (psi) | Jet Power (W) |
|---|---|---|---|
| 1 | 0.141 | 212.3 | 2.7 |
| 2 | 0.116 | 175.2 | 2.0 |
| 3 | 0.098 | 147.4 | 1.6 |
| 4 | 0.084 | 126.0 | 1.2 |
| 5 | 0.072 | 109.0 | 1.0 |
| 6 | 0.063 | 95.3 | 0.8 |
| 7 | 0.056 | 84.0 | 0.7 |

TABLE 6C-continued

| Model No. | Jet Impact Force (N) | Jet Impact Pressure (psi) | Jet Power (W) |
|---|---|---|---|
| 8 | 0.049 | 74.5 | 0.6 |
| 9 | 0.044 | 66.6 | 0.5 |

TABLE 6D

| Model No. | Flowrate per Orifice (m/s) | Total Flowrate (μL/s) | Time for Delivered Vol (ms) | Time from Start of Dose (ms) |
|---|---|---|---|---|
| 1 | 3.68E−06 | 14722.3 | | 0.0 |
| 2 | 3.34E−06 | 13375.8 | 3.56 | 3.6 |
| 3 | 3.07E−06 | 12270.4 | 3.90 | 7.5 |
| 4 | 2.84E−06 | 11342.7 | 4.23 | 11.7 |
| 5 | 2.64E−06 | 10550.1 | 4.57 | 16.3 |
| 6 | 2.47E−06 | 9862.8 | 4.90 | 21.2 |
| 7 | 2.31E−06 | 9259.3 | 5.23 | 26.4 |
| 8 | 2.18E−06 | 8723.7 | 5.56 | 32.0 |
| 9 | 2.06E−06 | 8244.0 | 5.89 | 37.8 |

The minimum (final) fluid pressure is about 105.4 psig, and the minimum (final) nozzle pressure is about 105.4 psig. The delivered volume of dispensable substance is 400 μL, and the final gas volume is 770 μL. The average velocity is 28.4 m/s. The total delivery time is 37.8 ms. The average velocity based on dispense time is 27.5 m/s.

Results—Initial Internal Pressure of 320 psig—4 Nozzles

The following properties were used in the model.

Initial internal pressure=320 psig

Fluid pressure=about 300 psig (peak; initial)

Nozzle pressure=about 300 psig (peak; initial)

Initial dose volume of dispensable substance=450 UL

Initial gas volume=370 μL

With these parameters, the modelling yielded the results shown in Tables 7A-7D (liquid pressure is the same as fluid pressure).

TABLE 7A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 22.1 | 20.7 | 300.0 | 36.5 |
| 2 | 50 | 420 | 18.5 | 17.1 | 247.9 | 33.1 |
| 3 | 100 | 470 | 15.8 | 14.4 | 208.9 | 30.3 |
| 4 | 150 | 520 | 13.7 | 12.3 | 178.7 | 28.0 |
| 5 | 200 | 570 | 12.0 | 10.7 | 154.7 | 26.0 |
| 6 | 250 | 620 | 10.7 | 9.3 | 135.3 | 24.3 |
| 7 | 300 | 670 | 9.6 | 8.2 | 119.3 | 22.8 |
| 8 | 350 | 720 | 8.7 | 7.3 | 106.0 | 21.5 |
| 9 | 400 | 770 | 7.9 | 6.5 | 94.7 | 20.3 |

TABLE 7B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.70E+03 | 7.23E−02 | 2.07E+06 | 20.68 | 0.00 |
| 2 | 1.54E+03 | 7.37E−02 | 1.71E+06 | 17.09 | 0.00 |
| 3 | 1.42E+03 | 7.51E−02 | 1.44E+06 | 14.40 | 0.00 |
| 4 | 1.31E+03 | 7.65E−02 | 1.23E+06 | 12.32 | 0.00 |
| 5 | 1.22E+03 | 7.78E−02 | 1.07E+06 | 10.67 | 0.00 |
| 6 | 1.14E+03 | 7.92E−02 | 9.33E+05 | 9.33 | 0.00 |
| 7 | 1.06E+03 | 8.05E−02 | 8.23E+05 | 8.23 | 0.00 |
| 8 | 1.00E+03 | 8.18E−02 | 7.31E+05 | 7.31 | 0.00 |
| 9 | 9.46E+02 | 8.31E−02 | 6.53E+05 | 6.53 | 0.00 |

TABLE 7C

| Model No. | Jet Impact Force (N) | Jet Impact Pressure (psi) | Jet Power (W) |
|---|---|---|---|
| 1 | 0.128 | 192.7 | 2.3 |
| 2 | 0.105 | 158.9 | 1.7 |
| 3 | 0.089 | 133.5 | 1.3 |
| 4 | 0.076 | 113.9 | 1.1 |
| 5 | 0.065 | 98.4 | 0.8 |
| 6 | 0.057 | 85.8 | 0.7 |
| 7 | 0.050 | 75.5 | 0.6 |
| 8 | 0.044 | 66.9 | 0.5 |
| 9 | 0.040 | 59.6 | 0.4 |

TABLE 7D

| Model No. | Flowrate per Orifice (m/s) | Total Flowrate (μL/s) | Time for Delivered Vol (ms) | Time from Start of Dose (ms) |
|---|---|---|---|---|
| 1 | 3.51E−06 | 14028.4 | | 0.0 |
| 2 | 3.18E−06 | 12736.9 | 3.74 | 3.7 |
| 3 | 2.92E−06 | 11676.1 | 4.10 | 7.8 |
| 4 | 2.70E−06 | 10785.3 | 4.45 | 12.3 |
| 5 | 2.51E−06 | 10023.7 | 4.81 | 17.1 |
| 6 | 2.34E−06 | 9362.7 | 5.16 | 22.2 |
| 7 | 2.20E−06 | 8781.9 | 5.51 | 27.8 |
| 8 | 2.07E−06 | 8266.0 | 5.87 | 33.6 |
| 9 | 1.95E−06 | 7803.5 | 6.22 | 39.8 |

The minimum (final) fluid pressure is about 94.7 psig, and the minimum (final) nozzle pressure is about 94.7 psig. The delivered volume of dispensable substance is 400 μL, and the final gas volume is 770 μL. The average velocity is 27.0 m/s. The total delivery time is 39.8 ms. The average velocity based on dispense time is 26.1 m/s.

Results—Summary

A summary of certain data for the ingestible devices with two nozzles is provided in Table 8 and FIGS. 33-47. "Drive Force Generator: Pre-compressed gas pressure (psig)" is the initial internal pressure, and "liquid pressure" is fluid pressure.

TABLE 8

| Drive Force Generator: Pre-compressed gas pressure (psig) | Peak Liquid Pressure (psig) | Peak Jet Velocity (m/s) | Peak Jet Power (W) |
|---|---|---|---|
| 320 | 300 | 36.5 | 2.3 |
| 300 | 280 | 35.2 | 2.1 |
| 270 | 250 | 33.2 | 1.8 |
| 220 | 200 | 29.7 | 1.3 |

A summary of certain data for the ingestible devices with four nozzles is provided in Table 9. "Drive Force Generator: Pre-compressed gas pressure (psig)" was the initial internal pressure, and "liquid pressure" is fluid pressure.

TABLE 9

| Drive Force Generator: Pre-compressed gas pressure (psig) | Peak Liquid Pressure (psig) | Peak Jet Velocity (m/s) | Peak Jet Power (W) |
|---|---|---|---|
| 350 | 330 | 38.3 | 2.7 |
| 320 | 300 | 36.5 | 2.3 |

Example 2—Jet Velocity Measurements

A high-speed video camera (Photron Fastcam SA3, using 2,000 frames per second) was used to measure the jet velocities of a dispensable substance (water) delivered from devices having different nozzle diameters and nozzle lengths. The receiving medium (external environment) was air. The nozzles were made of MicroFine Green Resin (an ABS-like material), using micro-resolution stereolithography (SLA).

The results are shown in Tables 10 AND 11. The first 12 nozzles in Table 10 correspond to nozzles depicted in FIGS. 6A-6L, respectively.

TABLE 10

| Nozzle Dia. (mm) | Nozzle Length (mm) | Throat Geometry | Internal Pressure (PSI) | Avg dispensing time (s) | Jet Dia at 5 mm | Peak (Initial) Jet Velocity based on dispensing time (m/s) | Peak (Initial) Jet Velocity based on Image processing |
|---|---|---|---|---|---|---|---|
| 0.35 | 0.5 | Rounded | 220 | 0.10 | 1.0 | 37.2 | 38.0 |
| 0.35 | 0.5 | Sharp | 220 | 0.12 | 1.5 | 32.1 | 33.5 |
| 0.35 | 1.5 | Rounded | 220 | 0.12 | 1.0 | 32.8 | 34.7 |
| 0.35 | 1.5 | Sharp | 220 | 0.13 | 0.8 | 29.7 | 36.0 |
| 0.35 | 1 | Rounded | 220 | 0.12 | 0.9 | 31.9 | 37.3 |
| 0.35 | 1 | Sharp | 220 | 0.12 | 0.9 | 32.3 | 32.0 |
| 0.5 | 0.5 | Rounded | 220 | 0.06 | 1.2 | 34.2 | 34.5 |
| 0.5 | 0.5 | Sharp | 220 | 0.07 | 1.3 | 28.9 | 28.0 |
| 0.5 | 1.5 | Rounded | 220 | 0.06 | 1.1 | 30.6 | 36.7 |
| 0.5 | 1.5 | Sharp | 220 | 0.07 | 1.3 | 27.9 | 26.5 |
| 0.5 | 1 | Rounded | 225 | 0.07 | 1.0 | 29.2 | 35.3 |
| 0.5 | 1 | Sharp | 220 | 0.08 | 1.1 | 25.3 | 32.0 |
| 0.5 | Detailed Geometry | | 220 | 0.06 | 1.2 | 29.7 | 33.3 |

TABLE 11

| Nozzle Dia (mm) | Nozzle entrance Shape | Avg Dispensing time (s) | Avg Velocity (m/s) |
|---|---|---|---|
| 0.35 | Rounded | 0.115 | 34.0 |
| 0.35 | Sharp | 0.124 | 31.4 |
| 0.5 | Rounded | 0.061 | 31.3 |
| 0.5 | Sharp | 0.070 | 27.4 |

Example 3—Comparison of PK/PD of Human Insulin Delivered by Subcutaneous or Jet Delivery in the Jejunum Using Euglycemic Clamp Technique in Swine A study was carried out to compare the pharmacokinetics (PK) and pharmacodynamics (PD) of regular human insulin (NOVOLIN® R) in swines after subcutaneous (SC) administration or intra-jejunal (IJ) administration via a single nozzle jet delivery device.

A total of 18 Yorkshire female swine in good health and weighing 60-70 kg each were included in this study. Swine were divided into two groups with 9 animals per group. All 9 animals in group 01 were administered a single subcutaneous injection of insulin aspart (NOVOLIN® R) (~40 U) on one side of the neck at a depth of ~5 mm. A sham surgical laparotomy was performed. All 9 animals in group 02 were administrated regular human insulin (NOVOLIN® R) (~40 U) delivered in the proximal jejunum by a jet delivery device placed by surgical laparotomy. The jet delivery device was configured with the single nozzle in an axial orientation. The device was held in place during the laparotomy insertion, and the nozzle outlet was directed to face the jejunal wall to direct the jet of the NOVOLIN® R to the GI tract. The device was pre-pressurized with compressed gas to have an internal pressure of about 225 psi, except where noted.

All animals were fasted overnight prior to the NOVOLIN® R administration. Swine were divided into two groups with 9 animals per group. Prior to NOVOLIN® R administration, the animals were anesthetized, and two vascular access catheters were placed. In all 18 animals, a laparotomy procedure was performed to expose the abdominal cavity. Animals remained under anesthesia during the entire procedure for the PK/PD study.

All 9 animals in group 01 were administered a single subcutaneous injection of insulin aspart (NOVOLIN® R) (~30 U) on one side of the neck at a depth of 5 mm.

All 9 animals in group 02 were dosed with regular human insulin (NOVOLIN® R) in the proximal jejunum by the single nozzle jet delivery device placed by surgical laparotomy.

For the laparotomy in group 02, a small segment of the jejunal mucosa and serosa was exposed by midline laparotomy and the jet delivery device was inserted through antimesenteric incision. Regular human insulin NOVOLIN® R (~40 U) was delivered by the jet delivery device, and the bowel and abdominal wall was closed.

For PK/PD blood collections, blood (approximately 3 mL, EDTA) samples were collected at −20, −10, 0, 10, 20, 30, 40, 50, 60, 75, 90, 105, 120, 150, 180, 210, 240, 270, 300, 330, 360, 390, and 420 minutes after dosing. Blood samples were kept on wet ice until centrifugation and separation of plasma. The plasma samples were stored −80° C. on the days of collection until delivered to AHDC Endocrinology Laboratory at Cornell University for insulin analyses. Glucose was monitored every five (5) minutes during the study by portable glucose analyzer (StatStrip (SS) hospital glucose monitoring system (Nova Biomedical, Waltham, MA)). At each time point, approximate 0.1 mL of blood was drawn and immediately placed on a glucose monitoring test strip, and the whole blood glucose concentration was measured by the SS in triplicate.

A euglycemic clamp procedure (ECP) was employed to compare pharmacokinetics and pharmacodynamics of regular human Insulin (NOVOLIN® R) delivered subcutaneously (SC) in the neck versus intra-jejunally (IJ) by the jet delivery device in the small intestine. ECP was used to quantify the amount of glucose required to maintain normoglycemia after exogenous bolus of insulin. ECP allowed both the glucose infusion rate (20% dextrose infusion) and total quantity to be calculated, which represented the effect of exogenous insulin on the disposition of blood glucose. ECP ensured pharmacologic suppression of the production of endogenous insulin. This study evaluated serum insulin concentration (pg/mL) over time and glucose infusion rate (to maintain a constant ~85 mg/dl BG) over the duration of the ECP (7 hours; 420 min.). The animals were anesthetized for the entire ECP. The endpoints included a comparison of selected pharmacokinetic parameters for insulin, including $t_{1/2}$ (min), $C_{max}$ (pg/mL), $T_{max}$ (min) and $AUC_{0-420min}$ (ng·h/mL), as well as pharmacodynamic parameters such as the rate (mg/kg/min) and amount of glucose (mg/kg) infused.

At the end of the study, all animals were euthanized and animals in group 02 underwent gross necropsy for histopathologic evaluation of the proximal jejunum where the NOVOLIN® R was administrated.

Results

Figure 48:
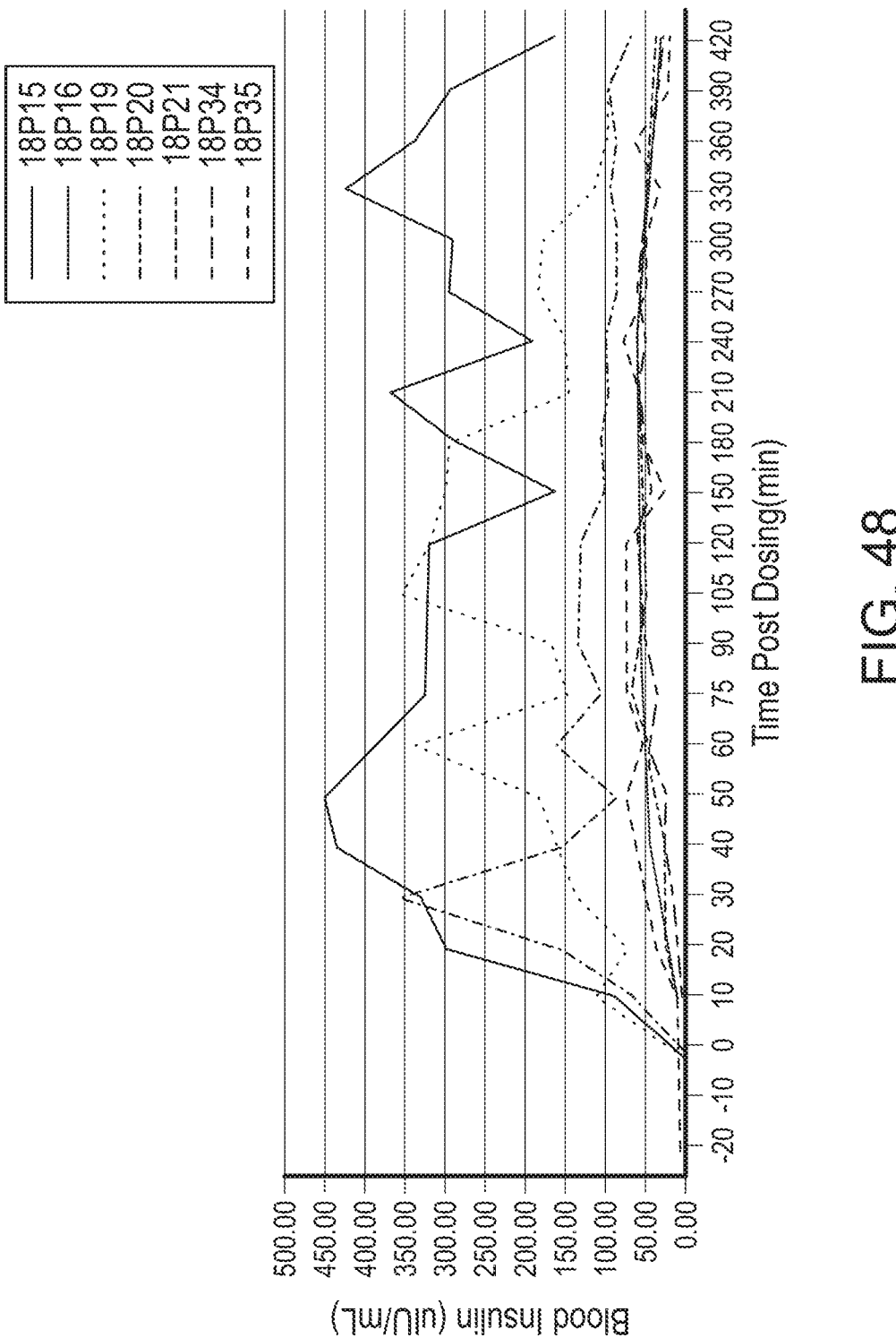
FIG. 48 shows blood insulin levels in swine after subcutaneous (SC) administration.
Figure 49:
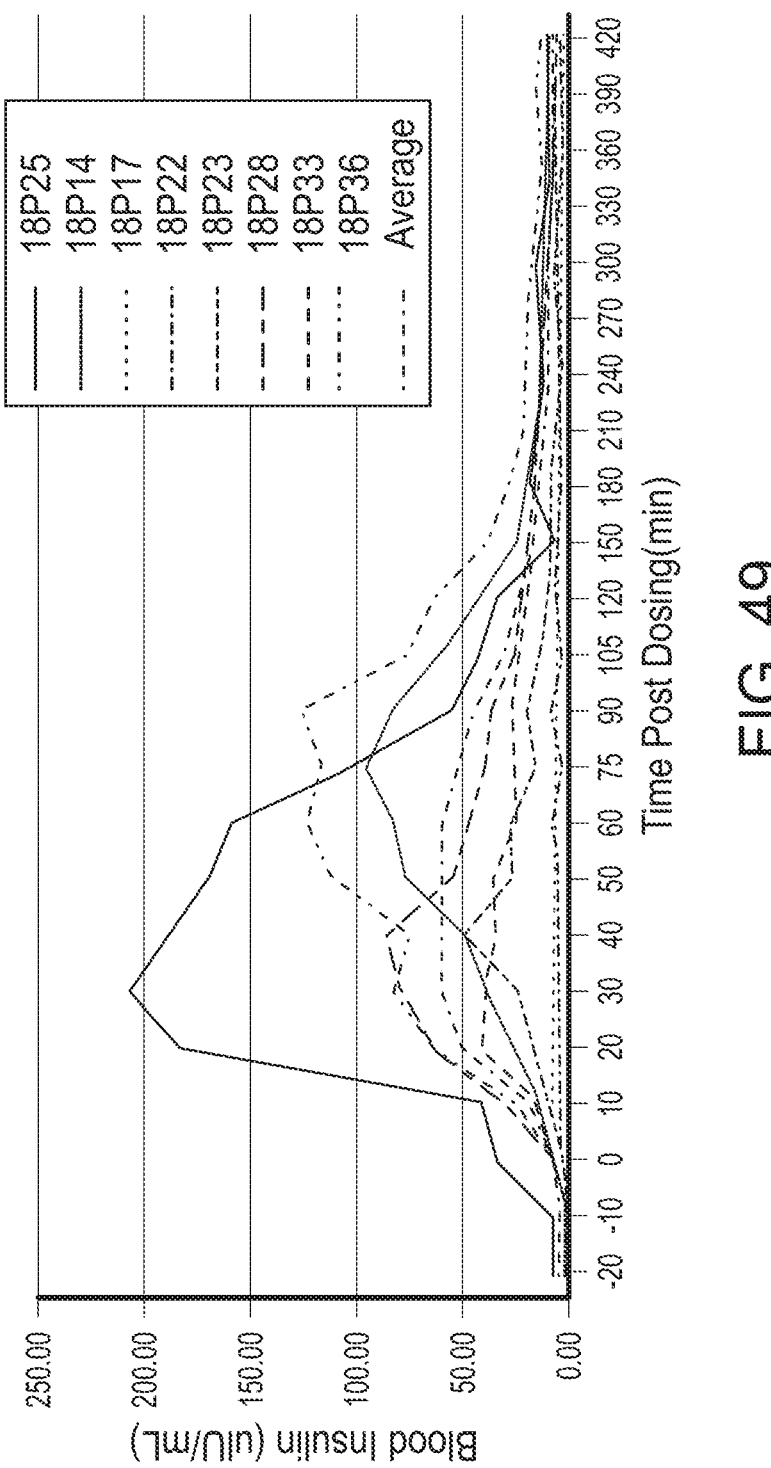
FIG. 49 shows blood insulin levels in swine after jejunum (IJ) administration.

FIG. 48 and FIG. 49 show blood insulin levels for each animal. The area under the concentration-time curve ($AUC_{0-420min}$) of the blood insulin, maximum plasma concentration $C_{max}$ (uIU/mL), and time to maximum plasma concentration ($T_{max}$) were calculated for each animal.

Figure 50:
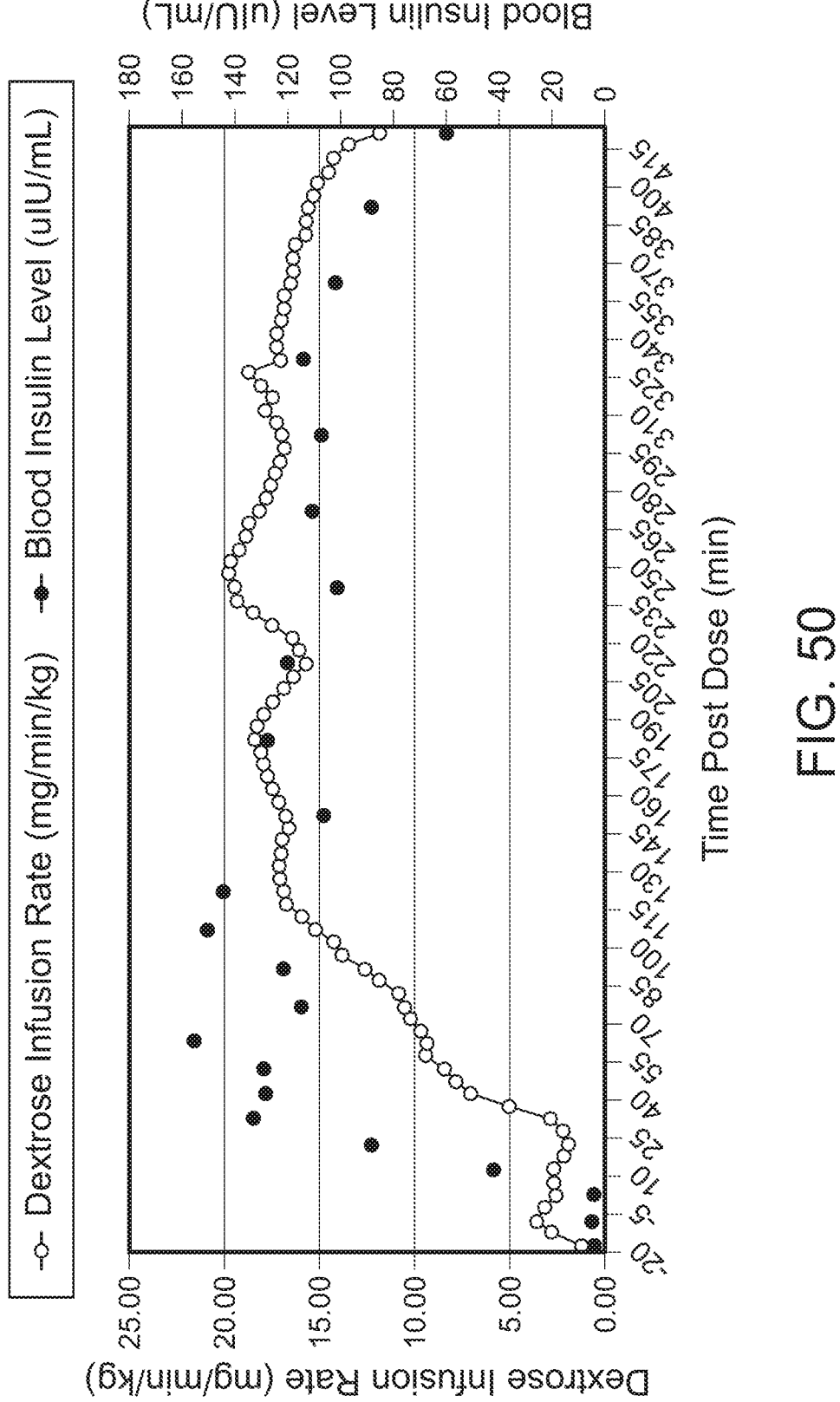
FIG. 50 shows blood insulin levels and dextrose infusion rates in the SC administration group.
Figure 51:
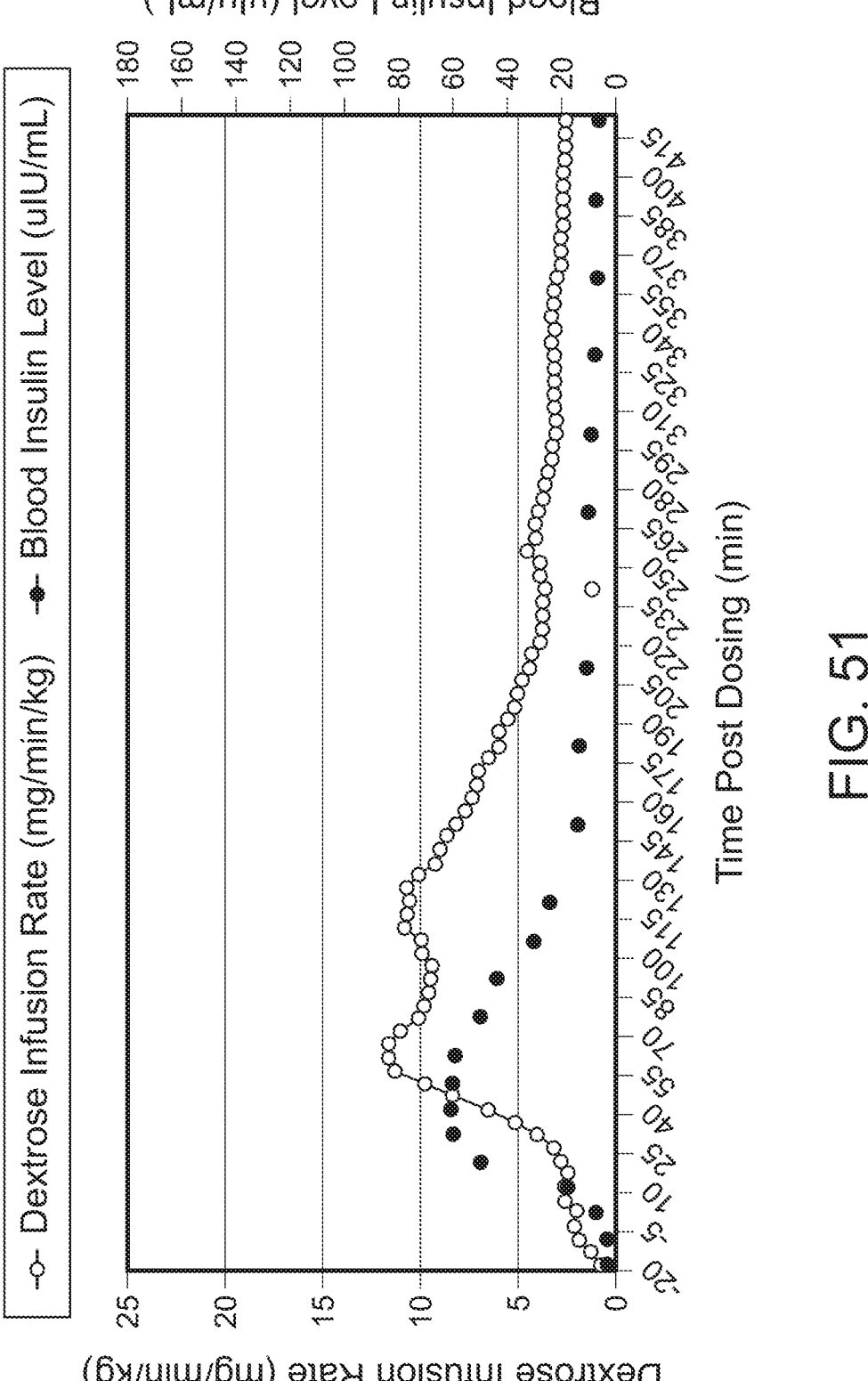
FIG. 51 shows blood insulin levels and dextrose infusion rates in the IJ administration group.

FIG. 50 and FIG. 51 show blood insulin levels (uIU/mL) and dextrose infusion rates (mg/min/kg) in SC and IJ administration groups, respectively.

Blood insulin results for SC and IJ administrations are shown in Tables 12 and 13, respectively.

TABLE 12

| | SC Administration | | | | | | | |
|---|---|---|---|---|---|---|---|---|
| Animal ID | 18P15 | 18P16 | 18P19 | 18P20 | 18P21 | 18P34 | 18P35 | Average* |
| $AUC_{(0-420min)}$ | 124486 | 20281 | 75580 | 45338 | 19729 | 17811 | 21211 | 46348 |
| $C_{max}$ (uIU/mL) | 451.00 | 60.74 | 354.00 | 356.60 | 65.71 | 59.18 | 73.34 | 202.94 |
| $T_{max}$ (min) | 50 | 180 | 105 | 30 | 75 | 120 | 50 | 87.14 |

TABLE 13

| | | | | IJ Administration | | | | | |
|---|---|---|---|---|---|---|---|---|---|
| Animal ID | 18P25 | 18P14 | 18P17 | 18P22 | 18P23 | 18P28 | 18P33 | 18P36 | Average* |
| $AUC_{(0-420\,min)}$ | 7677 | 11588 | 1389 | 2229 | 4024 | 8797 | 17046 | 17075 | 8728 |
| $C_{max}$ (ulU/mL) | 40.93 | 96.77 | 5.03 | 7.96 | 48.77 | 85.38 | 207.96 | 126.39 | 77.40 |
| $T_{max}$ (min) | 20 | 75 | 50 | 90 | 40 | 40 | 40 | 90 | 55.63 |

*Results from animal 18P29 and 18P24 were excluded from blood insulin PK analysis, blood glucose analysis, and Dextrose infusion calculation; animal 18P29 received only 30 U insulin, while animal 18P24 received 30 U insulin at 150 psig. Animal 18P18 was also excluded from the blood insulin calculation due to unknown abnormal results as compared with all the other animals.

The mean blood glucose level in SC administration group was 83.5 mg/dl, which was very similar to IJ administration group (89.6 mg/dL). The mean dextrose infusion rate was higher in the IJ administration group in the first 70 minutes after Novolin® R administration. From 75 minutes to 420 minutes post-Novolin® R administration, the mean dextrose infusion rate was higher in the SC administration group.

The AUC and the maximum plasma concentration $C_{max}$ in the SC administration group was higher than that of the IJ administration group. The time to maximum plasma concentration ($T_{max}$) was 55.63 minutes in jejunum administration group whereas in the subcutaneous administration group, $T_{max}$ was 87.14 minutes.

The blood insulin level in animal 18P18 (SC administration group) was significantly higher than the rest of the animals in the group. The reason was unknown. The blood insulin levels post-dosing in animal 18P17 and 18P22 were similar to the baseline indicating that IJ administration of the Novolin® R via the jet delivery device in these animals may not have been successful.

Example 4—Evaluation of Target Internal Pressure Range for Submucosal Delivery Using an Ingestible 2-Nozzle Jet Delivery Device by Bench Test Jetting of India Ink into Porcine Jejunal Tissue Ex Vivo A study was conducted to identify the internal pressure range for trans-epithelial delivery of a drug payload into porcine jejunal submucosal tissue ex vivo using India ink as a drug surrogate.

Test Article

India Ink was used in this study.

Ingestible Device Configuration

Each ingestible device used in this study was configured as a capsule containing a substance reservoir (volume: 450 L); two (2) gas reservoirs; a check valve; a floating piston; two (2) nozzles radially configured 180 degrees apart; a lid at one end of the capsule; and a pneumatic control line ((polyetheretherketone (PEEK) tubing) attached to the lid). The first gas reservoir was positioned behind the substance reservoir and was used to drive the substance (India ink) from the substance reservoir. The floating piston separated the substance reservoir from the first gas reservoir. The second gas reservoir was positioned beneath the lid and used only to open the lid. Although it was previously demonstrated that a single pressurized gas reservoir can be used to both open the lid and eject the substance (e.g., drug; data not shown), the use of two separate gas reservoirs in this study was intended to demonstrate independent assessment of the action of the triggering mechanism (lid opening) and the substance ejection parameters.

Configuration of ingestible device with tissue: Porcine jejunum tissue, previously flash frozen in liquid $N_2$ and then stored at −80° C., was thawed and used as the source tissue for testing. In a biological safety cabinet, one side of the jejunum was sealed with a zap strap and stopper. The ingestible device was then inserted into the lumen of the jejunum. Finally, a zap strap fixed the proximal portion of the jejunum to the pneumatic control line.

Device pressurization: An external pressure chamber was connected to an air compressor. Two pressure gauges were used: one was fitted onto the air compressor and a second NIST-certified pressure gauge was placed in-line with the pressure chamber and the air compressor.

The first and second gas reservoirs of each device were pressurized separately. To pressurize the first gas reservoir, the device was placed in the pressure chamber and then pressurized to its target internal pressure (200 psig to 350 psig). The pressure chamber was then depressurized back to ambient atmospheric pressure. The ingestible device was then removed from the chamber, after which it maintained the target internal pressure by way of the check valve. To pressurize the second gas reservoir, the ingestible device control line was directly attached to the air compressor via an in-line valve. The valve was turned manually to pressurize the second gas reservoir to 350 psig.

Ex Vivo Jetting Study Protocol and Results

Briefly, a total of five (5) capsules were used in this study and a single ingestible device was used per test. Prior to testing, each ingestible device (attached to the control line) was filled with a 450 μL payload of substance (India ink). The first gas reservoir was then pressurized with air to its target internal pressure of 200 psig, 250 psig, 300 psig or 350 psig, as described above; the pressure was read from the in-line NIST gauge, which was in agreement with the pressure reading from the air compressor gauge. At the time of testing, the pressurized device configured with tissue was placed within a blast shield. Then the second gas reservoir (initially at ambient atmospheric pressure) was quickly pressurized to 350 psig, as described above. Pressurizing the second gas reservoir opened the lid, exposing the ingestible device nozzles. The internal pressure in the first gas reservoir ejected the India ink from the substance reservoir through the two (2) radially-configured nozzles towards the porcine jejunum tissue surrounding the ingestible device. Pre- and post-deployment device weights and diameters were recorded throughout the study to confirm proper device loading/dispensing volumes and pressurization, respectively. The jejunal tissue was then removed from the ingestible device and rinsed in 10% neutral buffered formalin (NBF) and deionized water for photography. The deployed device was disinfected and dried prior to obtaining its post-pressurization weight.

Pressure tests were performed at 200 psig, 250 psig, 300 psig and 350 psig, and visual observations were made after washing the tissue. The results are summarized in Table 14. The test result was assigned as PASS if the substance delivered from the device passed through the jejunal tissue without tissue rupture or blow through of ink to the outside of the jejunal tissue, or FAIL if the substance delivered from the device was not observed to pass through the jejunal tissue or if tissue rupture or blow through of ink to the outside of the jejunal tissue occurred.

TABLE 14

| Device ID | Pressure Test (psi) | Result | Observations |
|---|---|---|---|
| 81 | 200 | FAIL | All ink deployed from device. No conclusive injection sites could be seen after washing the tissue, and no passing through tissue observed. |
| 52 | 250 | PASS | Two injection boluses observed, one of which was very faint. Each was markedly smaller than that observed with the 300 psig or 350 g psi injections. |
| 95 | 300 | PASS | All ink deployed from device. India ink observed inside of the lumen. One bolus clearly identified. Second injection site lost during excision process. |
| 92 | 300 | ABORT | Pressure leak detected prior to deployment. Test aborted. |
| 84 | 300 | PASS | All ink deployed from device. Two ink boluses observed. Possible asymmetry noted in bolus sizes. Ink deposited in the lumen. |
| 82 | 350 | PASS | All ink deployed from device. Two ink boluses observed, with one bolus noticeably smaller than other. |

Example 5—Identification of the Target Internal Pressure Range of an Ingestible 2-Nozzle Jet Delivery Device by Evaluating the Bioavailability of Adalimumab in Female Yorkshire Pigs A study was conducted to identify the target internal pressure range of an ingestible 2-nozzle jet delivery device required to achieve systemic uptake of adalimumab. In this study, the plasma pharmacokinetics of adalimumab were evaluated in female Yorkshire pigs after intravenous (IV), subcutaneous (SC), or intraduodenal (ID) administration via an endoscopically placed ingestible device.

Test Article

Adalimumab in an aqueous buffer having an adalimumab concentration of about 106 mg/mL.

Ingestible Device Configuration

Each ingestible device was configured as a capsule comprising a substance reservoir; a gas reservoir; a one-way duckbill valve; a piston; two nozzles radially configured 180 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig, 270 psig, or 220 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the amount of test article delivered was determined. Typically, approximately 0.050 mL was retained in the ingestible device after test article delivery was completed. Thus, approximately 0.400 mL of test article was dispensed from each ingestible device.

A summary of parameters for the delivery of the test article via the ingestible device is provided in Table 15. Initial and final refer to values at the beginning and end of the dispensing period for the test article, respectively.

TABLE 15

| Parameters for test article delivery from ingestible device | Internal pressure (pressure of pre-compressed gas): about 320 psig | Internal pressure (pressure of pre-compressed gas): about 270 psig | Internal pressure (pressure of pre-compressed gas): about 220 psig |
|---|---|---|---|
| Pre-compressed gas volume in ingestible device | about 370 microliters (initial) to about 770 microliters (final) | | |
| Nozzle diameter | 0.35 mm | | |
| Nozzle length | 2 mm | | |
| Nozzle throat geometry | circular, sharp-edged orifice | | |
| Piston diameter | 9.6 mm | | |

TABLE 15-continued

| Parameters for test article delivery from ingestible device | Internal pressure (pressure of pre-compressed gas): about 320 psig | Internal pressure (pressure of pre-compressed gas): about 270 psig | Internal pressure (pressure of pre-compressed gas): about 220 psig |
|---|---|---|---|
| Piston friction | 10N (one (1) O-ring on piston) | | |
| Friction pressure loss | about 20 psig | | |
| Nozzle stand-off distance | ≥1.5 mm | | |
| Device diameter | 11.6 mm | | |
| Device length | about 34 to 36 mm | | |
| Fluid pressure | about 300 psig (peak; initial) to about 95 psig (minimum; final) | about 250 psig (peak; initial) to about 77 psig (minimum; final) | about 200 psig (peak; initial) to about 59 psig (minimum; final |
| Jet velocity | about 36.5 m/s (peak; initial) to about 20 m/s (minimum; final) | about 33 m/s (peak; initial) to about 18 m/s (minimum; final) | about 30 m/s (peak; initial) to about 16 m/s (minimum; final) |
| Mean jet velocity | about 26 to 27 m/s | about 23 to 25 m/s | about 20 to 22 m/s |
| Fluid dispensing time (total) | about 80 ms | about 88 ms | about 100 ms |
| Jet impact force | about 0.13N (peak; initial) to about 0.04N (minimum; final) | about 0.11N (peak; initial) to about 0.03N (minimum; final) | about 0.09 (peak; initial) to about 0.02 (minimum; final) |
| Jet impact pressure | about 193 psig (peak; initial) to about 60 psig (minimum; final) | about 160 psig (peak; initial) to about 48 psig (minimum; final) | about 128 psig (peak; initial) to about 37 psig (minimum; final) |
| Jet power | about 2.3 W (peak; initial) to about 0.4 W (minimum; final) | about 1.8 W (peak; initial) to about 0.3 W (minimum; final) | about 1.3 W (peak; initial) to about 0.2 W (minimum; final) |
| Jet diameter | about 0.35 mm (initial) | about 0.35 mm (initial) | about 0.35 mm (initial) |

In Vivo Study Design

A total of 21 healthy female Yorkshire pigs (*Sus scrofa domesticus*) having a body weight of 25-30 kg were used in this study. Five (N=5) were used in each of dose Groups 1-3 (intraduodenal (ID) administration via an endoscopically placed ingestible device), and three (N=3) were used in each of dose Group 4 (SC administration) and dose Group 5 (IV administration). The study design is shown below in Table 16.

day 3: group 3 (n=3), and group 2 (n=2); Dose day 4: groups 4 (n=3), and group 5 (n=3). Following the 240-hour post-dose blood collection the animal was euthanized via euthanasia solution IV bolus dose.

Routes of Administration

For intraduodenal (ID) administration, the ingestible device was attached to an endoscope (Olympus OSF-V60 attached to an Olympus CV60 Tower) via a working channel and maneuvered into the pyloric sphincter with camera

TABLE 16

| Group # | Dose Route | N | Dose | Dose Conc. | Internal Device Pressure or Volume | Clinical Observations | Blood Collection Time Points | Termination & Necropsy |
|---|---|---|---|---|---|---|---|---|
| 1 | ID (Device) | 5 | 40 mg | 106 mg/mL | 220 PSIG | Twice on the day of each endoscopic event, and 24, 72, 144, and 240 hours post dose | Pre-dose, 1, 3, 6, 8, 24, 72, 144, and 240 hours post dose | Termination and necropsy of the injection site to assess signs of hematoma and gross lesions (Day 10 post-dose) |
| 2 | ID (Device) | 5 | 40 mg | 106 mg/mL | 270 PSIG | | | |
| 3 | ID (Device) | 5 | 40 mg | 106 mg/mL | 320 PSIG | | | |
| 4 | SC | 3 | 40 mg | 107 mg/mL | 0.373 mL | | | N/A, animals are to be survived |
| 5 | IV | 3 | 40 mg | 107 mg/mL | 0.373 mL | | | |

Figure 52:
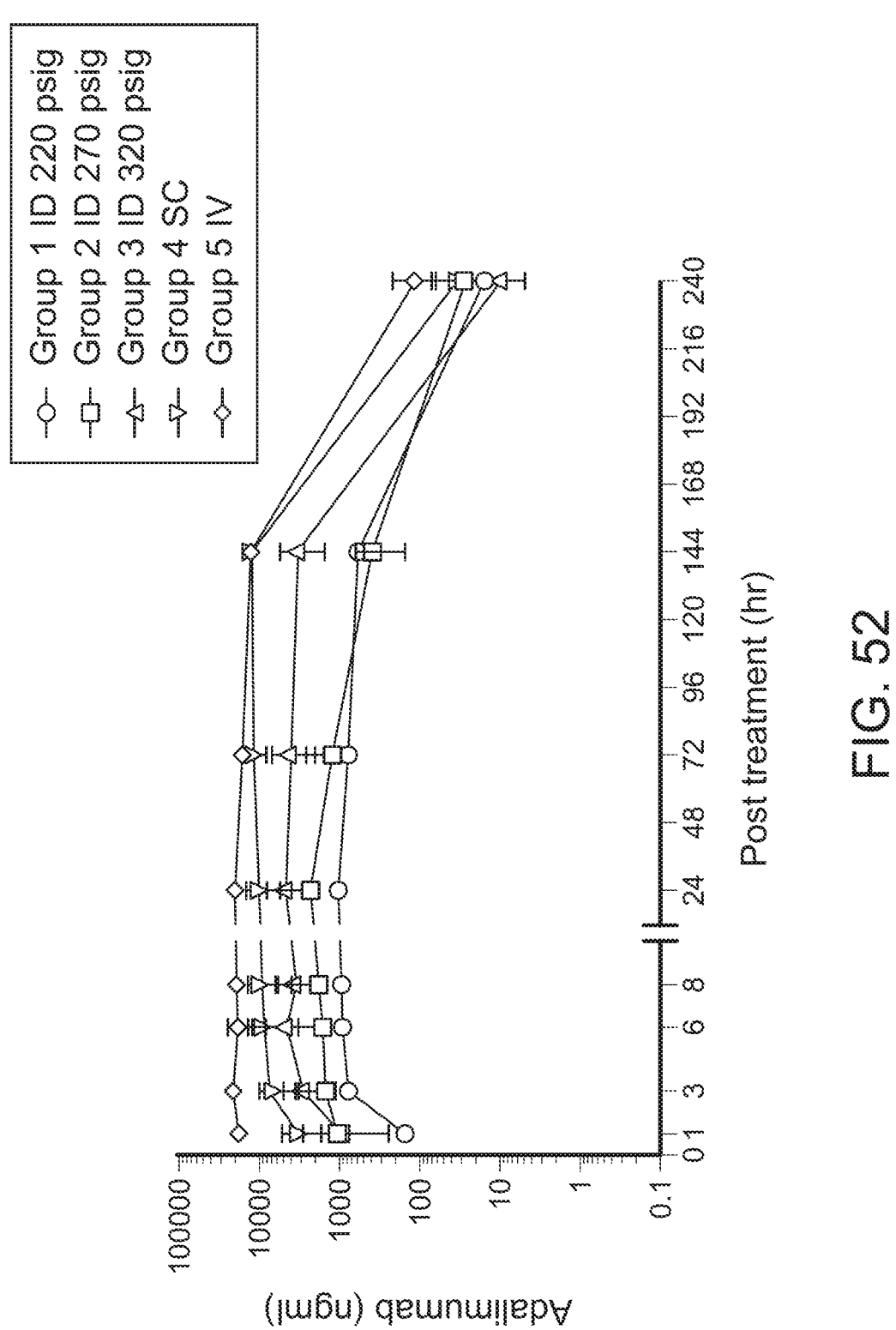
FIG. 52 shows adalimumab concentration in swine plasma over 10 days after: ID administration via the endoscopically placed ingestible device having an internal pressure of 220 psig, 270 psig or 320 psig; SC administration; and IV administration.

Animals were housed two per cage and fasted for a minimum of 12 hours prior to dosing. Food was returned at 4 hours post-dose. Water was supplied ad libitum. The dosing was as follows: Dose day 1: group 1 (n=3), and group 3 (n=2); Dose day 2: group 2 (n=3), and group 1 (n=2); Dose visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual obser- Results The results are summarized in Table 17. FIG. 52 charts the adalimumab plasma concentration over 10 days for each group.

TABLE 17

| | 2 Nozzle Jet Delivery Device | | | Controls | |
|---|---|---|---|---|---|
| | Group 1: 220 PSIG | Group 2: 270 PSIG | Group 3: 320 PSIG | Group 4: SC | Group 5: IV |
| Route | ID | ID | ID | SC | IV |
| N | 2 | 4 | 5 | 3 | 3 |
| $T_{max}$ (days) | 1 | 1 | 1 | 6 | 0.13 |
| $C_{max}$ (µg/mL) | 0.57 | 2.27 | 5.00 | 12.60 | 20.92 |
| AUC (µg · day/mL) (± SEM) | 3.32 ± 2.59 | 8.50 ± 4.16 | 32.31 ± 8.09 | 91.87 ± 12.58 | 122.67 ± 7.68 |
| AUC (µg · day/mL) Corrected for dose (± SEM) | 3.02 ± 2.31 | 8.19 ± 3.62 | 32.50 ± 8.10 | N/A | N/A |
| Bioavailability over IV[a] (%) | 2.46 ± 1.88 | 6.68 ± 2.95 | 26.25 ± 6.60 | 74.89 ± 10.26 | 100 |
| Bioavailability over SC[a] (%) | 3.28 ± 2.51 | 8.92 ± 3.94 | 35.38 ± 8.82 | 100 | Not calculated |

[a]AUC corrected for dose was used to calculate bioavailability.

vation of the injection site. The capsule and endoscope were then retracted out of the body.

For intravenous (IV) administration, the test article was administered intravenously via bolus dose into the marginal ear vein followed by a 1 mL flush with saline if necessary.

For subcutaneous (SC) administration, animals were placed in dorsal recumbence and the SC injection site asceptically prepared with alcohol. The test article was administered as an SC injection into a "skin tent" on the belly of the pig.

Sampling and Analysis

Plasma samples were collected at pre-dose, 1, 3, 6, 8, 24, 72, 144, and 240 hours post-dose in all animals. Each blood sample was collected from the pig jugular vein, or other suitable vessel via direct venipuncture, placed into a chilled tube containing K2-EDTA as the anticoagulant, and inverted several times to mix. Blood samples were kept on wet ice until centrifugation. Blood samples were centrifuged at a temperature of 4° C., at 3,000×g, for 5 minutes and chilled throughout processing. Plasma was collected into pre-labeled polypropylene tubes and placed in a freezer set to maintain −60 to −80° C. prior to analysis.

Samples were processed and analyzed by using an adalimumab (anti-TNF-alpha) ELISA kit from Alpha Diagnostics, Inc. (Catalog #200 310-AHG). All plasma samples were diluted by 1:100 dilution. Plasma samples were reanalyzed with a 1:1000 dilution from animals 6287, 6289, 6332, 6334, 6336, 6149, 6335, and 6337. Plasma samples close to the lower limit of quantification (LLOQ) were repeated with a 1:5 dilution from animals 6138 and 6137. The final concentrations of adalimumab in these two animals were lower than previously shown, suggesting that these values were at the limits of detection and were not reliable. Therefore, the data from animal 6138 and 6137 were not included in the final PK analysis. All data and pharmacokinetic parameters were analyzed and graphed by using GraphPad Prism version 7.00 for Windows, GraphPad Software, La Jolla California USA, www.graphpad.com (GraphPad Prism 7). The area under the concentration curve (AUC) was calculated with the trapezoidal rules.

Example 6—Evaluation of the Bioavailability of Dulaglutide after Intraduodenal Administration Via an Ingestible 2-Nozzle Jet Delivery Device in Female Yorkshire Pigs A study was performed to determine the plasma pharmacokinetics of dulaglutide in female Yorkshire pigs after intravenous (IV), subcutaneous (SC), or intraduodenal (ID) administration via an endoscopically placed ingestible device.

Test Article

TRULICITY® (dulaglutide solution) having a dulaglutide concentration of 1.5 mg/0.5 mL (i.e., 3 mg/mL) was used in this study. Dulaglutide is a long-acting glucagon-like peptide 1 (GLP-1) receptor agonist having a molecular weight of about 63 kDa. The molecule consists of 2 identical disulfide-linked chains, each containing a modified human GLP-1 analogue sequence covalently linked to a modified human immunoglobulin G4 (IgG4) heavy chain fragment (Fc) by a small peptide linker. The GLP-1 analogue portion of dulaglutide is approximately 90% homologous to native human GLP-1 (7-37).

Ingestible Device Configuration

Each ingestible device was configured as a capsule comprising a substance reservoir; a gas reservoir; a one-way duckbill valve; a piston; two nozzles radially configured 180 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device;

the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the Jet impact pressure: 193 psig (peak; initial) to about 60 psig (minimum; final)

Jet power: 2.3 W (peak; initial) to about 0.4 W (minimum; final)

Jet diameter: about 0.35 mm (initial)

Nozzle stand-off distance: ≥1.5 mm

Device diameter: 11.6 mm

Device length: about 34 to 36 mm

In Vivo Study Design

A total of 11 healthy female Yorkshire pigs (*Sus scrofa domesticus*) were used for the study: n=5 for ID administration, n=3 for IV administration, and n=3 for SC administration. Each pig weighed between about 25-30 kg at the initiation of the study. A 1.2 mg (~0.04 mg/kg) dose of the dulaglutide solution was administered to each pig by either ID administration via the endoscopically placed ingestible device (Group 1), IV administration (Group 2), or SC administration (Group 3). The study design is shown below in Table 18.

TABLE 18

| | | | | | | Blood | |
| | | | | Dose | | Collection | |
| Group | Dose | | | Conc. | Clinical | Time | Termination & |
| # | Route | N | Dose | (mg/mL) | Observations | Points | Necropsy |
|---|---|---|---|---|---|---|---|
| 1 | ID | 5 | 1.2 mg (0.4 mL) | 3 | Twice on the | Pre-dose, | At |
| 2 | IV | 3 | (~0.04 mg/kg) | | day of each | 1, 3, 6, 8, | termination, |
| 3 | SC | 3 | | | dose | 24, 72, | necropsy of |
| | | | | | administration, | 144, and | abdominal |
| | | | | | and 24, 72, | 240 hours | region to |
| | | | | | 144, and 240 | post dose | assess |
| | | | | | hours post | | signs of |
| | | | | | dose | | hematoma |
| | | | | | | | and gross |
| | | | | | | | lesions | amount of test article delivered was determined. Typically, approximately 0.050 mL was retained in the ingestible device after test article delivery was completed. Thus, approximately 0.400 mL of test article was dispensed from each ingestible device.

A summary of parameters for the delivery of the test article solution via the ingestible device is provided below. Initial and final refer to values at the beginning and end of the dispensing period for the test article, respectively.

Internal pressure (pressure of pre-compressed gas): about 320 psig

Pre-compressed gas volume in ingestible device: about 370 microliters (initial) to about 770 microliters (final)

Nozzle diameter: 0.35 mm

Nozzle length: 2 mm

Nozzle throat geometry: circular, sharp-edged orifice

Piston diameter: 9.6 mm

Piston friction: 10 N (one (1) O-ring on piston)

Friction pressure loss: about 20 psig

Fluid pressure: about 300 psig (peak; initial) to about 95 psig (minimum; final)

Jet velocity: about 36.5 m/s (peak; initial) to about 20 psig (minimum; final)

Mean jet velocity: about 26 to 27 m/s

Fluid dispensing time (total): about 80 ms

Jet impact force: about 0.13 N (peak; initial) to about 0.04 N (minimum; final)

Dulaglutide solution was administered at t=0 on the day of dosing. The animals were anesthetized with an intramuscular injection of a cocktail containing ketamine (approximately 10-20 mg/kg), xylazine (approximately 1-2 mg/kg) and atropine (approximately 0.02-0.04 mg/kg). The animals were intubated and maintained using isoflurane (approximately 3-5% in oxygen 1 to 4 L/min) as necessary until dosing was complete. The animals were wakened post dose. Routes of Administration For intraduodenal (ID) administration, the ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

For intravenous (IV) administration, the test article was administered intravenously via bolus dose into the marginal ear vein followed by a 1 mL flush with saline if necessary.

For subcutaneous (SC) administration, the test article was administered into the dorsal subcutaneous space directly at the base of the pig. Dose sites were gently shaved and circled with marker pen for identifying the injection site.

Sampling

Each blood sample (~2.0 mL) were taken from the jugular vein (or other suitable vessel) of each pig via direct venipuncture. The samples were collected into chilled tubes with K2EDTA as the anticoagulant, and inverted several times to mix. Blood samples were kept on wet ice until centrifugation. The blood samples were centrifuged at a temperature of 4° C., at 3,000×g, for 5 minutes. All samples were maintained chilled throughout processing. Plasma was collected into pre-labeled 2-mL microcentrifuge tubes and placed in a freezer set to maintain a temperature of –60° C. to –80° C. until further analysis by ELISA assay. The samples were taken prior to dosing, then again at 1, 3, 6, 8, 24, 72, 144, and 240 hours post-dose and sent to an off-site laboratory for bioanalytical analysis. Following the 240 hour post dose blood collection, the animals were euthanized via euthanasia solution IV bolus dose.

Analysis

Samples were processed and analyzed by using an enzyme-linked immunosorbent assay (ELISA) modified from a validated ELISA method for detecting dulaglutide in monkey serum (Vahle et al., Toxicol. Pathol. 43:1004-1014, 2015).

Briefly, 96-well microtiter plates were coated with mouse anti-human IgG (Fc) antibody (0.5 µg/mL) (Southern Bio- Non-compartmental analysis was used to determine PK parameters for each subject. $AUC_{T0-T240h}$, half-life, clearance, $C_{max}$ and $T_{max}$ were determined for each subject. The bioavailability of dulaglutide via ID administration (Group 1) in comparison to the IV (Group 2) and SC (Group 3) administrations was determined.

Results

Figure 53A:
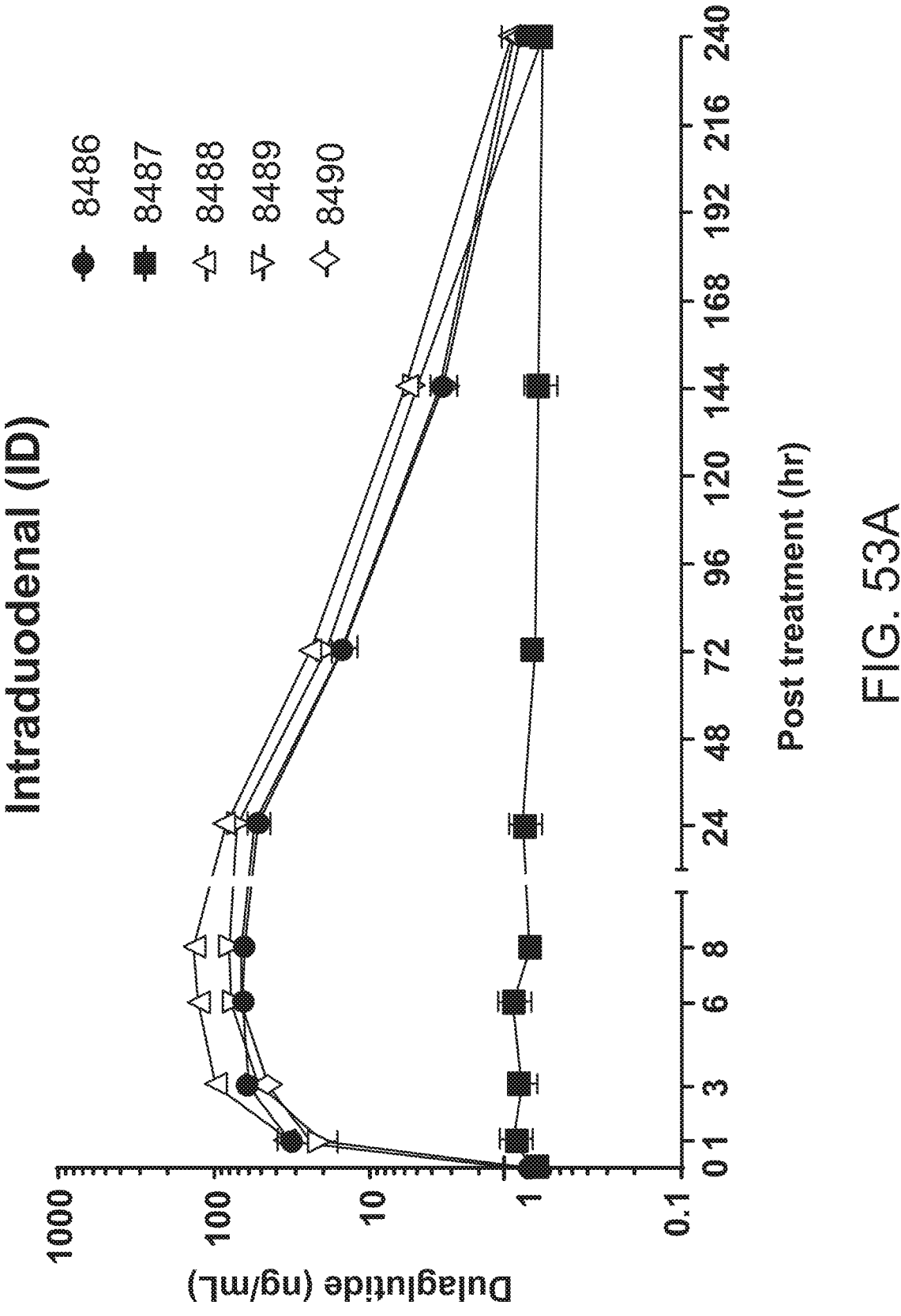
FIGS. 53A-53C show dulaglutide concentration in blood over time after: ID administration via the endoscopically placed ingestible device an internal pressure of 320 psig (FIG. 53A); SC administration (FIG. 53B); and IV administration (FIG. 53C).
Figure 53B:
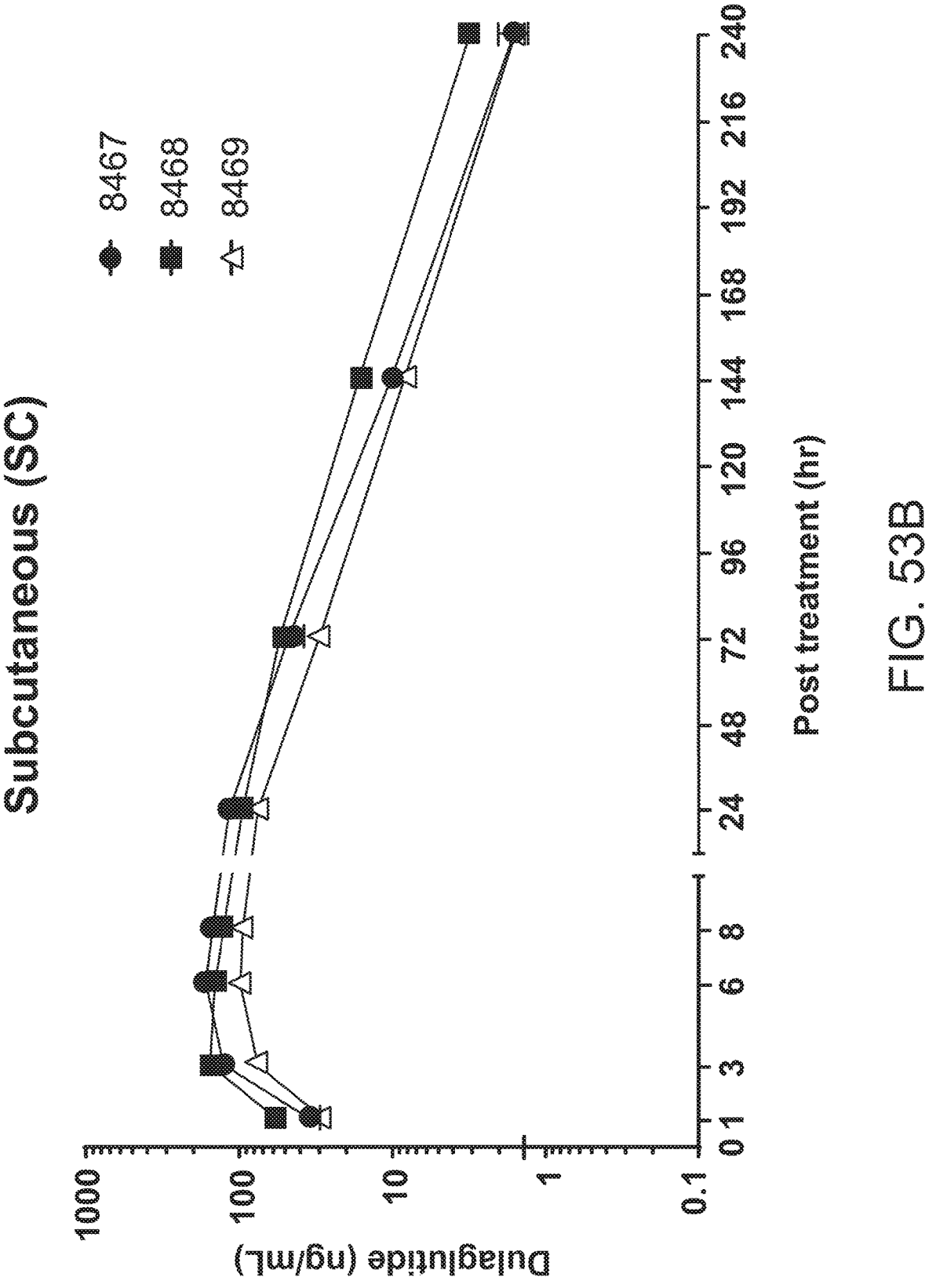
Figure 53C:
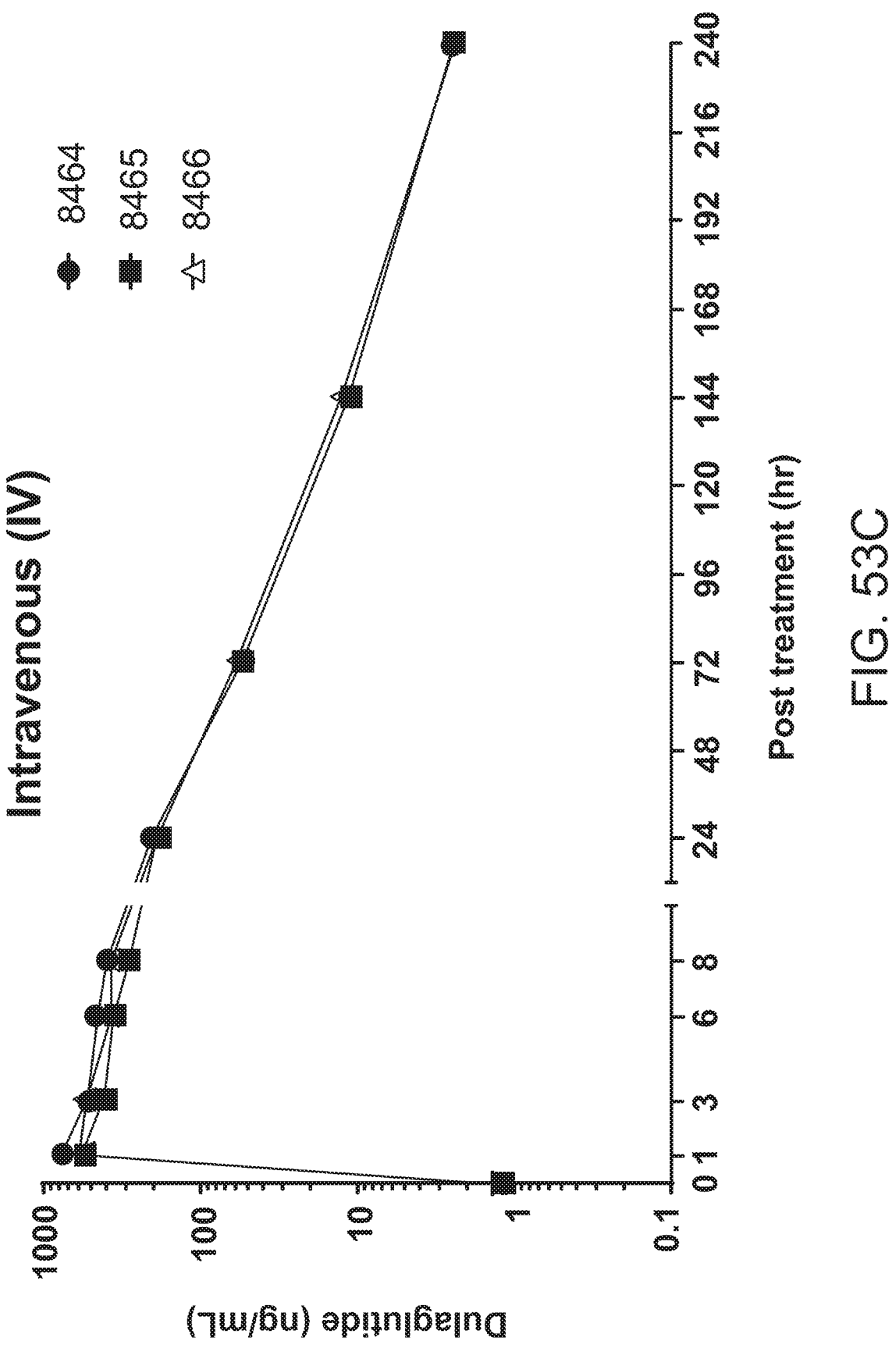

The results of the study are shown in Table 19 and in FIGS. 53A-53C and FIG. 54. FIGS. 53A-53C show the dulaglutide concentration in blood over time after: ID administration via the endoscopically placed ingestible device (FIG. 53A); SC administration (FIG. 53B); and IV administration (FIG. 53C). The plasma level of dulaglutide in one animal in Group 1 (no. 8487; ID) was below the limit of detection of the ELISA assay. Data obtained from this animal were excluded from subsequent bioavailability determinations. Prior to exclusion of these data, the ratio of the area under a curve (AUC) of the therapeutic agent concentration in systemic circulation versus time that was achieved when the drug was administered by the ID route ($AUC_{ID}$ (ng.hr/mL±SEM)) was 3890.00±94.73.

Figure 54:
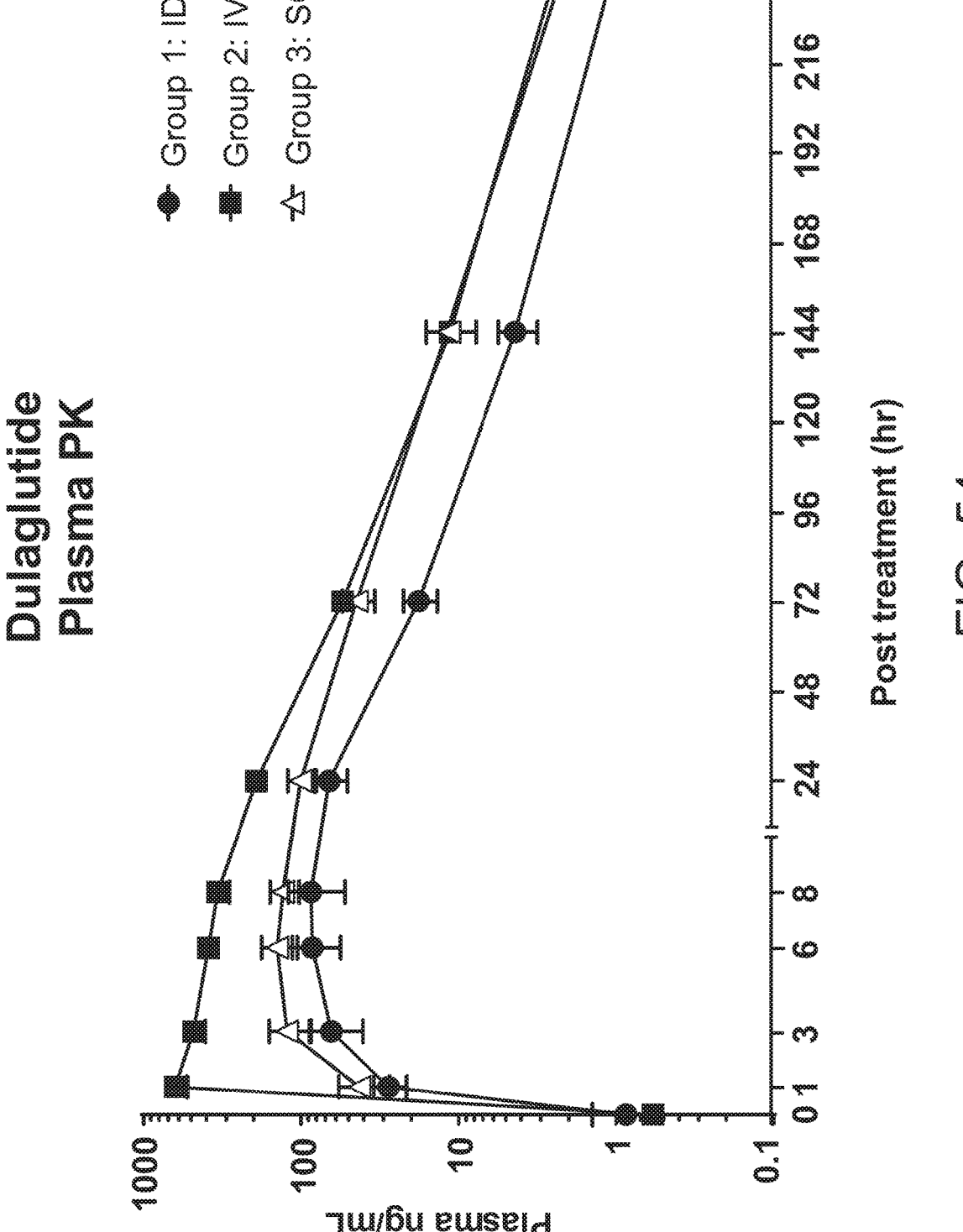
FIG. 54 shows the plasma concentration of dulaglutide over time via ID administration relative to IV or SC administration.

The bioavailability of dulaglutide via ID administration was determined relative to IV or SC administration. The results are shown in FIG. 54. For ID administration, the bioavailability relative to IV administration [($AUC)_{ID/IV}$*100%] was about 33%, while the bioavailability relative to SC administration [($AUC)_{ID/SC}$*100%] was about 61%.

TABLE 19

| | Dulaglutide plasma PK in swine | | |
| --- | --- | --- | --- |
| Route | ID | IV | SC |
| N | $4^a$ | 3 | 3 |
| $T_{max}$ (hr) | 8 | 1 | 6 |
| $C_{max}$ (ng) | 70.65 ± 19.18 | 632.93 ± 49.68 | 141.3 ± 17.09 |
| $(AUC)_{T0-T240\ h}$ ng · hr/mL ± SEM | $4355.86 ± 1094.57^a$ | 16429.33 ± 600.93 | 8869 ± 887.33 |
| Bioavailability relative to IV | $26.51 ± 6.55\%^a$ | 100% | $53.98\%^a$ |
| Bioavailability relative to SC | $49.11 ± 0.08\%^a$ | Not calculated | 100% |

$^a$The plasma level of one animal was lower than the detection limit (see FIG. 53A) and therefore excluded from the $AUC_{ID}$ and $AUC_{ID}$-based calculations. When this animal is included in the analysis, the bioavailability relative to SC administration is 43.9% [($AUC)_{ID/SC}$ * 100%], and the bioavailability relative to IV administration is 23.7% [($AUC)_{ID/IV}$ * 100%].

tech, Birmingham, AL) to capture dulaglutide in swine plasma. Dilutions of dulaglutide standards, quality control samples, and test samples were prepared in 10% swine plasma. Following preparation, the samples were incubated on the coated plates for 1 h at room temperature. The dulaglutide complex on the plate was bound with a mouse IgG2a kappa anti-GLP-1 antibody (ThermoFisher Scientific, Waltham, MA) and then detected using a mouse anti-mouse IgG2a-horseradish peroxidase (IgG2a-HPR) (Bethyl, Montgomery, TX) with tetramethylbenzidine (TMB) substrate. The standard curve ranged from 4.0-0.031 ng/ml, with 0.31 ng/ml being the lowest limit of quantitation. All plasma samples were diluted by 1:10, 1:50, or 1:100 depending on the concentration of the drug. All data and pharmacokinetic parameters were analyzed and graphed using GraphPad Prism version 7.00 for Windows, (GraphPad Software, La Jolla California USA). The area under the concentration curve (AUC) versus time was calculated with the trapezoidal rules from the first sample collection time points (pre-dose, time 0) to last time point of sample collection (240 h post-dose) (($AUC)_{T0-T240h}$)).

Example 7—Identification of the Target Internal Pressure Range of an Ingestible 4-Nozzle Jet Delivery Device by Evaluating the Bioavailability of Adalimumab after Intraduodenal (ID) Administration to Female Yorkshire Pigs A study was conducted to identify the target internal pressure range of an ingestible 4-nozzle jet delivery device required to achieve systemic uptake of adalimumab. In this study, the plasma pharmacokinetics of adalimumab were evaluated in female Yorkshire pigs after intraduodenal (ID) administration via an endoscopically placed ingestible device. The results were compared with those obtained after administration of adalimumab via a 2-nozzle jet delivery device, SC or IV (Example 5).

Test Article

Adalimumab in an aqueous buffer having an adalimumab concentration of about 106 mg/mL.

Ingestible Device Configuration

Each ingestible device was configured as a capsule comprising a substance reservoir; a gas reservoir; a one-way duckbill valve; a piston; four nozzles radially configured 90 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig or 350 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the amount of test article delivered was determined. Typically, approximately 0.050 mL was retained in the ingestible device after test article delivery was completed. Thus, approximately 0.400 mL of test article was dispensed from each jet delivery device.

A summary of parameters for the delivery of the test article via the ingestible device is provided in Table 20. Initial and final refer to values at the beginning and end of the dispensing period for the test article, respectively.

TABLE 20

| Parameters for test article delivery from ingestible device | Internal pressure (pressure of pre-compressed gas): about 320 psig | Internal pressure (pressure of pre-compressed gas): about 350 psig |
| --- | --- | --- |
| Pre-compressed gas volume in ingestible device | about 370 microliters (initial) to about 770 microliters (final) | |
| Nozzle diameter | 0.35 mm | |
| Nozzle length | 2 mm | |
| Nozzle stand-off distance | ≥1.5 mm | |
| Nozzle throat geometry | circular sharp-edged orifice | |
| Device diameter | 11.6 mm | |
| Device length | about 34 to 36 mm | |
| Piston diameter | 9.6 mm | |
| Piston friction | 10N (one (1) O-ring on piston) | |
| Friction pressure loss | about 20 psig | |
| Fluid pressure | about 300 psig (peak; initial) to about 95 psig (minimum; final) | about 330 psig (peak; initial) to about 105 psig (minimum; final) |
| Jet velocity | about 36.5 m/s (peak; initial) to about 21 m/s (minimum; final) | about 38 m/s (peak; initial) to about 21 m/s (minimum; final) |
| Mean jet velocity | about 26 m/s to 27 m/s | about 26 m/s to 27 m/s |
| Fluid dispensing time (total) | about 40 ms | about 40 ms |
| Jet impact force | about 0.13N (peak; initial) to about 0.04N (minimum; final) | about 0.14N (peak; initial) to about 0.04N (minimum; final) |
| Jet impact pressure | about 193 psig (peak; initial) to about 60 psig (minimum; final) | about 212 psig (peak; initial) to about 67 psig (minimum; final) |
| Jet power | about 2.3 W (peak; initial) to about 0.4 W (minimum; final) | about 2.7 W (peak; initial) to about 0.5 W (minimum; final) |
| Jet diameter | about 0.35 mm (initial) | about 0.35 mm (initial) |

In Vivo Study Design

A total of 9 healthy female Yorkshire pigs (*Sus scrofa domesticus*) having a body weight of 24-30 kg were used in this study. Five (N=5) were used in dose Group 1 and four (N=4) were used in dose Group 2. Each dose group received test article via intraduodenal (ID) administration. The study design is shown below in Table 21.

TABLE 21

| Group # | Dose Route | N | Dose | Dose Conc. | Internal Device Pressure | Clinical Observations | Blood Collection Time Points | Termination & Necropsy |
|---|---|---|---|---|---|---|---|---|
| 1 | ID (Device) | 5 | 40 mg | 106 mg/mL | 320 PSIG | Twice on the day of each endoscopic event, and 24, 72, 144, and 240 hours post dose | Pre-dose, 1, 3, 6, 8, 24, 72, 144, and 240 hours post dose | Termination and necropsy of injection site to assess signs of hematoma and gross lesions (Day 10 post dose) |
| 2 | ID (Device) | 4 | 40 mg | 106 mg/mL | 350 PSIG | | | |

Animals were housed two per cage and fasted for a minimum of 12 hours prior to dosing. Food was returned at 4 hours post-dose. Water was supplied ad libitum. The dosing was as follows: Dose day 1: group 1 (n=2), and group 2 (n=3); Dose day 2: group 2 (n=3), and group 1 (n=2). Following the 240-hour post-dose blood collection the animals were euthanized via intramuscular bolus dose of euthanasia solution.

Intraduodenal (ID) administration was performed as follows. The ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

Sampling

Each blood sample was collected from the pig jugular vein, or other suitable vessel via direct venipuncture, placed into a chilled tube containing K2-EDTA as the anticoagulant, and inverted several times to mix. Blood samples were kept on wet ice until centrifugation. Blood samples were centrifuged at a temperature of 4° C., at 3,000×g, for 5 minutes and chilled throughout processing. Plasma was collected into pre-labeled polypropylene tubes and placed in a freezer set to maintain −60 to −80° C. prior to analysis.

Plasma samples were collected at pre-dose, 1, 3, 6, 8, 24, 72, 144, and 240 hours post-dose in all animals and sent to an off-site laboratory for bioanalytical analysis. Samples were processed and analyzed by using an adalimumab (anti-TNF-alpha) ELISA kit from Alpha Diagnostics, Inc. (Catalog #200 310-AHG). All plasma samples were diluted by 1:100 dilution. Diluted samples were processed in duplicates and the mean Optical Density (O.D.) was measured using a SpectraMax plate reader and utilizing SoftMax Pro software for analysis. The Lower Limit of Quantification (LLOQ) was calculated by adding 10× the standard deviation value of the blanks O.D. to the average of the blank standard O.D. values. Mean concentrations of adalimumab were back interpolated to a 4-parameter log fit standard curve and subsequently multiplied by the dilution factor to obtain a final corrected adalimumab concentration.

All data and pharmacokinetic parameters were analyzed and graphed by using GraphPad Prism version 7.00 for Windows, GraphPad Software, La Jolla California USA, www.graphpad.com (GraphPad Prism 7). The area under the concentration curve (AUC) was calculated with the trapezoidal rules.

Results

Figure 55A:
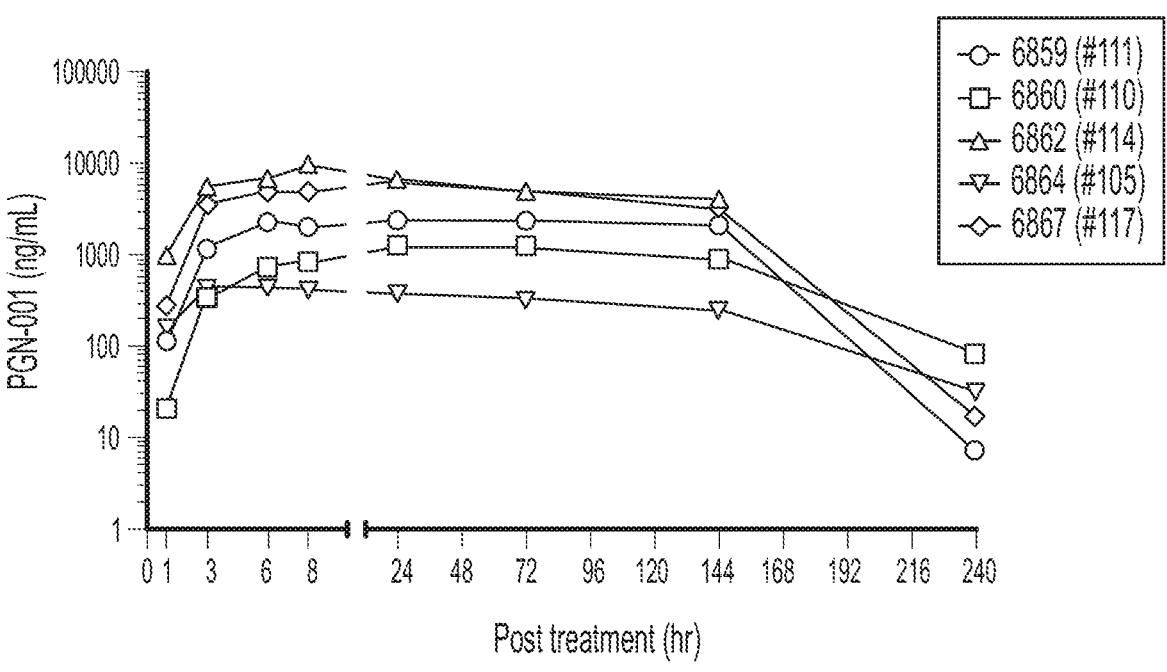
FIGS. 55A-55B show the plasma concentration of adalimumab over time in individual animals.
Figure 55B:
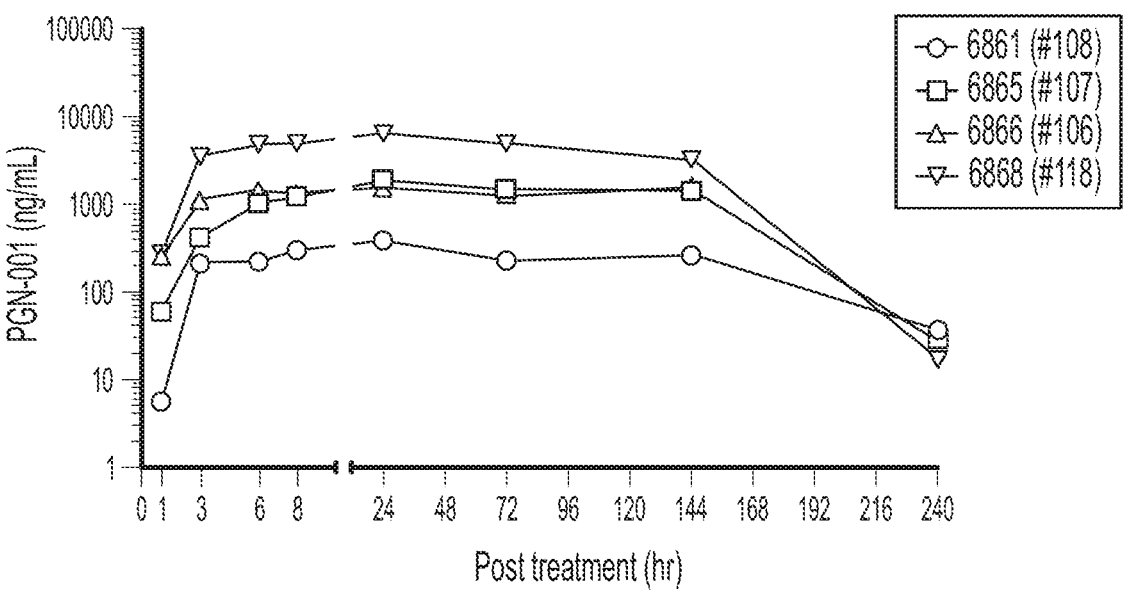

The plasma concentrations of adalimumab over time in individual animals are shown in FIGS. 55A-55B. FIG. 55A represents animals treated with adalimumab after ID administration via the endoscopically placed ingestible device having 4 nozzles and an internal pressure of 320 psig. FIG. 55B represents animals treated with adalimumab after ID administration via the endoscopically placed ingestible device having 4 nozzles and an internal pressure of 350 psig.

The PK results were compared to a subset of data from Example 5. The bioavailability was determined by comparison with Example 5 control arms (SC and IV administration). The results are summarized in Table 22.

TABLE 22

| | 4 Nozzle | | 2 Nozzle[a] | Controls[a] | |
|---|---|---|---|---|---|
| | Group 1: 320 PSIG | Group 2: 350 PSIG | Group 3: 320 PSIG | Group 4: SC | Group 5: IV |
| Route | ID | ID | ID | SC | IV |
| N | 4 | 4 | 5 | 3 | 3 |
| $T_{max}$ (day) | 1 | 1 | 1 | 6 | 0.13 |
| $C_{max}$ (ug/mL) | 3.64 | 2.63 | 5.00 | 12.60 | 20.92 |

TABLE 22-continued

| | 4 Nozzle | | 2 Nozzle[a] | Controls[a] | |
|---|---|---|---|---|---|
| | Group 1: 320 PSIG | Group 2: 350 PSIG | Group 3: 320 PSIG | Group 4: SC | Group 5: IV |
| $AUC_{0-10}$ (ug · day/mL) (± SEM) | 23.831 ± 5.512 | 14.603 ± 6.305 | 32.31 ± 8.09 | 91.87 ± 12.58 | 122.67 ± 7.68 |
| $AUC_{0-10}$ (ug · day/mL) Corrected for Dose (± SEM) | 23.997 ± 5.6147 | 15.171 ± 6.522 | 32.25 ± 8.10 | N/A | N/A |
| Bioavailability over IV[b] (± SEM) | 19.560 ± 4.577 | 12.367 ± 5.317 | 26.25 ± 6.60 | 74.89 ± 10.26 | 100 |
| Bioavailability over SC[b] (± SEM) | 26.120 ± 3.731 | 16.513 ± 4.334 | 35.38 ± 8.82 | 100 | Not calculated |

[a] Data from Example 5
[b] AUC corrected for dose was used to calculate bioavailability.

Figure 56:
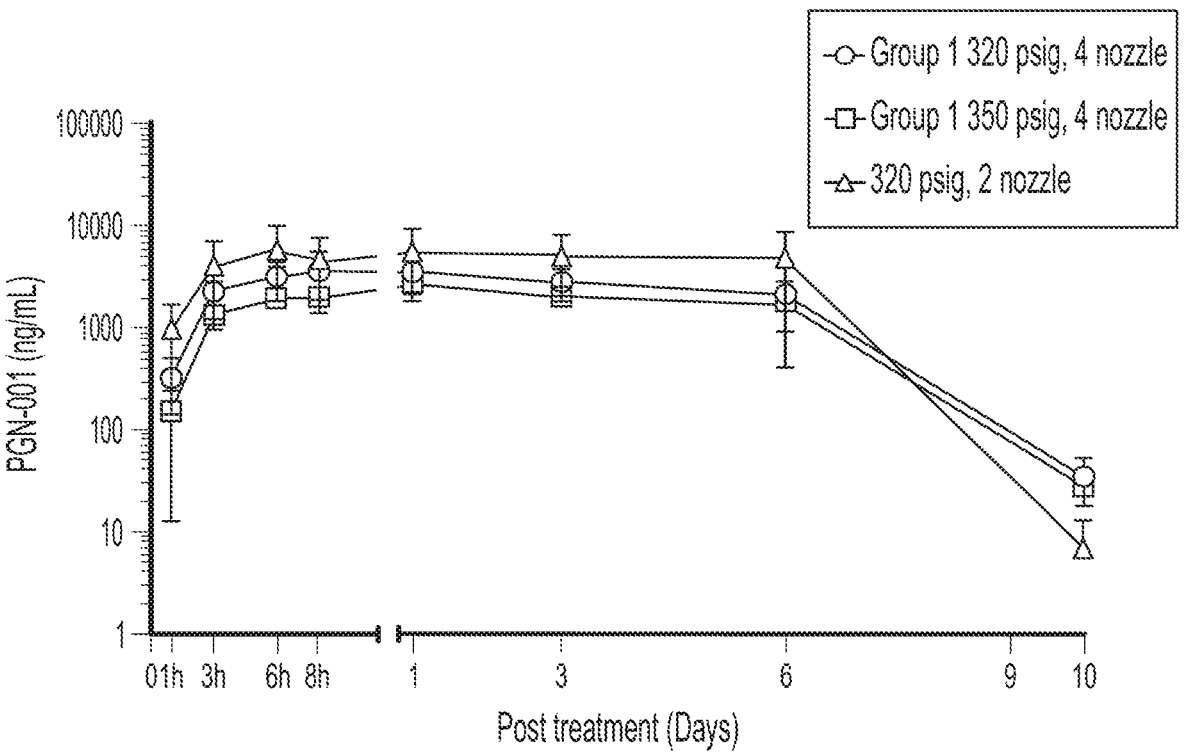
FIG. 56 shows the mean plasma concentration of adalimumab (ng/ml±SEM) over time (0-240 hours) after ID administration via the endoscopically placed ingestible device having: 4 nozzles and an internal pressure of 320 psig (Group 1); 4 nozzles and an internal pressure of 350 psig (Group 2); 2 nozzles and an internal pressure of 320 psig.

FIG. 56 shows the mean plasma concentration of adalimumab (ng/ml±SEM) over time (0-240 hours) after ID administration via the endoscopically placed ingestible device having: 4 nozzles and an internal pressure of 320 psig (Group 1); 4 nozzles and an internal pressure of 350 psig (Group 2); 2 nozzles and an internal pressure of 320 psig (Example 5, Group 3).

Example 8—Evaluation of the Stability and Integrity of Adalimumab After Delivery Via an Ingestible Device The effects that various drug dispensing variables, such as nozzle geometry and delivery pressure, have on the structure and function of the target drug adalimumab were evaluated. Delivery pressures up to 300 psi and nozzle dimensions down to 0.35 mm diameter were tested.

The experimental design is as follows. Briefly, a drug (adalimumab) was loaded into a jet device including a piston with a release mechanism. On the back side of the piston, pressure was provided by a hand pump, and the release mechanism was released to release the drug. The end fastener was screwed on to secure the nozzle insert and seal the chamber. The jet device was operated at a target pressure to dispense the drug into a polypropylene tube for collection and analysis. For the minimum pressure test, the jet was operated manually by slowly pushing the piston forward to dispense the drug. For the maximum pressure test, 300 pounds per square inch gauge (psig) were applied to the jet device, and the drug was carefully dispensed into a polypropylene collection tube. After each dose was delivered, the remaining gas pressure was relieved, and the nozzle was cleaned.

Target Binding

Tests were conducted to determine whether certain pressures and nozzle diameters used to deliver adalimumab with an ingestible device would result in physical damage to the drug and affect target drug binding.

Test Method

The drug (adalimumab) was loaded into the ingestible device and fired through a nozzle with varying diameters at various pressure conditions. Table 23 summarizes the samples and delivery conditions used.

TABLE 23

| CODE | SAMPLE | Description |
|---|---|---|
| | Description of Test Articles | |
| A | Adalimumab Standard Delivery | Adalimumab delivered from a standard pipette as manufactured. |
| B | Very low Pressure | 0 psi gauge pressure, load device and dispense |
| T1 | Low Pressure | 160 psi gauge pressure, 0.5 mm nozzle diameter |
| T2 | Target Delivery | 230 psi gauge pressure, 0.35 mm nozzle diameter |
| T3 | Aggressive Pressure | 300 psi gauge pressure, 0.35 mm nozzle diameter |
| NC | Negative Control | Adalimumab delivered from a standard syringe as manufactured and pre-processed using Pierce FAb preparation kit |
| C | PBS Control | PBS Control |
| AlphaLISA Kit Parts | AlphaLISA Anti-TNFα LOCI Kit | AlphaLISA LOCI Kit |

The drug was extracted utilizing the respective dispensing systems and tested by a competitive inhibition assay as described in Velayudhan et al., "Demonstration of functional similarity of proposed biosimilar ABP 501 to adalimumab," BioDrugs 30:339-351, 2016, and Barbeau et. al., "Application Note: Screening for inhibitors of TNFα/s TNFR1 Binding using AlphaScreen™ Technology," PerkinElmer Technical Note ASC-016, 2002.

Figure 57A:
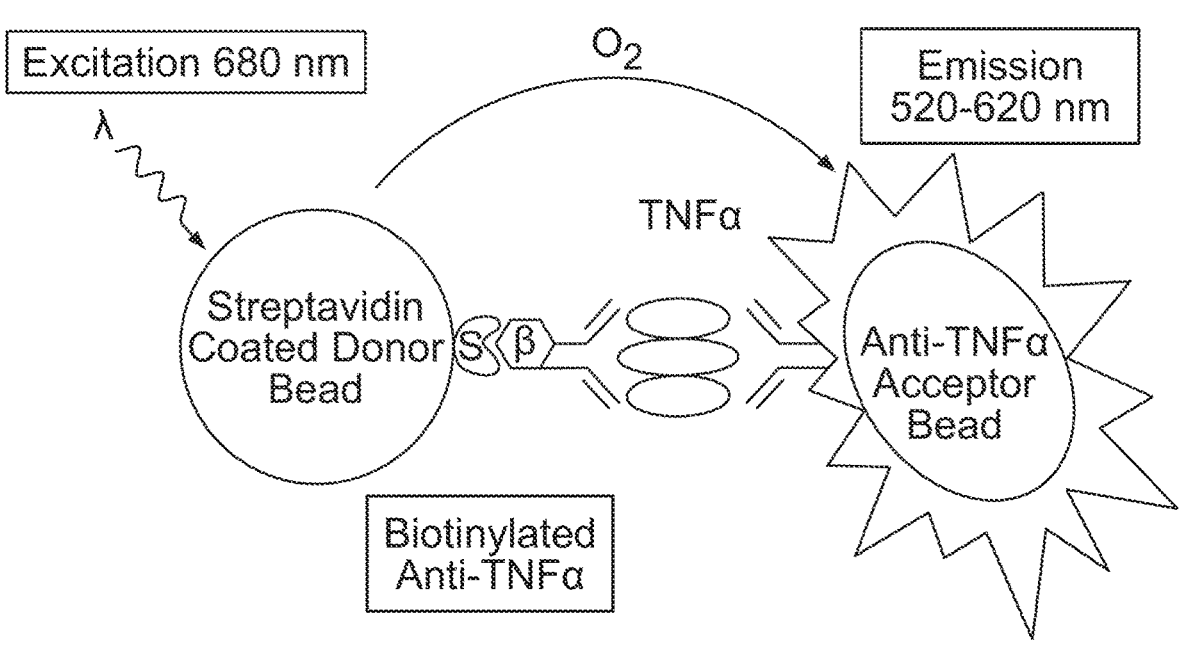
FIGS. 57A-57B illustrate the general principle of a competitive inhibition assay.
Figure 57B:
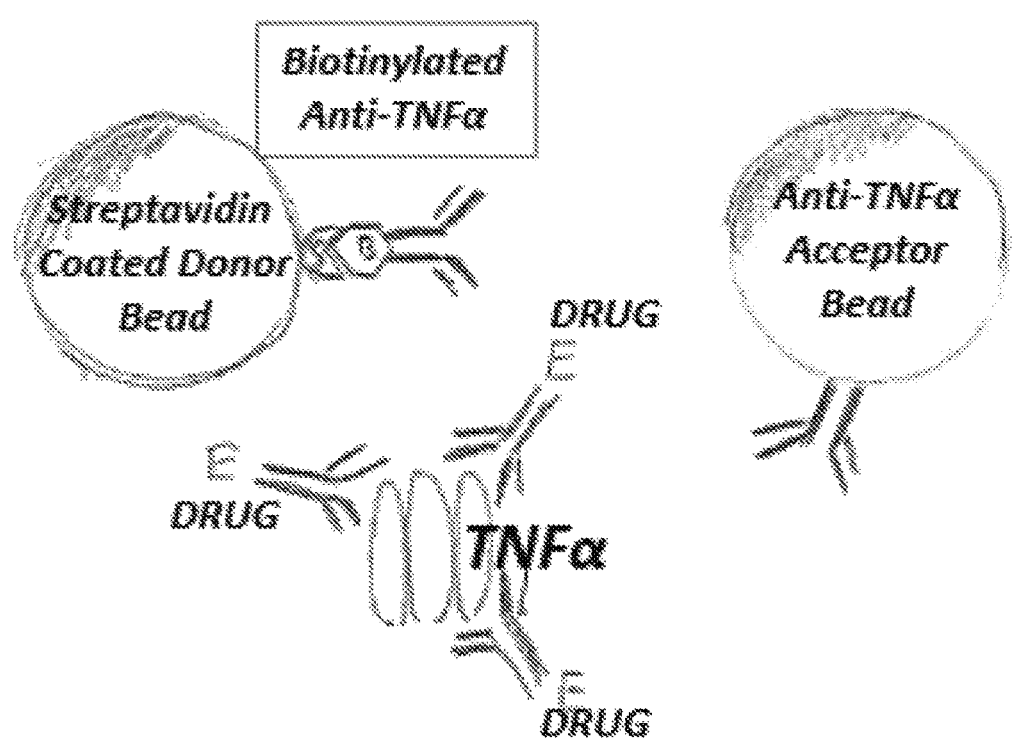

FIGS. 57A-57B illustrate the general principle of the assay. FIG. 57A shows binding of anti-TNFα to the TNFα receptor without drug, where uninhibited binding brings the Donor and Acceptor beads into close proximity for singlet oxygen transfer detection. FIG. 57B shows binding of anti-TNFα to TNFα that is inhibited by drug binding to TNFα, thus preventing binding to anti-TNFα antibodies and proximity oxygen singlet transfer detection.

Drug binding was detected using Luminescent Oxygen Channeling (LOCI™)—a competitive binding assay. Signal was detected by comparing to a non-drug carrier control and an artificially damaged drug using a commercial FAB fragmentation kit.

Drug function was determined through a competition binding assay comparing drug binding function for drug dispensed via standard delivery mechanism and drug delivered via the ingestible device with various pressures.

Results

Figure 58A:
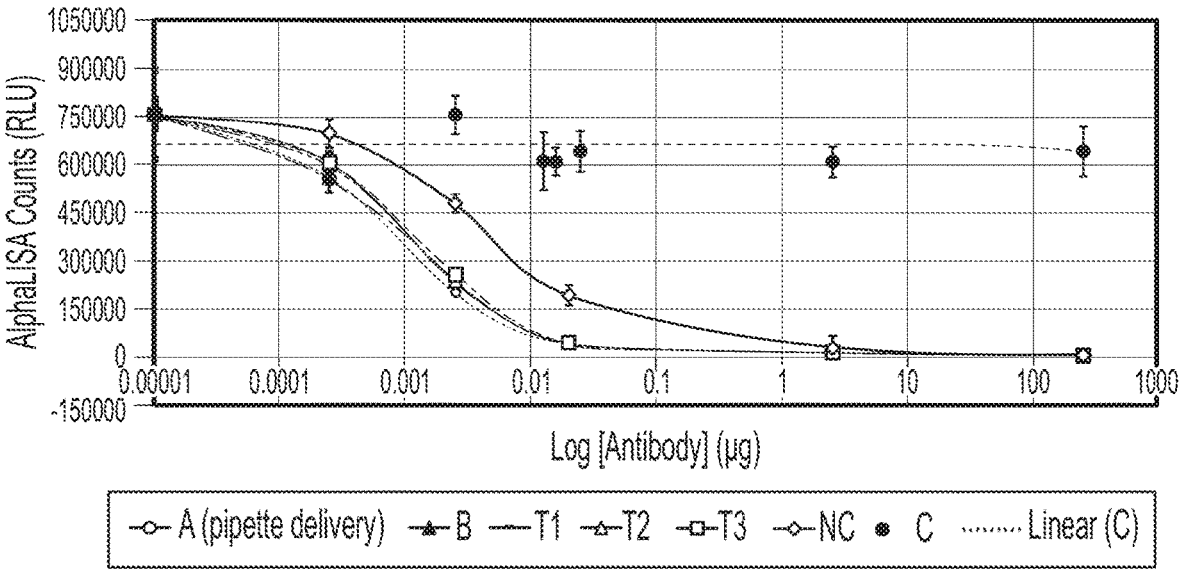
FIGS. 58A-58B are dose response curves of adalimumab binding to TNF-alpha.

The jet delivery pressures and nozzle dimensions utilized did not appear to affect the binding or function of the drug. Under the conditions evaluated in this experiment, the tested pressures did not significantly inhibit the ability of the drug to bind to the target TNFα as measured by the LOC1 competitive inhibition assay. Table 24 shows the $IC_{50}$ values of adalimumab binding to TNFα under the various conditions tested. FIG. 58A is a dose response curve generated after adalimumab (10,000 pg/mL) was dispensed into collection tubes under the conditions described in Table 23.

TABLE 24

| $IC_{50}$ of adalimumab binding to TNFα (10,000 pg/mL) | | | | | | | |
|---|---|---|---|---|---|---|---|
| | A | B | T1 | T2 | T3 | NC | C |
| IC50 (µg) | 0.0007 | 0.0008 | 0.0009 | 0.0009 | 0.001 | 0.0045 | NA |

Figure 58B:
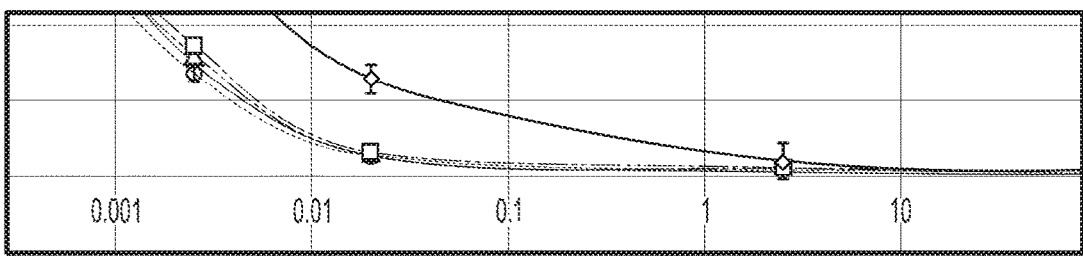

Any observable differences between the tested pressures and nozzle dimensions were within the standard deviation of the assay (FIG. 58B). The negative control (NC) sample curve was shifted to the right, demonstrating that damaged drug binds less to TNFα, allowing for an increase of singlet oxygen transfer due to the proximity of the Donor and Acceptor Beads.

Drug Structure

The purpose of this study was to evaluate the effects that nozzle geometry and delivery pressure have on drug structure when the drug is dispensed from a jet delivery device using different delivery pressures and nozzle sizes. Structural changes in the jet-delivered drug could potentially result in compromised functioning of the drug in vitro.

Test Method

The drug (adalimumab drug substance (DS)) was loaded into the simulated capsule jet delivery device and ejected using different pressures and nozzle geometries. Table 25 summarizes the samples and delivery conditions used.

TABLE 25

| Test articles | | |
|---|---|---|
| CODE | SAMPLE | Description |
| A | Adalimumab Standard Delivery | Adalimumab delivered from a standard pipette as manufactured. |
| B | Very low Pressure | 0 psi gauge pressure, load device and dispense |
| T1 | Low Pressure | 160 psi gauge pressure, 0.5 mm nozzle diameter |
| T2 | Target Delivery | 230 psi gauge pressure, 0.35 mm nozzle diameter |

TABLE 25-continued

| Test articles | | |
|---|---|---|
| CODE | SAMPLE | Description |
| T3 | Aggressive Pressure | 300 psi gauge pressure, 0.35 mm nozzle diameter |
| NC | Negative Control | Adalimumab processed using Pierce FAb preparation kit |
| PPC | Pre-papain Positive Control | Adalimumab DS, desalted and diluted; pre-papain column |
| $NC_{gel}$ | Negative Control for Gel Analysis | Old stock adalimumab processed using Pierce Fab preparation kit; known gel profile |
| $PC_{gel}$ | Positive Control for Gel Analysis | Old stock adalimumab delivered from a standard syringe as manufactured; known gel profile |

Figure 59:
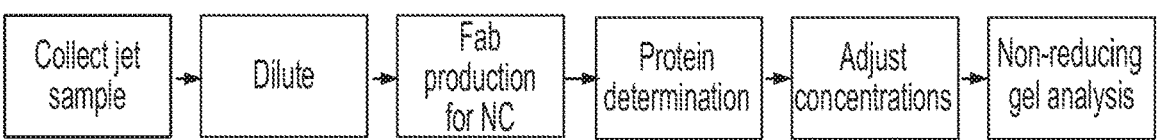
FIG. 59 is a flow chart of the experimental design.
Figure 60:
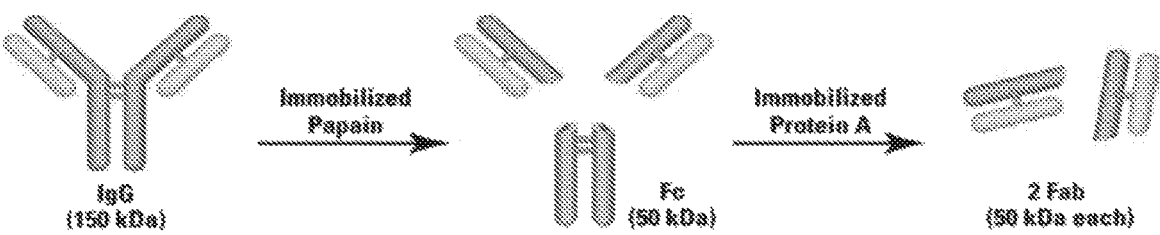
FIG. 60 shows the assay principle of negative control (NC) production.

The experimental design flow is shown in FIG. 59 and the assay principle is shown in FIG. 60. Briefly, OD280 nm readings were taken of pre- and post-dispensed samples, and pre- and post-papain digested adalimumab DS (whole IgG and Fab/Fc fragments, respectively) using a Cytation 5 plate reader and Take 3 micro-volume plate. The resulting protein concentrations were obtained using an extinction coefficient of 1.4 and Gen5 version 3.03.14 program. The samples were then diluted and the protein profiles were analyzed using non-reducing SDS-PAGE. Protein banding patterns of the dispensed samples were compared to that of the unmanipulated drug and the drug artificially damaged (enzymatically degraded) via the papain in a commercial Fab fragmentation kit (Pierce™ Fab Preparation Kit).

For gel analysis, protein was mixed with non-reducing sample buffer. Samples were not heated. 5 µg of samples and controls were loaded per lane of a SDS-PAGE gel (4% Acrylamide-Bis stacking, 12% resolving; see Table 26). The gel was electrophoresed at 195 V and stained in R-250 Coomassie Blue dye.

TABLE 26

| Gel Lane | Code | Quantity |
|---|---|---|
| 1 | MW Standard | 5 µL |
| 2 | A | 5 µg |
| 3 | B | 5 µg |
| 4 | T1 | 5 µg |
| 5 | T2 | 5 µg |
| 6 | T3 | 5 µg |
| 7 | NC | 5 µg |
| 8 | PPC | 5 µg |
| 9 | $PC_{gel}$ | 5 µg |
| 10 | $NC_{gel}$ | 5 µg |

Results

The results are shown in Table 27. None of the jet delivery pressures or nozzle sizes utilized appeared to affect the structure of the drug.

TABLE 27

| Code | Location | 280 Raw | 260 Raw | 320 Raw | 280 | 260 | 260/280 | mg/mL | Mean | CV (%) |
|---|---|---|---|---|---|---|---|---|---|---|
| A | B2 | 0.947 | 0.498 | 0.047 | 0.95 | 0.473 | 0.498 | 13.865 | 13.516 | 3.66 |
| | B3 | 0.902 | 0.478 | 0.049 | 0.902 | 0.451 | 0.5 | 13.166 | | |
| B | C2 | 0.89 | 0.469 | 0.046 | 0.894 | 0.445 | 0.498 | 13.053 | 12.997 | 0.611 |
| | C3 | 0.885 | 0.469 | 0.051 | 0.886 | 0.441 | 0.498 | 12.941 | | |
| T1 | D2 | 0.884 | 0.466 | 0.047 | 0.889 | 0.442 | 0.497 | 12.985 | 12.922 | 0.688 |
| | D3 | 0.87 | 0.458 | 0.047 | 0.881 | 0.437 | 0.497 | 12.859 | | |
| T2 | E2 | 0.872 | 0.461 | 0.049 | 0.874 | 0.435 | 0.497 | 12.765 | 12.782 | 0.193 |
| | E3 | 0.864 | 0.455 | 0.046 | 0.877 | 0.435 | 0.496 | 12.8 | | |
| T3 | F2 | 0.848 | 0.449 | 0.051 | 0.844 | 0.419 | 0.496 | 12.322 | 12.364 | 0.472 |
| | F3 | 0.841 | 0.443 | 0.045 | 0.85 | 0.421 | 0.496 | 12.405 | | |

TABLE 27-continued

| Code | Location | 280 Raw | 260 Raw | 320 Raw | 280 | 260 | 260/280 | mg/mL | Mean | CV (%) |
|---|---|---|---|---|---|---|---|---|---|---|
| NC | C2 | 0.552 | 0.333 | 0.044 | 0.537 | 0.284 | 0.529 | 7.832 | 7.807 | 0.463 |
| | C3 | 0.552 | 0.335 | 0.05 | 0.533 | 0.281 | 0.527 | 7.781 | | |
| PPC | B2 | 0.616 | 0.345 | 0.053 | 0.592 | 0.286 | 0.483 | 8.645 | 8.522 | 2.037 |
| | B3 | 0.587 | 0.327 | 0.041 | 0.575 | 0.28 | 0.486 | 8.4 | | |
| $PC_{gel}$ | B2 | 0.076 | 0.059 | 0.037 | 0.039 | 0.019 | 0.492 | 0.57 | 0.569 | 0.102 |
| | B3 | 0.076 | 0.059 | 0.037 | 0.039 | 0.019 | 0.493 | 0.569 | | |
| $NC_{gel}$ | B2 | 0.08 | 0.089 | 0.044 | 0.033 | 0.02 | 0.604 | 0.485 | 0.486 | 0.09 |
| | B3 | 0.084 | 0.093 | 0.049 | 0.033 | 0.019 | 0.582 | 0.486 | | |

Figure 61:
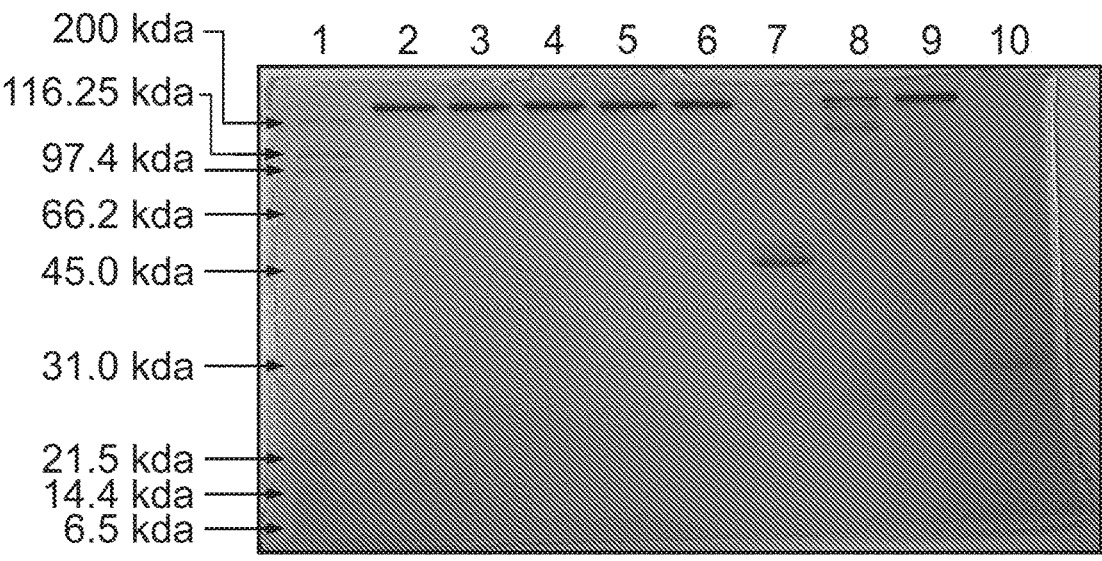
FIG. 61 shows the results of a gel analysis.

FIG. 61 shows the results of the gel analysis. All jet-delivered drug samples showed the same banding pattern as the unmanipulated drug. No subunit fragments were visible in their corresponding gel profiles, in comparison to intentionally degraded controls NC and $Nc_{gel}$. Banding for controls NC and $Nc_{gel}$ differed from each other. NC showed expected bands corresponding to Fab and Fc fragments (running at approx. 45-50 kda). $Nc_{gel}$ showed a lower MW band, likely due to further reduction of adalimumab (digested from a lower starting concentration than NC) to Fab heavy and light chain sub-components (approx. 25 kDa each). Undetermined fragments were also present (see column 8 of FIG. 61) as adalimumab was desalted, prior to its loading on the immobilized papain column.

No structural changes were evident and there was no physical indication that the drug had been inactivated through the dispensing pressures or nozzle sizes employed.

Example 9—Pharmacokinetic and Pharmacodynamic Assessment of Tofacitinib Citrate After Oral or Topical Intracecal Administration in a Dextran Sulfate Sodium (DSS)-Induced Colitis Mouse Model Study Design The overall study design is summarized in Table 28. Briefly, at least 10 days prior to the start of the study (Day −10), a cohort of male C57BL/6 mice underwent surgical implantation of a cecal cannula. Colitis was induced in 110 mice (Groups 2-7) by exposure to 3% DSS-treated drinking water from Day 0 to Day 5. Five animals (Group 1) served as no-disease controls; the other animals received a single dose of vehicle (Group 2) or tofacitinib citrate suspension containing about 0.5% excipients via oral gavage (PO;

Groups 3 and 4) or intracecal injection via the surgically implanted indwelling catheter (IC; Groups 5, 6 and 7) once on Day 12 (peak disease status). All animals were weighed daily and assessed visually for the presence of diarrhea and/or blood in stool. A subset of animals per group was sacrificed for terminal PK collections at various time points post-dose. Terminal samples (plasma, cecal contents, colon contents, cecal tissue and colon tissue) were collected at terminal sacrifice. All $K_2EDTA$ plasma and tissue homogenate (proximal colon, cecum and associated lumen contents) were stored at −80° C. until further analysis.

TABLE 28 b. Description of Treatment Groups

| Group Number | Number Animals | Cecal Cannula | Colitis Induction | Treatment | Dose (mg/kg) (Day 12)[1] | Route | PK Schedule |
|---|---|---|---|---|---|---|---|
| 1 | 5 | no | (a) | (a) | (a) | (a) | 24 h post-dose (n = 5) 24 h |
| 2 | 10 | | 3% DSS in | Control vehicle | 0 | PO | 1 and 24 h post-dose (n = 5 per |
| 3 | 20 | | drinking | Tofacitinib | 15 | | 1, 3, 12, 24 h |
| 4 | 20 | | water | citrate | 45 | | post-dose |
| 5 | 20 | yes | Days | suspension | 1 | IC | (n = 5 per |
| 6 | 20 | | 0-5 | | 3 | | timepoint) |
| 7 | 20 | | | | 10 | | |

DSS = dextran sulfate sodium; IC = Intracecal injection; PK = Pharmacokinetics; PO = oral gavage
(a) Five animals served as no-disease controls.
[1]All dose levels are expressed based on tofacitinib citrate salt form.

Sample Bioanalysis

Plasma samples and tissue homogenate (proximal colon, cecum and associated lumen contents) were assessed for tofacitinib. Briefly, samples were analyzed by LC-MS/MS against matrix-matched standard curves. Three additional samples were above their respective quantitation limits, and extrapolated data was reported.

To evaluate pharmacodynamic (PD) effects of tofacitinib in the DSS-induced colitis mouse model, several cytokines involved in the JAK/STAT signaling pathway, i.e., IL-6, GM-CSF, IL-15, IL-2, IL-12, IL-13, TNFα, and INF-γ, were measured in both plasma and colon tissue by ELISA.

The study design was complex and involved surgical procedure in a disease model. The PK/PD parameters were derived from limited timepoints and should be considered best estimates only.

All PK/PD concentrations are expressed as active drug moiety (anhydrous tofacitinib free base).

Pharmacokinetic Statistical Analysis

PK modeling was performed using mean plasma or tissue concentrations of tofacitinib versus time curves. The following PK parameters were calculated with a one-compartmental model using Excel software: time to maximum concentration: $T_{max}$; half-life: $t_{1/2}$, maximum concentration: $C_{max}$; clearance (Cl), area under the concentration-time curve from the start of dosing to the last protocol-specified time point: $AUC_{(0-24h)}$. The absolute oral bioavailability was estimated to be 74% based on: Xeljanz® (Tofacitinib tablets for oral administration) Prescribing Information Revised 11/2012.

Results

Drug Tissue Concentrations

Figures 62A, 62B:
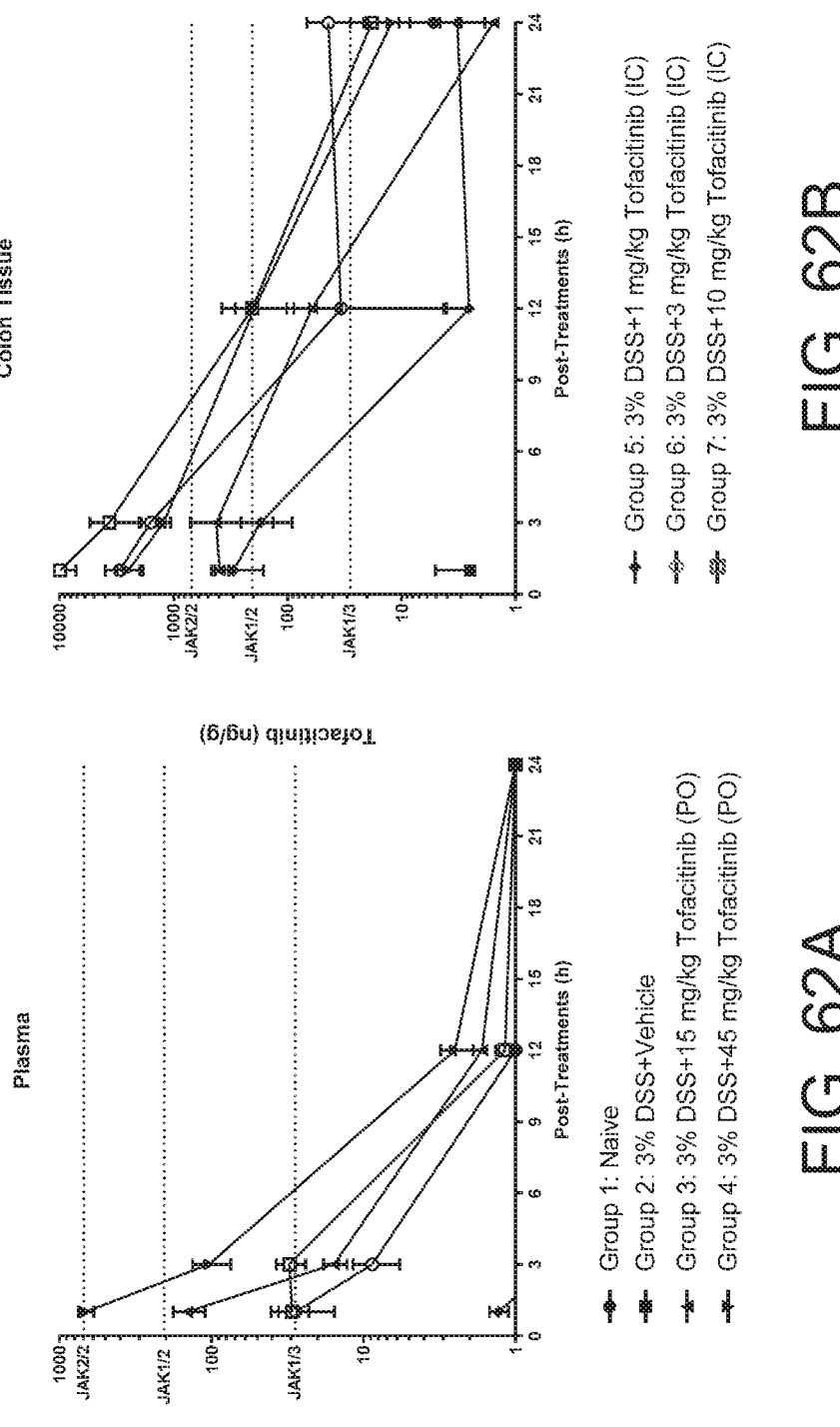
FIGS. 62A-62B show mean plasma (FIG. 62A) and colon tissue (FIG. 62B) concentrations of tofacitinib (free base) over a 24-hour period post-treatment with tofacitinib citrate or vehicle in a DSS-induced colitis mouse model. Dashed lines indicate in vitro $IC_{50}$ values for JAK1/3, JAK1/2 and JAK2/2 in whole blood. Error bars represent standard deviation.
Figures 63A, 63B, 63C:
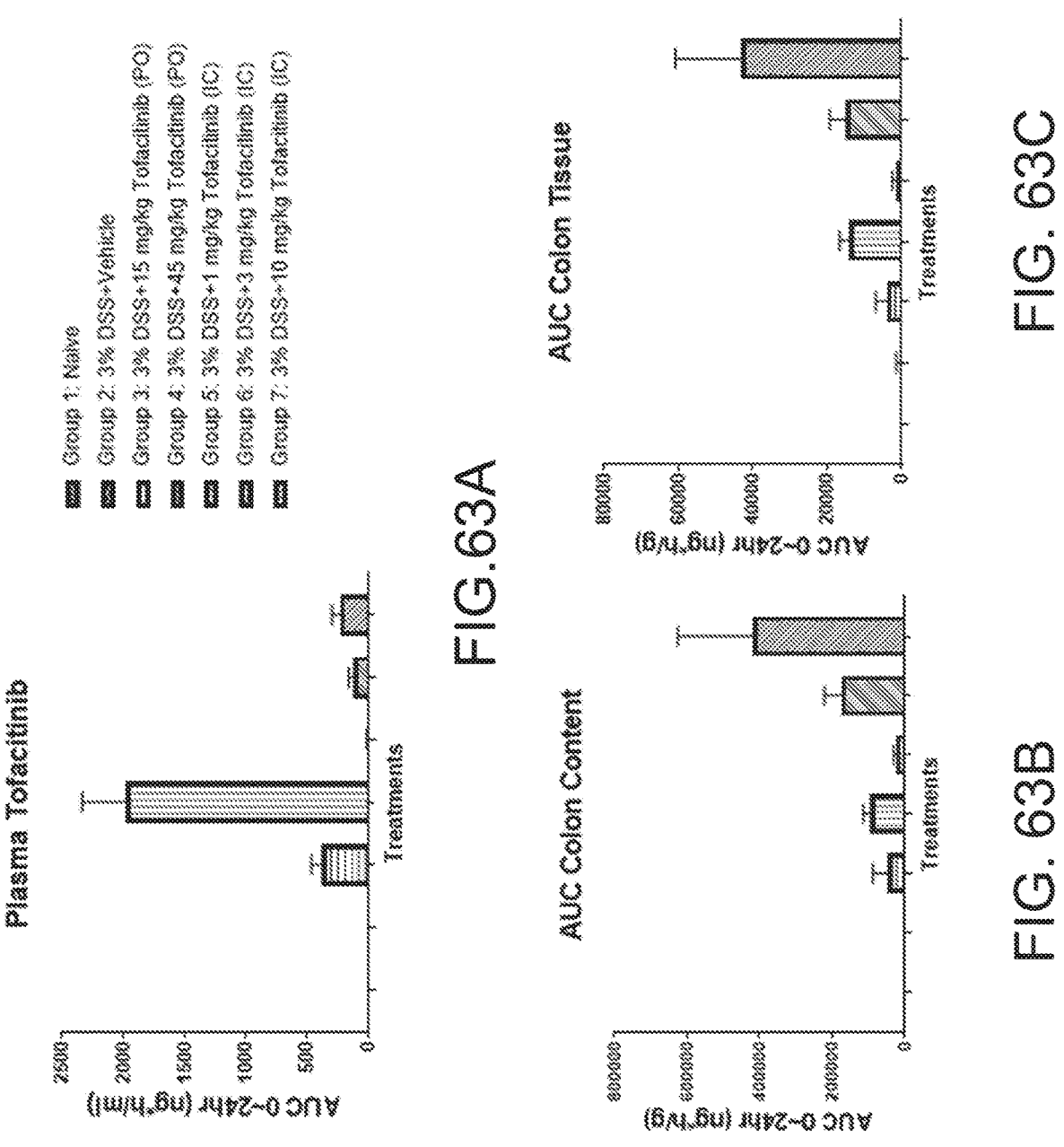
FIGS. 63A-63C show plasma (FIG. 63A), colon content (FIG. 63B) and colon tissue (FIG. 63C) tofacitinib exposure $(AUC_{0-24h})$ after treatment with vehicle or tofacitinib citrate via per oral (PO) or intracecal (IC) administration in a DSS-induced colitis mouse model.
Figure 64A:
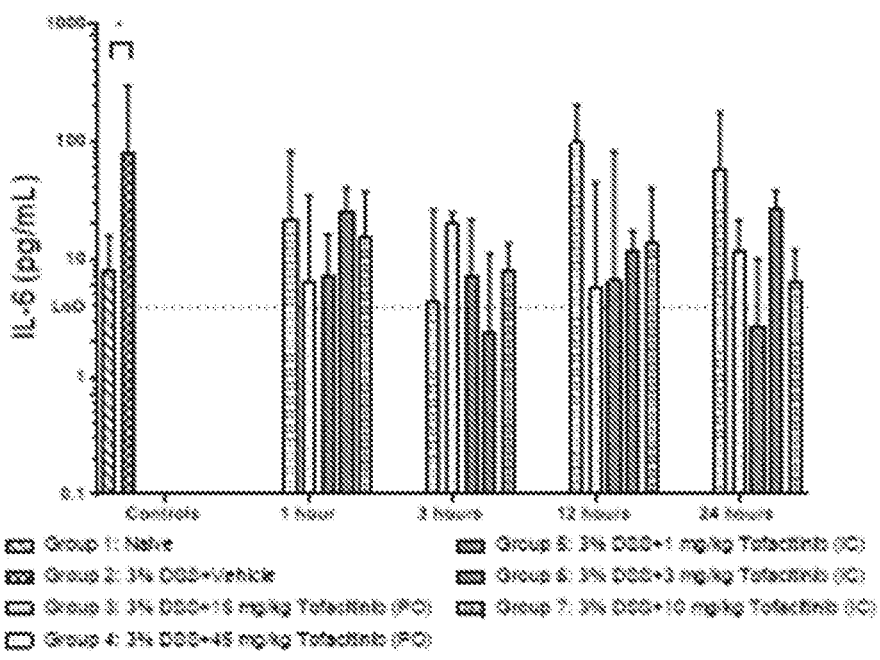
FIGS. 64A-64B show IL-6 concentrations in colon tissue over a 24-hour period post-treatment with vehicle or tofacitinib citrate via per oral (PO) or intracecal (IC) administration in a DSS-induced colitis mouse model on Study Day 12.
Figure 64B:
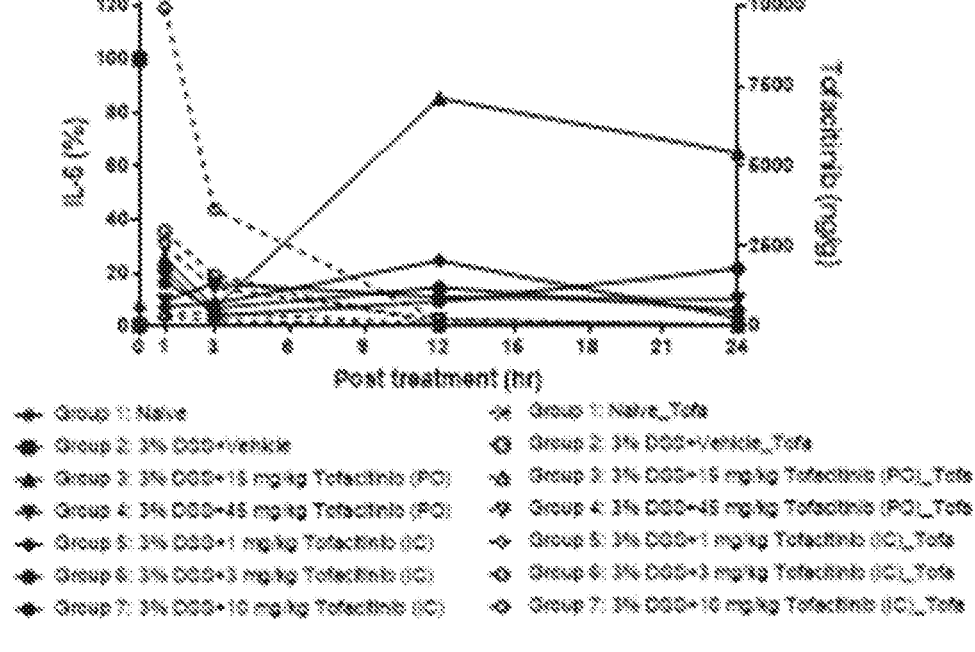

Animals dosed PO with tofacitinib citrate (Groups 3-4) demonstrated the highest mean plasma tofacitinib concentrations at all timepoints, while limited blood exposure was observed in animals treated IC (Groups 5-6) (See FIGS. 62A-62B). Plasma $T_{max}$ occurred between 1.2 and 1.6 h post-dose in all groups, regardless of dosing route. Colon tissue $T_{max}$ occurred between 1.43 and 1.86 h post-dose in all IC groups, and at 2.25 and 2.33 h post-dose in PO groups (Table 46). At similar dose levels, IC delivery of tofacitinib citrate (IC, 10 mg/kg) resulted in an 18-fold higher tofacitinib AUC colon tissue/plasma ratio when compared to PO delivery (PO, 15 mg/kg) (AUC ratio 193.76 vs. 10.6, respectively; Table 29). Plasma and tissue tofacitinib exposure $(AUC_{0-24\ h})$ are also shown in FIGS. 63A-63C.

groups and in the high dose PO group (45 mg/kg) (FIG. 64B). Recovery from IL-6 inhibition was observed in the low dose PO group (15 mg/kg) by 12 h post-dose.

The concentration of GM-CSF (a cytokine activated through stimulation of the JAK2/JAK2 pathway) was not significantly different between the DSS-treatment groups and the naïve group, nor was there a significant difference in GM-CSF levels between IC and PO treatment groups in either plasma or colon tissue, despite high exposure of tofacitinib found in colon tissue of IC groups dosed at 3 and 10 mg/kg (data not shown).

Example 10—Topical Intracecal Administration of Therapeutic Antibodies in a Colitis Animal Model that has Previously Received an Adoptive T-cell Transfer A set of experiments was performed to compare the efficacy of targeted intracecal (IC) anti-mouse-TNFα antibody (a surrogate for adalimumab) and anti-mouse-interleukin (IL) 12p40 antibody (a surrogate of anti-human-IL12p40 antibody) with systemic intraperitoneal (IP) injection in an adoptive T cell transfer induced chronic colitis mouse model.

TABLE 29

Pharmacokinetic and pharmacodynamic parameters for tofacitinib over 24 hours after a single dose administration of tofacitinib citrate suspension on Day 12 in DSS-induced colitis mouse model

| Group | | Biological | Cmax | AUC | Tissue/ | Tmax | T$_{1/2}$ | Clearance | IC$_{50}$ coverage (h)$^a$ | | |
|---|---|---|---|---|---|---|---|---|---|---|---|
| | | | | | | | | | Pharmacodynamics | | |
| Number | Route/Dose | Matrix | (ng/mL) | (ng · h/mL) | plasma ratio | (h) | (h) | (mL/h) | JAK1/3$^b$ | JAK1/2$^c$ | JAK2/2$^d$ |
| 3 | PO/15 | Plasma | 65.5 | 372.09 | 10.6 | 1.61 | 2.53 | 656.28 | 1 | 0 | 0 |
| | mg/kg | Colon tissue | 552.7 | 3954.9 | | 2.25 | 3.23 | 61.82 | 12 | 3 | 0 |
| 4 | PO/45 | Plasma | 467.1 | 1976.24 | 7.09 | 1.36 | 1.64 | 370.7 | 1 | 3 | 1 |
| | mg/kg | Colon tissue | 1774.9 | 14006.55 | | 2.33 | 3.4 | 52.3 | 12 | 12 | 3 |
| 5 | IC/1 | Plasma | 1.3 | 6.13 | 253.05 | 1.56 | 1.73 | 2653.91 | 0 | 0 | 0 |
| | mg/kg | Colon tissue | 271.7 | 1551.21 | | 1.61 | 2.56 | 10.5 | 3 | 3 | 0 |
| 6 | IC/3 | Plasma | 33.2 | 115.45 | 128.76 | 1.21 | 1.19 | 423.05 | 1 | 0 | 0 |
| | mg/kg | Colon tissue | 2960.2 | 14865.55 | | 1.43 | 2.23 | 3.29 | 24 | 3 | 3 |
| 7 | IC/10 | Plasma | 57.8 | 223.27 | 193.76 | 1.27 | 1.47 | 729.17 | 3 | 0 | 0 |
| | mg/kg | Colon tissue | 7644.9 | 43261.18 | | 1.86 | 2.16 | 3.76 | 24 | 12 | 3 |

PO = oral gavage; IC = intra-cecal injection; IC$_{50}$ = half-maximum inhibitory concentration; Groups 1 and 2: not applicable
$^a$Concentrations above the IC$_{50}$ over the 24-hour period;
$^b$IC$_{50}$ of JAK1/3 heterodimer = 56 nM$^e$ (28.25 ng/mL);
$^c$IC$_{50}$ of JAK1/2 heterodimer = 406 nM$^e$ (204.83 ng/mL);
$^d$IC$_{50}$ of JAK2/2 homodimer inhibition = 1377 nM$^e$ (694.7 ng/mL);
$^e$Meyer et al. (2010) J. Inflamm. 7-41

Cytokines

Inflammatory cytokine IL-6 has been shown to play a critical role in the response of uncontrolled intestinal inflammation through JAK1/JAK2 and JAK1/TYK2 signaling pathways (Meyer et al. (2010) J. Inflamm. 7-41).

FIGS. 64A-64B show results obtained for IL-6 in colon tissue on Day 12. IL-6 expression was induced by DSS treatment in both plasma (data not shown) and colon tissue (FIG. 64A) of PO and IC treatment groups; significant induction (p<0.05) was observed on Day 12 when compared with naïve animals (Group 1).

In plasma, inhibition of IL-6 expression was observed in groups treated with tofacitinib citrate via PO or IC administration at 1 h and 3 h post-treatment; recovery of IL-6 expression (50 to 100%) was observed at 12 h and 24 h post-treatment (data not shown).

In colon tissue, inhibition of IL-6 expression was sustained through 24 h post-dose in colon tissue in all IC treated Materials Test System Species/strain: Mice, C57Bl/6 (donors) and RAG2$^{-/-}$ (recipients; C57Bl/6 background)

Physiological state: Normal/immunodeficient

Age/weight range at start of study: 6-8 weeks (20-24 g)

Animal supplier: Taconic

Randomization: Mice were randomized into seven groups of 15 mice each, and two groups of eight mice each.

Justification: T cells isolated from male C57Bl/6 wild type donors were transferred into male RAG2$^{-/-}$ recipient mice to induce colitis.

Replacement: Animals were not replaced during the course of the study.

Animal Housing and Environment

Housing: Mice were housed in groups of 8-15 animals per cage prior to cannulation surgery. After cannulation surgery, cannulated animals were single-housed for seven days post-surgery. After this point, animals were again group-housed as described above. Non-cannulated animals (Group 9) were housed at 8 mice per cage. ALPHA-drie bedding was used. Prior to colitis induction (i.e., during the cannulation surgeries), bedding was changed a minimum of once per week. After colitis induction, bedding was changed every two weeks, with 1/4 of dirty cage material captured and transferred to the new cage. Additionally, bedding from Group 9 animals was used to supplement the bedding for all other groups at the time of cage change.

Acclimation: Animals were acclimatized for a minimum of 7 days prior to study commencement. During this period, the animals were observed daily in order to reject animals that presented in poor condition.

Environmental conditions: The study was performed in animal rooms provided with filtered air at a temperature of 70+/−5° F. and 50%+/−20% relative humidity. Animal rooms were set to maintain a minimum of 12 to 15 air changes per hour. The room was on an automatic timer for a light/dark cycle of 12 hours on and 12 hours off, with no twilight.

Food/water and contaminants: Animals were maintained with Labdiet 5053 sterile rodent chow. Sterile water was provided ad libitum.

Test Article: IgG Control
Name of the Test Article: InVivoMAb polyclonal rat IgG
Source: BioXCell, catalog #BP0290
Storage conditions: 4° C.
Vehicle: Sterile PBS
Dose: 0.625 mg/mouse; 0.110 mL/mouse IP and IC
Formulation:
Formulation Stability: Prepare fresh daily
For Group 3: On each day of dosing, dilute stock pAb to achieve 2.145 mL of a 5.68 mg/mL solution.

For Group 4: On each day of dosing, dilute stock pAb to achieve 2.145 mL of a 5.68 mg/mL solution
Test Article: Anti-IL12 p40
Name of the Test Article: InVivo MAb anti-mouse IL-12 p40
Source: BioXCell, catalog #BE0051
Storage conditions: 4° C.
Vehicle: Sterile PBS
Dose: 0.625 mg/mouse (IP and IC); 0.110 mL/mouse IP and IC
Formulation:
Formulation Stability: Prepare fresh daily
For Group 5: On each dosing day, the stock mAb was diluted to achieve 1.716 mL of a 5.68 mg/mL solution.
For Group 6: On each dosing day, the stock mAb was diluted to achieve 1.716 mL of a 5.68 mg/mL solution.
Test Article: anti-TNFα
Name of the Test Article: InVivoPlus anti-mouse TNFα, clone XT3.11
Source: BioXCell, catalog #BP0058
Storage conditions: 4° C.
Vehicle: Sterile PBS
Dose: 0.625 mg/mouse (IP and IC); 0.110 mL/mouse IP and IC
Formulation:
Formulation Stability: Prepare fresh daily
For Group 7: On each dosing day, the stock mAb was diluted to achieve 1.716 mL of a 5.68 mg/mL solution.
For Group 8: On each dosing day, the stock mAb was diluted to achieve 1.716 mL of a 5.68 mg/mL solution.
Methods
The details of the study design are summarized in Table 30. A detailed description of the methods used in this study is provided below.

TABLE 30

| | | | Cell | | | | Schedule | Blood | | |
| | No. | Cecal | Transfer | | | | (Days 0- | Collection | | Endpoints |
| Group | Animals | Cannula | (Day 0) | Treatment | Dose* | Route | 42**) | (RO) | Endoscopy | (Day 42) |
|---|---|---|---|---|---|---|---|---|---|---|
| 1 | 8 | YES | — | — | — | — | — | Day 13 | Days 14, 28, 42 | 3 Hours Post Dose: |
| 2 | 15 | | 0.5 × 10⁶ naïve T_H cells | Vehicle (PBS; IP) Vehicle (PBS; IC) | — | IP; IC | IP: 3x/week IC: QD | | | Colon weight/ length, stool |
| 3 | 15 | | | IgG Control (IP) Vehicle (PBS; IC) | 625 µg | | IP: 3x/week IC: QD | | | score Terminal |
| 4 | 15 | | | Vehicle (PBS; IP) IgG Control (IC) | 625 µg | | IP: 3x/week IC: QD | | | collection (all groups): |
| 5 | 15 | | | Anti-IL12p40 (IP) Vehicle (PBS; IC) | 625 µg | | IP: 3x/week IC: QD | | | Cecal Contents, Colon Contents, |
| 6 | 15 | | | Vehicle (PBS; IP) Anti-IL12p40 (IC) | 625 µg | | IP: 3x/week IC: QD | | | Plasma, small intestinal tissue, |
| 7 | 15 | | | Anti-TNFα (IP) Vehicle (PBS; IC) | 625 µg | | IP: 3x/week IC: QD | | | colon tissue, mLN, and |
| 8 | 15 | | | Vehicle (PBS; IP) Anti-TNFα (IC) | 625 µg | | IP: 3x/week IC: QD | | | Peyer's Patches |
| 9 | 8 | NO | — | — | — | — | — | — | — | — |

*Per mouse;

**Test Article was administered in 0.110 mL/animal IC or IP from Day 0–42;

IC = intracecal injection;

IP = intraperitoneal injection;

QD = once a day;

RO = Retro-Oribital eye bleed

A cohort of animals underwent surgical implantation of a cecal cannula at least 10 days to 2 weeks prior to the experiment for the ease of bolus topical delivery to the cecum. A sufficient number of animals underwent implantation to allow for enough cannulated animals to be enrolled in the main study. An additional n=8 animals (Group 9) served as no surgery/no disease controls.

Colitis was induced by intraperitoneal (IP) injection of $0.5\times10^6$ CD44/CD62L+ T-cells from C57BL/6 donor mice to male RAG2$^{-/-}$ recipient mice in Groups 2 to 8 on Day 0. The donor cells were processed by first harvesting spleens from 80 C57BI/6 mice and then isolating the CD44$^-$/CD62L$^+$ T cells using Miltenyi Magnetic-Activated Cell Sorting (MACS) columns.

To minimize variation due to methods of administration, animals were treated both by IP injection every third day (3×/wk) and IC injection once daily for 42 consecutive days (qdx42d) of either the test article or the control (vehicle solution or IgG control). Groups were as outlined in Table 30, also summarized as follows: Group 1=untreated (no disease controls); Group 2=vehicle [phosphate buffer saline (PBS)] (IP)+vehicle (IC); Group 3=IgG (IP)+vehicle (IC); Group 4=vehicle (IP)+IgG (IC); Group 5=anti-IL12p40 (IP)+vehicle (IC); Group 6=vehicle (IC)+anti-IL12p40 (IC); Group 7=anti-TNFα (IP)+vehicle (IC); Group 8=vehicle (IP)+anti-TNFα (IC); Group 9=no surgery, untreated (no-cannulation and no-disease controls (sentinel animals for bedding)). Treatment with test article was initiated on Day 0 and was continued until Day 42 as outlined in Table 30.

All recipient mice were weighed daily and assessed visually for the presence of diarrhea and/or bloody stool. The cages were changed every two weeks starting on Day 7, with care taken to capture ¼ of dirty cage material for transfer to the new cage. On Day 13, blood was collected via RO eye bleed, centrifuged, and plasma was aliquoted (50 μL and remaining) and frozen for downstream analysis. The pelleted cells were re-suspended in buffer to determine the presence of T cells by FACS analysis of CD45$^+$/CD4$^+$ events.

On Day 13, after dosing, peripheral blood from all surviving mice was analyzed by flow cytometry from the presence of CD45+/CD4+ T cells.

The mice underwent high definition video endoscopy on Days 14 (pre-dosing; baseline), 28, and 42 (before euthanasia) to assess the extent of colitis severity. Images were captured from each animal at the most severe region of disease identified during endoscopy. Stool consistency was scored during endoscopy using the parameters described herein on Days 14, 18 and 42.

Disease Activity Index (DAI) was calculated using a combination of body weight (BW) loss score, colitis score, stool consistency score. The DAI (combined value from 0 to 13) was calculated using colitis score, stool consistency score, and BW loss score to provide an overall evaluation of the disease intensity (see Table 31). The score from animals with unscheduled death was carried forward to limit any bias that may be introduced by mortality.

The animals from all groups were euthanized by $CO_2$ inhalation on Day 42 following endoscopy and three hours after dosing. Terminal blood samples were collected for bioanalysis of inflammatory cytokines, and tissues samples were collected and fixed for histopathological evaluation. Plasma obtained from these samples was split into two separate cryotubes, with 50 μL in one tube (Bioanalysis) and the remainder in a second tube (TBD). The cecum and colon contents were removed and the contents collected, weighed, and snap frozen in separate cryovials. The mesenteric lymph nodes were collected and flash-frozen in liquid nitrogen. The small intestine were excised and rinsed, and the most distal 2-cm of ileum was placed in formalin for 24 hours and then transferred to 70% ethanol for subsequent histological evaluation. The Peyer's patches were collected from the small intestine, and were flash-frozen in liquid nitrogen. The colon was rinsed, measured, weighed, and then trimmed to 6-cm in length and divided into 5 pieces as described in the above Examples. The most proximal 1-cm of colon was separately weighed, and flash-frozen for subsequent bio-analysis (PK) of test article levels. Of the remaining 5-cm of colon, the most distal and proximal 1.5-cm sections were each placed in formalin for 24 hours and then transferred to 70% ethanol for subsequent histological evaluation. The middle 2-cm portion was bisected longitudinally, and each piece was weighed, placed into two separate cryotubes, and snap frozen in liquid nitrogen; one of the samples was used for cytokine analysis and the other was used for myeloper-oxidase (MPO) analysis. All plasma and frozen colon tissue samples were stored at −80° C. until used for endpoint analysis.

The colon weight (mg) to length (cm) ratio was calculated for individual mice.

A more detailed description of the protocols used in this study are described below.

Cecal Cannulation

Animals were placed under isoflurane anesthesia, and the cecum was exposed via a mid-line incision in the abdomen. A small point incision was made in the distal cecum through which 1-2 cm of the cannula was inserted. The incision was closed with a purse-string suture using 5-0 silk. An incision was made in the left abdominal wall through which the distal end of the cannula was inserted and pushed subcutaneously to the dorsal aspect of the back. The site was washed copiously with warmed saline prior to closing the abdominal wall. A small incision was made in the skin of the back between the shoulder blades, exposing the tip of the cannula. The cannula was secured in place using suture, wound clips, and tissue glue. All of the animals received 1 mL of warm sterile saline (subcutaneous injection) and were monitored closely until fully recovered before returning to the cage. All animals received buprenorphine at 0.6 mg/kg BID for the first 3 days, and Baytril at 10 mg/kg QD for the first 5 days following surgery.

Disease Induction

Colitis was induced on Day 0 in male RAG2$^{-/-}$ mice by IP injection (200 μL) of $0.5\times10^6$ CD44$^-$/CD62L$^+$ T cells (in PBS) isolated and purified from C57BI/6 recipients.

Donor Cell Harvest

Whole spleens were excised from C57BI/6 mice and immediately placed in ice-cold PBS. The spleens were dissociated to yield a single cell suspension and the red blood cells were lysed. The spleens were then processed for CD4$^+$ enrichment prior to CD44$^-$CD62L$^+$ sorting by MACS.

Dosing

See Table 30.

Body Weight and Survival

The animals were observed daily (morbidity, survival, presence of diarrhea and/or bloody stool) in order to assess possible differences among treatment groups and/or possible toxicity resulting from the treatments. Animals were weighed daily and their percent body weight relative to Day 0 was calculated.

Animals Found Dead or Moribund

The animals were monitored on a daily basis and those exhibiting weight loss greater than 30% were euthanized, and did not have samples collected.

Endoscopy

Each mouse underwent video endoscopy on Days 14 (pre-dosing; baseline), 28, and 42 (before euthanasia) using a small animal endoscope (Karl Storz Endoskope, Germany), under isoflurane anesthesia. During each endoscopic procedure, still images as well as video were recorded to evaluate the extent of colitis and the response to treatment. Additionally, an image from each animal at the most severe region of disease identified during endoscopy was captured. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the scoring system described herein.

Sample Collection

Terminal blood (plasma and cell pellet), Peyer's patches (Groups 1-8 only), small intestine and colon mLN (Groups 1-8 only), cecum contents, colon contents, small intestine, and colon were collected at euthanasia, as follows.

Blood: Terminal blood was collected by cardiac puncture and plasma generated from these samples. The resulting plasma was split into two separate cryotubes with 50 μL in one tube (Bioanalysis), and the remainder in a second tube (TBD).

Mesenteric Lymph Nodes: The mesenteric lymph nodes were collected, weighed, snap-frozen in liquid nitrogen, and stored at −80° C.

Small Intestine: The small intestine was excised and rinsed, and the most distal 2-cm of ileum will be placed in formalin for 24 hours and then transferred to 70% ethanol for subsequent histological evaluation.

Peyer's Patches: The Peyer's patches were collected from the small intestine. The collected Peyer's patches were weighed, snap-frozen in liquid nitrogen, and stored at −80° C.

Cecum/Colon Contents: The cecum and colon were removed from each animal and contents collected, weighed, and snap-frozen in separate cryovials.

Colon: Each colon was rinsed, measured, weighed, and then trimmed to 6-cm in length and divided into 5 pieces as outlined herein. The most proximal 1-cm of colon was separately weighed, and snap frozen for subsequent bioanalysis (PK) of test article levels. Of the remaining 5-cm of colon, the most distal and proximal 1.5-cm sections were placed in formalin for 24 hours and then transferred to 70% ethanol for subsequent histological evaluation. The middle 2-cm portion was bisected longitudinally, and each piece weighed, placed into two separate cryotubes, and snap-frozen in liquid nitrogen; one of these samples was used for cytokine analysis and the other sample was used for myeloperoxidase analysis.

Cytokine Levels in Colon Tissue

Cytokine levels (IFNγ, IL-2, IL-4, IL-5, IL-1B, IL-6, IL-12 p40, and TNFα) were assessed in colon tissue homogenate (all groups) by multiplex analysis. Myeloperoxidase levels were assessed by ELISA in colon tissue homogenate (all groups).

Histopathology

Ileum, proximal colon, and distal colon samples from seventy-one mice were fixed in 10% neutral buffered formalin. Samples were trimmed into three cross sections per portion and processed routinely into two blocks per animal (ileum in one block, proximal and distal colon in a second block). One slide from each block was sectioned at approximately 5 microns and stained with hematoxylin and eosin (H&E). Glass slides were evaluated with light microscopy by a board-certified veterinary pathologist. Ileum, proximal colon, and distal colon samples were scored individually. Lesions in H&E-stained samples were given a severity score 0-51 (0=not present/normal, 1=minimal, <10% of tissue affected; 2=mild, 10-25% of tissue affected; 3=moderate, 26-50% of tissue affected; 4=marked, 51-79% of tissue affected; 5=severe, >75% of the tissue affected). Inflammation, crypt damage, erosion, and hyperplasia scores were added together to determine a sum colitis score for each sample.

Lymphocyte counts were performed in a subset of samples: proximal and distal colon from Groups 2 (vehicle), 7 (anti-TNF-alpha IP; vehicle IC), and 8 (anti-TNF-alpha IC; vehicle IP). In each piece of tissue, a randomly identified site was divided into approximately four segments extending from the lumen to the muscularis mucosae; 100 μm2 fields were used in the proximal colon, and 50 μm2 fields were used in the distal colon due to the differences in mucosal thickness. Using H&E-stained slides, the number of cells with lymphocyte morphology (small round nucleus with condensed chromatin) were counted within the overlying surface epithelium, in each field from lumen to muscularis mucosae, and within a 100 μm2 field surrounding an adjacent submucosal blood vessel.

Statistical Analysis

As presented in the figures, non-parametric data was analyzed by Kruskal-Wallis test with Dunn's multiple comparisons test used to compare all groups to one another and individual pair-wise comparisons was analyzed by Mann Whitney U-Test. All statistical analyses were performed using GraphPad Prism 7 (La Jolla, CA).

Results

Survival

The observed mortality rate was within the expected range given the design including surgical intervention, T-cell transfer in immunologically compromised animals followed by chronic development of colitis over a 6-week study period (Ostanin D V et al. Am J Physiol Gastrointest Liver Physiol. 2009, 296(2):G135-G146).

The survival of animals was compared; no significant difference in survival rate was found in treatments of anti-IL12p40 and anti-TNFα with either route of administration compared to vehicle or IgG controls (p>0.08, log-rank; Kaplan-Meier). The timing of animal deaths did not correspond to changes in efficacy endpoints, such as body weight, that were evaluated longitudinally. As noted above, changes in DAI score which includes, BW loss, stool consistency and colitis severity were carried forward to limit any bias that may be introduced by mortality.

Colon Weight: Length Ratio

The mean colon weight: length ratio was significantly elevated in vehicle control animals (Group 2) compared to naïve (Group 1); no other significant differences in mean colon weight: length ratio were observed.

Disease Activity Index

The Disease Activity Index was determined in each mouse using a total score from the scoring system depicted in Table 31.

TABLE 31

Disease Activity Index scoring system

| Disease Activity Index | Description | Score |
|---|---|---|
| Colitis | Normal | 0 |
| Severity | Loss of vascularity | 1 |
| | Loss of vascularity and friability | 2 |
| | Friability and erosions | 3 |
| | Ulcerations and bleeding | 4 |
| Stool | Normal | 0 |
| Consistency | Loose stool, soft, staying in shape | 1 |
| | Abnormal form with excess moisture | 2 |
| | Watery or diarrhea | 3 |
| | Bloody diarrhea | 4 |
| Body Weight | X < 0% or gain weight | 0 |
| Loss (%) | 2% ≤ X < 5% | 1 |
| | 5% ≤ X < 10% | 2 |
| | 10% ≤ X < 15% | 3 |
| | 15% ≤ X < 20% | 4 |
| | 20% ≤ X < 25% | 5 |
| | 25% ≤ X < 30% | 6 |
| | X ≥ 35% | 7 |
| Total Score | | 15 |

Figures 65, 66:
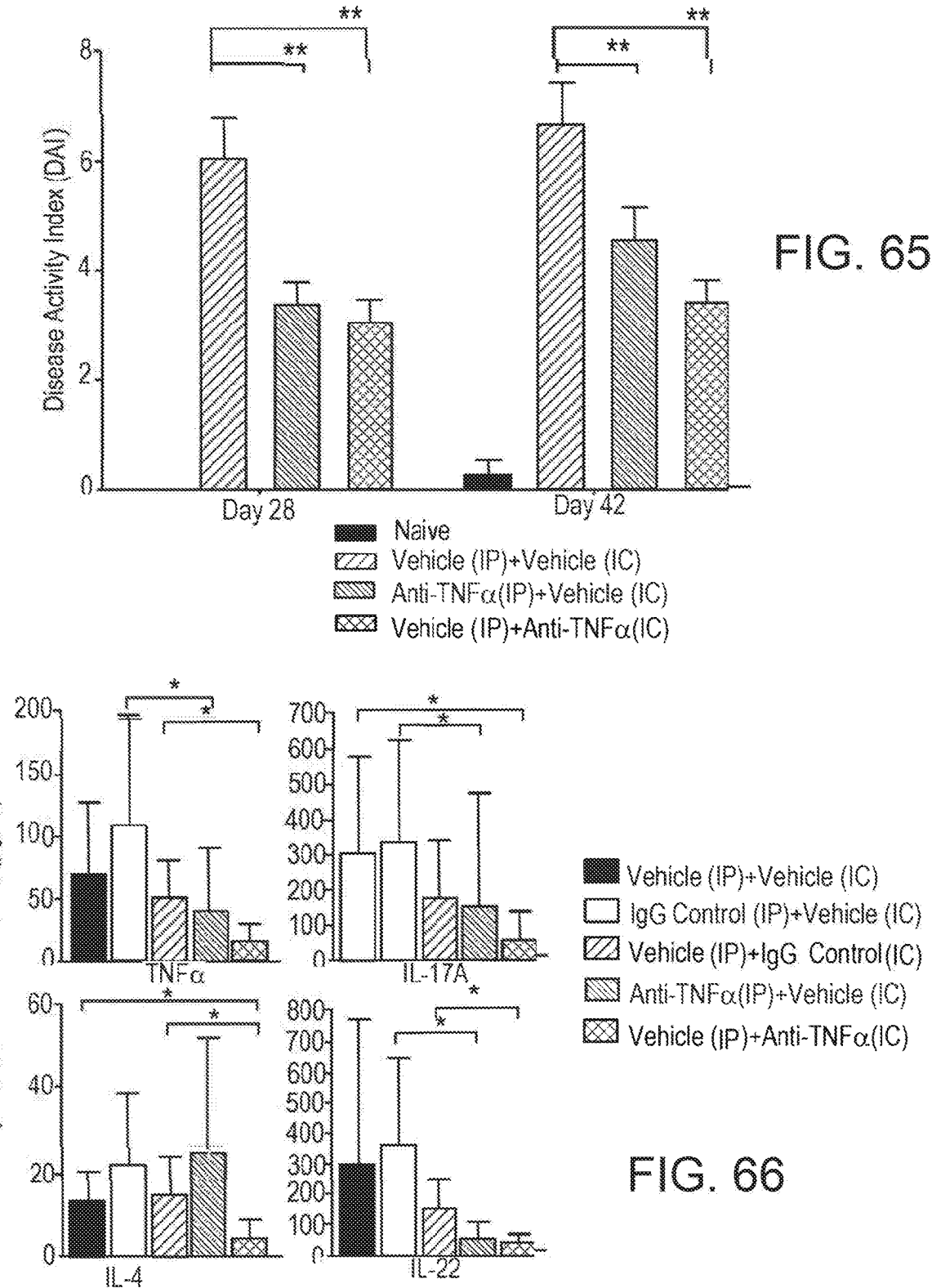
FIG. 65 is a graph showing the Disease Activity Index (DAI) of naïve mice (Group 1), mice administered vehicle only both intraperitoneally (IP) and intra-cecally (IC) (Group 2), mice administered an anti-TNFα antibody IP and vehicle IC (Group 7), and mice administered an anti-TNFα antibody IC and vehicle IP (Group 8) at Day 28 and Day 42 of the study described in Example 10.
FIG. 66 is a set of graphs showing the colonic tissue concentration of TNFα, IL-17A, IL-4, and IL-22 in mice administered vehicle only both IP and IC (Group 2), mice administered IgG control antibody IP and vehicle IC (Group 3), mice administered IgG control IC and vehicle IP (Group 4), mice administered anti-TNFα antibody IP and vehicle IC (Group 7), and mice administered anti-TNFα antibody IC and vehicle IP (Group 8) at Day 42 of the study described in Example 10.
Figure 67:
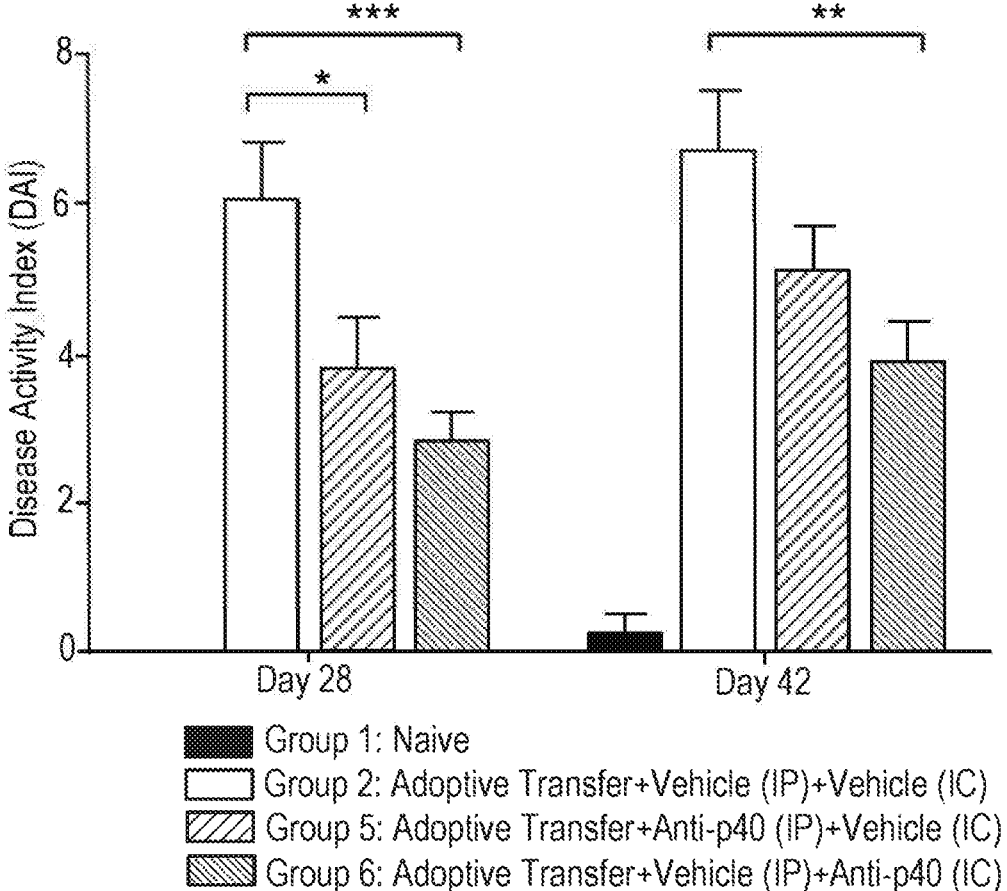
FIG. 67 is a graph showing the Disease Activity Index (DAI) of naïve mice (Group 1), mice administered vehicle only both IP and IC (Group 2), mice administered an anti-IL12 p40 antibody IP and vehicle IC (Group 5), and mice an anti-IL12 p40 antibody IC and vehicle IP (Group 6) at Day 28 and Day 42 of the study described in Example 10.

The data in FIG. 65 show that mice intracecally administered anti-TNFα antibody (Group 8) had decreased disease activity index (DAI) as compared to mice intraperitoneally administered anti-TNFα antibody (Group 7) at Day 42 of the study. The data in FIG. 67 show that mice intracecally administered anti-IL12 p40 antibody (Group 6) had decreased disease activity index (DAI) as compared to mice intraperitoneally administered anti-IL12 p40 antibody (Group 5) at Day 28 and Day 42 of the study.

Inflammatory Cytokines in Colonic Tissue

The concentration of inflammatory cytokines was evaluated in the colonic tissue in vehicle or IgG control groups.

A significant reduction of inflammatory cytokines, including IL 17A, IL-4, TNFα, and IL-22, were found in groups treated with anti-TNFα (IC (Group 8) or IP (Group 7)) when compared with vehicle (IP/IC) control or its respective IgG controls (IC or IP) in colon tissue (FIG. 66). Mice treated with anti-TNFα antibody IC (Group 8) had decreased levels of TNFα, IL-17A, and IL-4 in colonic tissue as compared to the levels in colonic tissue of mice treated with anti-TNFα IP (Group 7) when assessed at Day 42 of the study.

Figure 68:
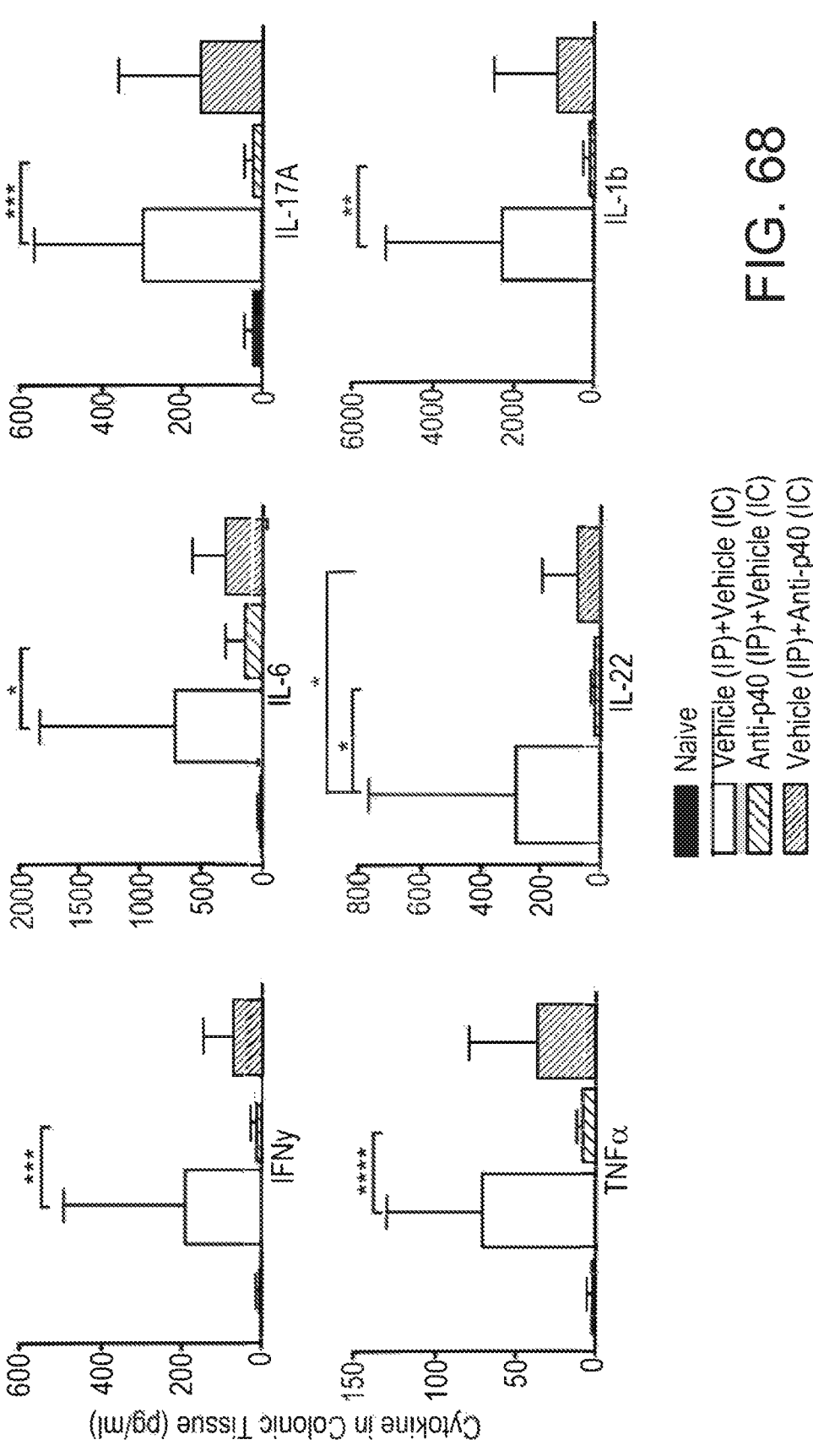
FIG. 68 is a set of graphs showing the colonic tissue concentration of IFN-gamma, IL-6, IL-17A, TNFα, IL-22, and IL-1b in naïve mice (Group 1), mice administered vehicle only both IP and IC (Group 2), mice administered anti-IL12 p40 antibody IP and vehicle IC (Group 5), and mice administered anti-IL12 p40 antibody IC and vehicle IP (Group 8) at Day 42 of the study described in Example 10.

A significant reduction of IL-22, IL-6, IL17A, TNFα, IL-1b, and IFNγ cytokine was found in groups treated with anti-IL12p40 (IP or IC) when compared with vehicle (IP/IC) control in colon tissue (FIG. 68). Mice intracecally administered anti-IL12 p40 antibody (Group 6) had decreased levels of IFNK, IL-6, IL-17A, TNFα, IL-22, and IL-1b in colonic tissue as compared to the levels in colonic tissue in vehicle-administered control mice (Group 2).

Body Weight Loss

Treatments with either systemic (IP) or topical (IC) administration of an anti-TNFα antibody or anti-IL12p40 antibody led to a significant decrease in body weight (BW) loss over time from Day 0 to Day 42.

Figure 69A:
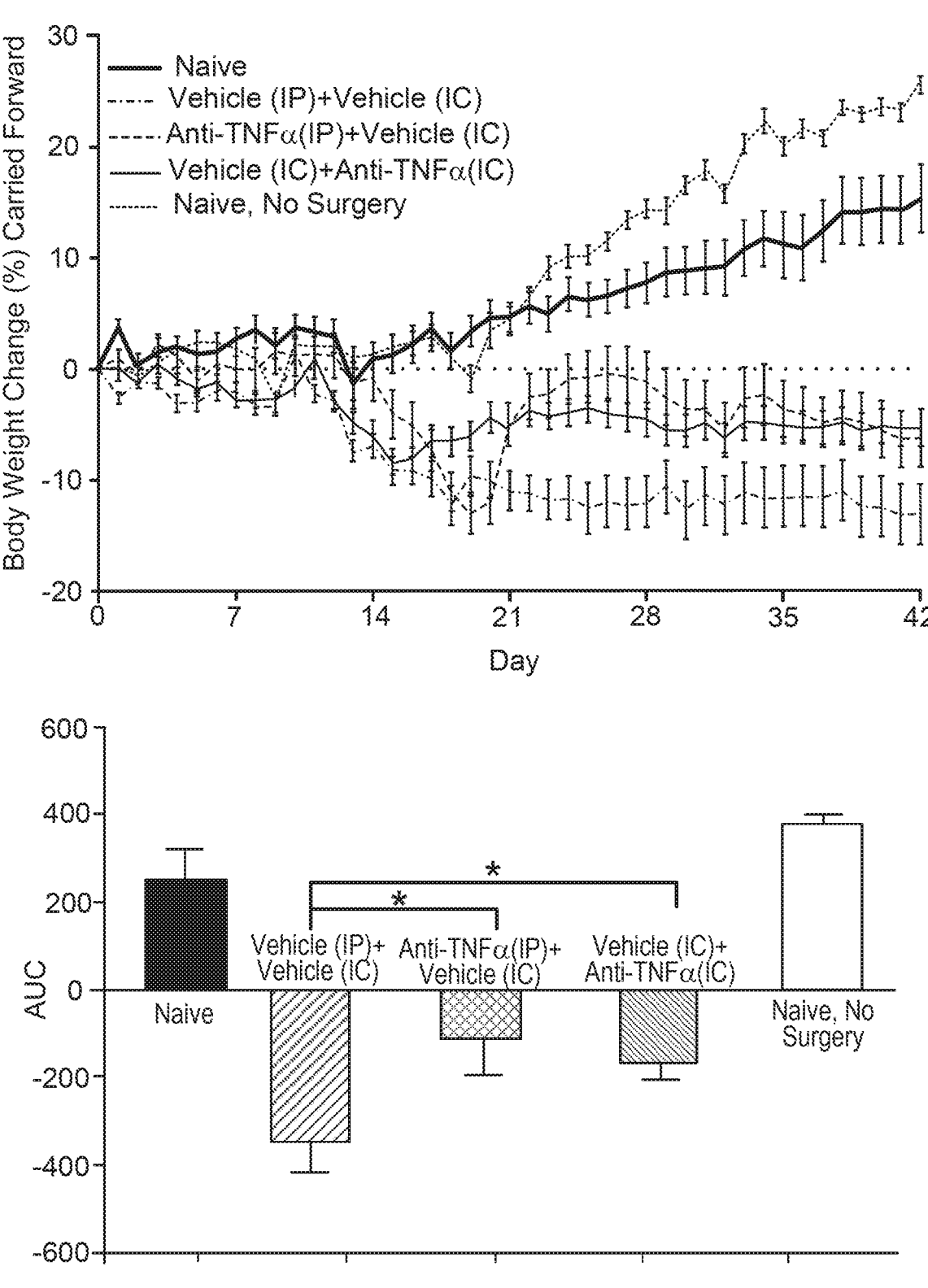
FIGS. 69A-69B show body weight changes (mean % SEM).
Figure 69B:
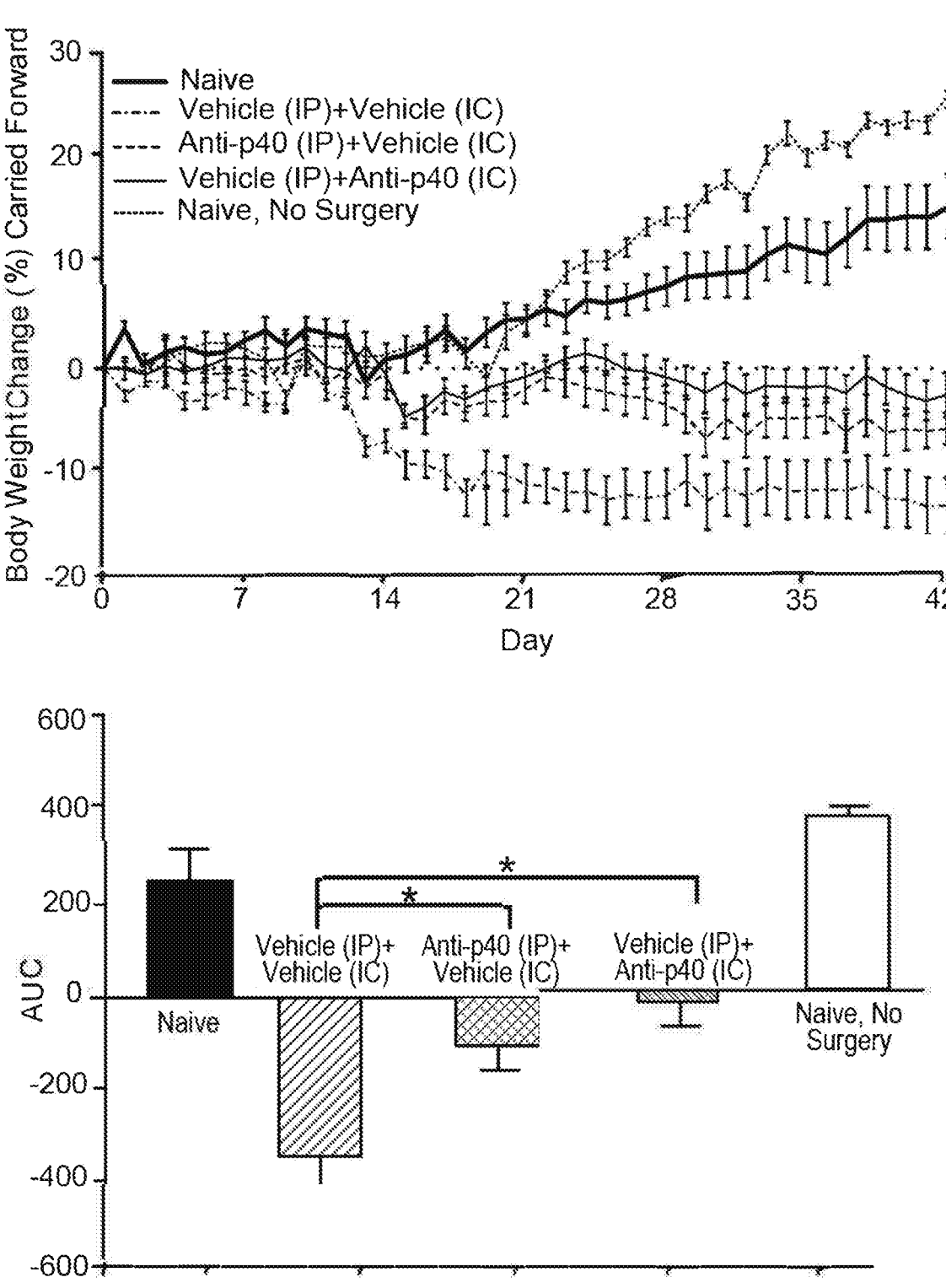

The change in body weight over the course of the experiment from Day 0 through Day 42 is shown in FIGS. 69A and 69B. No apparent signs of disease were observed within the first week after induction of colitis. In control groups treated with PBS vehicle and/or IgG, BW loss did not begin until Days 14 through 16 and continued in the 3rd and 4th week following transfer during the acute phase. The weight loss was maintained until study termination on Day 42. Administration of anti-TNFα antibody or anti-IL12p40 antibody through either IP or IC had a significant reduction in AUC of the BW loss (%) from Day 0 to Day 42 along with the weight increase maintained from Day 21 to Day 42 (FIGS. 69A and 69B). Overall, intracecal administration of anti-IL12p40 antibody had the earliest recovery of weight loss and most significant reduction in overall BW loss from Day 0~ Day 42 in comparison to the vehicle control group amount of all treatment groups (FIG. 69B).

Histopathology Colitis Score

Figure 70:
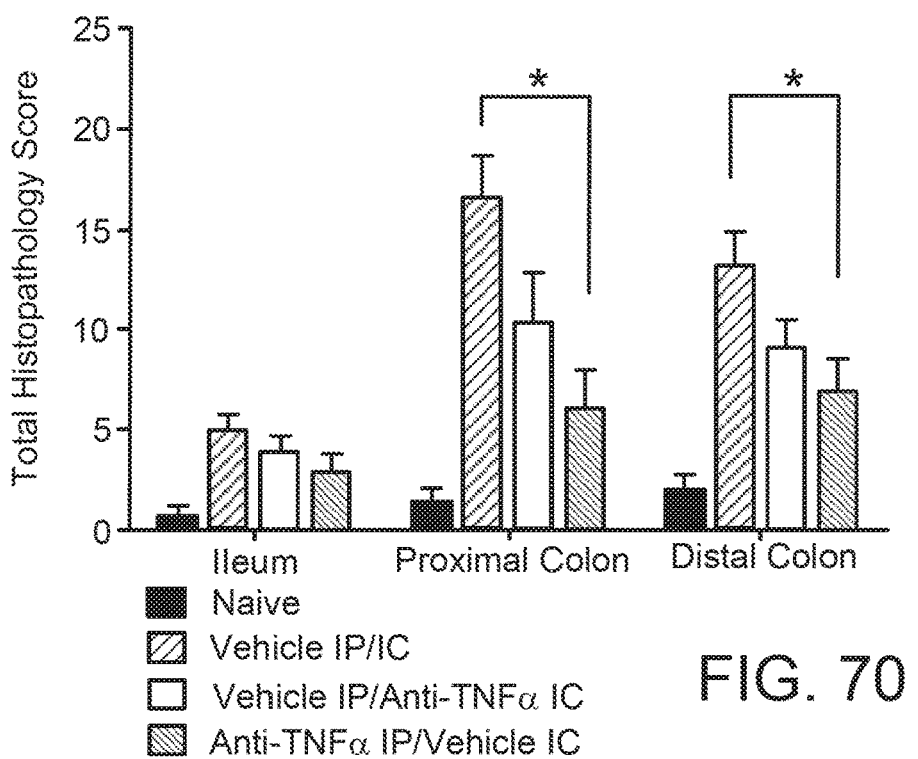
FIG. 70 shows total histopathology score (mean %±SEM) in ileum, proximal colon and distal colon tissues after targeted IC anti-TNF-alpha treatment compared with vehicle and IP treatment groups. Pair-wise comparisons by two-tailed Mann-Whitney U-Test for treatment effects; p<0.05*.

Lesions of ileitis and colitis, including inflammation, crypt damage, occasional erosions, and epithelial hyperplasia, were induced with the T-cell transfer in this model. Lesions were the least severe in ileum sections and the most severe in the proximal colon. Both IP and IC administration of anti-IL12p40 and anti-TNFα resulted in a reduction in sum ileitis/colitis scores compared to PBS vehicle control. Targeted IC anti-TNFα treatment showed a significant improvement in the mean histopathologic score when compared with the vehicle controls given by either route (IP or IC) in proximal and distal colon tissues (FIG. 70).

Lymphocyte Counts

Targeted IC anti-TNFα treatment showed the greatest magnitude of lymphocyte reductions in all counted fields, from inner lumen to submucosa of proximal colon when compared to the vehicle control group (Group 8 vs. Group 2, P<0.05*, FIG. 69A). A similar trend in lymphocyte count reductions was found in the distal colon, although to a lesser degree. Results are shown in FIGS. 71A-71D. Mean counts and scores for all fields were generally the highest in vehicle-treated animals (Group 2, data not shown) and lower in those given anti-TNFα by IP (Group 7, data not shown) or IC (Group 8, FIG. 71B).

Thus, significantly reduced body weight loss (%), decreased Disease Activity Index, improved histological score and reduced tissue inflammatory cytokines were found in animals receiving targeted (IC) anti-TNFα antibody when compared with vehicle controls. Targeted IC delivery was significantly more efficacious when compared to systemic (IP) anti-TNFα antibody in end points of total histologic score and lymphocyte count from inner lumen to submucosa of proximal colon.

Example 11—Evaluation of the Bioavailability of Semaglutide after Intraduodenal Administration Via an Ingestible 2-Nozzle Jet Delivery Device in Female Yorkshire Pigs A study was performed to determine the plasma pharmacokinetics of semaglutide in female Yorkshire pigs after intravenous (IV), subcutaneous (SC), or intraduodenal (ID) administration via an endoscopically placed ingestible device.

Test Article

OZEMPIC® (semaglutide solution) having a semaglutide concentration of 1.34 mg/mL was used in this study.

Ingestible Device Configuration

Each ingestible device was configured as a capsule comprising a substance reservoir; a gas reservoir; a one-way duckbill valve; a piston; two nozzles radially configured 180 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was Friction pressure loss: about 20 psig Fluid pressure: about 300 psig (peak; initial) to about 95 psig (minimum; final)

Jet velocity: about 36.5 m/s (peak; initial) to about 20 psig (minimum; final)

Mean jet velocity: about 26 to 27 m/s

Fluid dispensing time (total): about 80 ms

Jet impact force: about 0.13 N (peak; initial) to about 0.04 N (minimum; final)

Jet impact pressure: 193 psig (peak; initial) to about 60 psig (minimum; final)

Jet power: 2.3 W (peak; initial) to about 0.4 W (minimum; final)

Jet diameter: about 0.35 mm (initial)

Nozzle stand-off distance: ≥1.5 mm

Device diameter: 11.6 mm

Device length: about 34 to 36 mm

In Vivo Study Design

A total of 11 healthy female Yorkshire pigs (*Sus scrofa domesticus*) were used for the study: n=5 for ID administration, n=3 for IV administration, and n=3 for SC administration. Each pig weighed between about 25-30 kg at the initiation of the study. A fixed dose of 0.5 mg semaglutide per pig (~0.02 mg/kg) was administered intraduodenally (ID) via the endoscopically placed ingestible device (Group 1); a 0.02 mg/kg dose was administered to each pig in the IV (Group 2) and SC (Group 3) dose groups. The study design is shown below in Table 32.

TABLE 32

| | | | | | | Blood Collection | |
| Group # | Dose Route | N | Dose | Dose Conc. (mg/mL) | Clinical Observations | Time Points | Termination & Necropsy |
|---|---|---|---|---|---|---|---|
| 1 | ID | 5 | 0.5 mg | 1.34 | Twice on the day of each dose administration, and 24, 72, 144, and 240 hours post dose | Pre-dose, 1, 3, 6, 8, 24, 72, 144, and 240 hours post dose | At termination, necropsy of abdominal region to assess signs of hematoma and gross lesions |
| 2 | IV | 3 | (~0.02 mg/kg) | | | | |
| 3 | SC | 3 | (~0.02 mg/kg) | | | | |

<div>Study Design</div> completed, the ingestible device was weighed again, and the amount of test article delivered was determined. Typically, approximately 0.050 mL was retained in the ingestible device after test article delivery was completed. Thus, approximately 0.400 mL of test article was dispensed from each ingestible device. A summary of parameters for the delivery of the test article solution via the ingestible device is provided below. Initial and final refer to values at the beginning and end of the dispensing period for the test article, respectively.

Internal pressure (pressure of pre-compressed gas): about 320 psig

Pre-compressed gas volume in ingestible device: about 370 microliters (initial) to about 770 microliters (final)

Nozzle diameter: 0.35 mm

Nozzle length: 2 mm

Nozzle throat geometry: circular, sharp-edged orifice

Piston diameter: 9.6 mm

Piston friction: 10 N (one (1) O-ring on piston)

Semaglutide solution was administered at t=0 on the day of dosing. The animals were anesthetized with an intramuscular injection of a cocktail containing ketamine (approximately 10-20 mg/kg), xylazine (approximately 1-2 mg/kg) and atropine (approximately 0.02-0.04 mg/kg). The animals were intubated and maintained using isoflurane (approximately 3-5% in oxygen 1 to 4 L/min) as necessary until dosing was complete. The animals were wakened post dose.

Routes of Administration

For intraduodenal (ID) administration, the ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

For intravenous (IV) administration, the test article was administered intravenously via bolus dose into the marginal ear vein followed by a 1 mL flush with saline if necessary.

For subcutaneous (SC) administration, the test article was administered into the dorsal subcutaneous space directly at the base of the pig. Dose sites were gently shaved and circled with marker pen for identifying the injection site.

Sampling

Each blood sample (~2.0 mL) were taken from the jugular vein (or other suitable vessel) of each pig via direct venipuncture. The samples were collected into chilled tubes with K2EDTA as the anticoagulant, and inverted several times to mix. Blood samples were kept on wet ice until centrifugation. The blood samples were centrifuged at a temperature of 4° C., at 3,000×g, for 5 minutes. All samples were main-concentration curve (AUC) versus time was calculated with the trapezoidal rules from the first sample collection time points (pre-dose, time 0) to last time point of sample collection (240 h post-dose) ($(AUC)_{T0-T240h}$)). Non-compartmental analysis was used to determine PK parameters for each subject. $AUC_{T0-T240h}$, $C_{max}$ and $T_{max}$ were determined for each subject. The bioavailability of semaglutide via ID administration (Group 1) in comparison to the IV (Group 2) and SC (Group 3) administrations was determined.

Results

The results of the study are shown in Table 33 and in FIGS. 72A-72C show the semaglutide concentration in blood over time after: ID administration via the endoscopically placed ingestible device (FIG. 72A); IV administration (FIG. 72B); and SC administration (FIG. 72C).

The bioavailability of semaglutide via ID administration was determined relative to IV or SC administration. The results are shown in Table 33.

TABLE 33

| | Semaglutide plasma PK in swine | | |
|---|---|---|---|
| Route | ID | IV | SC |
| N | $4^a$ | 3 | 3 |
| $T_{max}$ (hr) | 6.67 ± 0.54 | 1.00 ± 0.00 | 18.67 ± 4.53 |
| $C_{max}$ (ng) | 33.57 ± 19.04 | 279.00 ± 9.67 | 98.47 ± 3.49 |
| $(AUC)_{T0-T240\ h}$ ng · hr/mL ± SEM | 1709.4 ± 1108.05 | 11371.67 ± 143.81 | 9695.00 ± 313.95 |
| Corrected $(AUC)_{T0-T240\ h}$ ng · hr/mL ± SEM | $1789.42 ± 1156.76^a$ | N/A | N/A |
| Bioavailability relative to IV ± SEM | $15.74 ± 10.17^a$ | 100% | 85.26 ± 2.96 |
| Bioavailability relative to SC ± SEM | $18.46 ± 11.95^a$ | Not calculated | 100% |

$^a$AUC corrected for dose was used to calculate bioavailability.

tained chilled throughout processing. Plasma was collected into pre-labeled 2-mL microcentrifuge tubes and placed in a freezer set to maintain a temperature of –60° C. to –80° C. until further analysis. The samples were taken prior to dosing, then again at 1, 3, 6, 8, 24, 72, 144, and 240 hours post-dose and sent to an off-site laboratory for bioanalytical analysis. Following the 240 hour post dose blood collection, the animals were euthanized via euthanasia solution IV bolus dose.

Analysis

Samples were processed and analyzed by using a modified LC-MS/MS method (Kapitza, C. et al., J. Clin. Pharm. (2015) 55 (5) pp. 497-504) to quantify in swine plasma in the concentration range 5-500 (for BLQ samples) and 50-1000 ng/ml to quantify in swine plasma. Liraglutide was used as an internal standard (IS). The analysis was carried out using a Waters Xevo-TQ-S LC-MS/MS spectrometer monitoring positive ions in the MRM mode with mass transitions m/z 1029.468>136.124 Da (semaglutide) and m/z 938.9>1266.99 Da (IS), respectively. The LC system was a Waters Acquity™ UPLC® system and the LC column an InfinityLab Poroshell 120 Bonus-RP, 2.1×150 mm, 2.7 μm. Quantification was performed by peak areas and weighted linear regression ($1/x^2$). The lower limit of quantification (LLOQ) for semaglutide was 5 ng/ml. All data and pharmacokinetic parameters were analyzed and graphed using GraphPad Prism version 7.00 for Windows, (GraphPad Software, La Jolla California USA). The area under the a AUC corrected for dose was used to calculate bioavailability.

Example 12—Evaluation of the Bioavailability of Adalimumab after Intraduodenal Administration Via Endoscopic Needle Injection in Female Yorkshire Pigs Two studies were conducted to evaluate the plasma pharmacokinetics of adalimumab in female Yorkshire pigs after intraduodenal (ID) administration via an endoscopic injection needle. The results were compared with those obtained after administration of adalimumab via a 2-nozzle jet delivery device, SC or IV (Example 5).

Test Article

Adalimumab in an aqueous buffer having an adalimumab concentration of about 100 mg/mL.

In Vivo Study Design

A total of 5 healthy female Yorkshire pigs (Sus scrofa domesticus) having a body weight of ~25-40 kg were used in these studies, 3 in a first study and 2 in a second study. Each animal received test article via intraduodenal (ID) administration via an injection needle. The study design is shown below in Table 34.

TABLE 34

| Study | Dose Route | N | Dose | Dose Conc. | Dose volume | Blood Collection Time Points |
|---|---|---|---|---|---|---|
| 1 | ID (endoscopic injection needle) | 3 | 40 mg | 100 mg/mL | 400 microliters | Pre-dose, 1, 3, 6, 8, 24, 72, 144, and 240 hours post dose |
| 2 | ID (endoscopic injection needle) | 2 | 40 mg | 100 mg/mL | 400 microliters | Pre-dose, 1, 3, 6, 8, 24, 72, 144, and 240 hours post dose |

Animals were housed one per cage and fasted for a minimum of 12 hours prior to dosing. Food was returned at 4 hours post-dose. Water was supplied ad libitum.

Intraduodenal (ID) administration was performed as follows. The endoscope (Olympus OSF-V60 attached to an Olympus CV60 Tower) configured with an endoscopic injection needle was maneuvered into the pyloric sphincter with camera visualization to identify the third (inferior/horizontal) part of the duodenum (D3). Following confirmation of placement of the endoscopic injection needle in the correct region, the endoscope was retracted out of the pyloric sphincter, leaving the injection device in the D3 region of the duodenum. Once it was confirmed that the endoscopic injection needle was placed in the correct region, approximately 0.5 mL of saline was injected within the lamina propria of the mucosa to create a small bleb in the mucosa. The formulation was then injected into the bleb and flushed with approximately 0.8 mL of saline. The animals were kept under anesthesia through the 1 hour blood collection time point. All other blood collections were performed on the pigs without the use of anesthesia.

Sampling

Each blood sample was collected from the pig jugular vein, or other suitable vessel via direct venipuncture, placed into a chilled tube containing K2-EDTA as the anticoagulant, and inverted several times to mix. Blood samples were kept on wet ice until centrifugation. Blood samples were centrifuged at a temperature of 4° C., at 3,000×g, for 5 minutes and chilled throughout processing. Plasma was collected into pre-labeled polypropylene tubes and placed in a freezer set to maintain −60 to −80° C. prior to analysis.

Plasma samples were collected at pre-dose, 1, 3, 6, 8, 24, 72, 144, and 240 hours post-dose in all animals and sent to an off-site laboratory for bioanalytical analysis. Samples were processed and analyzed by using an adalimumab (anti-TNF-alpha) ELISA kit from Alpha Diagnostics, Inc. (Catalog #200 310-AHG). All plasma samples were diluted by 1:100 dilution. Diluted samples were processed in duplicates and the mean Optical Density (O.D.) was measured using a SpectraMax plate reader and utilizing SoftMax Pro software for analysis. The Lower Limit of Quantification (LLOQ) was calculated by adding 10× the standard deviation value of the blanks O.D. to the average of the blank standard O.D. values. Mean concentrations of adalimumab were back interpolated to a 4-parameter log fit standard curve and subsequently multiplied by the dilution factor to obtain a final corrected adalimumab concentration. All data and pharmacokinetic parameters were analyzed and graphed by using GraphPad Prism version 7.00 for Windows, Graph-Pad Software, La Jolla California USA, www.graphpad.com (GraphPad Prism 7). The area under the concentration curve (AUC) was calculated with the trapezoidal rules.

Results

PK analysis showed that one animal from the first study and one animal from the second study had quantifiable levels of adalimumab in plasma. The mean $(AUC)_{T0\text{-}T240h}$ for these two animals was determined and the results are shown in FIG. 73 in comparison with subset of data from Example 5, specifically, Example 5 Group 3 (ID administration via ingestible jet delivery device having an internal pressure of 320 psig), Group 4 (SC) and Group 5 (IV).

Example 13—Workflow for Clinical Trial

The following workflow can be used in clinical trials testing the ingestible device 100 described above:

1. Capsule is pre-assembled with a target dispensing location identified.
2. Subject is briefed on device functionality and provides informed consent.
3. Capsule is pre-loaded with a quantified amount of therapeutic drug.
4. Capsule is pressurized (drive mechanism).
5. Capsule is shipped to the clinical site.
6. Subject arrives at clinical site fasted.
7. Site personnel ensures that subject swallows the capsule under medical supervision.
8. Capsule completes delivery of drug at pre-determined dispensing location.
9. Capsule naturally passes through GI tract and is excreted.

Other Embodiments

While certain embodiments have been provided, other embodiments are possible.

As an example, some embodiments have been described in which an ingestible device includes one or more pins. However, the disclosure is not limited in this sense. Rather, in such embodiments, any element having the appropriate shape and size, as well as being made of the appropriate material(s), may be used instead of (or, in some cases, in addition to) one or more of the pins.

As another example, while embodiments have been described in which the dispensable substance is released in a single stage. Other embodiments are possible. In some embodiments, multi-stage (e.g., two stage, three stage, four stage) release of the dispensable substance is used. Multi-staged release can be achieved, for example, via multiple elements (e.g., pins, plugs or the like) formed of different materials (e.g., different enteric materials) that degrade/dissolve erode under different conditions (e.g., different pH, temperature, enzyme concentration) present in different locations in the GI tract of a subject.

As an additional example, while embodiments have been described in which an ingestible device includes a seal or a coating, the disclosure is not limited in this sense. As another example, in some embodiments, the peak fluid pressure or the internal pressure on the pharmaceutical formulation inside the device, prior to release from the device, is at least about 100 psig, optionally ranging from about 100 psig to about 500 psig, and the mean jet velocity of each of the one or more jets upon release of the pharmaceutical formulation from the device ranges from about 10 m/s to about 50 m/s. In a further embodiment, the mean velocity of each of the one or more jets upon release of the pharmaceutical formulation from the device is about 10 or 20 m/s to about 50 m/s.

A number of embodiments have been described. Nevertheless, various modifications may be made without departing from the spirit and scope of the disclosure. Accordingly, other embodiments are within the scope of the following claims.

What is claimed is:

1. An ingestible device comprising:
a storage reservoir in a housing;
a dispensable substance in the storage reservoir;
one or more nozzles in the housing connecting into the storage reservoir, each nozzle extending through a curved sidewall of the housing;
a gas container in the housing containing a compressed gas providing an internal pressure of about 280 psig to about 390 psig; and
a piercer for piercing the gas container to release the compressed gas from the gas container the piercer exerting a force on an enteric material triggering component, the enteric material triggering component resisting the force until the device is triggered, releasing the compressed gas from the gas container after the ingestible device is ingested;
wherein the released compressed gas drives the dispensable substance into the submucosa of the gastrointestinal tract of a patient.

2. The ingestible device of claim 1 wherein the ingestible device is configured to deliver the dispensable substance as a jet through each nozzle with a peak jet power of each jet of about one Watt to about three Watts.

3. The ingestible device of claim 1 wherein the released compressed gas drives a sliding piston in the housing between the gas container and the storage reservoir.

4. The ingestible device of claim 1 wherein the ingestible device is configured to provide a peak fluid pressure on the dispensable substance of about 300 psig to about 375 psig.

5. The ingestible device of claim 1 wherein the ingestible device is configured to deliver the dispensable substance at a mean jet velocity of from about 20 m/s to about 50 m/s.

6. The ingestible device of claim 1 wherein the ingestible device is configured to deliver the dispensable substance to tissue of the gastrointestinal tract of a patient at a peak jet force of about 0.09 N to about 0.15 N.

7. The ingestible device of claim 1 wherein the device is configured to release a dispensable substance volume of 50 microliters to 500 microliters.

8. The ingestible device of claim 1 wherein one or more of the nozzles has a nozzle diameter of 0.25 millimeters to 0.45 millimeters.

9. The ingestible device of claim 1 wherein the device is configured to release a dispensable substance volume of 200 microliters to 400 microliters.

10. An ingestible device comprising:
a storage reservoir in a housing;
a dispensable substance in the storage reservoir;
one or more nozzles connecting into the storage reservoir, each nozzle extending through a sidewall of the housing;
a gas container in the housing containing a compressed gas, the gas container configured to provide an internal pressure of about 280 psig to about 390 psig;
a sliding piston in the housing between the gas container and the storage reservoir; and
an enteric material triggering component which triggers release of the compressed gas from the gas container after the ingestible device is ingested;
wherein the internal pressure is configured to deliver the dispensable substance into the submucosa of the gastrointestinal tract of a patient.

11. The ingestible device of claim 10 wherein the ingestible device is configured to deliver the dispensable substance as a jet through each nozzle with a peak jet power of each jet of about one Watt to about three Watts.

12. The ingestible device of claim 10 wherein the ingestible device is configured to provide a peak fluid pressure on the dispensable substance of about 300 psig to about 375 psig.

13. The ingestible device of claim 10 wherein the ingestible device is configured to deliver the dispensable substance at a mean jet velocity of from about 20 m/s to about 50 m/s.

14. The ingestible device of claim 10 wherein the ingestible device is configured to deliver the dispensable substance to tissue of the gastrointestinal tract of a patient at a peak jet force of about 0.09 N to about 0.15 N.

15. The ingestible device of claim 10 wherein the device is configured to release a dispensable substance volume of 50 microliters to 500 microliters.

16. The ingestible device of claim 10 wherein one or more of the nozzles has a nozzle diameter of 0.25 millimeters to 0.45 millimeters.

17. The ingestible device of claim 10 wherein the nozzles extend through a cylindrical sidewall of the housing.

18. The ingestible device of claim 10 wherein the enteric material triggering component exerts a restraining force which prevents release of compressed gas from the gas container until it is at least partially dissolved, degraded and/or eroded after the device is ingested.

* * * * *